US007662574B2

(12) United States Patent
Watanabe et al.

(10) Patent No.: US 7,662,574 B2

(45) Date of Patent: Feb. 16, 2010

(54) USE OF A G PROTEIN-COUPLED RECEPTOR AND ITS COGNIZANT LIGAND IN THE IDENTIFICATION OF COMPOUNDS THAT AFFECT PROLACTIN SECRETION

(75) Inventors: Takuya Watanabe, Osaka (JP); Kuniko Kikuchi, Ibaraki (JP); Yasuko Terao, Hyogo (JP); Yasushi Shintani, Hamburg (DE); Shuji Hinuma, Ibaraki (JP); Shoji Fukusumi, Ibaraki (JP); Ryo Fujii, Ibaraki (JP); Masaki Hosoya, Ibaraki (JP); Chieko Kitada, Osaka (JP)

(73) Assignee: Takeda Pharmaceutical Company Limited, Osaka-Shi (JP)

( * ) Notice: Subject to any disclaimer, the term of this patent is extended or adjusted under 35 U.S.C. 154(b) by 245 days.

(21) Appl. No.: 11/701,719

(22) Filed: Feb. 2, 2007

(65) Prior Publication Data

US 2007/0202550 A1 Aug. 30, 2007

Related U.S. Application Data

(60) Division of application No. 10/719,587, filed on Nov. 21, 2003, now Pat. No. 7,192,723, which is a continuation-in-part of application No. 09/831,758, filed as application No. PCT/JP99/06283 on Nov. 11, 1999, now abandoned.

(30) Foreign Application Priority Data

| | | |
|---|---|---|
| Mar. 8, 1999 | (JP) | 11-60030 |
| Apr. 14, 1999 | (JP) | 11-106812 |
| Jun. 14, 1999 | (JP) | 11-166672 |
| Aug. 4, 1999 | (JP) | 11-221640 |
| Sep. 14, 1999 | (JP) | 11-259818 |
| Nov. 13, 1999 | (JP) | 10-323759 |

(51) Int. Cl.
*G01N 33/567* (2006.01)
*C07K 14/705* (2006.01)

(52) U.S. Cl. .......................... 435/7.1; 435/7.2; 436/501

(58) Field of Classification Search ....................... None
See application file for complete search history.

(56) References Cited

U.S. PATENT DOCUMENTS 6,262,246 B1 * 7/2001 Gerald et al. .............. 536/23.5

FOREIGN PATENT DOCUMENTS

| | | |
|---|---|---|
| JP | 09-238686 | 9/1997 |
| WO | WO-97-24436 | 7/1997 |

OTHER PUBLICATIONS

Daniela Marazziti, et al.; "*Molecular Cloning and Chromosomal Localization of the Mouse Gpr37 Gene Encoding an Orphan G-Protein-Coupled Peptide Receptor Expressed in brain and Testis*"; Genomics 53, pp. 315-324; (1998); Article No. GE985433.
Dorland's Illustrated Medical Dictionary, 28th ed. (1994), p. 1361.
The Merck Index, 13th ed. (2001), p. 1392.
The Merck Mannual, 17th ed. (1999), p. 68.
Concise Oxford English Dictionary (1990), p. 954.

* cited by examiner

*Primary Examiner*—John D Ulm
(74) *Attorney, Agent, or Firm*—Edwards Angell Palmer & Dodge LLP; David G. Conlin, Esq.; Kathryn A. Piffat, Esq.

(57) ABSTRACT

The polypeptides in the present invention possess the effects of promoting and inhibiting the secretion of prolactin, and are thus useful as drugs for the prevention and treatment of various diseases, in terms of prolactin secretion stimulants, which are associated with the secretion of prolactin, such as hypoovarianism, spermatic underdevelopment, menopausal symptoms, hypothyroidism, etc. The polypeptides are useful as drugs for the prevention and treatment of various diseases, in terms of prolactin secretion inhibitors, which are associated with the secretion of prolactin, such as pituitary tumor, diencephalon tumor, menstrual disorder, autoimmune diseases, prolactinoma, sterility, impotence, amenorrhea, lactorrhea, acromegaly, Chiari-Frommel syndrome, Argonz-del Castilo syndrome, Forbes-Albright syndrome, lymphoma, Sheehan's syndrome, spermatogenesis disorder, etc.

1 Claim, 15 Drawing Sheets

Fig.1

```
                9           18          27          36          45          54
5'  ATG GAA ATT ATT TCA TCA AAA CTA TTC ATT TTA TTG ACT TTA GCC ACT TCA AGC
    --- --- --- --- --- --- --- --- --- --- --- --- --- --- --- --- --- ---
    Met Glu Ile Ile Ser Ser Lys Leu Phe Ile Leu Leu Thr Leu Ala Thr Ser Ser

               63          72          81          90          99          108
    TTG TTA ACA TCA AAC ATT TTT TGT GCA GAT GAA TTA GTG ATG TCC AAT CTT CAC
    --- --- --- --- --- --- --- --- --- --- --- --- --- --- --- --- --- ---
    Leu Leu Thr Ser Asn Ile Phe Cys Ala Asp Glu Leu Val Met Ser Asn Leu His

               117         126         135         144         153         162
    AGC AAA GAA AAT TAT GAC AAA TAT TCT GAG CCT AGA GGA TAC CCA AAA GGG GAA
    --- --- --- --- --- --- --- --- --- --- --- --- --- --- --- --- --- ---
    Ser Lys Glu Asn Tyr Asp Lys Tyr Ser Glu Pro Arg Gly Tyr Pro Lys Gly Glu

               171         180         189         198         207         216
    AGA AGC CTC AAT TTT GAG GAA TTA AAA GAT TGG GGA CCA AAA AAT GTT ATT AAG
    --- --- --- --- --- --- --- --- --- --- --- --- --- --- --- --- --- ---
    Arg Ser Leu Asn Phe Glu Glu Leu Lys Asp Trp Gly Pro Lys Asn Val Ile Lys

               225         234         243         252         261         270
    ATG AGT ACA CCT GCA GTC AAT AAA ATG CCA CAC TCC TTC GCC AAC TTG CCA TTG
    --- --- --- --- --- --- --- --- --- --- --- --- --- --- --- --- --- ---
    Met Ser Thr Pro Ala Val Asn Lys Met Pro His Ser Phe Ala Asn Leu Pro Leu

               279         288         297         306         315         324
    AGA TTT GGG AGG AAC GTT CAA GAA GAA AGA AGT GCT GGA GCA ACA GCC AAC CTG
    --- --- --- --- --- --- --- --- --- --- --- --- --- --- --- --- --- ---
    Arg Phe Gly Arg Asn Val Gln Glu Glu Arg Ser Ala Gly Ala Thr Ala Asn Leu

               333         342         351         360         369         378
    CCT CTG AGA TCT GGA AGA AAT ATG GAG GTG AGC CTC GTG AGA CGT GTT CCT AAC
    --- --- --- --- --- --- --- --- --- --- --- --- --- --- --- --- --- ---
    Pro Leu Arg Ser Gly Arg Asn Met Glu Val Ser Leu Val Arg Arg Val Pro Asn

               387         396         405         414         423         432
    CTG CCC CAA AGG TTT GGG AGA ACA ACA ACA GCC AAA AGT GTC TGC AGG ATG CTG
    --- --- --- --- --- --- --- --- --- --- --- --- --- --- --- --- --- ---
    Leu Pro Gln Arg Phe Gly Arg Thr Thr Thr Ala Lys Ser Val Cys Arg Met Leu

               441         450         459         468         477         486
    AGT GAT TTG TGT CAA GGA TCC ATG CAT TCA CCA TGT GCC AAT GAC TTA TTT TAC
    --- --- --- --- --- --- --- --- --- --- --- --- --- --- --- --- --- ---
    Ser Asp Leu Cys Gln Gly Ser Met His Ser Pro Cys Ala Asn Asp Leu Phe Tyr

               495         504         513         522         531         540
    TCC ATG ACC TGC CAG CAC CAA GAA ATC CAG AAT CCC GAT CAA AAA CAG TCA AGG
    --- --- --- --- --- --- --- --- --- --- --- --- --- --- --- --- --- ---
    Ser Met Thr Cys Gln His Gln Glu Ile Gln Asn Pro Asp Gln Lys Gln Ser Arg

    TAA 3'
    ---
    ***
```

Fig.3

```
                9              18             27             36             45             54
5'  ATG GAA ATT ATT TCA TCA AAA CTA TTC ATT TTA TTG ACT TTA GCC ACT TCA AGC
    --- --- --- --- --- --- --- --- --- --- --- --- --- --- --- --- --- ---
    Met Glu Ile Ile Ser Ser Lys Leu Phe Ile Leu Leu Thr Leu Ala Thr Ser Ser

                63             72             81             90             99            108
    TTG TTA ACA TCA AAC ATT TTT TGT GCA GAT GAA TTA GTG ATG TCC AAT CTT CAC
    --- --- --- --- --- --- --- --- --- --- --- --- --- --- --- --- --- ---
    Leu Leu Thr Ser Asn Ile Phe Cys Ala Asp Glu Leu Val Met Ser Asn Leu His

               117            126            135            144            153            162
    AGC AAA GAA AAT TAT GAC AAA TAT TCT GAG CCT AGA GGA TAC CCA AAA GGG GAA
    --- --- --- --- --- --- --- --- --- --- --- --- --- --- --- --- --- ---
    Ser Lys Glu Asn Tyr Asp Lys Tyr Ser Glu Pro Arg Gly Tyr Pro Lys Gly Glu

               171            180            189            198            207            216
    AGA AGC CTC AAT TTT GAG GAA TTA AAA GAT TGG GGA CCA AAA AAT GTT ATT AAG
    --- --- --- --- --- --- --- --- --- --- --- --- --- --- --- --- --- ---
    Arg Ser Leu Asn Phe Glu Glu Leu Lys Asp Trp Gly Pro Lys Asn Val Ile Lys

               225            234            243            252            261            270
    ATG AGT ACA CCT GCA GTC AAT AAA ATG CCA CAC TCC TTC GCC AAC TTG CCA TTG
    --- --- --- --- --- --- --- --- --- --- --- --- --- --- --- --- --- ---
    Met Ser Thr Pro Ala Val Asn Lys Met Pro His Ser Phe Ala Asn Leu Pro Leu

               279            288            297            306            315            324
    AGA TTT GGG AGG AAC GTT CAA GAA GAA AGA AGT GCT GGA GCA ACA GCC AAC CTG
    --- --- --- --- --- --- --- --- --- --- --- --- --- --- --- --- --- ---
    Arg Phe Gly Arg Asn Val Gln Glu Glu Arg Ser Ala Gly Ala Thr Ala Asn Leu

               333            342            351            360            369            378
    CCT CTG AGA TCT GGA AGA AAT ATG GAG GTG AGC CTC GTG AGA CGT GTT CCT AAC
    --- --- --- --- --- --- --- --- --- --- --- --- --- --- --- --- --- ---
    Pro Leu Arg Ser Gly Arg Asn Met Glu Val Ser Leu Val Arg Arg Val Pro Asn

               387            396            405            414            423            432
    CTG CCC CAA AGG TTT GGG AGA ACA ACA ACA GCC AAA AGT GTC TGC AGG ATG CTG
    --- --- --- --- --- --- --- --- --- --- --- --- --- --- --- --- --- ---
    Leu Pro Gln Arg Phe Gly Arg Thr Thr Thr Ala Lys Ser Val Cys Arg Met Leu

               441            450            459            468            477            486
    AGT GAT TTG TGT CAA GGA TCC ATG CAT TCA CCA TGT GCC AAT GAC TTA TTT TAC
    --- --- --- --- --- --- --- --- --- --- --- --- --- --- --- --- --- ---
    Ser Asp Leu Cys Gln Gly Ser Met His Ser Pro Cys Ala Asn Asp Leu Phe Tyr

               495            504            513            522            531            540
    TCC ATG ACC TGC CAG CAC CAA GAA ATC CAG AAT CCC GAT CAA AAA CAG TCA AGG
    --- --- --- --- --- --- --- --- --- --- --- --- --- --- --- --- --- ---
    Ser Met Thr Cys Gln His Gln Glu Ile Gln Asn Pro Asp Gln Lys Gln Ser Arg

               549            558            567            576            585
    AGA CTG CTA TTC AAG AAA ATA GAT GAT GCA GAA TTG AAA CAA GAA AAA TAA 3'
    --- --- --- --- --- --- --- --- --- --- --- --- --- --- --- --- ---
    Arg Leu Leu Phe Lys Lys Ile Asp Asp Ala Glu Leu Lys Gln Glu Lys ***
```

Fig.4

```
            9          18          27          36          45          54
5' ATG GAA ATT ATT TCA TTA AAA CGA TTC ATT TTA TTG ATG TTA GCC ACT TCA AGC
   --- --- --- --- --- --- --- --- --- --- --- --- --- --- --- --- --- ---
   Met Glu Ile Ile Ser Leu Lys Arg Phe Ile Leu Leu Met Leu Ala Thr Ser Ser

           63          72          81          90          99         108
   TTG TTA ACA TCA AAC ATC TTC TGC ACA GAC GAA TCA AGG ATG CCC AAT CTT TAC
   --- --- --- --- --- --- --- --- --- --- --- --- --- --- --- --- --- ---
   Leu Leu Thr Ser Asn Ile Phe Cys Thr Asp Glu Ser Arg Met Pro Asn Leu Tyr

          117         126         135         144         153         162
   AGC AAA AAG AAT TAT GAC AAA TAT TCC GAG CCT AGA GGA GAT CTA GGC TGG GAG
   --- --- --- --- --- --- --- --- --- --- --- --- --- --- --- --- --- ---
   Ser Lys Lys Asn Tyr Asp Lys Tyr Ser Glu Pro Arg Gly Asp Leu Gly Trp Glu

          171         180         189         198         207         216
   AAA GAA AGA AGT CTT ACT TTT GAA GAA GTA AAA GAT TGG GCT CCA AAA ATT AAG
   --- --- --- --- --- --- --- --- --- --- --- --- --- --- --- --- --- ---
   Lys Glu Arg Ser Leu Thr Phe Glu Glu Val Lys Asp Trp Ala Pro Lys Ile Lys

          225         234         243         252         261         270
   ATG AAT AAA CCT GTA GTC AAC AAA ATG CCA CCT TCT GCA GCC AAC CTG CCA CTG
   --- --- --- --- --- --- --- --- --- --- --- --- --- --- --- --- --- ---
   Met Asn Lys Pro Val Val Asn Lys Met Pro Pro Ser Ala Ala Asn Leu Pro Leu

          279         288         297         306         315         324
   AGA TTT GGG AGG AAC ATG GAA GAA GAA AGG AGC ACT AGG GCG ATG GCC CAC CTG
   --- --- --- --- --- --- --- --- --- --- --- --- --- --- --- --- --- ---
   Arg Phe Gly Arg Asn Met Glu Glu Glu Arg Ser Thr Arg Ala Met Ala His Leu

          333         342         351         360         369         378
   CCT CTG AGA CTC GGA AAA AAT AGA GAG GAC AGC CTC TCC AGA TGG GTC CCA AAT
   --- --- --- --- --- --- --- --- --- --- --- --- --- --- --- --- --- ---
   Pro Leu Arg Leu Gly Lys Asn Arg Glu Asp Ser Leu Ser Arg Trp Val Pro Asn

          387         396         405         414         423         432
   CTG CCC CAG AGG TTT GGA AGA ACA ACA ACA GCC AAA AGC ATT ACC AAG ACC CTG
   --- --- --- --- --- --- --- --- --- --- --- --- --- --- --- --- --- ---
   Leu Pro Gln Arg Phe Gly Arg Thr Thr Thr Ala Lys Ser Ile Thr Lys Thr Leu

          441         450         459         468         477         486
   AGT AAT TTG CTC CAG CAG TCC ATG CAT TCA CCA TCT ACC AAT GGG CTA CTC TAC
   --- --- --- --- --- --- --- --- --- --- --- --- --- --- --- --- --- ---
   Ser Asn Leu Leu Gln Gln Ser Met His Ser Pro Ser Thr Asn Gly Leu Leu Tyr

          495         504         513         522         531         540
   TCC ATG GCC TGC CAG CCC CAA GAA ATC CAG AAT CCT GGT CAA AAG AAC CTA AGG
   --- --- --- --- --- --- --- --- --- --- --- --- --- --- --- --- --- ---
   Ser Met Ala Cys Gln Pro Gln Glu Ile Gln Asn Pro Gly Gln Lys Asn Leu Arg

          549         558         567         576         585
   AGA CGG GGA TTC CAG AAA ATA GAT GAT GCA GAA TTG AAA CAA GAA AAA TAA 3'
   --- --- --- --- --- --- --- --- --- --- --- --- --- --- --- --- ---
   Arg Arg Gly Phe Gln Lys Ile Asp Asp Ala Glu Leu Lys Gln Glu Lys ***
```

Fig.5

```
              9           18          27          36          45          54
5' ATG GAA ATT ATT TCA TCA AAG CGA TTC ATT TTA TTG ACT TTA GCA ACT TCA AGC
   Met Glu Ile Ile Ser Ser Lys Arg Phe Ile Leu Leu Thr Leu Ala Thr Ser Ser
             63          72          81          90          99         108
   TTC TTA ACT TCA AAC ACC CTT TGT TCA GAT GAA TTA ATG ATG CCC CAT TTT CAC
   Phe Leu Thr Ser Asn Thr Leu Cys Ser Asp Glu Leu Met Met Pro His Phe His
            117         126         135         144         153         162
   AGC AAA GAA GGT TAT GGA AAA TAT TAC CAG GTG AGA GGA ATC CCA AAA GGG GTA
   Ser Lys Glu Gly Tyr Gly Lys Tyr Tyr Gln Leu Arg Gly Ile Pro Lys Gly Val
            171         180         189         198         207         216
   AAG GAA AGA AGT GTG ACT TTT CAA GAA CTC AAA GAT TGG GGG GCA AAG AAA GAT
   Lys Glu Arg Ser Val Thr Phe Gln Glu Leu Lys Asp Trp Gly Ala Lys Lys Asp
            225         234         243         252         261         270
   ATT AAG ATG AGT CCA GCC CCT GCC AAC AAA GTG CCC CAC TCA GCA GCC AAC CTT
   Ile Lys Met Ser Pro Ala Pro Ala Asn Lys Val Pro His Ser Ala Ala Asn Leu
            279         288         297         306         315         324
   CCC CTG AGG TTT GGG AGG AAC ATA GAA GAC AGA AGA AGC CCC AGG GCA CGG GCC
   Pro Leu Arg Phe Gly Arg Asn Ile Glu Asp Arg Arg Ser Pro Arg Ala Arg Ala
            333         342         351         360         369         378
   AAC ATG GAG GCA GGG ACC ATG AGC CAT TTT CCC AGC CTG CCC CAA AGG TTT GGG
   Asn Met Glu Ala Gly Thr Met Ser His Phe Pro Ser Leu Pro Gln Arg Phe Gly
            387         396         405         414         423         432
   AGA ACA ACA GCC AGA CGC ATC ACC AAG ACA CTG GCT GGT TTG CCC CAG AAA TCC
   Arg Thr Thr Ala Arg Arg Ile Thr Lys Thr Leu Ala Gly Leu Pro Gln Lys Ser
            441         450         459         468         477         486
   CTG CAC TCC CTG GCC TCC AGT GAA TCG CTC TAT GCC ATG ACC CGC CAG CAT CAA
   Leu His Ser Leu Ala Ser Ser Glu Ser Leu Tyr Ala Met Thr Arg Gln His Gln
            495         504         513         522         531         540
   GAA ATT CAG AGT CCT GGT CAA GAC CAA CCT AGG AAA CGC GTG TTC ACG GAA ACA
   Glu Ile Gln Ser Pro Gly Gln Glu Gln Pro Arg Lys Arg Val Phe Thr Glu Thr
            549         558         567         576         585         594
   GAT GAT GCA GAA AGG AAA CAA GAA AAA ATA GGA AAC CTC CAG CCA GTC CTT CAA
   Asp Asp Ala Glu Arg Lys Gln Glu Lys Ile Gly Asn Leu Gln Pro Val Leu Gln
            603         612
   GGG GCT ATG AAG CTG TGA  3'
   Gly Ala Met Lys Leu ***
```

Fig.6

```
                          10         20         30         40         50
hLPLRF.aa      1 MEIISSKLFI LLTLATSSLL TSNIFCADEL VMSNLHSKEN YDKYSEPRG-    50
bLPLRF.aa      1 MEIISLKRFI LLMLATSSLL TSNIFCTDES RMPNLYSKKN YDKYSEPRGD    50
rLPLRF.aa      1 MEIISSKRFI LLTLATSSFL TSNTLCSDEL MMPHFHSKEG YGKYYQLRGI    50

                          60         70         80         90        100
hLPLRF.aa     51 --YPKG--ER SLNFEELKDW GPKNVIKMST PAVNKMPHSF ANLPLRFGRN   100
bLPLRF.aa     51 LGWEK---ER SLTFEEVKDW APK--IKMNK PVVNKMPPSA ANLPLRFGRN   100
rLPLRF.aa     51 ---PKGVKER SVTFQELKDW GAKKDIKMSP APANKVPHSA ANLPLRFGRN   100

                         110        120        130        140        150
hLPLRF.aa    101 VQEERSAGAT ANLPLRSGRN MEVSLVRRVP NLPQRFGRTT TAKSVCRMLS   150
bLPLRF.aa    101 MEEERSTRAM AHLPLRLGKN REDSLSRWVP NLPQRFGRTT TAKSITKTLS   150
rLPLRF.aa    101 IEDRRSPRAR ANM------- -EAGTMSHFP SLPQRFGRTT -ARRITKTLA   150

                         160        170        180        190        200
hLPLRF.aa    151 DLCQGSMHSP CANDLFYSMT CQHQEIQNPD QKQSRRLLFK KIDDAELKQE   200
bLPLRF.aa    151 NLLQQSMHSP STNGLLYSMA CQPQEIQNPG QKNLRRRGFQ KIDDAELKQE   200
rLPLRF.aa    151 GLPQKSLHSL ASSESLYAMT RQHQEIQSPG QEQPRKRVFT ETDDAERKQE   200

                         210        220        230        240        250
hLPLRF.aa    201 K*-------- ------.... .......... .......... ..........   250
bLPLRE.aa    201 K*-------- ------.... .......... .......... ..........   250
rLPLRF.aa    201 KIGNLQPVLQ GAMKL*.... .......... .......... ..........   250
```

Fig.7

```
1    TTTAGACTTAGACGAAATGGAAATTATTTCATTAAAACGATTCATTTTATTGACTGTG  58
1                            MetGluIleIleSerLeuLysArgPheIleLeuLeuThrVal  14
59   GCAACTTCAAGCTTCTTAACATCAAACACCTTCTGTACAGATGAGTTCATGATGCCTCAT  118
15   AlaThrSerSerPheLeuThrSerAsnThrPheCysThrAspGluPheMetMetProHis  34
119  TTTCACAGCAAAGAAGGTGACGGAAAATACTCCCAGCTGAGAGGAATCCCAAAAGGGGAA  178
35   PheHisSerLysGluGlyAspGlyLysTyrSerGlnLeuArgGlyIleProLysGlyGlu  54
179  AAGGAAAGAAGTGTCAGTTTTCAAGAACTAAAAGATTGGGGGGCAAAGAATGTTATTAAG  238
55   LysGluArgSerValSerPheGlnGluLeuLysAspTrpGlyAlaLysAsnValIleLys  74
239  ATGAGTCCAGCCCCTGCCAACAAAGTGCCCCACTCAGCAGCCAACCTGCCCCTGAGATTT  298
75   MetSerProAlaProAlaAsnLysValProHisSerAlaAlaAsnLeuProLeuArgPhe  94
299  GGAAGGACCATAGATGAGAAAAGAAGCCCCGCAGCACGGGTCAACATGGAGGCAGGGACC  358
95   GlyArgThrIleAspGluLysArgSerProAlaAlaArgValAsnMetGluAlaGlyThr  114
359  AGGAGCCATTTCCCCAGCCTGCCCCAAAGGTTTGGGAGAACAACAGCCAGAAGCCCCAAG  418
115  ArgSerHisPheProSerLeuProGlnArgPheGlyArgThrThrAlaArgSerProLys  154
419  ACACCCGCTGATTTGCCACAGAAACCCCTGCACTCACTGGGCTCCAGCGAGTTGCTCTAC  538
135  ThrProAlaAspLeuProGlnLysProLeuHisSerLeuGlySerSerGluLeuLeuTyr  154
479  GTCATGATCTGCCAGCACCAAGAAATTCAGAGTCCTGGTGGAAAGCGAACGAGGAGAGGA  538
155  ValMetIleCysGlnHisGlnGluIleGlnSerProGlyGlyLysArgThrArgArgGly  174
539  GCGTTTGTGGAAACAGATGATGCAGAAAGGGAAACCAGAAAAATAGGAAACTCGAGCCCG  598
175  AlaPheValGluThrAspAspAlaGluArgLysProGluLys***                188
599  ACTTCAAGAGGCTACGGAGC                                          618
188                                                                188
```

USE OF A G PROTEIN-COUPLED RECEPTOR AND ITS COGNIZANT LIGAND IN THE IDENTIFICATION OF COMPOUNDS THAT AFFECT PROLACTIN SECRETION

CROSS-REFERENCES TO RELATED APPLICATIONS

The present application is a divisional application of U.S. Ser. No. 10/719,587, filed Nov. 21, 2003, the disclosure of which is incorporated herein by reference and which is a continuation-in-part application of U.S. Ser. No. 09/831,758, filed May 11, 2001, the disclosure of which is incorporated herein by reference and which claims priority under 35 U.S.C. §371 to PCT/JP99/06283, filed Nov. 11, 1999, the disclosure of which is incorporated herein by reference and which claims priority of Ser. No. 11/259,818, which was filed in Japan on Sep. 14, 1999; Ser. No. 11/221,640, which was filed in Japan on Aug. 4, 1999; Ser. No. 11/166,672, which was filed in Japan on Jun. 14, 1999; Ser. No. 11/106,812, which was filed in Japan on Apr. 14, 1999; Ser. No. 11/60,030, which was filed in Japan on Mar. 8, 1999; and Ser. No. 10/323,759, which was filed in Japan on Nov. 13, 1998; the entire contents of all of these applications listed in this paragraph being hereby incorporated herein by reference.

FIELD OF THE INVENTION

The present invention relates to a novel polypeptide (hereinafter sometimes referred to as a novel physiologically active polypeptide throughout the specification), its partial peptide, DNA encoding the same, as well as a receptor protein capable of recognizing the polypeptide as a ligand, its partial peptide and DNA encoding the same, and so on. In particular, the present invention relates to a novel polypeptide characterized by containing an RF amide-like structure and its partial peptide. The present invention also relates to a prolactin secretion regulatory agent comprising a novel physiologically active polypeptide, its partial peptide and the like.

BACKGROUND ART

Peptides play pivotal roles as the molecules for regulating various functions in vivo such as metabolism, growth, reproduction, maintenance of homeostasis, mental activities, biological protection or the like. These peptides are coupled to specific receptors on the cell membrane to transduce their information. So far, most of these physiologically active peptides have been isolated from tissue extracts, etc. based on their physiological activities followed by determination of their structures. Using these receptors, physiologically active peptides have recently been isolated from tissue extracts, etc.

On the other hand, the latest rapid progress of sequencing of genome or cDNA has made accessible to enormous information on DNAs. It is assumed that these DNAs would comprise the DNA encoding for physiologically active peptides hitherto unknown. However, most physiologically active peptides have only very short amino acid sequences. Therefore, even if one attempts to explore, from genomic DNA sequences or expressed sequence tag (EST), such unknown physiologically active peptides bearing a sequence in part similar to or a common motif to known physiologically active peptides, desired sequences similar to these known peptides are frequently found only in protein genes not at all associated with physiologically active peptides or in DNA sequences of non-translational region. It was thus extremely difficult to ascertain which the objective physiologically active peptide is in these peptides.

FMRF amide, one of physiologically active peptides, is a peptide isolated from the ganglia of bivalve, which structure was determined for the first time (Price, D. A. & Greenberg, M. J., Science, 197 670-671, 1977). Since then it has turned out that peptides having an RF amide structure at the C terminus and peptides having a structure similar to the RF amide structure are present over many species of the invertebrate animal. Many peptides having the RF amide structure are reported to be present especially in the nematodes. It is also known that most of these peptides are borne on one gene in such a state that a plurality of peptides is contiguous (Nelson, L. S., et al., Molecular Brain Research, 58, 103-111, 1998).

Turning to the vertebrate animal, LPLRF amide was isolated from the brain of chicken and identified to be an FMRF amide-like peptide having the RF amide structure. However, its gene structure remains yet unknown (Dockray, G. J., et al., Nature, 305, 328-330, 1983). In fish, C-RFa was recently reported to be a peptide with the RF amide structure. As peptides containing the RF amide structure in mammal, there are known two peptides purified and isolated from bovine (Yang, H.-Y. T., et al., Proc. Natl. Acad. Sci. USA, 82, 7757-7761, 1985) and neuropeptide SF (NSF) and neuropeptide AF(NAF) isolated from human cDNA, which are considered to correspond to the two peptides above. Recently, the present inventors identified prolactin-releasing peptides (PrRP) containing the RF amide structure in human, bovine and rats (Hinuma, S., et al., Nature, 393, 272-276, 1998).

Various reports have been published on the physiological activities of the FMRF amide peptides, which include, for example, acceleration or suppression of heartbeats, contraction or relaxation of various radular muscle, visceral muscle and retractor muscle, and hyperpolarization or depolarization of nerve cells. With respect to PrRP and LPLRF amides, prolactin-releasing stimulation activity, and nerve cell-stimulating effects or hypertension effects are reported, respectively.

As stated above, many important physiological activities have been reported on the RF amide structure-bearing peptides. However, it is totally unknown if there is any other peptide containing the RF amide or the like structure in mammals, except NSF, NAF or PrRP.

On the other hand, a variety of physiologically active substances such as hormones, neurotransmitters, etc. regulate the functions in vivo through specific receptor proteins located in a cell membrane. Many of these receptor proteins are coupled with guanine nucleotide-binding protein (hereinafter sometimes referred to as G protein) and mediate the intracellular signal transduction via activation of G protein. These receptor proteins possess the common structure, i.e. seven transmembrane domains and are thus collectively referred to as G protein-coupled receptors or seven-transmembrane receptors (7TMR).

G protein-coupled receptor proteins present on the cell surface of each functional cells and organs in the body, and play important physiological roles as the targets of molecules that regulate the functions of the cells and organs, e.g., hormones, neurotransmitters, physiologically active substances and the like. Receptors transmit signals into cells via binding with physiologically active substances, and the signals induce various reactions such as activation and inhibition of the cells.

To clarify the relationship between substances that regulate complex biological functions in various cells and organs and their specific receptor proteins, in particular, G protein-coupled receptor proteins would elucidate the functional mechanisms in various cells and organs in the body to provide a very important means for development of drugs closely associated with the functions.

For example, in various organs, their physiological functions are controlled in vivo through regulation by many hormones, hormone-like substances, neurotransmitters or physiologically active substances. In particular, physiologically active substances are found in numerous sites of the body and regulate the physiological functions through their corresponding receptor proteins. However, it is supposed that many unknown hormones, neurotransmitters or other physiologically active substances still exist in the body and, as for their receptor proteins, many of such proteins have not yet been reported. In addition, it is still unknown if there are subtypes of known receptor proteins.

One of the pathways to modulate biological functions mediated by the interactions of hormones or neurotransmitters with G protein-coupled receptors is the hypothalamus-pituitary system. In this system, the secretion of pituitary hormones from the pituitary gland is regulated by hypothalamic hormones (pituitatropic hormones), and the functions of the target cells/organs are regulated by the pituitary hormones released into the blood. Functions, which are important for the living body, including the maintenance of homeostasis and the control of development, metabolism and growth of a genital system and an individual organism, are regulated through this pathway.

The secretion of pituitary hormones is controlled by a positive feedback or a negative feedback mechanism by the hypothalamic hormone and the peripheral hormone secreted from the target endocrine glands.

It is also widely known that these hormones and factors as well as their receptors are not localized in the hypothalamus-pituitary system but are broadly distributed in the brain. This fact suggests that the substances called hypothalamic hormones are functioning as neurotransmitters or neuromodulators in the central nervous system.

Moreover, these substances are distributed even in the peripheral tissues as well and thought to be playing the role of important functions in the respective tissues.

It is also very important for development of drugs to clarify the relationship between substances that regulate elaborate functions in vivo and their specific receptor proteins. Furthermore, for efficient screening of agonists and antagonists to receptor proteins in development of drugs, it is required to clarify functional mechanisms of receptor protein genes expressed in vivo and express the genes in an appropriate expression system.

In recent years, random analysis of cDNA sequences has been actively studied as a means for analyzing genes expressed in vivo. The sequences of cDNA fragments thus obtained have been registered on and published to databases as Expressed Sequence Tag (EST). However, since many ESTs contain sequence information only, it is difficult to deduce their functions from the information.

It has thus been desired to find an unknown polypeptide (peptide) having RF amide-like structure or an unknown G protein-coupled receptor protein and using these peptides to develop a drug for the prevention, treatment or diagnosis for disease, comprising a novel physiologically active peptide, in particular, for regulating the secretion of pituitary hormones from the pituitary gland by regulating the secretion of hypothalamic hormones.

DISCLOSURE OF THE INVENTION

In order to solve the foregoing problems, the present inventors have made extensive studies and as a result, succeeded in preparing primers based on the sequence information such as EST and cloning cDNA having a novel base sequence by RT-PCR using poly(A)$^+$ RNA of human fetal brain as a template. The present inventors have thus found that polypeptides encoded by the thus obtained cDNA are useful peptides in which the C terminal structure is LPL RF amide-, LPL RS amide-, LPQ RF amide- or LPLRL amide-like.

Based on the EST information prepared by the degenerated PCR technique, the present inventors have succeeded in isolating cDNAs encoding novel G protein-coupled receptor proteins derived from rat cerebellum and from human hypothalamus and in sequencing their full base sequences. When the base sequences were translated into the amino acid sequences, 1 to 7 transmembranes domains were found to be on the hydrophobic plot, verifying that the proteins encoded by these cDNAs are seven-transmembrane type G protein-coupled receptor proteins.

The present inventors have made extensive studies and as a result, have found that physiologically active peptides characterized by containing an RF amide-like or RS amide-like structure, in particular, polypeptides characterized by containing the same or substantially the same amino acid sequence as the amino acid sequence represented by SEQ ID NO:1 or partial peptides thereof possess the function of regulating prolactin release.

Based on these findings, the present inventors have continued extensive studies and as a result, have come to accomplish the present invention.

Thus, the present invention relates to the following features.

(1) A polypeptide containing the same or substantially the same amino acid sequence as that represented by SEQ ID NO: 1, its amide or ester, or a salt thereof.

(2) A polypeptide or its amide or ester, or a salt thereof, according to (1), wherein substantially the same amino acid sequence is represented by SEQ ID NO: 8, SEQ ID NO: 14, SEQ ID NO: 18, SEQ ID NO: 33 or SEQ ID NO: 50.

(3) A partial peptide of the polypeptide according to (1), or its amide or ester, or a salt thereof.

(4) A partial peptide or its amide or ester, or a salt thereof, according to (3), comprising amino acid residues 81 (Met) to 92 (Phe) of SEQ ID NO: 1.

(5) A partial peptide or its amide or ester, or a salt thereof, according to (3), comprising amino acid residues 101 (Ser) to 112 (Ser) of SEQ ID NO: 1.

(6) A partial peptide or its amide or ester, or a salt thereof, according to (3), comprising amino acid residues 124 (Val) to 131 (Phe) of SEQ ID NO: 1.

(7) An amide of the partial peptide of the polypeptide according to (1), or a salt thereof.

(8) A DNA containing a DNA bearing a base sequence encoding the polypeptide according to (1).

(9) A DNA according to (8) having a base sequence represented by SEQ ID NO: 2, SEQ ID NO: 9, SEQ ID NO: 15, SEQ ID NO: 19, SEQ ID NO: 34 or SEQ ID NO: 51.

(10) A DNA containing a DNA encoding the partial peptide according to (3).

(11) A DNA according to (10), comprising bases 241 to 276 of the base sequence represented by SEQ ID NO: 2.

(12) A DNA according to (10), comprising bases 301 to 336 of the base sequence represented by SEQ ID NO: 2.

(13) A DNA according to (10), comprising bases 370 to 393 of the base sequence represented by SEQ ID NO: 2.

(14) A recombinant vector containing the DNA according to (8) or (10).

(15) A transformant transformed with the recombinant vector according to (14).

(16) A method for manufacturing the polypeptide or its amide or ester, or a salt thereof, according to (1) or the partial peptide or its amide or ester, or a salt thereof, according to (3), which comprises culturing said transformant according to (15) and producing and accumulating the polypeptide according to (1) or the partial peptide according to (3).

(17) An antibody to the polypeptide or its amide or ester, or a salt thereof, according to (1) or the partial peptide or its amide or ester, or a salt thereof according to (3).

(18) A diagnostic composition comprising the DNA according to (8) or (10) or the antibody according to (17).

(19) An antisense DNA having a complementary or substantially complementary base sequence to the DNA according to (8) or (10) and capable of suppressing expression of said DNA.

(20) A composition comprising the polypeptide or its amide or ester, or a salt thereof, according to (1) or the partial peptide, or its amide or ester, or a salt thereof, according to (3).

(21) A pharmaceutical composition comprising the polypeptide or its amide or ester, or a salt thereof, according to (1) or the partial peptide or its amide or ester, or a salt thereof, according to (3).

(22) A method for screening a compound that accelerates or inhibits the activity of the polypeptide or its amide or ester, or a salt thereof, according to (1) or the partial peptide or its amide or ester, or a salt thereof, according to (3), which comprises using the polypeptide or its amide or ester, or a salt thereof, according to (1) or the partial peptide or its amide or ester, or a salt thereof, according to (3).

(23) A method for screening according to (22), wherein the polypeptide or its amide or ester, or a salt thereof, according to (1) or the partial peptide or its amide or ester, or a salt thereof, according to (3) and a protein containing the same or substantially the same amino acid sequence as that represented by SEQ ID NO: 37, or a salt thereof, or the partial peptide or its amide or ester, or a salt thereof are used.

(24) A kit for screening a compound that accelerates or inhibits the activity of the polypeptide or its amide or ester, or a salt thereof, according to (1) or the partial peptide or its amide or ester, or a salt thereof, according to (3), comprising the polypeptide or its amide or ester, or a salt thereof, according to (1) or the partial peptide or its amide or ester, or a salt thereof, according to (3).

(25) A kit for screening according to (24), comprising the polypeptide or its amide or ester, or a salt thereof, according to (1) or the partial peptide or its amide or ester, or a salt thereof, according to (3) and a protein containing the same or substantially the same amino acid sequence as that represented by SEQ ID NO: 37 or the partial peptide or its amide or ester, or a salt thereof.

(26) A compound that accelerates or inhibits the polypeptide, or its amide or ester, or a salt thereof, according to (1) or the partial peptide, or its amide or ester, or a salt thereof, according to (3), which is obtainable using the screening method according to (22) or the screening kit according to (24).

(27) A pharmaceutical composition comprising a compound that accelerates or inhibits the polypeptide, or its amide or ester, or a salt thereof, according to (1) or the partial peptide, or its amide or ester, or a salt thereof, according to (3), which is obtainable using the screening method according to (22) or the screening kit according to (24).

(28) A protein or a salt thereof containing the same or substantially the same amino acid sequence as the amino acid sequence represented by SEQ ID NO: 37.

(29) A protein or its salt according to (28), wherein substantially the same amino acid sequence as the amino acid sequence represented by SEQ ID NO: 37 is the amino acid sequence represented by SEQ ID NO: 54.

(30) A partial peptide or its amide or ester, or a salt thereof, according to (28).

(31) A DNA containing a DNA having a base sequence encoding the protein according to (28) or the partial peptide according to (30).

(32) A DNA according to (31) having the base sequence represented by SEQ ID NO: 38, SEQ ID NO: 55 or SEQ ID NO: 56.

(33) A recombinant vector containing the DNA according to (31).

(34) A transformant transformed with the recombinant vector according to (33).

(35) A method for manufacturing the protein or its salt according to (28) or the partial peptide or its amide or ester, or a salt thereof, according to (30), which comprises culturing the transformant according to (34) and producing and accumulating the protein according to (28) or the partial peptide according to (30).

(36) An antibody to the protein or its salt according to (28) or the partial peptide or its amide or ester, or a salt thereof, according to (30).

(37) A diagnostic composition comprising the DNA according to (31) or the antibody according to (36).

(38) A ligand to the protein or its salt according to (28), which is obtainable by using the protein or its salt according to (28) or the partial peptide or its amide or ester or, a salt thereof, according to (30).

(39) A method for determination of a ligand to the protein or its salt according to (28), characterized by using the protein or its salt according to (28) or the partial peptide or its amide or ester, or a salt thereof, according to (30).

(40) A method for screening a compound that alters the binding property between a ligand and the protein or its salt according to (28), which comprises using the protein or its salt according to (28) or the partial peptide or its amide or ester, or a salt thereof, according to (30).

(41) A kit for screening a compound that alters the binding property between a ligand and the protein or its salt according to (28), comprising the protein or its salt according to (28) or the partial peptide or its amide or ester, or a salt thereof, according to (30).

(42) A compound that alters the binding property between a ligand and the protein or its salt according to (28), which is obtainable by using the screening method according to (40) or the screening kit according to (41).

(43) A pharmaceutical composition comprising a compound that alters the binding property between a ligand and the protein or its salt according to (28), which is obtainable by using the screening method according to (40) or the screening kit according to (41).

(44) A method for quantifying the protein or its salt according to (28), which comprises using the antibody of (36).

(45) A prolactin secretion regulatory agent comprising a polypeptide containing the same or substantially the same amino acid sequence as the amino acid sequence represented by SEQ ID NO: 1, its amide or ester, or a salt thereof.

(46) The agent according to (45), wherein substantially the same amino acid sequence is represented by SEQ ID NO: 8, SEQ ID NO: 14, SEQ ID NO: 18, SEQ ID NO: 33 or SEQ ID NO: 50.

(47) A prolactin secretion regulatory agent comprising a partial peptide of a polypeptide containing the same or substantially the same amino acid sequence as the amino acid sequence represented by SEQ ID NO: 1, its amide or ester, or a salt thereof.

(48) The prolactin secretion regulatory agent according to (47), comprising a partial peptide composed of acid residues 81 (Met) to 92 (Phe) of SEQ ID NO: 1, its amide or ester, or a salt thereof.

(49) The prolactin secretion regulatory agent according to (47), comprising a partial peptide composed of amino acid residues 101 (Ser) to 112 (Ser) of SEQ ID NO: 1, its amide or ester, or a salt thereof.

(50) The prolactin secretion regulatory agent according to (47), comprising a partial peptide composed of amino acid residues 124 (Val) to 131 (Phe) of SEQ ID NO: 1, its amide or ester, or a salt thereof.

(51) The prolactin secretion regulatory agent according to (47), comprising a partial peptide composed of amino acid residues 56 (Ser) to 92 (Phe) of SEQ ID NO: 1, its amide or ester, or a salt thereof.

(52) The prolactin secretion regulatory agent according to (47), comprising an amide of a partial peptide of a polypeptide containing the same or substantially the same amino acid sequence as the amino acid sequence represented by SEQ ID NO: 1, or a salt thereof.

(53) The prolactin secretion regulatory agent according to (52), comprising a partial peptide of a polypeptide containing the same or substantially the same amino acid sequence as the amino acid sequence represented by SEQ ID NO: 1, the C-terminal carboxyl of which is amidated, or a salt thereof.

(54) The prolactin secretion regulatory agent according to (45) or (47), which is a prolactin secretion stimulant.

(55) The prolactin secretion regulatory agent according to (45) or (47), which is a prolactin secretion inhibitor.

(56) The prolactin secretion stimulant according to (54), which is a medicament for the prevention or treatment of hypoovarianism, spermatic underdevelopment, osteoporosis, menopausal symptoms, agalactosis, hypothyroidism or renal insufficiency.

(57) The a prolactin secretion inhibitor according to (55), which is a medicament for the prevention or treatment of hyperprolactinemia, pituitary tumor, diencephalon tumor, menstrual disorder, stress, autoimmune diseases, prolactinoma, sterility, impotence, amenorrhea, lactorrhea, acromegaly, Chiari-Frommel syndrome, Argonz-del Castilo syndrome, Forbes-Albright syndrome, breast cancer lymphoma or Sheehan's syndrome, or spermatogenesis disorder.

(58) The prolactin secretion regulatory agent according to (45) or (47), which is a galactosis stimulant for livestock mammal.

(59) The prolactin secretion regulatory agent according to (45) or (47), which is a test agent for prolactin secretion function.

(60) A prolactin secretion regulatory agent comprising a compound or its salt that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, which is obtainable using:

A method of screening a compound or its salt that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, which comprises using (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof; or, A kit for screening a compound or its salt that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof; the kit comprising (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof.

(61) A prolactin secretion regulatory agent comprising a compound or its salt that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, which is obtainable using:

(I) A method of screening a compound or its salt that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, which comprises using (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, and (iii) a protein containing the same or substantially the same amino acid sequence represented by SEQ ID NO: 37 or a salt thereof, or its partial peptide, its amide or ester, or a salt thereof; or, (II) A kit for screening a compound or its salt that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof; the kit comprising (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, and (iii) a protein containing the same or substantially the same amino acid sequence represented by SEQ ID NO: 37 or a salt thereof, or its partial peptide, its amide or ester, or a salt thereof.

(62) (1) A peptide containing an amino acid sequence composed of 81 (Met) to 92 (Phe) of SEQ ID NO: 1, its amide or ester, or a salt thereof, (2) a peptide containing an amino acid sequence composed of 101(Ser) to 112 (Ser) of SEQ ID NO: 1, its amide or ester, or a salt thereof, (3) a peptide containing an amino acid sequence composed of 124(Val) to 131 (Phe) of SEQ ID NO: 1, its amide or ester, or a salt thereof, (4) a peptide containing an amino acid sequence composed of 56 (Ser) to 92 (Phe) of SEQ ID NO: 1, its amide or ester, or a salt thereof, (5) a peptide containing an amino acid sequence composed of 81 (Met) to 92 (Phe) of SEQ ID NO: 14, its amide or ester, or a salt thereof, (6) a peptide containing an amino acid sequence composed of 101 (Ser) to 112 (Leu) of SEQ ID NO: 14, its amide or ester, or a salt thereof, (7) a peptide containing an amino acid sequence composed of 58 (Ser) to 92 (Phe) of SEQ ID NO: 14, its amide or ester, or a salt thereof, (8) a peptide containing an amino acid sequence composed of 83 (Val) to 94 (Phe) of SEQ ID NO: 33, its amide or ester, or a salt thereof, (9) a peptide containing an amino acid sequence composed of 118 (Phe) to 125 (Phe) of SEQ ID NO: 33, its amide or ester, or a salt thereof, (10) a peptide containing an amino acid sequence composed of 58 (Ser) to 94 (Phe) of SEQ ID NO: 33, its amide or ester, or a salt thereof, or (11) a peptide containing an amino acid sequence composed of 58 (Ser) to 94 (Phe) of SEQ ID NO: 50, its amide or ester, or a salt thereof.

(63) An amide of the peptide according to (62), or a salt thereof.

(64) The peptide according to (62) wherein the C-terminal carboxyl is amidated, its amide or ester, or a salt thereof.

(65) A DNA encoding the peptide according to (62).

(66) The DNA according to (65), containing (1) a 241-276 base sequence of SEQ ID NO: 2, (2) a 301-336 base sequence of SEQ ID NO: 2, (3) a 370-393 base sequence of SEQ ID NO: 2, (4) a 166-276 base sequence of SEQ ID NO: 2, (5) a 241-276 base sequence of SEQ ID NO: 15, (6) a 301-336 base sequence of SEQ ID NO: 15, (7) a 172-276 base sequence of SEQ ID NO: 15, (8) a 247-282 base sequence of SEQ ID NO: 34, (9) a 352-375 base sequence of SEQ ID NO: 34, (10) a 172-282 base sequence of SEQ ID NO: 34, or (11) a 172-282 base sequence of SEQ ID NO: 51.

(67) An antibody to the peptide according to (62), or its amide or ester, or a salt thereof.

(68) A diagnostic comprising the DNA according to (65) or the antibody according to (67).

(69) An antisense DNA having a base sequence complementary or substantially complementary to the DNA according to (65) and capable of inhibiting expression of the DNA.

(70) An agent comprising the peptide according to (62), or its amide or ester, or a salt thereof.

(71) A pharmaceutical composition comprising the peptide according to (62), or its amide or ester, or a salt thereof.

(72) The pharmaceutical composition according to (71), which is a prolactin secretion regulatory agent.

(73) A method of screening a compound or its salt that promotes or inhibits the activity of the peptide according to (62), or its amide or ester, or a salt thereof, which comprises using the peptide according to (62), or its amide or ester, or a salt thereof.

(74) The method of screening according to (73), wherein a protein containing the same or substantially the same amino acid sequence represented by SEQ ID NO: 37 or a salt thereof, or its partial peptide, its amide or ester, or a salt thereof is further used.

(75) A kit for screening a compound or its salt that promotes or inhibits the activity of the peptide according to (62), or its amide or ester, or a salt thereof, which comprises using the peptide according to (62), or its amide or ester, or a salt thereof.

(76) A compound or its salt that promotes or inhibits the activity of the peptide according to (62), or its amide or ester, or a salt thereof, which is obtainable using the screening method according to (73) or the screening kit according to (75).

(77) Use of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, for the manufacture of a medicament having a prolactin secretion regulating activity.

(78) A method of regulating the secretion of prolactin, which comprises administering to a mammal (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof.

(79) Use of a compound or its salt that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, for the manufacture of a medicament having a prolactin secretion regulating activity, which is obtainable using:

A method of screening a compound or its salt that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, which comprises using (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof; or, A kit for screening a compound or its salt that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof; the kit comprising (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof.

(80) Use of a compound or its salt that that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, for the manufacture of a medicament having a prolactin secretion regulating activity, which is obtainable using:

(I) A method of screening a compound or its salt that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, which comprises using (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, and (iii) a protein containing the same or substantially the same amino acid sequence represented by SEQ ID NO: 37 or a salt thereof, or its partial peptide, its amide or ester, or a salt thereof; or, (II) A kit for screening a compound or its salt that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof; the kit comprising (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, and (iii) a protein containing the same or substantially the same amino acid sequence represented by SEQ ID NO: 37 or a salt thereof, or its partial peptide, its amide or ester, or a salt thereof.

(81) A method of regulating the secretion of prolactin, which comprises administering to a mammal a compound or its salt that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, for the manufacture of a medicament having a prolactin secretion regulating activity, which is obtainable using:

A method of screening a compound or its salt that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, which comprises using (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof. or, A kit for screening a compound or its salt that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof; the kit comprising (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof.

(82) A method of regulating the secretion of prolactin, which comprises administering to a mammal a compound or its salt that that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, for the manufacture of a medicament having a prolactin secretion regulating activity, which is obtainable using:

(I) A method of screening a compound or its salt that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, which comprises using (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, and (iii) a protein containing the same or substantially the same amino acid sequence represented by SEQ ID NO: 37 or a salt thereof, or its partial peptide, its amide or ester, or a salt thereof; or, (II) A kit for screening a compound or its salt that promotes or inhibits the activity of (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof; the kit comprising (i) a polypeptide containing the same or substantially the same amino acid sequence as the amino acid sequence represented by SEQ ID NO: 1, its amide or ester, or a salt thereof, or (ii) a partial peptide of a polypeptide containing the same or substantially the same amino acid sequence as the amino acid sequence represented by SEQ ID NO: 1, its amide or ester, or a salt thereof, and (iii) a protein containing the same or substantially the same amino acid sequence represented by SEQ ID NO: 37 or a salt thereof, or its partial peptide, its amide or ester, or a salt thereof.

The present invention further relates to the following:

(83) A polypeptide, its amide or ester, or a salt thereof, according to (1), wherein substantially the same amino acid sequence as the amino acid sequence shown by SEQ ID NO: 1 is an amino acid sequence possessing homology of at least about 70%, preferably at least about 80%, more preferably at least about 90% and most preferably about 95%, to the amino acid sequence shown by SEQ ID NO: 1.

(84) A polypeptide, its amide or ester, or a salt thereof, according to (1), wherein substantially the same amino acid sequence as the amino acid sequence shown by SEQ ID NO: 1 is (i) an amino acid sequence represented by SEQ ID NO: 1, SEQ ID NO: 8, SEQ ID NO: 14, SEQ ID NO: 18, SEQ ID NO: 33 or SEQ ID NO: 50, of which 1 to 20 (preferably 1 to 15, more preferably 1 to 5 and most preferably 1 to 3) amino acids are deleted; (ii) an amino acid sequence represented by SEQ ID NO: 1, SEQ ID NO: 8, SEQ ID NO: 14, SEQ ID NO: 18, SEQ ID NO: 33 or SEQ ID NO: 50, to which 1 to 20 (preferably 1 to 15, more preferably 1 to 5 and most preferably 1 to 3) amino acids are added; (iii) an amino acid sequence represented by SEQ ID NO: 1, SEQ ID NO: 8, SEQ ID NO: 14, SEQ ID NO: 18, SEQ ID NO: 33 or SEQ ID NO: 50, into which 1 to 20 (preferably 1 to 15, more preferably 1 to 5 and most preferably 1 to 3) amino acids are inserted, (iv) an amino acid sequence represented by SEQ ID NO: 1, SEQ ID NO: 8, SEQ ID NO: 14, SEQ ID NO: 18, SEQ ID NO: 33 or SEQ ID NO: 50, in which 1 to 20 (preferably 1 to 15, more preferably 1 to 5 and most preferably 1 to 3) amino acids are substituted by other amino acids; and (v) a combination of the above amino acid sequences.

(85) DNA containing DNA having a base sequence which is hybridizable with the base sequence encoding DNA according to (8) or (10) under highly stringent conditions.

(86) A recombinant vector containing DNA according to (85).

(87) A transformant transformed with the recombinant vector according to (86).

(88) A method for manufacturing the polypeptide, it amide or ester, or a salt thereof, encoded by DNA according to (85), which comprises culturing the transformant according to (87), producing and accumulating the polypeptide encoded by DNA according to (85) and harvesting the polypeptide.

(89) A polypeptide, its amide or ester, or a salt thereof, encoded by DNA according to (85), which is manufactured by the method according to (88).

(90) A protein or its salt according to (28), wherein substantially the same amino acid sequence as the amino acid sequence shown by SEQ ID NO: 37 is an amino acid sequence possessing homology of at least about 50%, preferably at least about 70%, more preferably at least about 80%, further more preferably at least about 90% and most preferably about 95%, to the amino acid sequence shown by SEQ ID NO: 37.

(91) A protein or its salt according to (28), wherein substantially the same amino acid sequence as the amino acid sequence shown by SEQ ID NO: 37 is (i) an amino acid sequence represented by SEQ ID NO: 37, of which 1 to 20 (preferably 1 to 15, more preferably 1 to 5 and most preferably 1 to 3) amino acids are deleted; (ii) an amino acid sequence represented by SEQ ID NO: 37, to which 1 to 20 (preferably 1 to 15, more preferably 1 to 5 and most preferably 1 to 3) amino acids are added; (iii) an amino acid sequence represented by SEQ ID NO: 37, in which 1 to 20 (preferably 1 to 15, more preferably 1 to 5 and most preferably 1 to 3) amino acids are substituted by other amino acids; or (iv) a combination of the above amino acid sequences.

(92) DNA containing DNA having a base sequence which is hybridizable with the base sequence encoding DNA according to (31) under highly stringent conditions.

(93) A recombinant vector containing DNA according to (92).

(94) A transformant transformed with the recombinant vector according to (93).

(95) A method for manufacturing the polypeptide, it amide or ester, or a salt thereof, encoded by DNA according to (92), which comprises culturing the transformant according to (94), producing and accumulating the polypeptide encoded by DNA according to (92) and harvesting the polypeptide.

(96) A polypeptide, its amide or ester, or a salt thereof, encoded by DNA according to (92), which is manufactured by the method according to (95).

(97) A method for screening according to (22), which comprises measuring and comparing (i) the activity of the polypeptide, its amide or ester, or a salt thereof, according to (1), or the partial peptide, its amide or ester, or a salt thereof, according to (3), where its receptor is brought in contact with the polypeptide, its amide or ester, or a salt thereof, according to (1) or the partial peptide, its amide or ester, or a salt thereof, according to (3) and (ii) the activity of the polypeptide, its amide or ester, or a salt thereof, according to (1), or the partial peptide, its amide or ester, or a salt thereof, according to (3), where its receptor and a test compound are brought in contact with polypeptide, its amide or ester, or a salt thereof, according to (1) or the partial peptide, its amide or ester, or a salt thereof, according to (3).

(98) A method for screening according to (97), wherein the receptor is a protein containing the same or substantially the same amino acid sequence as the amino acid sequence shown by SEQ ID NO: 37, or a salt thereof, or its partial peptide, its amide or ester or a salt thereof.

(99) A pharmaceutical composition comprising a compound that accelerates the activity of the polypeptide or its amide or ester, or a salt thereof, according to (1) or the partial peptide or its amide or ester, or a salt thereof, according to (3), which is obtainable using the screening method according to (22) or the screening kit according to (24).

(100) A pharmaceutical composition comprising a compound that inhibits the activity of the polypeptide or its amide or ester, or a salt thereof, according to (1) or the partial peptide or its amide or ester, or a salt thereof, according to (3), which is obtainable using the screening method according to (22) or the screening kit according to (24).

(101) A method for quantifying the polypeptide, its amide or ester, or a salt thereof, according to (1) or the partial peptide, its amide or ester, or a salt thereof, according to (3) in a test sample fluid, which comprises competitively reacting the antibody according to (17) with a test sample fluid and the polypeptide, its amide or ester, or a salt thereof, according to (1) or the partial peptide, its amide or ester, or a salt thereof, according to (3), which is labeled, and measuring the ratio of the labeled polypeptide, amide or ester or salt according to (1) or the labeled partial peptide, amide or ester or salt according to (3) in the test sample fluid.

(102) A method for quantifying the polypeptide, its amide or ester or, a salt thereof, according to (1) or the partial peptide, its amide or ester or, a salt thereof, according to (3) in a test sample fluid, which comprises reacting a test sample fluid simultaneously or sequentially with the antibody of (17) immobilized on a carrier and labeled antibody of (17) and then measuring the activity of a labeling agent on the immobilized carrier.

(103) A method for quantifying the protein or its salt according to (28) or the partial peptide, its amide or ester, or a salt thereof, according to (30) in a test sample fluid, which comprises competitively reacting the antibody according to (36) with a test sample fluid and the protein or its salt according to (28) or the partial peptide, its amide or ester, or a salt thereof, according to (30), which is labeled, and measuring the ratio of the antibody-bound labeled protein, amide or ester or salt according to (1) or the antibody-bound labeled partial peptide, amide or ester or salt according to (30) in the test sample fluid. And, (104) A method for quantifying the polypeptide, its amide or ester, or a salt thereof, according to (28) or the partial peptide, its amide or ester, or a salt thereof, according to (30) in a test sample fluid, which comprises reacting a test sample fluid simultaneously or sequentially with the antibody of (36) immobilized on a carrier and labeled antibody of (36) and then measuring the activity of a labeling agent on the immobilized carrier.

BRIEF DESCRIPTION OF THE DRAWINGS

FIG. 1 shows the base sequence of DNA encoding the polypeptide (human type) of the present invention obtained in Example 2 (SEQ ID NO: 2), and the amino acid sequence (SEQ ID NO: 1) deduced from the base sequence.

FIG. 3 shows the base sequence of DNA encoding the polypeptide (human type) of the present invention obtained in Example 3 (SEQ ID NO: 9), and the amino acid sequence (SEQ ID NO: 8) deduced from the base sequence.

FIG. 4 shows the base sequence of DNA encoding the polypeptide (bovine type) of the present invention obtained in Example 4 (SEQ ID NO: 15), and the amino acid sequence (SEQ ID NO: 14) deduced from the base sequence.

FIG. 5 shows the base sequence of DNA encoding the polypeptide (rat type) of the present invention obtained in Example 5 (SEQ ID NO: 19), and the amino acid sequence (SEQ ID NO: 18) deduced from the base sequence.

FIG. 6 shows comparison of the amino acid sequences of the polypeptides of the present invention obtained in Examples 3, 4 and 5 (SEQ ID NOS: 8, 14, and 18).

FIG. 7 shows the base sequence of DNA encoding the polypeptide (mouse type) of the present invention obtained in Example 6 (SEQ ID NO: 34), and the amino acid sequence (SEQ ID NO: 33) deduced from the base sequence.

Also, the time period for administration is made 0 minutes, and * indicates a risk percentage of $p<0.05$, and ** indicates a risk percentage of $p<0.01$.

Figure 11:
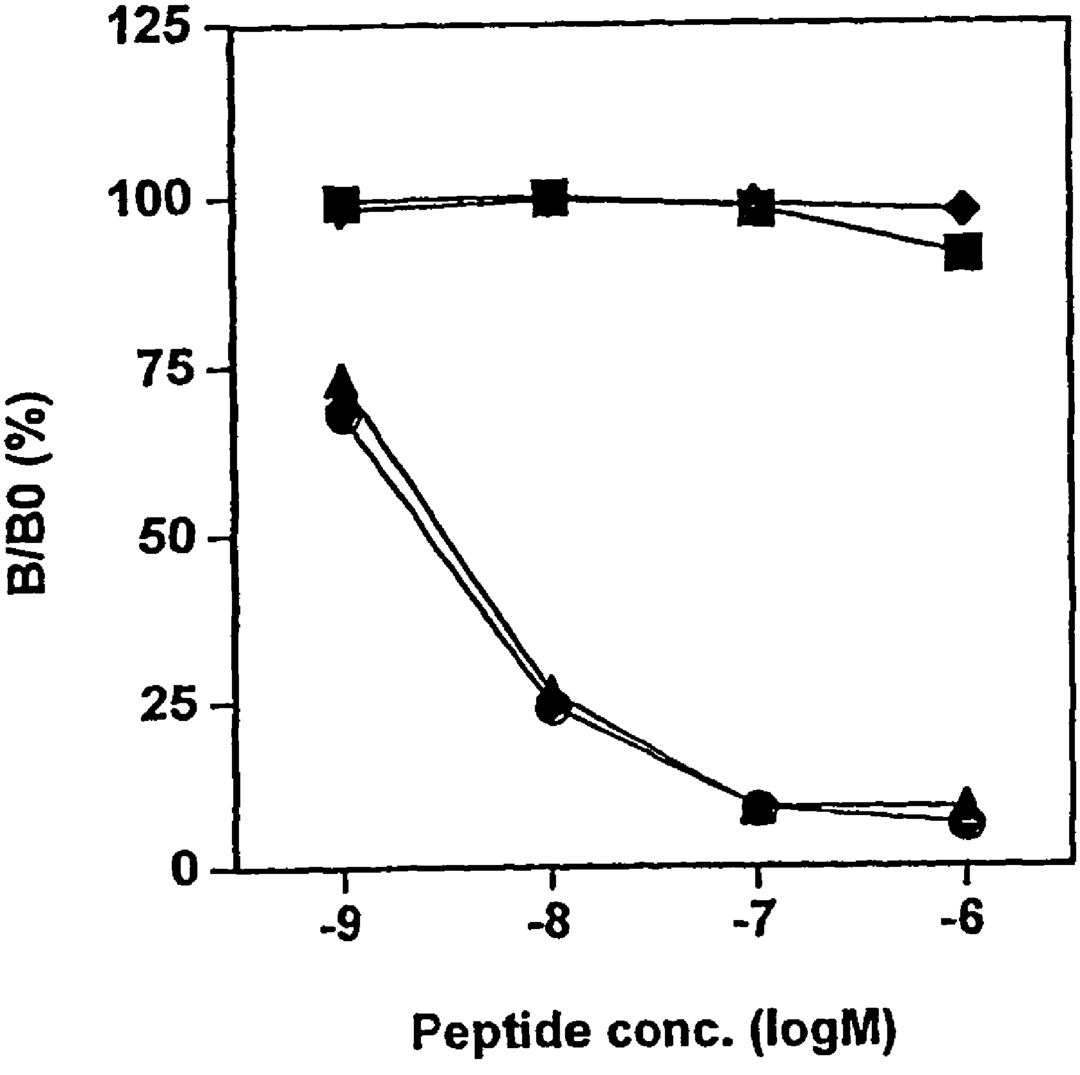

FIG. 11 shows the results of the reactivity of an RF amide-related peptide in competitive EIA using anti-rat RFRP-1 monoclonal antibody 1F3, which was carried out in Example 13.

To a 96-well plate coated with anti-mouse IgGAM antibody, 50 μl of anti-rat RFRP-1 monoclonal antibody and 50 μl of the peptide in concentrations indicated on the abscissa were added. After incubation at 4° C. for 16 hours, HRP-rat RFRP-1 was added followed by incubation at room temperature for further 2 hours. After the plate was washed, the HRP activity was measured as absorbance at 450 nm. B denotes absorbance when the peptide was added and $B_0$ denotes absorbance when the peptide was not added.

In the figure, -●- denotes the peptide composed of 83 (Val)-94 (Phe) amino acid sequence of the amino acid sequence shown by SEQ ID NO: 50, in which the C-terminal carboxyl is amidated (VPHSAANLPLRF—$NH_2$), -▲- denotes the peptide composed of 90 (Leu)-94 (Phe) amino acid sequence of the amino acid sequence shown by SEQ ID NO: 50, in which the C-terminal carboxyl is amidated (LPLRF—$NH_2$), -■- denotes the peptide composed of 124 (Val)-131 (Phe) amino acid sequence of the amino acid sequence shown by SEQ ID NO: 50, in which the C-terminal carboxyl is amidated (VPNLPQRF—$NH_2$), and -◆- denotes the peptide composed of 128 (Pro)-131 (Phe) amino acid sequence of the amino acid sequence shown by SEQ ID NO: 50, in which the C-terminal carboxyl is amidated (PQRF—$NH_2$).

Figure 12:
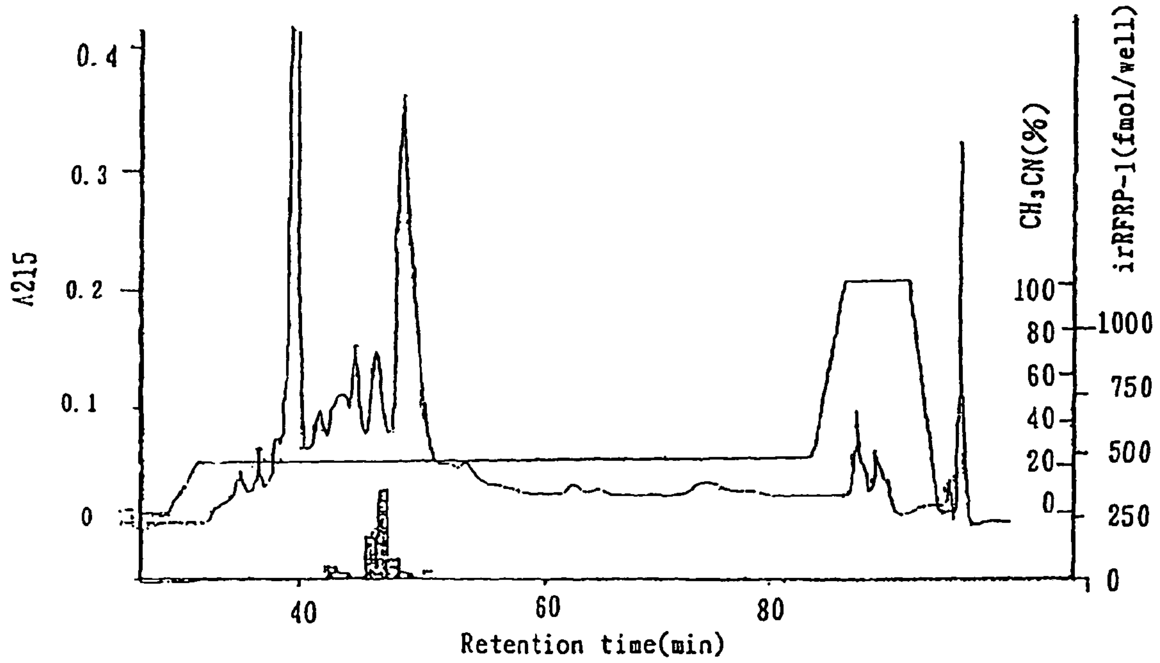

FIG. 12 shows the chromatographic pattern of endogenous RFRP-1 finally purified from bovine hypothalamus, which was performed in Example 15.

The chromatogram shows μRPC C2/dC18 SC 2.1/10 at the final purification step, wherein the ordinate indicates absorbance at 215 nm and the concentration of acetonitrile for elution, and the abscissa indicates retention time. In the figure, the black column shows RFRP-1-like immune activity when measured by competitive EIA using anti-rat RFRP-1 monoclonal antibody 1F3 in each fraction.

Figure 13:
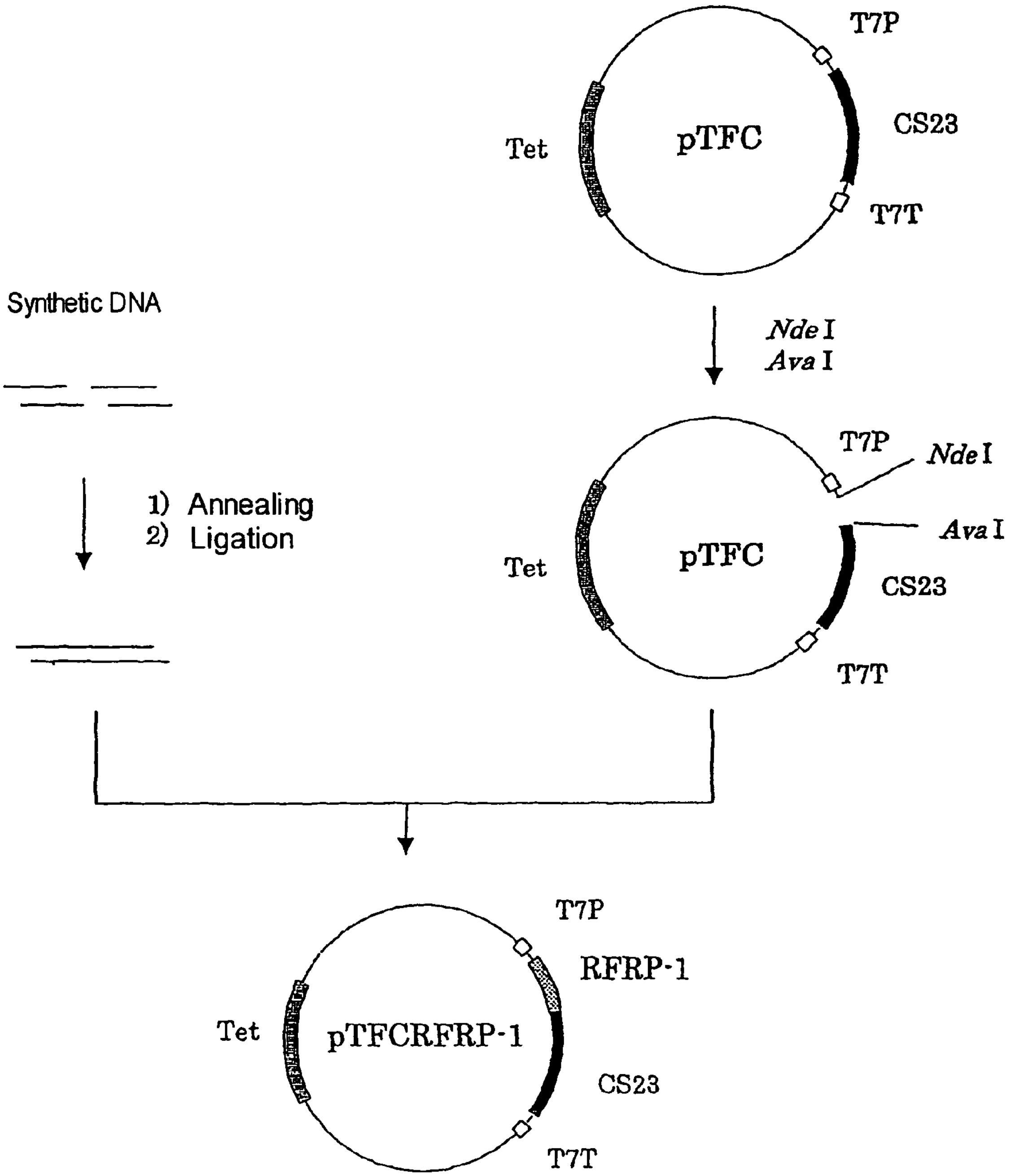

FIG. 13 shows the construction for plasmid pTFCRFRT-1 obtained in Example 17.

Figure 14:
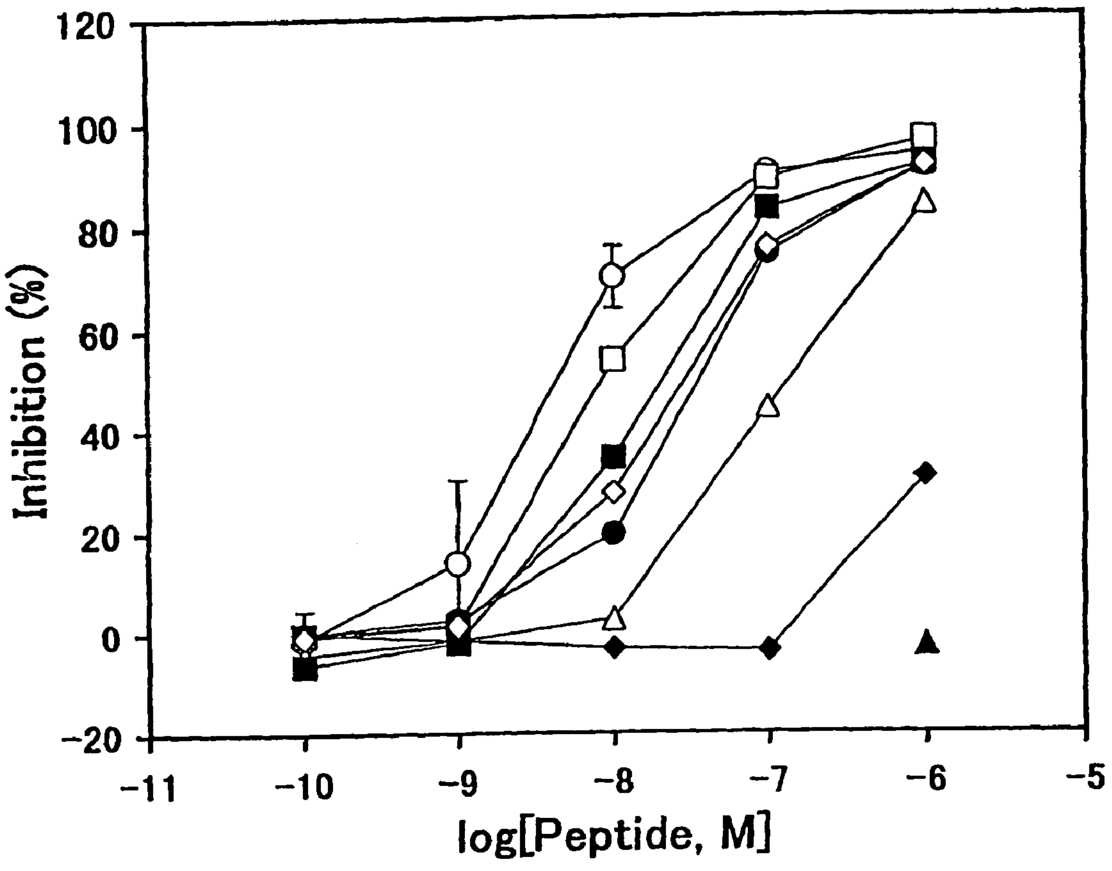

FIG. 14 shows the activities of various peptides for inhibiting the increased cAMP production in cells by forskolin treatment performed in Example 21, in which -○- denotes hRFRP-1-12 (peptide having the 81 (Met) to 92 (Phe) amino acid sequence in SEQ ID NO: 1), -■- denotes hRFRP-1-37 (peptide having the 56 (Ser) to 92 (Phe) amino acid sequence in SEQ ID NO: 1), -◇- denotes rRFRP-1-37 (peptide having the 58 (Ser) to 94 (Phe) amino acid sequence in SEQ ID NO: 50), -▲- denotes hRFRP-2-12 (peptide having the 101 (Phe) to 112 (Ser) amino acid sequence in SEQ ID NO: 1), -□- denotes hRFRP-3-8 (peptide having the 124 (Val) to 131 (Phe) amino acid sequence in SEQ ID NO: 1), -◆- denotes PQRFamide (peptide shown by Pro-Gln-Arg-Phe-$NH_2$), -●- denotes LPLRFamide (peptide shown by Leu-Pro-Leu-Arg-Phe-$NH_2$), and -▲- denotes NPFF (peptide shown by Asn-Pro-Phe-Phe).

Figure 15:
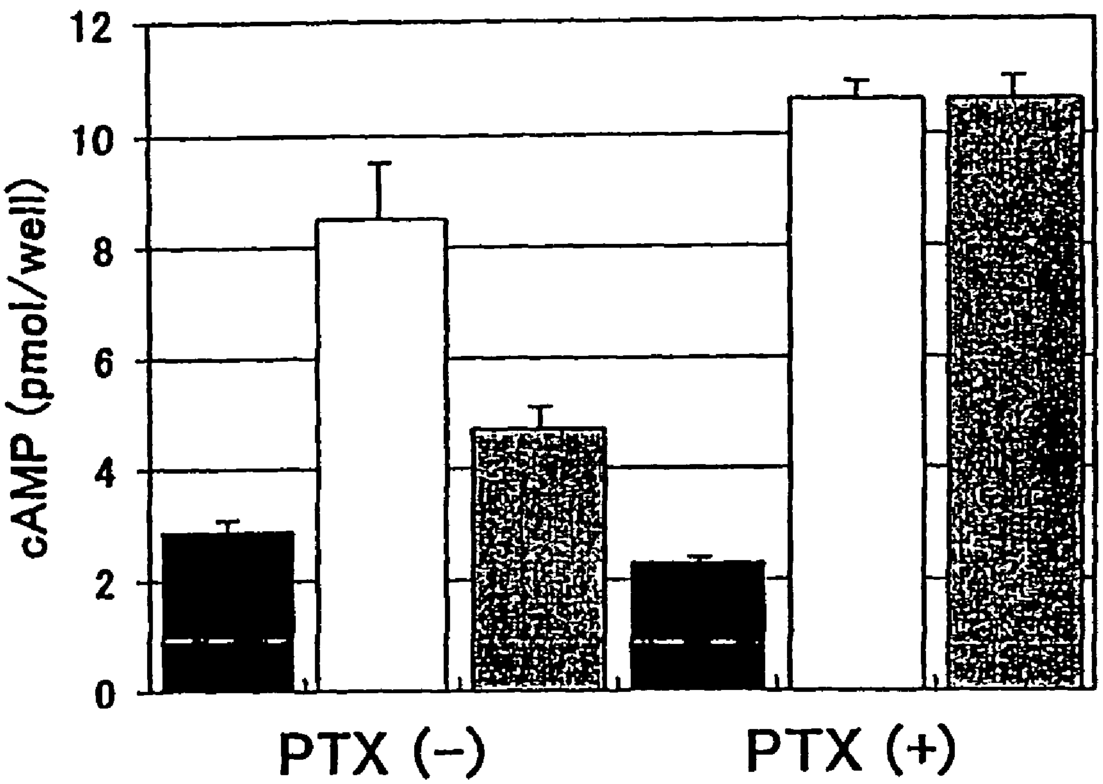

FIG. 15 is the figure showing the effect of pertussis toxin on activation of human 0T7T022 receptor by RFRP peptide using as an indicator the cAMP production inhibiting activity, which was carried out in Example 22.

BEST MODE OF EMBODIMENT OF THE INVENTION

The polypeptide of the present invention having the same or substantially the same amino acid sequence as the amino acid sequence shown by SEQ ID NO: 1 (hereinafter referred to as the polypeptide of the present invention) may be any polypeptide derived from any cells of human and other warm-blooded animals (e.g. guinea pig, rat, mouse, chicken, rabbit, swine, sheep, bovine, monkey, etc.) such as retina cell, liver cell, splenocyte, nerve cell, glial cell, β cell of pancreas, bone marrow cell, mesangial cell, Langerhans' cell, epidermic cell, epithelial cell, endothelial cell, fibroblast, fibrocyte, myocyte, fat cell, immune cell (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte, interstitial cell, etc., the corresponding precursor cells, stem cells, cancer cells, etc., or any tissues where such cells are present, such as brain or any of brain regions (e.g., retina, olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; polypeptides derived from hemocyte type cells or their cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.); the polypeptides may also be synthetic polypeptides.

The amino acid sequence which has substantially the same amino acid sequence as that represented by SEQ ID NO: 1 includes an amino acid sequence having at least about 70% homology, preferably at least about 80% homology, more preferably at least about 90% homology, and most preferably at least about 95% homology, to the amino acid sequence represented by SEQ ID NO: 1.

Examples of the polypeptide which has substantially the same amino acid sequence as that shown by SEQ ID NO: 1 include a polypeptide containing the 22-180 amino acid sequence of the amino acid sequence represented by SEQ ID NO: 1, etc.

More specifically, substantially the same amino acid sequence as that represented by SEQ ID NO: 1 includes amino acid sequences represented by SEQ ID NO: 8, SEQ ID NO: 14, SEQ ID NO: 18, SEQ ID NO: 33 or SEQ ID NO: 50, and the like.

Examples of the polypeptide which has substantially the same amino acid sequence as that represented by SEQ ID NO: 1 include a polypeptide having substantially the same amino acid sequence as that represented by SEQ ID NO: 1 (e.g., amino acid sequence shown by SEQ ID NO: 8, SEQ ID NO: 14, SEQ ID NO: 18, SEQ ID NO: 33 or SEQ ID NO: 50) and having the prolactin secretion regulating activity substantially equivalent to the polypeptide containing the amino acid sequence represented by SEQ ID NO: 1.

The term "substantially equivalent" is used to mean that the nature of these activities is equivalent (for example, biochemically or pharmacologically). Therefore, it is preferred that the these activities such as a cell-stimulating activity, a somatostatin secretion regulating activity, etc. are equivalent in strength (e.g., about 0.1 to about 100 times, preferably about 0.5 to about 10 times, more preferably about 0.5 to about 2 times), and it is allowable that even differences among grades such as the strength of these activities and molecular weight of the polypeptide are present.

The cell-stimulating activity can be determined according to a modification from publicly known methods, for example, in accordance with the screening method, which will be later described. The prolactin secretion regulating activity can be determined according to a modification from publicly known methods, for example, in accordance with Example 1, which will be later described.

The polypeptides of the present invention include so-called muteins such as polypeptides comprising (i) an amino acid sequence represented by SEQ ID NO: 1, SEQ ID NO: 8, SEQ ID NO: 14, SEQ ID NO: 18, SEQ ID NO: 33 or SEQ ID NO: 50, of which 1 to 20 (preferably 1 to 15, more preferably 1 to 5 and most preferably 1 to 3) amino acids are deleted; (ii) an amino acid sequence represented by SEQ ID NO: 1, SEQ ID NO: 8, SEQ ID NO: 14, SEQ ID NO: 18, SEQ ID NO: 33 or SEQ ID NO: 50, to which 1 to 20 (preferably 1 to 15, more preferably 1 to 5 and most preferably 1 to 3) amino acids are added; (iii) an amino acid sequence represented by SEQ ID NO: 1, SEQ ID NO: 8, SEQ ID NO: 14, SEQ ID NO: 18, SEQ ID NO: 33 or SEQ ID NO: 50, into which 1 to 20 (preferably 1 to 15, more preferably 1 to 5 and most preferably 1 to 3) amino acids are inserted, (iv) an amino acid sequence represented by SEQ ID NO: 1, SEQ ID NO: 8, SEQ ID NO: 14, SEQ ID NO: 18, SEQ ID NO: 33 or SEQ ID NO: 50, in which 1 to 20 (preferably 1 to 15, more preferably 1 to 5 and most preferably 1 to 3) amino acids are substituted by other amino acids; and (v) a combination of the above amino acid sequences.

When an amino acid sequence(s) are inserted, deleted or substituted as described above, the positions of such insertion, deletion or substitution are not particularly limited.

Specific examples of the polypeptide which contains substantially the same amino acid sequence as that shown by SEQ ID NO: 1 are a polypeptide containing substantially the same amino acid sequence as that shown by SEQ ID NO: 8, a polypeptide containing substantially the same amino acid sequence as that shown by SEQ ID NO: 14, a polypeptide containing substantially the same amino acid sequence as that shown by SEQ ID NO: 18, a polypeptide containing substantially the same amino acid sequence as that shown by SEQ ID NO: 33, a polypeptide containing substantially the same amino acid sequence as that shown by SEQ ID NO: 50 and the like.

Throughout the present specification, the polypeptides are represented in accordance with the conventional way of describing polypeptides, that is, the N-terminus (amino terminus) at the left hand and the C-terminus (carboxyl terminus) at the right hand. In the polypeptides of the present invention including the polypeptide containing the amino acid sequence shown by SEQ ID NO: 1, the C-terminus is usually in the form of a carboxyl group (—COOH) or a carboxylate (—$COO^-$) but may be in the form of an amide (—$CONH_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; and the like. In addition, pivaloyloxymethyl or the like which is used widely as an ester for oral administration may also be used.

Where the polypeptide of the present invention contains a carboxyl group (or a carboxylate) at a position other than the C-terminus, it may be amidated or esterified and such an amide or ester is also included within the polypeptide of the present invention. The ester group may be the same group as that described with respect to the above C-terminal.

Furthermore, examples of the polypeptide of the present invention include variants of the above polypeptides, wherein the amino group at the N-terminus (e.g., methionine residue) of the polypeptide is protected with a protecting group (e.g., a $C_{1-6}$ acyl group such as a $C_{1-6}$ alkanoyl group e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated proteins such as glycoproteins having sugar chains. These polypeptides are sometimes merely referred to as the polypeptide of the present invention.

Specific examples of the polypeptide of the present invention include a human-derived polypeptide containing the amino acid sequence represented by SEQ ID NO: 1 (FIG. 1), a human-derived polypeptide containing the amino acid sequence represented by SEQ ID NO: 8 (FIG. 3), a bovine-derived polypeptide containing the amino acid sequence represented by SEQ ID NO: 14 (FIG. 4), a rat-derived polypeptide containing the amino acid sequence represented by SEQ ID NO: 18 (FIG. 5), a mouse-derived polypeptide containing the amino acid sequence represented by SEQ ID NO: 33 (FIG. 7), a rat-derived polypeptide containing the amino acid sequence represented by SEQ ID NO: 50, etc. Preferably employed are, for example, the human-derived polypeptide containing the amino acid sequence represented by SEQ ID NO: 1, the human-derived polypeptide containing the amino acid sequence represented by SEQ ID NO: 8, and the bovine-derived polypeptide containing the amino acid sequence represented by SEQ ID NO: 14.

The polypeptides of the present invention may also be the precursors of the partial peptides below and in this case, may not necessarily require the activities (e.g., a cell stimulating activity or the like) of the following partial peptides.

The partial peptides of the polypeptides of the present invention (hereinafter sometimes referred to as the partial peptide of the present invention) may be any partial peptides of the polypeptides of the present invention described above, and those having the prolactin secretion regulating activity, which is expressed by adding the receptors of the polypeptide of the present invention (specifically, proteins containing the same or substantially the same amino acid sequence as the amino acid sequence shown by SEQ ID NO: 37, or salts thereof.

The partial peptide of the present invention may contain an amino acid sequence, wherein 1 to 5 (preferably 1 to 3) amino acids are deleted, an amino acid sequence, to which 1 to 5 (preferably 1 to 3) amino acids are added, an amino acid sequence, wherein 1 to 5 (preferably 1 to 3) amino acids are inserted, or an amino acid sequence, wherein 1 to 5 (preferably 1 to 3) amino acids are substituted by other amino acids. The partial peptide may contain a combination of the above amino acid sequences.

In the partial peptide of the present invention, the C-terminus is normally a carboxyl group (—COOH) or carboxylate (—$COO^-$) but the C-terminus may be in the form of an amide (—$CONH_2$) or an ester (—COOR) (wherein R has the same significance as defined above), as has been described with the polypeptide of the present invention. In particular, preferred are the partial peptides having an amide (—$CONH_2$) at the C-terminus.

Where the partial peptide of the receptor protein of the present invention contains a carboxyl group (or a carboxylate) at a position other than the C-terminus, it may be amidated or esterified and such an amide or ester is also included within the receptor protein of the present invention. The ester group may be the same group as the ester described with respect to the above C-terminal.

As in the polypeptide of the present invention described above, the partial peptide of the present invention further includes conjugated peptides such as those in which the amino group of the N-terminal amino acid residue (e.g., methionine residue) is protected by a protecting group, those in which the N-terminal residue is cleaved in vivo and the produced glutamine residue is pyroglutaminated, those in which substituents on the side chains of amino acids in the molecule are protected by appropriate protecting groups and conjugated proteins such as so-called glycoproteins having sugar chains. Hereinafter, these partial peptides are sometimes merely referred to as the partial peptide of the present invention.

As the partial peptide of the polypeptide of the present invention, preferred are peptides containing the RF amide, RS amide or RL amide structure, more preferably peptides containing the RF amide or RS amide structure, and most preferably peptides containing the RF amide structure.

The RF amide structure refers to the peptide structure, the C-terminus of which is arginine-phenylalanine-$NH_2$. The RS amide structure is used to mean the peptide structure, the C-terminus of which is arginine-serine-$NH_2$. In the RL amide structure, the C-terminus of the peptide is arginine-leucine-$NH_2$ structure.

Among these peptides, preferred examples include:

(1) A peptide containing the amino acid sequence of 56 (Ser)-92 (Phe), 73 (Met)-92 (Phe), 81 (Met)-92 (Phe), 84 (Ser)-92 (Phe), 101 (Ser)-112 (Ser), 115 (Asn)-131 (Phe), 124 (Val)-131 (Phe), 1 (Met)-92 (Phe), 1 (Met)-112 (Ser) or 1 (Met)-131 (Phe) in the amino acid sequence shown by SEQ ID NO: 1;

(2) A peptide containing the amino acid sequence of 56 (Ser)-92 (Phe), 73 (Met)-92 (Phe), 81 (Met)-92 (Phe), 84 (Ser)-92 (Phe), 101 (Ser)-112 (Ser), 115 (Asn)-131 (Phe), 124 (Val)-131 (Phe), 1 (Met)-92 (Phe), 1 (Met)-112 (Ser) or 1 (Met)-131 (Phe) in the amino acid sequence shown by SEQ ID NO: 8;

(3) A peptide containing the amino acid sequence of 58 (Ser)-92 (Phe), 81 (Met)-92 (Phe), 101 (Ser)-112 (Leu), 124 (Val)-131 (Phe), 1 (Met)-92 (Phe) or 1 (Met)-131 (Phe) in the amino acid sequence shown by SEQ ID NO: 14;

(4) A peptide containing the amino acid sequence of 58 (Ser)-94 (Phe), 83 (Val)-94 (Phe), 84 (Pro)-94 (Phe) or 118 (Phe)-125 (Phe) in the amino acid sequence shown by SEQ ID NO: 33;

(5) A peptide containing the amino acid sequence of 58 (Ser)-94 (Phe) or 84 (Pro)-94 (Phe) in the amino acid sequence shown by SEQ ID NO: 50.

Particularly preferred are:

(1) A peptide containing the amino acid sequence of 56 (Ser)-92 (Phe), 73 (Met)-92 (Phe), 81 (Met)-92 (Phe), 84 (Ser)-92 (Phe), 101 (Ser)-112 (Ser), 115 (Asn)-131 (Phe) or 124 (Val)-131 (Phe) in the amino acid sequence shown by SEQ ID NO: 1;

(2) A peptide containing the amino acid sequence of 56 (Ser)-92 (Phe), 73 (Met)-92 (Phe), 81 (Met)-92 (Phe), 84

(Ser)-92 (Phe), 101 (Ser)-112 (Ser), 115 (Asn)-131 (Phe) or 124 (Val)-131 (Phe) in the amino acid sequence shown by SEQ ID NO: 8;

(3) A peptide containing the amino acid sequence of 58 (Ser)-92 (Phe), 81 (Met)-92 (Phe), 101 (Ser)-112 (Leu) or 124 (Val)-131 (Phe) in the amino acid sequence shown by SEQ ID NO: 14;

(4) A peptide containing the amino acid sequence of 58 (Ser)-94 (Phe), 83 (Val)-94 (Phe), 84 (Pro)-94 (Phe) or 118 (Phe)-125 (Phe) in the amino acid sequence shown by SEQ ID NO: 33;

(5) A peptide containing the amino acid sequence of 58 (Ser)-94 (Phe) or 84 (Pro)-94 (Phe) in the amino acid sequence shown by SEQ ID NO: 50;

and the like;

among others, preferred are:

(1) A peptide containing the amino acid sequence of 56 (Ser)-92 (Phe), 73 (Met)-92 (Phe), 81 (Met)-92 (Phe), 84 (Ser)-92 (Phe), 101 (Ser)-112 (Ser), 115 (Asn)-131 (Phe) or 124 (Val)-131 (Phe) in the amino acid sequence shown by SEQ ID NO: 1;

(2) A peptide containing the amino acid sequence of 56 (Ser)-92 (Phe), 73 (Met)-92 (Phe), 81 (Met)-92 (Phe), 84 (Ser)-92 (Phe), 101 (Ser)-112 (Ser), 115 (Asn)-131 (Phe) or 124 (Val)-131 (Phe) in the amino acid sequence shown by SEQ ID NO: 8;

(3) A peptide containing the amino acid sequence of 58 (Ser)-92 (Phe), 81 (Met)-92 (Phe), 101 (Ser)-112 (Leu) or 124 (Val)-131 (Phe) in the amino acid sequence shown by SEQ ID NO: 14;

(4) A peptide containing the amino acid sequence of 58 (Ser)-94 (Phe), 83 (Val)-94 (Phe) or 118 (Phe)-125 (Phe) in the amino acid sequence shown by SEQ ID NO: 33;

(5) A peptide containing the amino acid sequence of 58 (Ser)-94 (Phe) in the amino acid sequence shown by SEQ ID NO: 50;

and the like;

among others, preferred are:

(1) A peptide containing the amino acid sequence of 56 (Ser)-92 (Phe), 73 (Met)-92 (Phe), 81 (Met)-92 (Phe), 84 (Ser)-92 (Phe), 115 (Asn)-131 (Phe) or 124 (Val)-131 (Phe) in the amino acid sequence shown by SEQ ID NO: 1;

(2) A peptide containing the amino acid sequence of 56 (Ser)-92 (Phe), 73 (Met)-92 (Phe), 81 (Met)-92 (Phe), 84 (Ser)-92 (Phe), 115 (Asn)-131 (Phe) or 124 (Val)-131 (Phe) in the amino acid sequence shown by SEQ ID NO: 8;

(3) A peptide containing the amino acid sequence of 58 (Ser)-92 (Phe), 81 (Met)-92 (Phe) or 124 (Val)-131 (Phe) in the amino acid sequence shown by SEQ ID NO: 14;

among others, preferred are:

(1) A peptide containing the amino acid sequence of 56 (Ser)-92 (Phe), 73 (Met)-92 (Phe), 81 (Met)-92 (Phe) or 84 (Ser)-92 (Phe) in the amino acid sequence shown by SEQ ID NO: 1;

(2) A peptide containing the amino acid sequence of 56 (Ser)-92 (Phe), 73 (Met)-92 (Phe), 81 (Met)-92 (Phe) or 84 (Ser)-92 (Phe) in the amino acid sequence shown by SEQ ID NO: 8;

(3) A peptide containing the amino acid sequence of 58 (Ser)-92 (Phe) or 81 (Met)-92 (Phe) in the amino acid sequence shown by SEQ ID NO: 14;

among others, preferred are:

(1) A peptide containing the amino acid sequence of 81 (Met)-92 (Phe) in the amino acid sequence shown by SEQ ID NO: 1;

(2) A peptide containing the amino acid sequence of 81 (Met)-92 (Phe), 84 (Ser)-92 (Phe) in the amino acid sequence shown by SEQ ID NO: 8;

(3) A peptide containing the amino acid sequence of 81 (Met)-92 (Phe) in the amino acid sequence shown by SEQ ID NO: 14;

among others, preferred are:

(1) A peptide containing the amino acid sequence of 81 (Met)-92 (Phe) in the amino acid sequence shown by SEQ ID NO: 1;

(2) A peptide containing the amino acid sequence of 81 (Met)-92 (Phe), 84 (Ser)-92 (Phe) in the amino acid sequence shown by SEQ ID NO: 8.

Also, preferred examples of the partial peptide of the present invention include:

(a) A peptide containing the amino acid sequence of 81 (Met)-92 (Phe) in the amino acid sequence shown by SEQ ID NO: 1;

(b) A peptide containing the amino acid sequence of 101 (Ser)-112 (Ser) in the amino acid sequence shown by SEQ ID NO: 1;

(c) A peptide containing the amino acid sequence of 124 (Val)-131 (Phe) in the amino acid sequence shown by SEQ ID NO: 1;

(d) A peptide containing the amino acid sequence of 56 (Ser)-92 (Phe) in the amino acid sequence shown by SEQ ID NO: 1;

(e) A peptide containing the amino acid sequence of 81 (Met)-92 (Phe) in the amino acid sequence shown by SEQ ID NO: 14;

(f) A peptide containing the amino acid sequence of 101 (Ser)-112 (Leu) in the amino acid sequence shown by SEQ ID NO: 14;

(g) A peptide containing the amino acid sequence of 58 (Ser)-92 (Phe) in the amino acid sequence shown by SEQ ID NO: 14;

(h) A peptide containing the amino acid sequence of 83 (Val)-94 (Phe) in the amino acid sequence shown by SEQ ID NO: 33;

(i) A peptide containing the amino acid sequence of 118 (Phe)-125 (Phe) in the amino acid sequence shown by SEQ ID NO: 33;

(j) A peptide containing the amino acid sequence of 58 (Ser)-94 (Phe) in the amino acid sequence shown by SEQ ID NO: 33;

(k) A peptide containing the amino acid sequence of 58 (Ser)-94 (Phe) in the amino acid sequence shown by SEQ ID NO: 50; and the like.

In particular, the amides of these peptides are desirable (preferably, peptides wherein the C-terminal carboxyl group (—COOH) is amidated (—$CONH_2$)).

Specific examples include a peptide having the amino acid sequence shown by 81(Met)-92(Phe) in SEQ ID NO: 1 wherein the C-terminus is amidated (—$CONH_2$) (SEQ ID NO: 39), a peptide having the amino acid sequence shown by 101(Ser)-112(Ser) in SEQ ID NO: 1 wherein the C-terminus is amidated (—$CONH_2$) (SEQ ID NO: 41) and a peptide having the amino acid sequence shown by 124(Val)-131(Phe) in SEQ ID NO: 1 wherein the C-terminus is amidated (—$CONH_2$) (SEQ ID NO: 40).

Among others, preferred are the peptide (SEQ ID NO: 39) having the 81 (Met)-92 (Phe) amino acid sequence in SEQ ID NO: 1, wherein the C-terminus is amidated (—$CONH_2$) and the peptide (SEQ ID NO: 40) having the 124 (Val)-131 (Phe) amino acid sequence in SEQ ID NO: 1 wherein the C-terminus is amidated (—$CONH_2$), with particular preference of the peptide (SEQ ID NO: 39) having the 81 (Met)-92 (Phe) amino acid sequence in SEQ ID NO: 1, wherein the C-terminus is amidated (—$CONH_2$).

The partial peptide of the present invention may contain an amino acid sequence wherein 1 to 5 (preferably 1 to 3) amino acids are deleted, an amino acid sequence to which 1 to 5 (preferably 1 to 3) amino acids are added, an amino acid sequence wherein 1 to 5 (preferably 1 to 3) amino acids are inserted, or an amino acid sequence wherein 1 to 5 (preferably 1 to 3) amino acids are substituted by other amino acids. The partial peptide may contain a combination of the above amino acid sequences.

In the partial peptide of the present invention, the C-terminus is normally a carboxyl group (—COOH) or carboxylate (—$COO^-$) but the C-terminus may be in the form of an amide (—$CONH_2$) or an ester (—COOR) (wherein R has the same significance as defined above), as has been described with the polypeptide of the present invention. In particular, preferred are the partial peptides having an amide (—$CONH_2$) at the C-terminus.

As in the polypeptide of the present invention described above, the partial peptide of the present invention further includes conjugated peptides is such as those in which the amino group of the N-terminal amino acid residue (e.g., methionine residue) is protected by a protecting group, those in which the N-terminal residue is cleaved in vivo and the produced glutamine residue is pyroglutaminated, those in which substituents on the side chains of amino acids in the molecule are protected by appropriate protecting groups and conjugated proteins such as so-called glycoproteins having sugar chains.

The partial peptide of the present invention can be employed as an antigen for producing an antibody and therefore, does not necessarily require the cell stimulating activity, the somatostatin secretion regulating activity, etc.

The polypeptide, amides or esters of the present invention or the partial peptide, amides or esters of the present invention may be used in the form of salts with physiologically acceptable acids (e.g., inorganic acids or organic acids) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The polypeptide of the present invention or salts thereof, or the partial peptide of the present invention or salts thereof may be manufactured by a publicly known method used to purify a polypeptide from human or other warm-blooded animal cells or tissues described above. Alternatively, the polypeptide of the present invention or salts thereof may also be manufactured by culturing a transformant containing DNA encoding the polypeptide of the present invention, as will be later described. Furthermore, the polypeptide of the present invention or salts thereof may also be manufactured by the methods for synthesizing proteins, which will also be described hereinafter, or by modified methods.

Where the polypeptide or salts thereof are manufactured from human or mammalian tissues or cells, human or mammalian tissues or cells are homogenized, then extracted with an acid or the like, and the extract is isolated and purified by a combination of chromatography techniques such as reverse phase chromatography, ion exchange chromatography, and the like.

To synthesize the polypeptide of the present invention, its partial peptide or its salts or amides, commercially available resins that are used for polypeptide synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective polypeptide according to various condensation methods publicly known in the art. At the end of the reaction, the polypeptide is excised from the resin and at the same time, the protecting groups are removed. Then, intramolecular disulfide bond-forming reaction is performed in a highly diluted solution to obtain the objective polypeptide, partial peptide or amides thereof.

For condensation of the protected amino acids described above, a variety of activation reagents for polypeptide synthesis may be used, but carbodiimides are particularly preferably employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents that are known to be usable for polypeptide condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitrites such as acetonitrile, propionitrile, etc.; esters such as methyl acetate, ethyl acetate, etc.; and appropriate mixtures of these solvents. The reaction temperature is appropriately chosen from the range known to be applicable to polypeptide binding reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower $C_{1-6}$ alkanoyl group, such as acetyl group, an aroyl group such as benzoyl group, and a group derived from carbonic acid such as benzyloxycarbonyl group and ethoxycarbonyl group. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting amino acids include the corresponding acid anhydrides, azides, activated esters (esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)). As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the polypeptide or partial peptide of the present invention, for example, the α-carboxyl group of the carboxy terminal amino acid is first protected by amidation; the peptide (polypeptide) chain is then extended from the amino group side to a desired length. Thereafter, a polypeptide in which only the protecting group of the N-terminal α-amino group has been eliminated from the polypeptide and a polypeptide in which only the protecting group of the C-terminal carboxyl group has been eliminated are manufactured. The two polypeptides are condensed in a mixture of the solvents described above. The details of the condensation reaction are the same as described above. After the protected polypeptide obtained by the condensation is purified, all the protecting groups are eliminated by the method described above to give the desired crude polypeptide. This crude polypeptide is purified by various known purification means. Lyophilization of the major fraction gives the amide of the desired polypeptide or partial peptide.

To prepare the esterified polypeptide or partial peptide of the present invention, for example, the α-carboxyl group of the carboxy terminal amino acid is condensed with a desired alcohol to prepare the amino acid ester, which is followed by procedure similar to the preparation of the amidated polypeptide above to give the desired esterified polypeptide or partial peptide.

The partial peptide or salts of the present invention can be manufactured by publicly known methods for peptide synthesis, or by cleaving the polypeptide of the present invention with an appropriate peptidase. For the methods for peptide synthesis, for example, either solid phase synthesis or liquid phase synthesis may be used. That is, the partial peptide or amino acids that can construct the polypeptide of the present invention are condensed with the remaining part of the partial peptide of the present invention. Where the product contains protecting groups, these protecting groups are removed to give the desired peptide. Publicly known methods for condensation and elimination of the protecting groups are described in 1)-5) below.

1) M. Bodanszky & M. A. Ondetti: Peptide Synthesis, Interscience Publishers, New York (1966)

2) Schroeder & Luebke: The Peptide, Academic Press, New York (1965)

3) Nobuo Izumiya, et al.: *Peptide Gosei-no-Kiso to Jikken* (Basics and experiments of peptide synthesis), published by Maruzen Co. (1975)

4) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

5) Haruaki Yajima ed.: *Zoku lyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the partial peptide of the present invention. When the partial peptide obtained by the above methods is in a free form, the peptide can be converted into an appropriate salt by a publicly known method; when the protein is obtained in a salt form, it can be converted into a free form or a different salt form by a publicly known method.

The DNA encoding the polypeptide of the present invention may be any DNA so long as it contains the base sequence encoding the polypeptide of the present invention described above. Such a DNA may also be any one of genomic DNA, genomic DNA library, cDNA derived from the cells or tissues described above, cDNA library derived from the cells or tissues described above and synthetic DNA.

The vector to be used for the library may be any of bacteriophage, plasmid, cosmid, phagemid and the like. In addition, the DNA can be amplified by reverse transcriptase polymerase chain reaction (hereinafter abbreviated as RT-PCR) with total RNA or mRNA fraction prepared from the above-described cells or tissues.

Specifically, the DNA encoding the polypeptide of the present invention may be any one of, for example, DNA having the base sequence represented by SEQ ID NO: 2, SEQ ID NO: 9, SEQ ID NO: 15, SEQ ID NO: 19, SEQ ID NO: 34 or SEQ ID NO: 51 or any DNA having a base sequence hybridizable to the base sequence represented by SEQ ID NO: 2, SEQ ID NO: 9, SEQ ID NO: 15, SEQ ID NO: 19, SEQ ID NO: 34 or SEQ ID NO: 51 under high stringent conditions and encoding a polypeptide which has the activities substantially equivalent to those of the polypeptide of the present invention (e.g., a cell stimulating activity, etc.).

Specific examples of the DNA that is hybridizable to the base sequence represented by SEQ ID NO: 2, SEQ ID NO: 9, SEQ ID NO: 15, SEQ ID NO: 19, SEQ ID NO: 34 or SEQ ID NO: 51 under high stringent conditions include DNA having at least about 70% homology, preferably at least about 80% homology, more preferably at least about 90% homology and most preferably at least about 95% homology, to the base sequence represented by SEQ ID NO: 2.

The hybridization can be carried out by publicly known methods or by a modification thereof, for example, according to the method described in Molecular Cloning, 2nd Ed., J. Sambrook et al., Cold Spring Harbor Lab. Press, (1989). A commercially available library may also be used according to the instructions of the attached manufacturer's protocol. The hybridization can be carried out preferably under high stringent conditions.

The high stringent conditions used herein are, for example, those in a sodium concentration at about 19 mM to about 40 mM, preferably about 19 mM to about 20 mM at a temperature of about 50° C. to about 70° C., preferably about 60° C. to about 65° C. In particular, hybridization conditions in a sodium concentration at about 19 mM at a temperature of about 65° C. are most preferred.

More specifically, for the DNA encoding the polypeptide having the amino acid sequence represented by SEQ ID NO: 1, there may be employed DNA having the base sequence represented by SEQ ID NO: 2 and, DNA having the base sequence represented by SEQ ID NO: 9 may be used for the DNA encoding the polypeptide having the amino acid sequence represented by SEQ ID NO: 8. For the DNA encoding the polypeptide having the amino acid sequence represented by SEQ ID NO: 14, DNA having the base sequence represented by SEQ ID NO: 15 may be employed and, DNA having the base sequence represented by SEQ ID NO: 19 may be used as the DNA encoding the polypeptide having the amino acid sequence represented by SEQ ID NO: 18. As the DNA encoding the polypeptide having the amino acid sequence represented by SEQ ID NO: 33, there may be employed DNA having the base sequence represented by SEQ ID NO: 34 and, DNA having the base sequence represented by SEQ ID NO: 51 may be used for the DNA encoding the polypeptide having the amino acid sequence represented by SEQ ID NO: 50.

The DNA encoding the partial peptide of the present invention may be any DNA so long as it contains the base sequence encoding the partial peptide of the present invention described above. The DNA may also be any of genomic DNA, genomic DNA library, cDNA derived from the cells and tissues described above, cDNA library derived from the cells and tissues described above and synthetic DNA.

Specifically, the DNA encoding the partial peptide of the present invention may be any one of, for example, DNA having a partial base sequence of the DNA having the base sequence represented by SEQ ID NO: 2, SEQ ID NO: 9, SEQ ID NO: 15, SEQ ID NO: 19, SEQ ID NO: 34 or SEQ ID NO: 51 or any DNA having a partial base sequence of the DNA having a base sequence hybridizable to the base sequence represented by SEQ ID NO: 2, SEQ ID NO: 9, SEQ ID NO: 15, SEQ ID NO: 19, SEQ ID NO: 34 or SEQ ID NO: 51 under high stringent conditions and encoding a polypeptide which has the activities substantially equivalent to those of the polypeptide of the present invention.

Specific examples of the DNA that is hybridizable to the base sequence represented by SEQ ID NO: 2, SEQ ID NO: 9, SEQ ID NO: 15, SEQ ID NO: 19, SEQ ID NO: 34 or SEQ ID NO: 51 are the same as described above.

Methods for the hybridization and the high stringent conditions that can be used are also the same as described above.

The polypeptide encoded by the DNA that is hybridizable to the base sequence represented by SEQ ID NO: 2, SEQ ID NO: 9, SEQ ID NO: 15, SEQ ID NO: 19, SEQ ID NO: 34 or SEQ ID NO: 51 can be manufactured in a manner similar to the method for manufacturing the polypeptide of the present invention, which will be described hereinafter. Examples of the amides, esters and salts of the polypeptide include those as described for the amides, esters and salts of the polypeptide of the present invention described above.

Specifically, the DNA encoding the partial peptide of the present invention includes:

(1) A DNA encoding the peptide containing the amino acid sequence of 56 (Ser)-92 (Phe), 73 (Met)-92 (Phe), 81 (Met)-92 (Phe), 84 (Ser)-92 (Phe), 101 (Ser)-112 (Ser), 115 (Asn)-131 (Phe), 124 (Val)-131 (Phe), 1 (Met)-92 (Phe), 1 (Met)-112 (Ser) or 1 (Met)-131 (Phe) in the amino acid sequence shown by SEQ ID NO: 1; or a DNA containing the base sequence hybridizable thereto under high stringent conditions;

(2) A DNA encoding the peptide containing the amino acid sequence of 56 (Ser)-92 (Phe), 73 (Met)-92 (Phe), 81 (Met)-92 (Phe), 84 (Ser)-92 (Phe), 101 (Ser)-112 (Ser), 115 (Asn)-131 (Phe), 124 (Val)-131 (Phe), 1 (Met)-92 (Phe), 1 (Met)-112 (Ser) or 1 (Met)-131 (Phe) in the amino acid sequence shown by SEQ ID NO: 8; or a DNA containing the base sequence hybridizable thereto under high stringent conditions;

(3) A DNA encoding the peptide containing the amino acid sequence of 58 (Ser)-92 (Phe), 81 (Met)-92 (Phe), 101 (Ser)-112 (Leu), 124 (Val)-131 (Phe), 1 (Met)-92 (Phe) or 1 (Met)-131 (Phe) in the amino acid sequence shown by SEQ ID NO: 14; or a DNA containing the base sequence hybridizable thereto under high stringent conditions;

(4) A DNA encoding the peptide containing the amino acid sequence of 58 (Ser)-94 (Phe), 83 (Val)-94 (Phe), 84 (Pro)-94 (Phe) or 118 (Phe)-125 (Phe) in the amino acid sequence shown by SEQ ID NO: 33; or a DNA containing the base sequence hybridizable thereto under high stringent conditions;

(5) A DNA encoding the peptide containing the amino acid sequence of 58 (Ser)-94 (Phe) or 84 (Pro)-94 (Phe) in the amino acid sequence shown by SEQ ID NO: 50; and the like.

More specifically, the DNA includes:

A DNA containing a DNA (DNA having 241-276 bases of the base sequence represented by SEQ ID NO: 2) having the base sequence represented by SEQ ID NO: 42 as the DNA having the base sequence encoding the peptide containing the 81 (Met)-92(Phe) amino acid sequence in the amino acid sequence represented by SEQ ID NO: 1;

DNA containing the DNA (DNA having 301-336 bases of the base sequence represented by SEQ ID NO: 2) having the base sequence represented by SEQ ID NO: 43 as the DNA having the base sequence encoding the peptide containing the 101(Ser)-112(Ser) amino acid sequence in the amino acid sequence represented by SEQ ID NO: 1;

DNA containing the DNA (DNA having 370-393 bases of the base sequence represented by SEQ ID NO: 2) having the base sequence represented by SEQ ID NO: 44 as the DNA having the base sequence encoding the peptide containing the 124(Val)-131(Phe) amino acid sequence in the amino acid sequence represented by SEQ ID NO: 1;

DNA containing the DNA (DNA having 1-276 bases of the base sequence represented by SEQ ID NO: 2) having the base sequence represented by SEQ ID NO: 45 as the DNA having the base sequence encoding the peptide containing the 1 (Met)-92(Phe) amino acid sequence in the amino acid sequence represented by SEQ ID NO: 1;

DNA containing the DNA (DNA having 1-336 bases of the base sequence represented by SEQ ID NO: 2) having the base sequence represented by SEQ ID NO: 46 as the DNA having the base sequence encoding the peptide containing the 1 (Met)-112(Ser) amino acid sequence in the amino acid sequence represented by SEQ ID NO: 1; and, DNA containing the DNA (DNA having 1-393 bases of the base sequence represented by SEQ ID NO: 2) having the base sequence represented by SEQ ID NO: 47 as the DNA having the base sequence encoding the peptide containing the 1(Met)-131(Phe) amino acid sequence in the amino acid sequence represented by SEQ ID NO: 1.

The DNA further includes:

As the DNA encoding the peptide containing the 56 (Ser)-92 (Phe) amino acid sequence in the amino acid sequence represented by SEQ ID NO: 1, a DNA containing the 166-276 base sequence represented by SEQ ID NO: 2;

As the DNA encoding the peptide containing the 73 (Met)-92 (Phe) amino acid sequence in the amino acid sequence represented by SEQ ID NO: 1, a DNA containing the 217-276 base sequence represented by SEQ ID NO: 2;

As the DNA encoding the peptide containing the 84 (Ser)-92 (Phe) amino acid sequence in the amino acid sequence represented by SEQ ID NO: 1, a DNA containing the 253-276 base sequence represented by SEQ ID NO: 2;

As the DNA encoding the peptide containing the 115 (Asn)-131 (Phe) amino acid sequence in the amino acid sequence represented by SEQ ID NO: 1, a DNA containing the 346-393 base sequence represented by SEQ ID NO: 2;

As the DNA encoding the peptide containing the 56 (Ser)-92 (Phe) amino acid sequence in the amino acid sequence represented by SEQ ID NO: 8, a DNA containing the 169-276 base sequence represented by SEQ ID NO: 9;

As the DNA encoding the peptide containing the 73 (Met)-92 (Phe) amino acid sequence in the amino acid sequence represented by SEQ ID NO: 8, a DNA containing the 220-276 base sequence represented by SEQ ID NO: 9;

As the DNA encoding the peptide containing the 81 (Met)-92 (Phe) amino acid sequence in the amino acid sequence represented by SEQ ID NO: 8, a DNA containing the 244-276 base sequence represented by SEQ ID NO: 9;

As the DNA encoding the peptide containing the 84 (Ser)-92 (Phe) amino acid sequence in the amino acid sequence represented by SEQ ID NO: 8, a DNA containing the 253-276 base sequence represented by SEQ ID NO: 9;

As the DNA encoding the peptide containing the 101 (Ser)-112 (Ser) amino acid sequence in the amino acid sequence represented by SEQ ID NO: 8, a DNA containing the 304-336 base sequence represented by SEQ ID NO: 9;

As the DNA encoding the peptide containing the 115 (Asn)-131 (Phe) amino acid sequence in the amino acid sequence represented by SEQ ID NO: 8, a DNA containing the 346-393 base sequence represented by SEQ ID NO: 9;

As the DNA encoding the peptide containing the 124 (Val)-131 (Phe) amino acid sequence in the amino acid sequence represented by SEQ ID NO: 8, a DNA containing the 373-393 base sequence represented by SEQ ID NO: 9;

As the DNA encoding the peptide containing the 1 (Met)-92 (Phe) amino acid sequence in the amino acid sequence represented by SEQ ID NO: 8, a DNA containing the 1-276 base sequence represented by SEQ ID NO: 9;

As the DNA encoding the peptide containing the 1 (Met)-112 (Ser) amino acid sequence in the amino acid sequence represented by SEQ ID NO: 8, a DNA containing the 1-336 base sequence represented by SEQ ID NO: 9;

As the DNA encoding the peptide containing the 1 (Met)-131 (Phe) amino acid sequence in the amino acid sequence represented by SEQ ID NO: 8, a DNA containing the 1-393 base sequence represented by SEQ ID NO: 9;

As the DNA encoding the peptide containing the 58 (Ser)-92 (Phe) amino acid sequence in the amino acid sequence represented by SEQ ID NO: 14, a DNA containing the 172-276 base sequence represented by SEQ ID NO: 15;

As the DNA encoding the peptide containing the 81 (Met)-92 (Phe) amino acid sequence in the amino acid sequence represented by SEQ ID NO: 14, a DNA containing the 241-276 base sequence represented by SEQ ID NO: 15;

As the DNA encoding the peptide containing the 101 (Ser)-112 (Leu) amino acid sequence in the amino acid sequence represented by SEQ ID NO: 14, a DNA containing the 301-336 base sequence represented by SEQ ID NO: 15;

As the DNA encoding the peptide containing the 124 (Val)-131 (Phe) amino acid sequence in the amino acid sequence represented by SEQ ID NO: 14, a DNA containing the 370-393 base sequence represented by SEQ ID NO: 15;

As the DNA encoding the peptide containing the 1 (Met)-92 (Phe) amino acid sequence in the amino acid sequence represented by SEQ ID NO: 14, a DNA containing the 1-276 base sequence represented by SEQ ID NO: 15;

As the DNA encoding the peptide containing the 1 (Met)-131 (Phe) amino acid sequence in the amino acid sequence represented by SEQ ID NO: 14, a DNA containing the 1-393 base sequence represented by SEQ ID NO: 15;

As the DNA encoding the peptide containing the 58 (Ser)-94 (Phe) amino acid sequence in the amino acid sequence represented by SEQ ID NO: 33, a DNA containing the 172-282 base sequence represented by SEQ ID NO: 34;

As the DNA encoding the peptide containing the 83 (Val)-94 (Phe) amino acid sequence in the amino acid sequence represented by SEQ ID NO: 33, a DNA containing the 247-282 base sequence represented by SEQ ID NO: 34;

As the DNA encoding the peptide containing the 84 (Pro)-94 (Phe) amino acid sequence in the amino acid sequence represented by SEQ ID NO: 33, a DNA containing the 250-282 base sequence represented by SEQ ID NO: 34;

As the DNA encoding the peptide containing the 118 (Phe)-125 (Phe) amino acid sequence in the amino acid sequence represented by SEQ ID NO: 33, a DNA containing the 352-375 base sequence represented by SEQ ID NO: 34;

As the DNA encoding the peptide containing the 58 (Ser)-94 (Phe) amino acid sequence in the amino acid sequence represented by SEQ ID NO: 50, a DNA containing the 172-282 base sequence represented by SEQ ID NO: 51;

As the DNA encoding the peptide containing the 84 (Pro)-94 (Phe) amino acid sequence in the amino acid sequence represented by SEQ ID NO: 50, a DNA containing the 250-282 base sequence represented by SEQ ID NO: 51; and the like.

The polypeptide of the present invention or its partial peptide, the receptor protein of the present invention or its partial peptide, which will be described hereinafter, and DNA encoding these proteins or peptides may be labeled in a publicly known manner. Specific examples include those labeled with an isotope, those labeled with fluorescence (labeling with, e.g., fluorescein, etc.), those biotinated and those labeled with enzyme.

For cloning of the DNA that completely encodes the polypeptide or its partial peptide of the present invention (hereinafter sometimes collectively referred to as the polypeptide of the present invention in the following description of cloning and expression of the DNA encoding these polypeptides or the like), the DNA may be either amplified by publicly known PCR using synthetic DNA primers containing a part of the base sequence of the polypeptide of the present invention, or the DNA inserted into an appropriate vector can be selected by hybridization with a labeled DNA fragment or synthetic DNA that encodes a part or entire region of the polypeptide of the present invention. The hybridization can be carried out, for example, according to the method described in Molecular Cloning, 2nd (J. Sambrook et al., Cold Spring Harbor Lab. Press, 1989). The hybridization may also be performed using commercially available library in accordance with the protocol described in the attached instructions.

Conversion of the base sequence of DNA can be effected by publicly known methods such as the Gapped duplex method or the Kunkel method or its modification by using a publicly known kit available as Mutan™-G or Mutan™-K (both manufactured by Takara Shuzo Co., Ltd., trademark).

The cloned DNA encoding the polypeptide of the present invention can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector of the polypeptide of the present invention can be manufactured, for example, by (a) excising the desired DNA fragment from the DNA encoding the polypeptide of the present invention, (b) and then ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SR α promoter, SV40 promoter, HIV-LTR promoter, CMV promoter, HSV-TK promoter, etc.

Among them, CMV (cytomegalovirus) promoter or SR α promoter is preferably used. Where the host is bacteria of the genus *Escherichia*, preferred examples of the promoter include trp promoter, lac promoter, recA promoter, λPL promoter, Ipp promoter, T7 promoter, etc. In the case of using bacteria of the genus *Bacillus* as the host, preferred example of the promoter are SPO1 promoter, SPO2 promoter and penP promoter. When yeast is used as the host, preferred examples of the promoter are PHO5 promoter, PGK promoter, GAP promoter and ADH promoter. When insect cells are used as the host, preferred examples of the promoter include polyhedrin prompter and P10 promoter.

In addition to the foregoing examples, the expression vector may further optionally contain an enhancer, a splicing signal, a poly A addition signal, a selection marker, SV40 replication origin (hereinafter sometimes abbreviated as SV40ri) etc. Examples of the selection marker include dihydrofolate reductase (hereinafter sometimes abbreviated as dhfr) gene [methotrexate (MTX) resistance], ampicillin resistant gene (hereinafter sometimes abbreviated as $Amp^r$), neomycin resistant gene (hereinafter sometimes abbreviated as Neo, G418 resistance), etc. In particular, when dhfr gene is used as the selection marker together with dhfr gene, selection can also be made on thymidine free media.

If necessary and desired, a signal sequence that matches with a host is added to the N-terminus of the polypeptide of the present invention. Examples of the signal sequence that can be used are PhoA signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MF α signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector comprising the DNA encoding the polypeptide of the present invention thus constructed, transformants can be manufactured.

Examples of the host, which may be employed, are bacteria belonging to the genus *Escherichia* or *Bacillus*, yeast, insect cells, insects and animal cells, etc.

Specific examples of the bacteria belonging to the genus *Escherichia* include *Escherichia coli* K12 DH1 (Proc. Natl. Acad. Sci. U.S.A., 60, 160 (1968)), JM103 (Nucleic Acids Research, 9, 309 (1981)), JA221 (Journal of Molecular Biology, 120, 517 (1978)), HB101 (Journal of Molecular Biology, 41, 459 (1969)), C600 (Genetics, 39, 440 (1954)), etc.

Examples of the bacteria belonging to the genus *Bacillus* include *Bacillus subtilis* MI114 (Gene, 24, 255 (1983)), 207-21 (Journal of Biochemistry, 95, 87 (1984)), etc.

Examples of yeast include *Saccharomyces cereviseae* AH22, $AH22R^-$, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from *Estigmena acrea*, etc.; and for the virus BmNPV, *Bombyx mori* N cell (BmN cell), etc. is used. Examples of the Sf cell which can be used are Sf9 cell (ATCC CRL1711) and Sf21 cell (both cells are described in Vaughn, J. L. et al., In Vivo, 13, 213-217 (1977).

As the insect, for example, a larva of *Bombyx mori* can be used (Maeda et al., Nature, 315, 592 (1985)).

Examples of animal cells include monkey cell COS-7, Vero, Chinese hamster cell CHO (hereinafter referred to as CHO cell), dhfr gene deficient Chinese hamster cell CHO (hereinafter simply referred to as CHO($dhfr^-$) cell), mouse L cell, mouse AtT-20, mouse myeloma cell, rat GH3, human FL cell, etc.

Bacteria belonging to the genus *Escherichia* can be transformed, for example, by the method described in Proc. Natl. Acad. Sci. U.S.A., 69, 2110 (1972) or Gene, 17,107 (1982).

Bacteria belonging to the genus *Bacillus* can be transformed, for example, by the method described in Molecular & General Genetics, 168, 111 (1979).

Yeast can be transformed, for example, by the method described in Methods in Enzymology, 194, 182-187 (1991) or Proc. Natl. Acad. Sci. U.S.A., 75, 1929 (1978).

Insect cells or insects can be transformed, for example, according to the method described in Bio/Technology, 6, 47-55(1988).

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263-267 (1995), published by Shujunsha, or Virology, 52, 456 (1973).

Thus, the transformant transformed with the expression vector containing the DNA encoding the polypeptide can be obtained.

Where the host is bacteria belonging to the genus *Escherichia* or the genus *Bacillus*, the transformant can be appropriately incubated in a liquid medium which contains materials required for growth of the transformant such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast, vitamins, growth promoting factors etc. may also be added to the medium. Preferably, pH of the medium is adjusted to about 5 to about 8.

A preferred example of the medium for incubation of the bacteria belonging to the genus *Escherichia* is M9 medium supplemented with glucose and Casamino acids (Miller, Journal of Experiments in Molecular Genetics, 431-433, Cold Spring Harbor Laboratory, New York, 1972). If necessary and desired, a chemical such as 3 β-indolylacrylic acid can be added to the medium thereby to activate the promoter efficiently.

Where the bacteria belonging to the genus *Escherichia* are used as the host, the transformant is usually cultivated at about 15° C. to about 43° C. for about 3 hours to about 24 hours. If necessary and desired, the culture may be aerated or agitated.

Where the bacteria belonging to the genus *Bacillus* are used as the host, the transformant is cultivated generally at about 30° C. to about 40° C. for is about 6 hours to about 24 hours. If necessary and desired, the culture can be aerated or agitated.

Where yeast is used as the host, the transformant is cultivated, for example, in Burkholder's minimal medium (Bostian, K. L. et al., Proc. Natl. Acad. Sci. U.S.A., 77, 4505 (1980)) or in SD medium supplemented with 0.5% Casamino acids (Bitter, G. A. et al., Proc. Natl. Acad. Sci. U.S.A., 81, 5330 (1984)). Preferably, pH of the medium is adjusted to about 5 to about 8. In general, the transformant is cultivated at about 20° C. to about 35° C. for about 24 hours to about 72 hours. If necessary and desired, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary and desired, the culture can be aerated or agitated.

Where animal cells are employed as the host, the transformant is cultivated in, for example, MEM medium containing about 5% to about 20% fetal bovine serum (Science, 122, 501 (1952)), DMEM medium (Virology, 8, 396 (1959)), RPMI 1640 medium (The Journal of the American Medical Association, 199, 519 (1967)), 199 medium (Proceeding of the Society for the Biological Medicine, 73, 1 (1950)), etc. Preferably, pH of the medium is adjusted to about 6 to about 8. The transformant is usually cultivated at about 30° C. to about 40° C. for about 15 hours to about 60 hours and, if necessary and desired, the culture can be aerated or agitated.

As described above, the polypeptide of the present invention can be produced in the cell membrane of the transformant, etc.

The polypeptide of the present invention can be separated and purified from the culture described above by the following procedures.

When the polypeptide of the present invention is extracted from the culture or cells, after cultivation the transformant or cell is collected by a publicly known method and suspended in an appropriate buffer. The transformant or cell is then disrupted by publicly known methods such as ultrasonication, a treatment with lysozyme and/or freeze-thaw cycling, followed by centrifugation, filtration, etc. Thus, the crude extract of the polypeptide or its partial peptide of the present invention can be obtained. The buffer used for the procedures may contain a protein modifier such as urea or guanidine hydrochloride, or a surfactant such as Triton X-100™, etc. When the polypeptide or its partial peptide of the present invention is secreted in the culture broth, after completion of the cultivation the supernatant can be separated from the transformant or cell to collect the supernatant by a publicly known method.

The supernatant or the polypeptide of the present invention contained in the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the polypeptide of the present invention thus obtained is in a free form, it can be converted into the salt by publicly known methods or modifications thereof. On the other hand, when the polypeptide is obtained in the form of a salt, it can be converted into the free form or in the form of a different salt by publicly known methods or modifications thereof.

The polypeptide of the present invention produced by the recombinant can be treated, prior to or after the purification, with an appropriate protein modifying enzyme so that the protein or partial peptide can be appropriately modified to partially remove a polypeptide. Examples of the protein-modifying enzyme include trypsin, chymotrypsin, arginyl endopeptidase, protein kinase, glycosidase and the like.

The activity of the thus produced polypeptide of the present invention or salts thereof can be determined by a binding test to a labeled ligand and by an enzyme immunoassay using a specific antibody.

Specific examples of the receptor for the polypeptide, its amides or esters or salts of the present invention or the partial peptide or its esters, amides or salts (hereinafter sometimes collectively referred to as the receptor protein) include receptor proteins which possess the same or substantially the same amino acid sequence as the amino acid sequence shown by SEQ ID NO: 37.

The receptor protein of the present invention may be any polypeptide derived from any cells of human and other mammals (e.g. guinea pig, rat, mouse, rabbit, swine, sheep, bovine, monkey, etc.) such as splenocyte, nerve cell, glial cell, β cell of pancreas, bone marrow cell, mesangial cell, Langerhans' cell, epidermic cell, epithelial cell, endothelial cell, fibroblast, fibrocyte, myocyte, fat cell, immune cell (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte or interstitial cell, etc.; the corresponding precursor cells, stem cells, cancer cells, etc.) or hemocyte type cells; or any tissues where such cells are present, such as brain or any of brain regions (e.g., olfactory bulb, amygdaloid nucleus, basal ganglia, hippocampus, thalamus, hypothalamus, subthalamic nucleus, cerebral cortex, medulla oblongata, cerebellum, occipital pole, frontal lobe, temporal lobe, putamen, caudate nucleus, corpus callosum, substantia nigra), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, peripheral blood cells, prostate, testis, ovary, placenta, uterus, bone, joint, skeletal muscle, etc. (especially brain or any of brain regions). The receptor protein may also be a synthetic protein.

The amino acid sequence which has substantially the same amino acid sequence as that represented by SEQ ID NO: 37 includes an amino acid sequence having at least about 50% homology, preferably at least about 70% homology, more preferably at least about 80% homology, much more preferably at least about 90% homology and most preferably at least about 95% homology, to the amino acid sequence represented by SEQ ID NO: 37.

The protein which has substantially the same amino acid sequence as that shown by SEQ ID NO: 37 is preferably a protein having substantially the same amino acid sequence shown by SEQ ID NO: 37 and having the activities substantially equivalent to the amino acid sequence shown by SEQ ID NO: 37. A specific example of such protein is a protein containing the amino acid sequence represented by SEQ ID NO: 54.

The substantially equivalent activities are, for example, a ligand binding activity, a signal transduction activity, a somatostatin secretion regulating activity, etc. The term "substantially equivalent" is used to mean that the nature of these activities is equivalent. Therefore, it is preferred that these activities such as ligand binding activity, a signal transduction activity, etc. are equivalent in strength (e.g., about 0.1 to about 100 times, preferably about 0.5 to about 20 times, more preferably about 0.5 to about 2 times), and it is allowable that even differences among grades such as the strength of these activities and molecular weight of the polypeptide are present.

The activities such as a ligand binding activity, a signal transduction activity, or the like can be assayed according to a publicly known method, for example, by means of ligand determination or screening, which will be later described.

The receptor protein of the present invention which can be employed include proteins comprising (i) an amino acid sequence represented by SEQ ID NO: 37 or SEQ ID NO: 54, of which at least 1 or 2 (preferably 1 to 30, more preferably 1 to 10 and most preferably several (1 or 2)) amino acids are deleted; (ii) an amino acid sequence represented by SEQ ID NO: 37 or SEQ ID NO: 54, to which at least 1 or 2 (preferably 1 to 30, more preferably 1 to 10 and most preferably several (1 or 2)) amino acids are added; (iii) an amino acid sequence represented by SEQ ID NO: 37 or SEQ ID NO: 54, in which at least 1 or 2 (preferably 1 to 30, more preferably 1 to 10 and most preferably several (1 or 2)) amino acids are substituted by other amino acids; and (v) a combination of the above amino acid sequences.

Throughout the present specification, the receptor proteins are represented in accordance with the conventional way of describing peptides, that is, the N-terminus (amino terminus) at the left hand and the C-terminus (carboxyl terminus) at the right hand. In the receptor proteins of the present invention including the receptor proteins containing the amino acid sequence shown by SEQ ID NO: 37, the C-terminus is usually in the form of a carboxyl group (—COOH) or a carboxylate (—$COO^-$) but may be in the form of an amide (—$CONH_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; an aralkyl having 7 to 14 carbon atoms such as a phenyl-$C_{1-2}$ alkyl group, e.g., benzyl, phenethyl, etc.; an α-naphthyl-$C_{1-12}$ alkyl group such as α-naphthylmethyl, etc.; and the like. In addition, pivaloyloxymethyl or the like which is used widely as an ester for oral administration may also be used.

Where the receptor protein of the present invention contains a carboxyl group (or a carboxylate) at a position other than the C-terminus, it may be amidated or esterified and such an amide or ester is also included within the receptor protein of the present invention. The ester group may be the same group as that described with respect to the above C-terminal.

Furthermore, examples of the receptor protein of the present invention include variants of the above receptor protein, wherein the amino group at the N-terminus (e.g., methionine residue) of the peptide is protected with a protecting group (e.g., a $C_{1-6}$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins having sugar chains.

Specific examples of the receptor protein of the present invention include a rat-derived receptor protein containing the amino acid sequence represented by SEQ ID NO: 37, a human-derived receptor protein containing the amino acid sequence represented by SEQ ID NO: 54, etc.

As the partial peptide of the receptor protein of the present invention, any partial peptide described for the receptor protein can be used. For example, a part of the receptor protein molecule of the present invention which is exposed to outside of a cell membrane or the like can be used so long as it has a receptor binding activity.

Specifically, the partial peptide of the receptor protein having the amino acid sequence represented by SEQ ID NO: 37 or SEQ ID NO: 54 is a peptide containing the parts, which have been analyzed to be extracellular domains (hydrophilic domains) in the hydrophobic plotting analysis. A peptide containing a hydrophobic domain part can be used as well. In addition, the peptide may contain each domain separately or plural domains together.

In the receptor protein of the present invention, the partial peptide is a peptide having at least 20, preferably at least 50 and more preferably at least 100 amino acids, in the amino acid sequence, which constitutes the receptor protein of the present invention.

The substantially the same amino acid sequence includes an amino acid sequence having at least about 50% homology, preferably at least about 70% homology, more preferably at least about 80% homology, much more preferably at least about 90% homology and most preferably at least about 95% homology, to the amino acid sequence represented.

Herein the term "substantially equivalent activities" refers to the same significance as defined hereinabove. The "substantially equivalent activities" can be assayed by the same method as described above.

In the partial peptide of the receptor protein of the present invention, at least 1 or 2 (preferably 1 to 10, more preferably several (1 or 2)) amino acids may be deleted; at least 1 or 2 (preferably 1 to 20, more preferably 1 to 10 and most preferably several (1 or 2)) amino acids may be added; or at least 1 or 2 (preferably 1 to 10, more preferably several (1 or 2)), amino acids may be substituted by other amino acids.

In the partial peptide in the receptor protein of the present invention, the C-terminus is usually in the form of a carboxyl group (—COOH) or a carboxylate (—$COO^-$) but may be in the form of an amide (—$CONH_2$) or an ester (—COOR), as in the polypeptide of the present invention described above.

Where the receptor protein of the present invention contains a carboxyl group (or a carboxylate) at a position other than the C-terminus, it may be amidated or esterified and such an amide or ester is also included within the receptor protein of the present invention. The ester group may be the same group as that described with respect to the above C-terminal.

Furthermore, examples of the partial peptide of the receptor protein in the present invention include variants of the above peptides, wherein the amino group at the N-terminal methionine residue is protected with a protecting group, those wherein the N-terminal region is cleaved in vivo and the Gln formed is pyroglutaminated, those wherein a substituent on the side chain of an amino acid in the molecule is protected with a suitable protecting group, or conjugated proteins such as glycoproteins having sugar chains, as in the receptor protein of the present invention described above.

As the salts of the receptor protein or its partial peptide in the present invention, physiologically acceptable acid addition salts are particularly preferred. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The receptor protein or salts of the present invention may be manufactured by a publicly known method used to purify a receptor protein from human or other mammalian cells or tissues described above, or by preparing a transformant containing the DNA encoding the receptor protein of the present invention (a host similar to the host of the transformant containing the DNA encoding the polypeptide of the present invention described above may be used) in a manner similar to the aforesaid method for preparing the transformant containing the DNA encoding the polypeptide of the present invention, culturing the resulting transformant in a manner similar to the aforesaid method for preparing the transformant containing the DNA encoding the polypeptide of the present invention. Furthermore, the receptor protein or salts of the present invention may also be manufactured by the aforesaid methods for synthesizing polypeptides or by modified methods.

Where the receptor protein or salts thereof are manufactured from human or mammalian tissues or cells, human or mammalian tissues or cells are homogenized, then extracted with an acid or the like, and the extract is isolated and purified by a combination of chromatography techniques such as reverse phase chromatography, ion exchange chromatography, and the like.

The partial peptide of the receptor protein or salts thereof in the present invention can be manufactured by a publicly known method used to synthesize a peptide or, by cleaving the receptor protein of the present invention with an appropriate peptidase.

The receptor protein or salts of the present invention, its partial peptide, amides, esters or salts can be synthesized by the aforesaid method for synthesizing the polypeptide, amides, esters or salts of the present invention.

For the polynucleotide encoding the receptor protein of the present invention, any polynucleotide can be used as long as it contains the base sequence (DNA or RNA, preferably DNA) encoding the receptor protein of the present invention. Such a polynucleotide may be DNA and RNA including mRNA encoding the receptor protein of the present invention. The polynucleotide may be double-stranded or single-stranded. Where the polynucleotide is double-stranded, it may be double-stranded DNA, double-stranded RNA or DNA:RNA hybrid. Where the polynucleotide is single-stranded, it may be a sense strand (i.e., a coding strand) or an antisense strand (i.e., a non-coding strand).

Using the polynucleotide encoding the receptor protein of the present invention, mRNA of the receptor protein of the present invention can be quantified by, for example, the publicly known method published in separate volume of *Jikken Igaku* 15 (7) "New PCR and its application" (1997) or the modified method.

The DNA encoding the receptor protein of the present invention may be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

Specifically, the DNA encoding the receptor protein of the present invention may be any DNA having the base sequence shown by SEQ ID NO: 38, SEQ ID NO: 55 or SEQ ID NO: 56, or the base sequence hybridizable to the base sequence represented by SEQ ID NO: 38, SEQ ID NO: 55 or SEQ ID NO: 56 under high stringent conditions and encoding a polypeptide which has the activities substantially equivalent to those of the receptor protein of the present invention (e.g., a ligand binding activity, a signal transduction activity or a somatostatin secretion regulating activity, etc.).

Specific examples of the DNA that is hybridizable to the base sequence represented by SEQ ID NO: 38, SEQ ID NO: 55 or SEQ ID NO: 56 include DNA having at least about 70% homology, preferably at least about 80% homology, more preferably at least about 90% homology and most preferably at least about 95% homology, to the base sequence represented by SEQ ID NO: 38, SEQ ID NO: 55 or SEQ ID NO: 56.

The hybridization can be carried out by publicly known methods or by a modification thereof, for example, according to the method described in Molecular Cloning, 2nd Ed., J. Sambrook et al., Cold Spring Harbor Lab. Press, (1989). A commercially available library may also be used according to the instructions of the attached manufacturer's protocol. The is hybridization can be carried out preferably under high stringent conditions.

The high stringent conditions used herein refer to the conditions, for example, in a sodium concentration of about 19 mM to about 40 mM, preferably about 19 mM to about 20 mM at a temperature of about 50° C. to about 70° C., preferably about 60° C. to about 65° C. In particular, hybridization conditions in a sodium concentration of about 19 mM at a temperature of about 65° C. are most preferred.

The polypeptide encoded by the DNA, which is hybridizable to the base sequence shown by SEQ ID NO: 38, SEQ ID NO: 55 or SEQ ID NO: 56 can be manufactured by methods similar to those for manufacturing the polypeptide of the present invention, described above. Examples of the amides, esters or salts of the polypeptide are the same as those for the amides, esters or salts of the polypeptide of the present invention described above.

More specifically, for the DNA encoding the receptor protein having the amino acid sequence represented by SEQ ID NO: 37, DNA having the base sequence represented by SEQ ID NO: 38 may be employed; and DNA having the base sequence represented by SEQ ID NO: 55 or SEQ ID NO: 56 may be used for the DNA encoding the receptor protein having the amino acid sequence represented by SEQ ID NO: 54.

The polypeptide containing a part of the base sequence of DNA encoding the receptor protein of the present invention or a part of the base sequence complementary to the DNA is used to mean that not only the DNA encoding the partial peptide of the present invention described below but also RNA are embraced.

According to the present invention, antisense polynucleotides (nucleic acids) that can inhibit replication or expression of the G protein-coupled receptor protein gene can be designed and synthesized based on the cloned or determined base sequence information of the DNA encoding the G protein-coupled receptor protein. Such a polynucleotide (nucleic acid) is capable of hybridizing with RNA of G protein coupled receptor protein gene to inhibit the synthesis or function of said RNA or capable of modulating the expression of a G protein-coupled receptor protein gene via interaction with G protein coupled receptor protein-associated RNA. Polynucleotides complementary to selected sequences of RNA associated with G protein-coupled receptor protein and polynucleotides specifically hybridizable with the selected sequences of RNA associated with G protein-coupled receptor protein are useful in modulating or controlling the expression of a G protein coupled receptor protein gene in vivo and in vitro, and in treating or diagnosing disease later described. The term "corresponding" is used to mean homologous to or complementary to a particular sequence of the base sequence or nucleic acid including the gene. The term "corresponding" between nucleotides, base sequences or nucleic acids and peptides (proteins) usually refers to amino acids of a peptide (protein) under the order derived from the sequence of nucleotides (nucleic acids) or their complements. 5' end hairpin loop, 5' end 6-base-pair repeats, 5' end untranslated region, polypeptide translation initiation codon, protein coding region, ORF translation initiation codon, 3' untranslated region, 3' end palindrome region, and 3' end hairpin loop in the G protein-coupled receptor protein gene may be selected as preferred target regions, though any other region may be selected as a target in G protein coupled receptor protein genes.

Any DNA can be used as the DNA encoding the partial peptide of the receptor protein of the present invention so long as DNA contains the base sequence encoding the partial peptide of the present invention described above. The DNA may be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using mRNA fraction prepared from the cells and tissues described above.

Specifically, the DNA encoding the partial peptide of the present invention may be any DNA having the base sequence shown by SEQ ID NO: 38, SEQ ID NO: 55 or SEQ ID NO: 56, or the base sequence hybridizable to the base sequence represented by SEQ ID NO: 38, SEQ ID NO: 55 or SEQ ID NO: 56 under high stringent conditions and encoding a polypeptide which has the activities substantially equivalent to those of the receptor protein of the present invention (e.g., a ligand binding activity, a signal transduction activity, etc.).

Antibodies to the polypeptide of the present invention, partial peptide or esters or amides, or salts thereof, or antibodies to the receptor protein of the present invention or its salts or the partial peptide, its amides or esters may be any of polyclonal antibodies and monoclonal antibodies, as long as they are capable of recognizing the polypeptide of the present invention, partial peptide or esters or amides, of salts thereof, or antibodies to the receptor protein of the present invention or its salts or the partial peptide, its amides or esters.

The antibodies to the polypeptide of the present invention, partial peptide or esters or amides, or salts thereof, or antibodies to the receptor protein of the present invention or its salts or the partial peptide, its amides or esters (hereinafter in the description of antibodies sometimes merely referred to as the receptor protein of the present invention) may be manufactured by publicly known methods for manufacturing antibodies or antisera, using as antigens the polypeptide of the present invention or the receptor protein of the present invention.

[Preparation of Monoclonal Antibody]

(a) Preparation of Monoclonal Antibody-producing Cells

The polypeptide or receptor protein of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every two to six weeks and two to ten times in total. Examples of the applicable warm-blooded animals are monkeys, rabbits, dogs, guinea pigs, mice, rats, sheep, goats and chickens, with the use of mice and rats being preferred.

In the preparation of monoclonal antibody-producing cells, a warm-blooded animal, e.g., mice, immunized with an antigen wherein the antibody titer is noted is selected, then spleen or lymph node is collected after two to five days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled polypeptide, which will be described later, with the antiserum followed by assaying the binding activity of the labeling agent bound to the antibody. The fusion may be carried out, for example, by the known method by Koehler and Milstein (Nature, 256, 495, 1975). Examples of the fusion accelerator are polyethylene glycol (PEG), Sendai virus, etc., of which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubating at 20 to 40° C., preferably at 30 to 37° C. for 1 to 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with the polypeptide (protein) as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the polypeptide labeled with a radioactive substance or an enzyme and detecting the monoclonal antibody bound to the solid phase.

The monoclonal antibody can be selected according to publicly known methods or their modifications. In general, the selection can be effected in a medium for animal cells supplemented with HAT (hypoxanthine, aminopterin and thymidine). Any selection and growth medium can be employed as far as the hybridoma can grow there. For example, RPMI 1640 medium containing 1% to 20%, preferably 10% to 20% fetal bovine serum, GIT medium (Wako Pure Chemical Industries, Ltd.) containing 1% to 10% fetal bovine serum, a serum free medium for cultivation of a hybridoma (SFM-101, Nissui Seiyaku Co., Ltd.) and the like can be used for the selection and growth medium. The cultivation is carried out generally at 20° C. to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins (for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody.

[Preparation of Polyclonal Antibody]

The polyclonal antibody of the present invention can be manufactured by publicly known methods or modifications thereof. For example, a warm-blooded animal is immunized with an immunogen (polypeptide antigen) per se, or a complex of immunogen and a carrier protein is formed and a warm-blooded animal is immunized with the complex in a manner similar to the method described above for the manufacture of monoclonal antibodies. The product containing the antibody to the polypeptide of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin or hemocyanin is coupled to hapten in a carrier-to-hapten weight ratio of approximately 0.1 to 20, preferably about 1 to about 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once every 2 to 6 weeks and 3 to 10 times in total.

The polyclonal antibody can be collected from the blood, ascites, etc., preferably from the blood of warm-blooded animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The antisense DNA having a complementary or substantial complementary base sequence to the DNA coding for the polypeptide of the present invention or its partial peptide or the DNA coding for the receptor protein of the present invention or its partial peptide (hereinafter these DNAs are collectively referred to as the DNA of the present invention in the following description of antisense DNA) can be any antisense DNA so long as it possesses a base sequence complementary or substantially complementary to that of the DNA of the present invention and capable of suppressing expression of the DNA.

The base sequence substantially complementary to the DNA of the present invention may, for example, be a base sequence having at least about 70% homology, preferably at least about 80% homology, more preferably at least about 90% homology and most preferably at least about 95% homology, to the full-length base sequence or partial base sequence of the base sequence complementary to the DNA of the present invention (i.e., complementary strand to the DNA of the present invention). In the entire base sequence of the complementary strand to the DNA of the present invention, an antisense DNA having at least about 70% homology, preferably at least about 80% homology, more preferably at least about 90% homology and most preferably at least about 95% homology, to the complementary strand of the base sequence which encodes the N-terminal region of the polypeptide of the present invention or the receptor protein of the present invention (e.g., the base sequence around the initiation codon). These antisense DNAs can be synthesized using a publicly known DNA synthesizer, etc.

Hereinafter the utilities of the following substances (1) through (3) are described: (1) the polypeptide of the present invention, its amides or esters, or its partial peptide or its amides or esters, or salts thereof (hereinafter sometimes merely referred to as the polypeptide of the present invention); (2) the receptor protein of the present invention or its salts, or its partial peptide or its amides or esters or salts thereof (hereinafter sometimes merely referred to as the receptor protein of the present invention); and (3) DNA encoding the polypeptide of the present invention or its partial peptide or the receptor protein of the polypeptide or its partial peptide (hereinafter sometimes merely referred to as the DNA of the present invention), antibodies to the polypeptide or the present invention, its amides or esters, or its partial peptide or its amides or esters, or salts thereof (hereinafter sometimes merely referred to as the antibody of the present invention) and the antisense DNA.

(1) Therapeutic and Prophylactic Agent for the Diseases with which the Polypeptide of the Present Invention or the Receptor Protein of the Present Invention is Associated Since the polypeptide of the present invention has a cell stimulating activity to the receptor protein of the present invention, any abnormality or deficiency in the DNA encoding the polypeptide of the present invention or any abnormality or deficiency in the receptor protein of the present invention would cause a variety of diseases such as hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer, rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive *staphylococcal* infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorder, pollakiuria, uremia, neurodegenerative disease, etc. Therefore, the polypeptide of the present invention, the receptor protein of the present invention and the DNA of the present invention can be used as a pharmaceutical composition for the treatment and prevention of various diseases as described above.

The polypeptide of the present invention, the receptor protein of the present invention and the DNA of the present invention can also be used as the therapeutic/prophylactic agent for macular edema cystoid.

Moreover, since the polypeptide of the present invention, the receptor protein of the present invention and the DNA of the present invention are associated with secretion control (also termed secretion regulation; hereinafter the same) of somatostatin, they are useful as:

(1) therapeutic agents for tumors such as acromegaly, TSH-producing tumor, non-secretory (non-functional) pituitary tumor, ectopic ACTH (adrenocorticotropine)-producing tumor, medullary thyroid cancer, VIP-producing tumor, glucagon-producing tumor, gastrin-producing tumor, insulinoma, carcinoid tumor, etc.;

(2) therapeutic agents for insulin-dependent or insulin-independent diabetes mellitus, or various diseases associated with the diabetes, i.e., diabetic complications (e.g., diabetic retinopathy, diabetic nephropathy, diabetic neuropathy, Down's syndrome, orthostatic hypotension, etc.);

(3) agents for improving hyperinsulinism or for the treatment of obesity, bulimia, etc. caused by the suppression of appetite;

(4) therapeutic agents for acute pancreatitis, chronic pancreatitis, pancreatic/intestinal fistula, hemorrhagic ulcer, peptic ulcer, gastritis, hyperchylia, reflux esophagitis, etc.;

(5) agents for alleviating various conditions accompanied by *Helicobacter pylori* bacterial infections (e.g., an agent for suppressing accentuated gastrin secretion, etc.);

(6) agents for suppressing secretion of amylase accompanied by endoscopic cholangio pancreatography and for the postoperative treatment in pancreas surgery;

(7) agents for the treatment of diarrhea caused by reduced absorption or accentuated secretion in small intestine or abnormal motility of digestive tract (Short bowel syndrome, etc.), diarrhea caused by drugs in chemotherapy of cancer, etc., diarrhea caused by congenital small intestine atrophy, diarrhea caused by neuro-endocrinal tumor such as VIP-producing tumor, etc., diarrhea caused by AIDS, diarrhea caused by graft-versus-host reaction accompanied by spinal transplant, etc., diarrhea caused by diabetes mellitus, diarrhea caused by blocking nervous plexus in the abdominal cavity, diarrhea caused by systemic screlosis, diarrhea caused by eosinophilia, etc.;

(8) agents for the treatment of Dumping syndrome, hypersensitive colitis, Crohn's disease, inflammatory bowel disease, etc.;

(9) agents for the treatment of tumor or cancer (e.g., thyroid cancer, colon cancer, breast cancer, prostatic cancer, small cell lung cancer, non-small cell lung cancer, pancreatic cancer, gastric cancer, bile duct cancer, liver cancer, bladder cancer, ovary cancer, melanoma, osteosarcoma, chondrosarcoma, malignant pheochromocytoma, neuroblastoma, brain tumor, thymoma, kidney cancer, etc.), leukemia (e.g., leukemia/chronic lymphoid leukemia of basophil leukocyte, chronic myeloid leukemia, Hodgkin's disease, non-Hodgkin's lymphoma, etc.), these agents may also be used alone or in combination with other carcinostatic agents (e.g., tamoxifen, LHRH agonist, LHRH antagonist, interferon-$\alpha$, $\beta$ and $\gamma$, interleukin-2, etc.);

(10) agents for the prevention and treatment of hypertrophic cardiomyopathy, arteriosclerosis, valvular disease, myocardial infarction (especially myocardial infarction after percutaneous transluminal angioplasty) or regeneration of blood vessels;

(11) agents for the treatment of hemorrhage in esophagal venous cancer, cirrhosis or peripheral vessel disease;

(12) agents for the treatment of disease accompanied by regulation of secretion of physiologically active substances acting on the immune system, such as systemic or regional inflammation (e.g., multiple arthritis, rheumatoid arthritis, psoriasis, sunburn, eczema, allergy (e.g., asthma, atopic dermatitis, allergic rhinitis, etc.), etc.;

(13) agents for the treatment of, for example, dementia (e.g., Alzheimer's disease, Alzheimer's senile dementia, vascular/multiple dementia, etc.), schizophrenia, epilepsy, depression, general anxiety disorder, sleeping disorder, multiple sclerosis, etc.;

(14) agents for the treatment of eye disease (e.g., glaucoma, etc.), etc.;

(15) agents for the prevention and treatment of acute bacterial meningitis, acute viral encephalitis, adult respiratory distress syndrome, bacterial pneumonia, severe systemic fungal infectious disease, tuberculosis, spinal injury, bone fracture, hepatic insufficiency, pneumonia, alcoholic hepatitis, hepatitis A, hepatitis B, hepatitis C, AIDS infectious disease, human papilloma virus infectious disease, influenza infectious disease, cancer metastasis, multiple myeloma, osteomalacia, osteoporosis, Behcet's disease of bone, nephritis, renal insufficiency, sepsis, septic shock, hypercalcemia, hypercholesterolemia, hyperglyceridemia, hyperlipemia, systemic lupus erythematosus, transient cerebral ischemia, alcoholic hepatitis, etc.

(16) Furthermore, the polypeptide of the present invention, receptor protein of the present invention and the DNA of the present invention are also used for healing organ transplantation, burn, wound, alopecia, etc.

(17) These substances of the present invention are also useful as analgesics for suppression or alleviation of chronic or acute pains (pains accompanied by, e.g., postoperative pain, inflammatory pain, toothache, bone disease (e.g., arthritis, rheumatoid, osteoporosis, etc.)).

When a patient has a reduced level of, or deficient in the polypeptide of the present invention or the receptor protein of the present invention in his or her body, the DNA of the present invention can provide its role sufficiently or properly for the patient, (a) by administering the DNA of the present invention to the patient to express the polypeptide of the present invention or the receptor protein of the present invention in vivo, (b) by inserting the DNA of the present invention into a cell, expressing the polypeptide of the present invention or the receptor protein of the present invention and then transplanting the cell to the patient, or (c) by administering the polypeptide of the present invention or the receptor protein of the present invention to the patient.

Where the DNA of the present invention is used as the prophylactic/therapeutic agents described above, the DNA per se is administered directly to human or other warm-blooded animal; alternatively, the DNA is inserted into an appropriate vector such as retrovirus vector, adenovirus vector, adenovirus-associated virus vector, etc. and then administered to human or other warm-blooded animal in a conventional manner. The DNA of the present invention may also be administered as naked DNA, or with adjuvants to assist its uptake by gene gun or through a catheter such as a catheter with a hydrogel.

Where the polypeptide of the present invention or the receptor protein of the present invention is used as the aforesaid therapeutic/prophylactic agents, the polypeptide or the protein is advantageously used on a purified level of at least 90%, preferably at least 95%, more preferably at least 98% and most preferably at least 99%.

The polypeptide of the present invention or the receptor protein of the present invention can be used orally, for example, in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured by mixing the polypeptide of the present invention or the receptor protein of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate $_6$™ and HCO-50), etc. Examples of the oily medium include sesame oil and soybean oil, which may also be used in combination with a dissolution aid such as benzyl benzoate and benzyl alcohol. The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

The vector in which the DNA of the present invention is inserted may also be prepared into pharmaceutical preparations in a manner similar to the procedures above. Such preparations are generally used parenterally.

Since the thus obtained pharmaceutical preparation is safe and low toxic, the preparation can be administered to human or other warm-blooded animal (e.g., rat, mouse, guinea pig, rabbit, chicken, sheep, swine, bovine, horse, cat, dog, monkey, etc.).

The dose of the polypeptide of the present invention or the receptor protein of the present invention varies depending on target disease, subject to be administered, route for administration, etc.; for example, in oral administration for the treatment of nerve disease, the dose is normally about 0.1 mg to about 100 mg, preferably about 1.0 to about 50 mg, and more preferably about 1.0 to about 20 mg per day for adult (as 60 kg body weight). In parenteral administration, the single dose varies depending on subject to be administered, target disease, etc. but it is advantageous for the treatment of nerve disease to administer the active ingredient intravenously at a daily dose of about 0.01 to about 30 mg, preferably about 0.1 to about 20 mg, and more preferably about 0.1 to about 10 mg for adult (as 60 kg body weight). For other animal species, the corresponding dose as converted per 60 kg body weight can be administered.

(2) Screening of Drug Candidate Compounds for Disease

Because of the cell stimulating activity or the like by the polypeptide of the present invention to the receptor protein of the present invention, a compound that accelerates or inhibits the functions (e.g., the cell stimulating activity, etc.) of the polypeptide of the present invention or the receptor protein of the present invention, or its salts (these compounds are also referred to as a compound that alter the binding property between the polypeptide of the present invention and the receptor protein of the present invention, or its salts; hereinafter the same) can be used as drugs for the treatment/prevention of diseases such as hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, bone fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer, rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicella-zoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorder, pollakiuria, uremia, neurodegenerative disease, etc.

The compound or its salts that accelerate or inhibit the functions (e.g., the cell stimulating activity or the like) of the polypeptide of the present invention or the receptor protein of the present invention can also be used as the therapeutic and prophylactic agent for macular edema cystoid.

Furthermore, since the polypeptide of the present invention or the receptor protein of the present invention are associated with secretion control of somatostatin, the compound or its salts that accelerate or inhibit the functions (e.g., the cell stimulating activity or the like) of the polypeptide of the present invention or the receptor protein of the present invention are useful as:

(1) therapeutic agents for tumors such as acromegaly, TSH-producing tumor, non-secretory (non-functional) pituitary tumor, ectopic ACTH (adrenocorticotropine)-producing tumor, medullary thyroid cancer, VIP-producing tumor, glucagon-producing tumor, gastrin-producing tumor, insulinoma, carcinoid tumor, etc.;

(2) therapeutic agents for insulin-dependent or insulin-independent diabetes mellitus, or various diseases associated with the diabetes, i.e., diabetic complications (e.g., diabetic retinopathy, diabetic nephropathy, diabetic neuropathy, Down's syndrome, orthostatic hypotension, etc.);

(3) agents for improving hyperinsulinism or for the treatment of obesity, bulimia, etc. caused by the suppression of appetite;

(4) therapeutic agents for acute pancreatitis, chronic pancreatitis, pancreatic/intestinal fistula, hemorrhagic ulcer, peptic ulcer, gastritis, hyperchylia, reflux esophagitis, etc.;

(5) agents for alleviating various conditions accompanied by *Helicobacter pylori* bacterial infections (e.g., an agent for suppressing accentuated gastrin secretion, etc.);

(6) agents for suppressing secretion of amylase accompanied by endoscopic cholangio pancreatography and for the postoperative treatment in pancreas surgery;

(7) agents for the treatment of diarrhea caused by reduced absorption or accentuated secretion in small intestine or abnormal motility of digestive tract (Short bowel syndrome, etc.), diarrhea caused by drugs in chemotherapy of cancer, etc., diarrhea caused by congenital small intestine atrophy, diarrhea caused by neuro-endocrinal tumor such as VIP-producing tumor, etc., diarrhea caused by AIDS, diarrhea caused by graft-versus-host reaction accompanied by spinal transplant, etc., diarrhea caused by diabetes mellitus, diarrhea caused by blocking nervous plexus in the abdominal cavity, diarrhea caused by systemic screlosis, diarrhea caused by eosinophilia, etc.;

(8) agents for the treatment of Dumping syndrome, hypersensitive colitis, Crohn's disease, inflammatory bowel disease, etc.;

(9) agents for the treatment of tumor or cancer (e.g., thyroid cancer, colon cancer, breast cancer, prostatic cancer, small cell lung cancer, non-small cell lung cancer, pancreatic cancer, gastric cancer, bile duct cancer, liver cancer, bladder cancer, ovary cancer, melanoma, osteosarcoma, chondrosarcoma, malignant pheochromocytoma, neuroblastoma, brain tumor, thymoma, kidney cancer, etc.), leukemia (e.g., leukemia/chronic lymphoid leukemia of basophil leukocyte, chronic myeloid leukemia, Hodgkin's disease, non-Hodgkin's lymphoma, etc.), these agents may also be used alone or in combination with other carcinostatic agents (e.g., tamoxifen, LHRH agonist, LHRH antagonist, interferon-$\alpha$, $\beta$ and $\gamma$, interleukin-2, etc.);

(10) agents for the prevention and treatment of hypertrophic cardiomyopathy, arteriosclerosis, valvular disease, myocardial infarction (especially myocardial infarction after percutaneous transluminal angioplasty) or regeneration of blood vessels;

(11) agents for the treatment of hemorrhage in esophagal venous cancer, cirrhosis or peripheral vessel disease;

(12) agents for the treatment of disease accompanied by regulation of secretion of physiologically active substances acting on the immune system, such as systemic or regional inflammation (e.g., multiple arthritis, rheumatoid arthritis, psoriasis, sunburn, eczema, allergy (e.g., asthma, atopic dermatitis, allergic rhinitis, etc.), etc.;

(13) agents for the treatment of, for example, dementia (e.g., Alzheimer's disease, Alzheimer's senile dementia, vascular/multiple dementia, etc.), schizophrenia, epilepsy, depression, general anxiety disorder, sleeping disorder, multiple sclerosis, etc.;

(14) agents for the treatment of eye disease (e.g., glaucoma, etc.), etc.;

(15) agents for the prevention and treatment of acute bacterial meningitis, acute viral encephalitis, adult respiratory distress syndrome, bacterial pneumonia, severe systemic fungal infectious disease, tuberculosis, spinal injury, bone fracture, hepatic insufficiency, pneumonia, alcoholic hepatitis, hepatitis A, hepatitis B, hepatitis C, AIDS infectious disease, human papilloma virus infectious disease, influenza infectious disease, cancer metastasis, multiple myeloma, osteomalacia, osteoporosis, Behcet's disease of bone, nephritis, renal insufficiency, sepsis, septic shock, hypercalcemia, hypercholesterolemia, hyperglyceridemia, hyperlipemia, systemic lupus erythematosus, transient cerebral ischemia, alcoholic hepatitis, etc.

(16) The compound or its salts are also used for healing organ transplantation, burn, wound, alopecia, etc.

(17) The compound or its salts are also useful as analgesics for suppression or alleviation of chronic or acute pains (pains accompanied by, e.g., postoperative pain, inflammatory pain, toothache, bone disease (e.g., arthritis, rheumatoid, osteoporosis, etc.)).

Therefore, the polypeptide of the present invention or the receptor protein of the present invention is useful as reagents for screening the compound or its salts that accelerate or inhibit the functions of the polypeptide of the present invention or the receptor protein of the present invention.

That is, the present invention provides:

(1) a method for screening the compound or its salts that accelerate the functions (e.g., a cell stimulating activity, a somatostatin secretion regulating activity, etc.) of the polypeptide of the present invention, its amides or esters, or salts thereof, the partial peptide, its amides or esters, or salts thereof (hereinafter sometimes merely referred to as the accelerator), or the compound or its salts that inhibit the functions of the polypeptide of the present invention, its amides or esters, or salts thereof, the partial peptide, its amides or esters, or salts thereof (hereinafter sometimes merely referred to as the inhibitor), which comprises using the polypeptide of the present invention, its amides or esters, or salts thereof, or the partial peptide, its amides or esters, or salts thereof.

The present invention further provides:

(2) a method for screening the compound or its salts that accelerate the functions (e.g., a cell stimulating activity, a somatostatin secretion regulating activity, etc.) of the receptor protein of the present invention or its salts, or the partial peptide, its amides or esters, or salts thereof (hereinafter sometimes merely referred to as the accelerator), or the compound or its salts that inhibit the functions of the receptor protein of the present invention or its salts, the partial peptide, its amides or esters, or salts thereof (hereinafter sometimes merely referred to as the inhibitor), which comprises using the receptor protein of the present invention or its salts, or the partial peptide, its amides or esters, or salts thereof.

More specifically, the present invention provides:

(3) a method for screening the compound or its salts that accelerate the functions (e.g., a cell stimulating activity, a somatostatin secretion regulating activity, etc.) of the polypeptide of the present invention, its amides or esters, or salts thereof, the partial peptide, its amides or esters, or salts thereof, or the receptor protein of the present invention or its salts, or the partial peptide, its amides or esters, or salts thereof (hereinafter sometimes merely referred to as the accelerator), or, the compound or its salts that inhibits the functions (e.g., a cell stimulating activity, a somatostatin secretion regulating activity, etc.) of the polypeptide of the present invention, its amides or esters, or salts thereof, the partial peptide, its amides or esters, or salts thereof, or the receptor protein of the present invention or its salts, or the partial peptide, its amides or esters, or salts thereof (hereinafter sometimes merely referred to as the inhibitor), which comprises using the polypeptide of the present invention, its amides or esters, or salts thereof, or the partial peptide, its amides or esters, or salts thereof, or the receptor protein of the present invention or its salts, or the partial peptide, its amides or esters, or salts thereof (specifically the protein containing the same or substantially the same amino acid sequence as the amino acid sequence shown by SEQ ID NO:37, or salts thereof, or the partial peptide, its amides or esters, or salts thereof).

The present invention further provides:

(3) a method for screening the compound or its salts that accelerate the functions (e.g., a cell stimulating activity, a somatostatin secretion regulating activity, etc.) of the polypeptide of the present invention, its amides or esters, or salts thereof, the partial peptide, its amides or esters, or salts thereof, or the receptor protein of the present invention or its salts, or the partial peptide, its amides or esters, or salts thereof (hereinafter sometimes merely referred to as the accelerator), or, the compound or its salts that inhibits the functions (e.g., a cell stimulating activity, a somatostatin secretion regulating activity, etc.) of the polypeptide of the present invention, its amides or esters, or salts thereof, the partial peptide, its amides or esters, or salts thereof, or the receptor protein of the present invention or its salts, or the partial peptide, its amides or esters, or salts thereof (hereinafter sometimes merely referred to as the inhibitor), which comprises measuring (i) the activity of the polypeptide of the present invention, its amides or esters, or salts thereof, or the partial peptide, its amides or esters, or salts thereof, when the receptor protein of the present invention or its salts, or the partial peptide, its amides or esters, or salts thereof (specifically the protein containing the same or substantially the same amino acid sequence as the amino acid sequence shown by SEQ ID NO:37, or salts thereof, or the partial peptide, its amides or esters, or salts thereof) is brought into contact with the polypeptide of the present invention, its amides or esters, or salts thereof, or the partial peptide, its amides or esters, or salts thereof, and (ii) the activity of the polypeptide of the present invention, its amides or esters, or salts thereof, or the partial peptide, its amides or esters, or salts thereof, when the receptor protein of the present invention or its salts, or the partial peptide, its amides or esters, or salts thereof (specifically the protein containing the same or substantially the same amino acid sequence as the amino acid sequence shown by SEQ ID NO:37, or salts thereof, or the partial peptide, its amides or esters, or salts thereof) and a test compound are brought into contact with the polypeptide of the present invention, its amides or esters, or salts thereof, or the partial peptide, its amides or esters, or salts thereof;

and comparing the activities;

and the like.

(1) The polypeptide of the present invention, its amides or esters, or salts thereof, or the partial peptide of the present invention, its amides or esters, or salts thereof (hereinafter sometimes collectively referred to as the polypeptide of the present invention) has the activities of regulating the secretion of prolactin, namely, prolactin secretion-stimulating and -inhibiting activities. That is, first, the polypeptide of the present invention has prolactin secretion-stimulating activity and thus finds application as a prophylactic and therapeutic drug for various diseases associated with prolactin hyposecretion. On the other hand, the polypeptide of the present invention has a high affinity to the receptor proteins and, therefore, when used in an increased dose, causes desensitization for prolactin secretion so that the polypeptide also exhibits the prolactin secretion-inhibiting activity. In this sense, the polypeptide can be used as a prophylactic and therapeutic drug for various diseases associated with prolactin hypersecretion.

Thus, the polypeptide of the present invention as the prolactin secretion stimulant is useful as prophylactic and therapeutic drugs for various diseases associated with prolactin secretion, such as hypoovarianism, spermatic underdevelopment, osteoporosis, menopausal symptoms, agalactosis, hypothyroidism, renal insufficiency, etc.

In addition, the polypeptide of the present invention has an effect of arousing sexual desire (pheromone-like activity) based on the prolactin secretion stimulating activity, and is useful also as a sexual desire-stimulating agent.

Moreover, the polypeptide of the present invention as the prolactin secretion inhibitor is useful as prophylactic and therapeutic drugs for various diseases associated with prolactin secretion, such as hyperprolactinemia, pituitary tumor, diencephalon tumor, menstrual disorder, stress, autoimmune diseases, prolactinoma, sterility, impotence, amenorrhea, lactorrhea, acromegaly, Chiari-Frommel syndrome, Argonz-del Castilo syndrome, Forbes-Albright syndrome, breast cancer lymphoma or Sheehan's syndrome, or spermatogenesis disorder, etc.

Furthermore, the polypeptide of the present invention is also useful as an anticonceptive, based on the prolactin secretion inhibiting activity.

In addition, the polypeptide of the present invention is useful not only as a testing agent to examine the function of prolactin secretion but also as a veterinary drug such as a lactation stimulant for livestock mammals including bovine, goat, swine, etc. Furthermore, an application of the polypeptide to the production of useful substances is expected, which involves producing a useful substance in the body of livestock mammals and secreting the substance into milk, or the like.

Furthermore, the polypeptide of the present invention has the activity of regulating placenta functions and is thus useful as a prophylactic or therapeutic agent for ciliary tumor, hydatid mole, invasive mole, miscarriage, fetal underdevelopment, glucose metabolism abnormality, lipid metabolism abnormality or labor induction.

The prolactin secretion regulating activities of the polypeptide of the present invention can be attained in accordance with the method described in Neuroendocrinology, 62, 1995, 198-206 or Neuroscience Letters, 203, 1996, 164-170, or its modifications. It is desired to perform the method described in EXAMPLES hereinafter.

In the case that the polypeptide of the present invention is used as the aforesaid pharmaceuticals or veterinary drugs, it may be implemented by a conventional means. The polypeptide may be used orally, for example, in the form of tablets, if necessary, sugarcoated, capsules, elixirs, microcapsules etc., or parenterally in the form of injectable preparations such as a sterile solution or a suspension in water or with other pharmaceutically acceptable liquid. These preparations can be manufactured by mixing the polypeptide or its salts with a physiologically acceptable known carrier, a flavoring agent, an excipient, a vehicle, an antiseptic agent, a stabilizer, a binder, etc., in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol), a polyalcohol (e.g., propylene glycol and polyethylene glycol), a nonionic surfactant (e.g., polysorbate 80(™) and HCO-50), etc. Examples of the oily medium include sesame oil and soybean oil, which may also be used in combination with a dissolution aid such as benzyl benzoate and benzyl alcohol. The prophylactic/therapeutic agent described above may further be formulated with a buffer (e.g., phosphate buffer, sodium acetate buffer), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule aseptically.

Since the thus obtained pharmaceutical preparation is safe and low toxic, the preparation can be administered to mammal (e.g., human, mouse, rat, guinea pig, rabbit, sheep, swine, bovine, cat, dog, monkey, hamadryad, chimpanzee, etc.).

The dose of the polypeptide of the present invention varies depending on conditions, etc.; in oral administration, generally to the adult patient with hypothyroidism (as 60 kg body weight), the dose is normally about 0.1 to about 100 mg, preferably about 1.0 to about 50 mg, and more preferably about 1.0 to about 20 mg per day. In parenteral administration, the single dose varies depending on subject to be administered, conditions, route for administration, etc. but it is advantageous to administer the active ingredient intravenously to the adult patient with hypothyroidism (as 60 kg body weight) at a daily dose of about 0.01 to about 30 mg, preferably about 0.1 to about 20 mg, and more preferably about 0.1 to about 10 mg. For other animal species, the corresponding dose as converted per 60 kg body weight can be administered.

(2) Also, the compound or its salts, which are obtainable using the method of screening the compound or its salts that promote or inhibit the activity of the polypeptide of the present invention characterized by using the polypeptide of the present invention, or using the kit for screening the compound or its salts that promote or inhibit the activity of the polypeptide of the present invention, comprising the polypeptide of the present invention; or, the compound or its salts, which are obtainable using the method of screening the compound or its salts that promote or inhibit the activity of the polypeptide of the present invention characterized by using the polypeptide of the present invention and the receptor protein of the present invention or its partial peptide, its amides or esters or salts thereof (hereinafter sometimes merely referred to as the receptor protein of the present invention), or using the kit for screening the compound or its salts that promote or inhibit the activity of the polypeptide of the present invention, comprising the receptor protein of the present invention; may also be used as prophylactic and therapeutic agents for various diseases associated with prolactin hyposecretion when they have the prolactin secretion stimulating activity, and when they have the prolactin secretion inhibiting activity, as prophylactic and therapeutic agents for various diseases associated with prolactin hypersecretion.

When the compound or its salts thus obtained have the prolactin secretion stimulating activity, they can be used as prophylactic and therapeutic agents for various diseases associated with prolactin hyposecretion;

The compound or its salts as the prolactin secretion stimulants are useful as prophylactic and therapeutic drugs for various diseases associated with prolactin secretion, such as hypoovarianism, spermatic underdevelopment, osteoporosis, menopausal symptoms, agalactosis, hypothyroidism, renal insufficiency, etc.

In addition, the compound or its salts have the effect of arousing sexual desire (pheromone-like activity) based on the prolactin secretion stimulating activity, and is useful as a sexual desire-stimulating agent.

On the other hand, when the compound or its salts thus obtained have the prolactin secretion inhibiting activity, they can be used as prophylactic and therapeutic agents for various diseases associated with prolactin hypersecretion;

The compound or its salts as the prolactin secretion inhibitors are useful as prophylactic and therapeutic drugs for various diseases associated with prolactin secretion, such as hyperprolactinemia, pituitary tumor, diencephalon tumor, menstrual disorder, stress, autoimmune diseases, prolactinoma, sterility, impotence, amenorrhea, lactorrhea, acromegaly, Chiari-Frommel syndrome, Argonz-del Castilo syndrome, Forbes-Albright syndrome, breast cancer lymphoma or Sheehan's syndrome, or spermatogenesis disorder, etc.

Furthermore, the compound or its salts thus obtained are useful as anticonceptives, based on the prolactin secretion inhibiting activity.

In addition, the compound or its salts thus obtained are useful not only as testing agents to examine the function of prolactin secretion but also as a veterinary drug such as lactation stimulants for livestock mammals including bovine, goat, swine, etc. Furthermore, an application to the production of useful substances is expected, which involves producing a useful substance in the body of livestock mammals and secreting the substance into milk, or the like.

Furthermore, the compound or its salts thus obtained have the activity of regulating the functions of placenta and are thus useful as prophylactic or therapeutic agents for ciliary tumor, hydatid mole, invasive mole, miscarriage, fetal underdevelopment, glucose metabolism abnormality, lipid metabolism abnormality or labor induction.

The prolactin secretion regulating activities of the compound or its salts obtained can be attained in accordance with the method described in Neuroendocrinology, 62, 1995, 198-206 or Neuroscience Letters, 203, 1996, 164-170, or its modifications. It is desired to perform the method described in EXAMPLES hereinafter.

In the case that the compound or its salts obtained is used as the aforesaid pharmaceuticals or veterinary drugs, it may be implemented by a conventional means. The compound or its salts may be used orally, for example, in the form of tablets, if necessary, sugarcoated, capsules, elixirs, microcapsules etc., or parenterally in the form of injectable preparations such as a sterile solution or a suspension in water or with other pharmaceutically acceptable liquid. These preparations can be manufactured by mixing the compound or its salts with a physiologically acceptable known carrier, a flavoring agent, an excipient, a vehicle, an antiseptic agent, a stabilizer, a binder, etc., in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol), a polyalcohol (e.g., propylene glycol and polyethylene glycol), a nonionic surfactant (e.g., polysorbate 80(™) and HCO-50), etc. Examples of the oily medium include sesame oil and soybean oil, which may also be used in combination with a dissolution aid such as benzyl benzoate and benzyl alcohol. The prophylactic/therapeutic agent described above may further be formulated with a buffer (e.g., phosphate buffer, sodium acetate buffer), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule aseptically.

Since the thus obtained pharmaceutical preparation is safe and low toxic, the preparation can be administered to mammal (e.g., human, mouse, rat, guinea pig, rabbit, sheep, swine, bovine, cat, dog, monkey, hamadryad, chimpanzee, etc.).

The dose of the compound or its salts obtained varies depending on conditions, etc.; in oral administration, generally to the adult patient with hypothyroidism (as 60 kg body weight), the dose is normally about 0.1 to about 100 mg, preferably about 1.0 to about 50 mg, and more preferably about 1.0 to about 20 mg per day. In parenteral administration, the single dose varies depending on subject to be administered, conditions, route for administration, etc. but it is advantageous to administer the active ingredient intravenously to the adult patient with hypothyroidism (as 60 kg body weight) at a daily dose of about 0.01 to about 30 mg, preferably about 0.1 to about 20 mg, and more preferably about 0.1 to about 10 mg. For other animal species, the corresponding dose as converted per 60 kg body weight can be administered.

(3) The method and the kit for screening the compound or its salt that promotes or inhibits the activity of the polypeptide of the present invention will be described below in detail.

The method for screening the compound or its salts that promote or inhibit the activities of the polypeptide of the present invention which comprises using the polypeptide of the present invention, is a method for screening the compound or its salts that promote or inhibit the activities of the polypeptide of the present invention which comprises using, preferably, the polypeptide of the present invention and the receptor protein of the present invention or its partial peptide, its amides or esters, or salts thereof, the partial peptide, its amides or esters, or salts thereof (hereinafter sometimes merely referred to as the receptor protein of the present invention).

The screening method is carried out specifically by measuring the activities of the polypeptide of the present invention (i) when the receptor protein of the present invention is brought in contact with the polypeptide of the present invention and (ii) when the receptor protein of the present invention and a test compound are brought in contact with the polypeptide of the present invention, and comparing them.

Specifically, the screening method described above is characterized by measuring the cell stimulating activities of the polypeptide of the present invention and a test compound or the binding amount of the polypeptide of the present invention and a test compound to the receptor protein of the present invention, in the cases (i) and (ii), and comparing these activities. The cell stimulating activity, etc. of the polypeptide in the present invention can be measured in accordance with publicly known methods, for example, Dockray, G. J., et al., Nature, 305, 328-330, 1983, Fukusumi, S., et al., Biochem. Biophys. Res. Commun., 232, 157-163, 1997, Hinuma, S., et al., Nature, 393, 272-276, 1998, Tatemoto, K., et al., Biochem. Biophys. Res. Commun., 251, 471-476, 1998, etc., or modifications thereof.

The binding amount of the polypeptide of the present invention and a test compound to the receptor protein of the present invention can be measured by a modification of the methods for "determination of a ligand (agonist) to the receptor protein of the present invention" which will be described hereinafter.

The binding amounts of the polypeptide of the present invention and a test compound to the receptor protein of the present invention or the cell stimulating activities can be measured by the methods described below, or a modification thereof.

Examples of such a test compound are a peptide, a protein, a non-peptide compound, a synthetic compound, a fermentation product, a cell extract, a plant extract, an animal tissue extract and the like. These compounds may be novel compounds or publicly known compounds.

To perform the screening method described above, the polypeptide of the present invention is suspended in a buffer suitable for screening to prepare a specimen of the polypeptide of the present invention. Any buffer having pH of approximately 4 to 10 (desirably a pH of approximately 6 to 8) such as a phosphate buffer, Tris-hydrochloride buffer, etc. may be used, so far as it does not interfere the reaction between the polypeptide of the present invention and the receptor protein of the present invention.

For example, when a test compound increases the cell stimulating activity, etc. in (ii) described above by at least about 20%, preferably at least 30%, more preferably at least about 50%, as compared to the case of (i) above, the test compound can be selected to be a compound that promotes the cell stimulating activity, etc. of the polypeptide of the present invention. On the other hand, a test compound can be selected to be a compound that inhibits the cell stimulating activity, etc. of the polypeptide of the present invention, when the test compound inhibits the cell stimulating activity, etc. in (ii) described above by at least about 20%, preferably at least 30%, more preferably at least about 50%, as compared to the case of (i) above.

It is desirable, before conducting these tests, to examine the binding ability of a test compound to the receptor protein of the present invention to see if the test compound is capable of binding to the receptor protein of the present invention, which is effected by the methods (1) to (3) later described for the "determination of ligand (agonist) to the receptor protein of the present invention".

It is desirable, before conducting these tests, to examine the binding ability of a test compound to the receptor protein of the present invention to see if the test compound is capable of binding to the receptor protein of the present invention, which is effected by the methods (1) to (3) later described for the "determination of the polypeptide of the present invention and a test compound to the receptor protein of the present invention".

As an indicator that the test compound described above is judged to be such a compound or its salts that promote or inhibit the activities of the polypeptide of the present invention, there are binding amounts of the polypeptide of the present invention and a test compound to the receptor protein of the present invention, and the activity that inhibits the binding between the polypeptide of the present invention and the labeled compound. According to the binding test system described in, e.g., Hosoya, M. et al., Biochem. Biophys. Res. Commun., 194 (1), 133-134, 1993, a test compound that inhibits the binding of the labeled compound by 10% or more in a concentration of $1\times10^{-2}$ M or less is highly likely to be the compound or its salts that promote or inhibit the activities of the polypeptide of the present invention. However, since the binding inhibition activity is a relative value based on the binding of the labeled compound, the activity is not essential for judging the test compound to be a compound or its salts that promote or inhibit the activities of the polypeptide of the present invention.

The kit for screening of the present invention comprises the polypeptide of the present invention, its amides or esters, or salts thereof, the partial peptide, its amides or esters, or salts thereof. Preferably, the kit for screening of the present invention further comprises the receptor to the polypeptide of the present invention, its amides or esters, or salts thereof, the partial peptide, its amides or esters, or salts thereof, that is, the receptor protein of the present invention or its salts, the partial peptide, its amides or esters, or salts thereof (specifically, the protein containing the same or substantially the same amino acid sequence as that shown by SEQ ID NO:37).

Examples of the screening kit according to the present invention include the following:

1. Reagent for Screening (1) Assay and Wash Buffers

Hanks' Balanced Salt Solution (manufactured by Gibco) supplemented with 0.05% of bovine serum albumin (manufactured by Sigma).

The buffers may be sterilized by filtration through a membrane filter with a 0.45 μm pore size and stored at 4° C., or may be prepared at use.

(2) A Receptor Preparation

CHO cells in which the receptor protein of the present invention is expressed are subcultured at $5\times10^5$ cells/well on a 12-well plate followed by culturing at 37° C. under a 5% $CO_2$ and 95% air for 2 days.

(3) Labeled Ligand

The polypeptide of the present invention is labeled with commercially available [$^3$H], [$^{125}$I], [$^{14}$C], [$^{35}$S], etc. The product in the form of an aqueous solution is stored at 4° C. or at −20° C., which will be diluted at use to 1 μM with a buffer for the assay.

(4) Standard Ligand Solution

The polypeptide of the present invention is dissolved in PBS containing 0.1% of bovine serum albumin (manufactured by Sigma) to make the volume 1 mM and then stored at −20° C.

2. Method for Assay (1) CHO cells are cultured in a 12-well tissue culture plate to express the receptor protein of the present invention. After washing the CHO cells twice with 1 ml of buffer for the assay, 490 μl of the buffer for assay is added to each well.

(2) After 5 μl of a test compound solution of $10^{-3}$ to $10^{-10}$ M is added, 5 μl of a labeled ligand is added to the system followed by culturing at room temperature for an hour. To determine the amount of the non-specific binding, 5 μl of the ligand of $10^{-3}$ M is added to the system, instead of the test compound.

(3) The reaction mixture is removed from the well, which is washed three times with 1 ml each of the buffer for assay. The labeled ligand bound to the cells is dissolved in 0.2N NaOH-1% SDS and mixed with 4 ml of a liquid scintillator A (manufactured by Wako Pure Chemical).

(4) Radioactivity is measured using a liquid scintillation counter (manufactured by Beckman) and percent of the maximum binding (PMB) is calculated in accordance with the following [equation 1]:

$$PMB=[(B-NSB)/(B_0-NSB)]\times 100 \quad \text{[equation 1]}$$

wherein:

PMB:percent of the maximum binding

B: value when a sample is added

NSB: non-specific binding $B_0$: maximum binding

The compound or its salt, which is obtainable by the screening method or by the screening kit of the present invention, is the compound selected from the test compounds described above, such as peptides, proteins, non-peptide compounds, synthetic compounds, fermentation products, cells extracts, plant extracts, animal tissue extracts, plasma, etc. and the compound that promotes or inhibits the activities (e.g., a cell stimulating activity, etc.) of the polypeptide of the present invention.

As the salts of the compound, there may be employed similar salts to those of the polypeptide of the present invention described above.

When the compound or salts thereof obtainable by the screening method or the screening kit of the present invention are used as the therapeutic and prophylactic agents described above, a conventional means may be applied to making pharmaceutical preparations. For example, the compound or its salts may be prepared into tablets, capsules, elixirs, microcapsules, sterile solutions, suspensions, etc.

Since the thus obtained preparation is safe and low toxic, it can be administered to human or warm-blooded animal (e.g., mouse, rat, rabbit, sheep, swine, bovine, horse, chicken, cat, dog, monkey, etc.).

The dose of the compound or salts thereof varies depending on activity, target disease, subject to be administered, method for administration, etc.; for example, in oral administration of the compound that accelerates the functions of the polypeptide of the present invention, the dose is normally about 0.1 to about 100 mg, preferably about 1.0 to about 50 mg, more preferably about 1.0 to about 20 mg per day for adult (as 60 kg body weight). In parenteral administration, the single dose varies depending on subject to be administered, target disease, etc. but it is advantageous to administer, for example, the compound that accelerates the functions of the polypeptide of the present invention intravenously at a daily dose of about 0.01 to about 30 mg, preferably about 0.1 to about 20 mg, more preferably about 0.1 to about 10 mg for adult (as 60 kg body weight). For other animal species, the corresponding dose as converted per 60 kg weight can be administered.

Turning to the compound that inhibits the functions of the polypeptide of the present invention when it is orally administered, the dose is normally about 0.1 to about 100 mg, preferably about 1.0 to about 50 mg, more preferably about 1.0 to about 20 mg per day for adult (as 60 kg body weight). In parenteral administration, the single dose varies depending on subject to be administered, target disease, etc. When the compound that inhibits the functions of the polypeptide of the present invention is administered to adult (as 60 kg body weight) generally in the form of injection, it is advantageous to administer the compound intravenously at a daily dose of about 0.01 to about 30 mg, preferably about 0.1 to about 20 mg, more preferably about 0.1 to about 10 mg. For other animal species, the corresponding dose as converted per 60 kg weight can be administered.

(3) Quantification for the polypeptide of the present invention, its amides or esters, or salts thereof, the partial peptide, its amides or esters, or salts thereof, and the receptor protein of the present invention or salts thereof, or the partial peptide, its amides or esters, or salts thereof:

The antibody to the polypeptide of the present invention or the receptor protein of the present invention (hereinafter sometimes merely referred to as the antibody of the present invention) is capable of specifically recognizing the polypeptide of the present invention or the receptor protein of the present invention and thus, can be used for a quantification of the polypeptide of the present invention or the receptor protein of the present invention in a test sample fluid, in particular, for a quantification by sandwich immunoassay.

That is, the present invention provides:

(i) a method for quantification of the polypeptide of the present invention or the receptor protein of the present invention in a test sample fluid, which comprises competitively reacting the antibody of the present invention, a test sample fluid and the labeled polypeptide of the present invention or the labeled receptor protein of the present invention, and measuring the ratio of the labeled polypeptide of the present invention or the labeled receptor protein of the present invention bound to said antibody; and, (ii) a method for quantification of the polypeptide of the present invention or the receptor protein of the present invention in a test sample fluid, which comprises reacting the test sample fluid simultaneously or continuously with the antibody of the present invention immobilized on a carrier and a labeled antibody of the present invention, and then measuring the activity of the labeling agent on the insoluble carrier.

In the method (ii) for quantification described above, it is preferred that one antibody is capable of recognizing the N-terminal region of the polypeptide of the present invention or the receptor protein of the present invention, while another antibody is capable of recognizing the C-terminal region of the polypeptide of the present invention or the receptor protein of the present invention.

The monoclonal antibody to the polypeptide of the present invention or the receptor protein of the present invention may be used to assay the polypeptide of the present invention or the receptor protein of the present invention. Moreover, the polypeptide of the present invention or the receptor protein of the present invention can be detected by means of a tissue staining as well. For these purposes, the antibody molecule per se may be used or $F(ab')_2$, Fab' or Fab fractions of the antibody molecule may also be used.

There is no particular limitation for the assaying method using the antibody to the polypeptide of the present invention or the receptor protein of the present invention; any method may be used so far as it relates to a method in which the amount of antibody, antigen or antibody-antigen complex can be detected by a chemical or a physical means, depending on or corresponding to the amount of antigen (e.g., the amount of the polypeptide) in a test sample fluid to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be described later, is particularly preferred.

Examples of the labeling agent used in the assay method using the labeling substance are radioisotopes, enzymes, fluorescent substances and luminescent substances, etc. Examples of the radioisotope are [$^{125}$I], [$^{131}$I], [$^{3}$H], [$^{14}$C], etc. Preferred examples of the enzyme are those that are stable and have a high specific activity, which include β-galactosidase, β-glucosidase, alkaline phosphatase, peroxidase and malate dehydrogenase. Examples of the fluorescent substance are fluorescamine, fluorescein isothiocyanate, etc. Examples of the luminescent substance are luminol, a luminol derivative, luciferin, lucigenin, etc. Furthermore, the biotin-avidin system may also be used for binding of an antibody or antigen to a labeling agent.

In the immobilization of antigens or antibodies, physical adsorption may be used. Alternatively, chemical binding that is conventionally used for immobilization of proteins or enzymes may be used as well. Examples of the carrier include insoluble polysaccharides such as agarose, dextran and cellulose; synthetic resins such as polystyrene, polyacrylamide and silicone; glass; etc.

In the sandwich method, a test sample fluid is reacted with an immobilized monoclonal antibody of the present invention (first reaction), then reacted with another labeled monoclonal antibody of the present invention (second reaction) and the activity of the labeling agent on the insoluble carrier is assayed, whereby the amount of the polypeptide of the present invention or the receptor protein of the present invention in the test sample fluid can be quantified. The first and second reactions may be carried out in a reversed order, simultaneously or sequentially with an interval. The type of the labeling agent and the method for immobilization may be the same as those described hereinabove. In the immunoassay by the sandwich method, it is not always necessary that the antibody used for the labeled antibody and for the solid phase should be one type or one species but a mixture of two or more antibodies may also be used for the purpose of improving the measurement sensitivity, etc.

In the method for assaying the polypeptide of the present invention or the receptor protein of the present invention by the sandwich method according to the present invention, preferred monoclonal antibodies of the present invention used for the first and the second reactions are antibodies, which binding sites to the polypeptide of the present invention or the receptor protein of the present invention are different from one another. Thus, the antibodies used in the first and the second reactions are those wherein, when the antibody used in the second reaction recognizes the C-terminal region of the polypeptide of the present invention or the receptor protein, the antibody recognizing the site other than the C-terminal regions, e.g., recognizing the N-terminal region, is preferably used in the first reaction.

The monoclonal antibody of the present invention may be used in an assay system other than the sandwich method, such as a competitive method, an immunometric method and a nephrometry.

In the competitive method, an antigen in a test sample fluid and a labeled antigen are competitively reacted with an antibody, then the unreacted labeled antigen (F) and the labeled antigen bound to the antibody (B) are separated (i.e., B/F separation) and the labeled amount of either B or F is measured to determine the amount of the antigen in the test sample fluid. In the reactions for such a method, there are a liquid phase method in which a soluble antibody is used as the antibody and the B/F separation is effected by polyethylene glycol while a second antibody to the antibody is used, and a solid phase method in which an immobilized antibody is used as the first antibody or a soluble antibody is used as the first antibody while an immobilized antibody is used as the second antibody.

In the immunometric method, an antigen in a test sample fluid and an immobilized antigen are competitively reacted with a given amount of a labeled antibody followed by separating the solid phase from the liquid phase; or an antigen in a test sample fluid and an excess amount of labeled antibody are reacted, then an immobilized antigen is added to bind an unreacted labeled antibody to the solid phase and the solid phase is separated from the liquid phase. Thereafter, the labeled amount of any of the phases is measured to determine the antigen amount in the test sample fluid.

In the nephrometry, the amount of insoluble sediment, which is produced as a result of the antigen-antibody reaction in a gel or in a solution, is measured. Even when the amount of an antigen in a test sample fluid is small and only a small amount of the sediment is obtained, a laser nephrometry utilizing laser scattering can be suitably used.

In applying each of those immunoassays to the assay method for the present invention, any special conditions or operations are not required to set forth. The assay system for the polypeptide of the present invention may be constructed in addition to conditions or operations conventionally used for each of the methods, taking the technical consideration of one skilled in the art into account consideration. For the details of such conventional technical means, a variety of reviews, reference books, etc. may be referred to (for example, Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by lgaku Shoin, 1987); "Methods in Enzymology" Vol. 70 (Immuochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (published by Academic Press); etc.)

As described above, the polypeptide of the present invention or the receptor protein of the present invention can be quantified with high sensitivity, using the antibody of the present invention.

Furthermore, when a decrease or increase in level of the polypeptide of the present invention or the receptor protein of the present invention is detected by quantifying the level of the polypeptide of the present invention or the receptor protein using the antibody of the present invention, it can be diagnosed that the following diseases are involved or it is highly likely to suffer from these disease in the future. Examples of such diseases are hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer, rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicella-zoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive *staphylococcal* infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorder, pollakiuria, uremia, neurodegenerative disease, etc.

Where a decrease or increase in the level of the polypeptide of the present invention or the receptor protein of the present invention is detected, it can be diagnosed as well that a disease such as macular edema cystoid or the like is involved or it is highly likely to suffer from such a disease in the future.

Moreover, since the polypeptide of the present invention, the receptor protein of the present invention and the DNA of the present invention are associated with secretion control of somatostatin, it can be diagnosed that the following diseases are involved or there is a high possibility to suffer from these diseases in the future, when a decreased or increased level of the polypeptide of the present invention or the receptor protein of the present invention is detected. Examples of these diseases are:

(1) acromegaly, TSH-producing tumor, non-secretory (non-functional) pituitary tumor, ectopic ACTH (adrenocorticotropine)-producing tumor, medullary thyroid cancer, VIP-producing tumor, glucagon-producing tumor, gastrin-producing tumor, insulinoma, carcinoid tumor;

(2) insulin-dependent or insulin-independent diabetes mellitus, or various diseases associated with the diabetes, i.e., diabetic complications (e.g., diabetic retinopathy, diabetic nephropathy, diabetic neuropathy, Down's syndrome, orthostatic hypotension, etc.);

(3) obesity, bulimia, etc. caused by improving hyperinsulinism or the suppression of appetite;

(4) acute pancreatitis, chronic pancreatitis, pancreatic/intestinal fistula, hemorrhagic ulcer, peptic ulcer, gastritis, hyperchylia, reflux esophagitis;

(5) various conditions accompanied by *Helicobacter pylori* bacterial infections (e.g., an agent for suppressing accentuated gastrin secretion, etc.);

(6) oversecretion of amylase accompanied by endoscopic cholangio pancreatography;

(7) diarrhea caused by reduced absorption or accentuated secretion in small intestine or abnormal motility of digestive tract (Short bowel syndrome, etc.), diarrhea caused by drugs in chemotherapy of cancer, etc., diarrhea caused by congenital small intestine atrophy, diarrhea caused by neuro-endocrinal tumor such as VIP-producing tumor, etc., diarrhea caused by AIDS, diarrhea caused by graft-versus-host reaction accompanied by spinal transplant, etc., diarrhea caused by diabetes mellitus, diarrhea caused by blocking nervous plexus in the abdominal cavity, diarrhea caused by systemic screlosis, diarrhea caused by eosinophilia;

(8) Dumping syndrome, hypersensitive colitis, Crohn's disease, inflammatory bowel disease;

(9) tumor or cancer (e.g., thyroid cancer, colon cancer, breast cancer, prostatic cancer, small cell lung cancer, non-small cell lung cancer, pancreatic cancer, gastric cancer, bile duct cancer, liver cancer, bladder cancer, ovary cancer, melanoma, osteosarcoma, chondrosarcoma, malignant pheochromocytoma, neuroblastoma, brain tumor, thymoma, kidney cancer, etc.), leukemia (e.g., leukemia/chronic lymphoid leukemia of basophil leukocyte, chronic myeloid leukemia, Hodgkin's disease, non-Hodgkin's lymphoma, etc.);

(10) hypertrophic cardiomyopathy, arteriosclerosis, valvular disease, myocardial infarction (especially myocardial infarction after percutaneous transluminal angioplasty) or regeneration of blood vessels;

(11) hemorrhage in esophagal venous cancer, cirrhosis or peripheral vessel disease;

(12) disease accompanied by regulation of secretion of physiologically active substances acting on the immune system, such as systemic or regional inflammation (e.g., multiple arthritis, rheumatoid arthritis, psoriasis, sunburn, eczema, allergy (e.g., asthma, atopic dermatitis, allergic rhinitis, etc.);

(13) dementia (e.g., Alzheimer's disease, Alzheimer's senile dementia, vascular/multiple dementia, etc.), schizophrenia, epilepsy, depression, general anxiety disorder, sleeping disorder, multiple sclerosis;

(14) eye disease (e.g., glaucoma, etc.);

(15) acute bacterial meningitis, acute viral encephalitis, adult respiratory distress syndrome, bacterial pneumonia, severe systemic fungal infectious disease, tuberculosis, spinal injury, bone fracture, hepatic insufficiency, pneumonia, alcoholic hepatitis, hepatitis A, hepatitis B, hepatitis C, AIDS infectious disease, human papilloma virus infectious disease, influenza infectious disease, cancer metastasis, multiple myeloma, osteomalacia, osteoporosis, Behcet's disease of bone, nephritis, renal insufficiency, sepsis, septic shock, hypercalcemia, hypercholesterolemia, hyperglyceridemia, hyperlipemia, systemic lupus erythematosus, transient cerebral ischemia, alcoholic hepatitis;

(16) burn, wound, alopecia;

(17) chronic or acute pains (pains accompanied by, e.g., postoperative pain, inflammatory pain, toothache, bone disease (e.g., arthritis, rheumatoid, osteoporosis, etc.)).

The antibody of the present invention can be employed for detecting the polypeptide of the present invention or the receptor protein of the present invention which may be present in a test sample fluid such as a body fluid, a tissue, etc. The antibody can also be used for preparation of an antibody column for purification of the polypeptide of the present invention or the receptor protein of the present invention, detection of the receptor protein of the present invention in the fractions upon purification, and analysis of the behavior of the polypeptide of the present invention or the receptor protein of the present invention in the cells under investigation.

(4) Gene Diagnostic Agent

By using the DNA of the present invention, e.g., as a probe, an abnormality (gene abnormality) of the DNA or mRNA coding for the polypeptide of the present invention or the receptor protein of the present invention in human or warm-blooded animal (e.g., rat, mouse, guy pig, rabbit, chicken, sheep, swine, bovine, horse, cat, dog, monkey, etc.) can be detected. Therefore, the DNA of the present invention is useful as a gene diagnostic agent for the damage to the DNA or mRNA, its mutation, or its decreased expression, or increased expression or overexpression of the DNA or mRNA.

The gene diagnosis described above using the DNA of the present invention can be performed by, for example, the publicly known Northern hybridization assay or the PCR-SSCP assay (Genomics, 5, 874-879 (1989); Proceedings of the National Academy of Sciences of the United States of America, 86, 2766-2770 (1989)).

In case that decreased expression or overexpression is detected by, e.g., the Northern hybridization, it can be diagnosed that the following diseases are involved or it is highly likely to suffer from these disease in the future. Examples of such diseases are hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer, rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorder, pollakiuria, uremia, neurodegenerative disease, etc.

In case that a decreased expression or overexpression is detected by the Northern hybridization, it can also be diagnosed that a disease such as macular edema cystoid or the like is involved or it is highly likely to suffer from such a disease in the future.

In addition, since the polypeptide of the present invention, the receptor protein of the present invention and the DNA of the present invention are associated with secretion control of somatostatin, the decrease in expression or overexpression detected by the Northern hybridization results in such a diagnosis that the following diseases are involved or there is a high possibility to suffer from these diseases in the future. Examples of the diseases are:

(1) acromegaly, TSH-producing tumor, non-secretory (non-functional) pituitary tumor, ectopic ACTH (adrenocorticotropine)-producing tumor, medullary thyroid cancer, VIP-producing tumor, glucagon-producing tumor, gastrin-producing tumor, insulinoma, carcinoid tumor;

(2) insulin-dependent or insulin-independent diabetes mellitus, or various diseases associated with the diabetes, i.e., diabetic complications (e.g., diabetic retinopathy, diabetic nephropathy, diabetic neuropathy, Down's syndrome, orthostatic hypotension, etc.);

(3) obesity, bulimia, etc. caused by improving hyperinsulinism or the suppression of appetite;

(4) acute pancreatitis, chronic pancreatitis, pancreatic/intestinal fistula, hemorrhagic ulcer, peptic ulcer, gastritis, hyperchylia, reflux esophagitis;

(5) various conditions accompanied by *Helicobacter pylori* bacterial infections (e.g., an agent for suppressing accentuated gastrin secretion, etc.);

(6) oversecretion of amylase accompanied by endoscopic cholangio pancreatography and for the postoperative treatment in pancreas surgery;

(7) diarrhea caused by reduced absorption or accentuated secretion in small intestine or abnormal motility of digestive tract (Short bowel syndrome, etc.), diarrhea caused by drugs in chemotherapy of cancer, etc., diarrhea caused by congenital small intestine atrophy, diarrhea caused by neuro-endocrinal tumor such as VIP-producing tumor, etc., diarrhea caused by AIDS, diarrhea caused by graft-versus-host reaction accompanied by spinal transplant, etc., diarrhea caused by diabetes mellitus, diarrhea caused by blocking nervous plexus in the abdominal cavity, diarrhea caused by systemic screlosis, diarrhea caused by eosinophilia;

(8) Dumping syndrome, hypersensitive colitis, Crohn's disease, inflammatory bowel disease;

(9) tumor or cancer (e.g., thyroid cancer, colon cancer, breast cancer, prostatic cancer, small cell lung cancer, non-small cell lung cancer, pancreatic cancer, gastric cancer, bile duct cancer, liver cancer, bladder cancer, ovary cancer, melanoma, osteosarcoma, chondrosarcoma, malignant pheochromocytoma, neuroblastoma, brain tumor, thymoma, kidney cancer, etc.), leukemia (e.g., leukemia/chronic lymphoid leukemia of basophil leukocyte, chronic myeloid leukemia, Hodgkin's disease, non-Hodgkin's lymphoma, etc.), these agents may also be used alone or in combination with other carcinostatic agents (e.g., tamoxifen, LHRH agonist, LHRH antagonist, interferon-$\alpha$, $\beta$, and $\gamma$, interleukin-2, etc.);

(10) hypertrophic cardiomyopathy, arteriosclerosis, valvular disease, myocardial infarction (especially myocardial infarction after percutaneous transluminal angioplasty) or regeneration of blood vessels;

(11) hemorrhage in esophagal venous cancer, cirrhosis or peripheral vessel disease;

(12) disease accompanied by regulation of secretion of physiologically active substances acting on the immune system, such as systemic or regional inflammation (e.g., multiple arthritis, rheumatoid arthritis, psoriasis, sunburn, eczema, allergy (e.g., asthma, atopic dermatitis, allergic rhinitis, etc.);

(13) dementia (e.g., Alzheimer's disease, Alzheimer's senile dementia, vascular/multiple dementia, etc.), schizophrenia, epilepsy, depression, general anxiety disorder, sleeping disorder, multiple sclerosis;

(14) eye disease (e.g., glaucoma, etc.);

(15) acute bacterial meningitis, acute viral encephalitis, adult respiratory distress syndrome, bacterial pneumonia, severe systemic fungal infectious disease, tuberculosis, spinal injury, bone fracture, hepatic insufficiency, pneumonia, alcoholic hepatitis, hepatitis A, hepatitis B, hepatitis C, AIDS infectious disease, human papilloma virus infectious disease, influenza infectious disease, cancer metastasis, multiple myeloma, osteomalacia, osteoporosis, Behcet's disease of bone, nephritis, renal insufficiency, sepsis, septic shock, hypercalcemia, hypercholesterolemia, hyperglyceridemia, hyperlipemia, systemic lupus erythematosus, transient cerebral ischemia, alcoholic hepatitis;

(16) burn, wound, alopecia;

(17) chronic or acute pains (pains accompanied by, e.g., postoperative pain, inflammatory pain, toothache, bone disease (e.g., arthritis, rheumatoid, osteoporosis, etc.)).

(5) Pharmaceutical Composition Comprising Antisense DNA

Antisense DNA that binds to the DNA of the present invention complemenarily to inhibit expression of the DNA can be used as the agent for the treatment/prevention of diseases such as hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer, rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive *staphylococcal* infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, is severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorder, pollakiuria, uremia, neurodegenerative disease, etc.

The antisense DNA that binds to the DNA of the present invention and can inhibit expression of the DNA can also be used as the therapeutic/prophylactic agent for macular edema cystoid.

In addition, since the polypeptide of the present invention or the receptor protein of the present invention are associated with secretion control of somatostatin, the antisense DNA that binds to the DNA of the present invention and can inhibit expression of the DNA are useful as:

(1) therapeutic agents for tumors such as acromegaly, TSH-producing tumor, non-secretory (non-functional) pituitary tumor, ectopic ACTH (adrenocorticotropine)-producing tumor, medullary thyroid cancer, VIP-producing tumor, glucagon-producing tumor, gastrin-producing tumor, insulinoma, carcinoid tumor, etc.;

(2) therapeutic agents for insulin-dependent or insulin-independent diabetes mellitus, or various diseases associated with the diabetes, i.e., diabetic complications (e.g., diabetic retinopathy, diabetic nephropathy, diabetic neuropathy, Down's syndrome, orthostatic hypotension, etc.);

(3) agents for improving hyperinsulinism or for the treatment of obesity, bulimia, etc. caused by the suppression of appetite;

(4) therapeutic agents for acute pancreatitis, chronic pancreatitis, pancreatic/intestinal fistula, hemorrhagic ulcer, peptic ulcer, gastritis, hyperchylia, reflux esophagitis, etc.;

(5) agents for alleviating various conditions accompanied by *Helicobacter pylori* bacterial infections (e.g., an agent for suppressing accentuated gastrin secretion, etc.);

(6) agents for suppressing secretion of amylase accompanied by endoscopic cholangio pancreatography and for the postoperative treatment in pancreas surgery;

(7) agents for the treatment of diarrhea caused by reduced absorption or accentuated secretion in small intestine or abnormal motility of digestive tract (Short bowel syndrome, etc.), diarrhea caused by drugs in chemotherapy of cancer, etc., diarrhea caused by congenital small intestine atrophy, diarrhea caused by neuro-endocrinal tumor such as VIP-producing tumor, etc., diarrhea caused by AIDS, diarrhea caused by graft-versus-host reaction accompanied by spinal transplant, etc., diarrhea caused by diabetes mellitus, diarrhea caused by blocking nervous plexus in the abdominal cavity, diarrhea caused by systemic screlosis, diarrhea caused by eosinophilia, etc.;

(8) agents for the treatment of Dumping syndrome, hypersensitive colitis, Crohn's disease, inflammatory bowel disease, etc.;

(9) agents for the treatment of tumor or cancer (e.g., thyroid cancer, colon cancer, breast cancer, prostatic cancer, small cell lung cancer, non-small cell lung cancer, pancreatic cancer, gastric cancer, bile duct cancer, liver cancer, bladder cancer, ovary cancer, melanoma, osteosarcoma, chondrosarcoma, malignant pheochromocytoma, neuroblastoma, brain tumor, thymoma, kidney cancer, etc.), leukemia (e.g., leukemia/chronic lymphoid leukemia of basophil leukocyte, chronic myeloid leukemia, Hodgkin's disease, non-Hodgkin's lymphoma, etc.), these agents may also be used alone or in combination with other carcinostatic agents (e.g., tamoxifen, LHRH agonist, LHRH antagonist, interferon-$\alpha$, $\beta$ and $\gamma$, interleukin-2, etc.);

(10) agents for the prevention and treatment of hypertrophic cardiomyopathy, arteriosclerosis, valvular disease, myocardial infarction (especially myocardial infarction after percutaneous transluminal angioplasty) or regeneration of blood vessels;

(11) agents for the treatment of hemorrhage in esophagal venous cancer, cirrhosis or peripheral vessel disease;

(12) agents for the treatment of disease accompanied by regulation of secretion of physiologically active substances acting on the immune system, such as systemic or regional inflammation (e.g., multiple arthritis, rheumatoid arthritis, psoriasis, sunburn, eczema, allergy (e.g., asthma, atopic dermatitis, allergic rhinitis, etc.), etc.;

(13) agents for the treatment of, for example, dementia (e.g., Alzheimer's disease, Alzheimer's senile dementia, vascular/multiple dementia, etc.), schizophrenia, epilepsy, depression, general anxiety disorder, sleeping disorder, multiple sclerosis, etc.;

(14) agents for the treatment of eye disease (e.g., glaucoma, etc.), etc.;

(15) agents for the prevention and treatment of acute bacterial meningitis, acute viral encephalitis, adult respiratory distress syndrome, bacterial pneumonia, severe systemic fungal infectious disease, tuberculosis, spinal injury, bone fracture, hepatic insufficiency, pneumonia, alcoholic hepatitis, hepatitis A, hepatitis B, hepatitis C, AIDS infectious disease, human papilloma virus infectious disease, influenza infectious disease, cancer metastasis, multiple myeloma, osteomalacia, osteoporosis, Behcet's disease of bone, nephritis, renal insufficiency, sepsis, septic shock, hypercalcemia, hypercholesterolemia, hyperglyceridemia, hyperlipemia, systemic lupus erythematosus, transient cerebral ischemia, alcoholic hepatitis, etc.

(16) The antisense DNA can also be used for healing organ transplantation, burn, wound, alopecia, etc.

(17) The antisense DNA is also useful as analgesics for suppression or alleviation of chronic or acute pains (pains accompanied by, e.g., postoperative pain, inflammatory pain, toothache, bone disease (e.g., arthritis, rheumatoid, osteoporosis, etc.)).

In the case that the antisense DNA described above is used as the therapeutic/prophylactic agent, the therapeutic/prophylactic agents for various diseases described above comprising the DNA of the present invention apply similarly to the antisense DNA.

For example, when the antisense DNA is used, the antisense DNA is administered directly, or the antisense DNA is inserted into an appropriate vector such as retrovirus vector, adenovirus vector, adenovirus-associated virus vector, etc. followed by treating in a conventional manner. The antisense DNA may be administered as it stands, or with a physiologically acceptable carrier to assist its uptake by gene gun or through a catheter such as a catheter with a hydrogel.

In addition, the antisense DNA may also be employed as an oligonucleotide probe for diagnosis to examine the presence of the DNA of the present invention in tissues or cells and states of its expression.

(6) Pharmaceutical Composition Comprising the Antibody of the Present Invention

The antibody of the present invention which possesses the effect to neutralize the activities of the polypeptide of the present invention or the receptor peptide of the present invention can be used as drugs for the treatment/prevention of diseases such as hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive *staphylococcal* infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorder, pollakiuria, uremia, neurodegenerative disease, etc.

In addition, the antibody of the present invention having the effect of neutralizing the polypeptide of the present invention or the receptor protein of the present invention can also be used as the therapeutic/prophylactic agent for macular edema cystoid.

Moreover, since the polypeptide of the present invention or the receptor protein of the present invention are associated with secretion control of somatostatin, the antibody of the present invention having the effect of neutralizing the polypeptide of the present invention or the receptor protein of the present invention are useful as:

(1) therapeutic agents for tumors such as acromegaly, TSH-producing tumor, non-secretory (non-functional) pituitary tumor, ectopic ACTH (adrenocorticotropine)-producing tumor, medullary thyroid cancer, VIP-producing tumor, glucagon-producing tumor, gastrin-producing tumor, insulinoma, carcinoid tumor, etc.;

(2) therapeutic agents for insulin-dependent or insulin-independent diabetes mellitus, or various diseases associated with the diabetes, i.e., diabetic complications (e.g., diabetic retinopathy, diabetic nephropathy, diabetic neuropathy, Down's syndrome, orthostatic hypotension, etc.);

(3) agents for improving hyperinsulinism or for the treatment of obesity, bulimia, etc. caused by the suppression of appetite;

(4) therapeutic agents for acute pancreatitis, chronic pancreatitis, pancreatic/intestinal fistula, hemorrhagic ulcer, peptic ulcer, gastritis, hyperchylia, reflux esophagitis, etc.;

(5) agents for alleviating various conditions accompanied by *Helicobacter pylori* bacterial infections (e.g., an agent for suppressing accentuated gastrin secretion, etc.);

(6) agents for suppressing secretion of amylase accompanied by endoscopic cholangio pancreatography and for the postoperative treatment in pancreas surgery;

(7) agents for the treatment of diarrhea caused by reduced absorption or accentuated secretion in small intestine or abnormal motility of digestive tract (Short bowel syndrome, etc.), diarrhea caused by drugs in chemotherapy of cancer, etc., diarrhea caused by congenital small intestine atrophy, diarrhea caused by neuro-endocrinal tumor such as VIP-producing tumor, etc., diarrhea caused by AIDS, diarrhea caused by graft-versus-host reaction accompanied by spinal transplant, etc., diarrhea caused by diabetes mellitus, diarrhea caused by blocking nervous plexus in the abdominal cavity, diarrhea caused by systemic screlosis, diarrhea caused by eosinophilia, etc.;

(8) agents for the treatment of Dumping syndrome, hypersensitive colitis, Crohn's disease, inflammatory bowel disease, etc.;

(9) agents for the treatment of tumor or cancer (e.g., thyroid cancer, colon cancer, breast cancer, prostatic cancer, small cell lung cancer, non-small cell lung cancer, pancreatic cancer, gastric cancer, bile duct cancer, liver cancer, bladder cancer, ovary cancer, melanoma, osteosarcoma, chondrosarcoma, malignant pheochromocytoma, neuroblastoma, brain tumor, thymoma, kidney cancer, etc.), leukemia (e.g., leukemia/chronic lymphoid leukemia of basophil leukocyte, chronic myeloid leukemia, Hodgkin's disease, non-Hodgkin's lymphoma, etc.), these agents may also be used alone or in combination with other carcinostatic agents (e.g., tamoxifen, LHRH agonist, LHRH antagonist, interferon-α, β and γ, interleukin-2, etc.);

(10) agents for the prevention and treatment of hypertrophic cardiomyopathy, arteriosclerosis, valvular disease, myocardial infarction (especially myocardial infarction after percutaneous transluminal angioplasty) or regeneration of blood vessels;

(11) agents for the treatment of hemorrhage in esophagal venous cancer, cirrhosis or peripheral vessel disease;

(12) agents for the treatment of disease accompanied by regulation of secretion of physiologically active substances acting on the immune system, such as systemic or regional inflammation (e.g., multiple arthritis, rheumatoid arthritis, psoriasis, sunburn, eczema, allergy (e.g., asthma, atopic dermatitis, allergic rhinitis, etc.), etc.;

(13) agents for the treatment of, for example, dementia (e.g., Alzheimer's disease, Alzheimer's senile dementia, vascular/multiple dementia, etc.), schizophrenia, epilepsy, depression, general anxiety disorder, sleeping disorder, multiple sclerosis, etc.;

(14) agents for the treatment of eye disease (e.g., glaucoma, etc.), etc.;

(15) agents for the prevention and treatment of acute bacterial meningitis, acute viral encephalitis, adult respiratory distress syndrome, bacterial pneumonia, severe systemic fungal infectious disease, tuberculosis, spinal injury, bone fracture, hepatic insufficiency, pneumonia, alcoholic hepatitis, hepatitis A, hepatitis B, hepatitis C, AIDS infectious disease, human papilloma virus infectious disease, influenza infectious disease, cancer metastasis, multiple myeloma, osteomalacia, osteoporosis, Behcet's disease of bone, nephritis, renal insufficiency, sepsis, septic shock, hypercalcemia, hypercholesterolemia, hyperglyceridemia, hyperlipemia, systemic lupus erythematosus, transient cerebral ischemia, alcoholic hepatitis, etc.

(16) Furthermore, the antibody of the present invention is also used for healing organ transplantation, burn, wound, alopecia, etc.

(17) The antibody of the present invention is also useful as analgesics for suppression or alleviation of chronic or acute pains (pains accompanied by, e.g., postoperative pain, inflammatory pain, toothache, bone disease (e.g., arthritis, rheumatoid, osteoporosis, etc.)).

The pharmaceutical agent comprising the antibody of the present invention for the treatment and prevention of the aforesaid diseases may be administered orally or parenterally to human or mammal (e.g., rat, rabbit, sheep, swine, bovine, cat, dog, monkey, etc.) as a liquid preparation in its original form, or as a pharmaceutical composition in an appropriate drug form. The dose varies depending on subject to be administered, target disease, conditions, route for administration, etc.; for example, when used for the treatment and prevention of adult patient with neuropathy, the antibody of the present invention is intravenously administered normally in the dose of about 0.01 mg to about 20 mg/kg body weight, preferably about 1.0 to about 10 mg/kg body weigh, and more preferably about 0.1 to about 5 mg per day once to about 5 times a day, preferably once to about 3 times. In parenteral administration in other route and in oral administration, a dose similar to those given above can be administered. Where conditions are serious, the dose may be increased depending on the conditions.

The antibody of the present invention may be administered in itself or as an appropriate pharmaceutical composition. The pharmaceutical composition used for the administration described above contains a pharmacologically acceptable carrier with the aforesaid compounds or salts thereof, a diluent or excipient. Such a composition is provided in the preparation suitable for oral or parenteral administration.

That is, examples of the composition for oral administration include solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, etc.

Examples of the composition for parenteral administration that can be used are injections, suppositories, etc. and the injections include the form of intravenous, subcutaneous, transcutaneous, intramuscular and drip injections. Such injections are prepared by publicly known methods, e.g., by dissolving, suspending or emulsifying the aforesaid antibody or its salts in a sterile aqueous or oily liquid medium. For the aqueous medium for injection, for example, physiological saline and isotonic solutions containing glucose and other adjuvant, etc. are used. Appropriate dissolution aids, for example, alcohol (e.g. ethanol), polyalcohol (e.g. propylene glycol, polyethylene glycol), nonionic surfactant (e.g. polysorbate 80™, HCO-50 (polyoxyethylene (50 mol) adduct of hydrogenated castor oil)) may be used in combination. For the oily solution, for example, sesame oil, soybean oil and the like are used, and dissolution aids such as benzyl benzoate and benzyl alcohol may be used in combination. The thus-prepared liquid for injection is normally filled in an appropriate ampoule. The suppository used for rectal administration is prepared by mixing the aforesaid antibody or its salts with conventional suppository base.

The oral or parenteral pharmaceutical composition described above is advantageously prepared in a unit dosage form suitable for the dose of the active ingredient. Examples of such unit dosage form include tablets, pills, capsules, injections (ampoules), suppositories, etc. It is preferred that the antibody described above is contained generally in a dose of 5 to 500 mg per unit dosage form, 5 to 100 mg especially for injections and 10 to 250 mg for other preparations.

Each composition described above may further contain other active components unless formulation with the antibody causes any adverse interaction.

(7) DNA Transgenic Animal

The present invention provides a non-human mammal bearing DNA encoding the polypeptide of the present invention or the receptor protein of the present invention, which is exogenous (hereinafter abbreviated as the exogenous DNA of the present invention) or its variant DNA (sometimes simply referred to as the exogenous variant DNA of the present invention).

Thus, the present invention provides:

(1) a non-human mammal bearing the exogenous DNA or its variant DNA;

(2) the mammal according to (1), wherein the non-human mammal is a rodent;

(3) the mammal according to (2), wherein the rodent is mouse or rat; and, (4) a recombinant vector bearing the exogenous DNA of the present invention or its variant DNA and capable of expressing in a mammal.

The non-human mammal bearing the exogenous DNA of the present invention or its variant DNA (hereinafter simply referred to as the DNA transgenic animal of the present invention) can be created by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method etc. In addition, it is possible to transfect the exogenous DNA of the present invention into a somatic cell, a living organ, a tissue cell, or the like by the DNA transfection methods, and utilize the transformant for cell culture, tissue culture, etc. In addition, these cells may be fused with the above-described germinal cell by a publicly known cell fusion method to create the transgenic animal of the present invention.

Examples of the non-human mammal that can be used include bovine, swine, sheep, goat, rabbits, dogs, cats, guinea pigs, hamsters, rats, mice and the like. Above all, preferred are rodents, especially mice (e.g., C57BI/6 strain, DBA2 strain, etc. for a pure line and for a cross line, B6C3F$_1$ strain, BDF$_1$ strain B6D2F$_1$ strain, BALB/c strain, ICR strain, etc.) or rats (Wistar, SD, etc.), since they are relatively short in ontogeny and life cycle from a standpoint of creating model animals for human disease.

"Mammals" in a recombinant vector that can be expressed in the mammals include the aforesaid non-human mammals and human.

The exogenous DNA of the present invention refers to the DNA of the present invention that is once isolated and extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean DNA that expresses the abnormal polypeptide or receptor protein of the present invention and exemplified by DNA that expresses a polypeptide for suppressing the functions of the normal polypeptide or receptor protein of the present invention.

The exogenous DNA of the present invention may be any one of those derived from a mammal of the same species as, or a different species from, the mammal as the target animal. In transfecting the DNA of the present invention, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the polypeptide of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include (1) promoters for DNA derived from viruses (e.g., simian virus, cytomegalovirus, Moloney leukemia virus, JC virus, breast cancer virus, poliovirus, etc.), and (2) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase β I subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), polypeptide chain elongation factor 1 α (EF-1 α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle, α actin, preproencephalin A, vasopressin, etc. Among them, cytomegalovirus promoters, human polypeptide elongation factor 1 α(EF-1 α) promoters, human and chicken β actin promoters etc., which protein can highly express in the whole body are preferred.

It is preferred that the vectors described above have a sequence for terminating the transcription of the desired messenger RNA in the DNA transgenic animal (generally termed terminator); for example, a sequence of each DNA derived from viruses and various mammals. SV40 terminator of the simian virus, etc. are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal polypeptide or receptor protein of the present invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using complementary DNA prepared by a publicly known method from RNA of liver, kidney, thyroid cell or fibroblast origin as a starting material. In addition, an exogenous abnormal DNA can be obtained using complementary DNA prepared by a publicly known method from RNA of human fibroblast origin as a starting material. Alternatively, the translational region for a normal polypeptide translational region obtained by the cell or tissue described above can be made variant by point mutagenesis.

The translational region can be prepared by a conventional DNA engineering technique in which the DNA is ligated downstream the aforesaid promoter and if desired, upstream the translation termination site, as a DNA construct capable of being expressed in the transgenic animal.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA in all of the germinal cells and somatic cells thereof.

The non-human mammal in which the normal exogenous DNA of the present invention has been transfected can be passaged as the DNA-bearing animal under ordinary rearing environment, by confirming that the exogenous DNA is stably retained by mating.

By the transfection of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfection means that the DNA of the present invention is excessively present in all of the germinal cells and somatic cells thereof. The offspring of the animal that inherits the exogenous DNA of the present invention have excessively the DNA of the present invention in all of the germinal cells and somatic cells thereof.

By obtaining a homozygotic animal having the transfected DNA in both of homologous chromosomes and mating a male and female of the animal, all offspring can be passaged to retain the DNA.

In a non-human mammal bearing the normal DNA of the present invention, the normal DNA of the present invention has expressed to a high level, and may eventually develop the function inactive type inadaptability of the polypeptide of the present invention or the receptor protein of the present invention by accelerating the functions of endogenous normal DNA. Therefore, the animal can be utilized as a pathologic model animal for such a disease. Specifically, using the normal DNA transgenic animal of the present invention, it is possible to elucidate the mechanism of the function inactive type inadaptability of the polypeptide or the receptor protein of the present invention and the pathological mechanism of the disease associated with the receptor protein of the present invention and to determine how to treat the disease.

Further, since a mammal transfected the exogenous normal DNA of the present invention exhibits an increasing symptom of the polypeptide or the receptor protein of the present invention librated, the animal is usable for screening of treatment agent for the disease associated with the polypeptide or the receptor protein of the present invention.

On the other hand, non-human mammal having the exogenous abnormal DNA of the present invention can be passaged under normal breeding conditions as the DNA-bearing animal by confirming the stable retaining of the exogenous DNA via crossing. Further, the exogenous DNA to be subjected can be utilized as a starting material by inserting the DNA into the plasmid described above. The DNA construct with promoter can be prepared with conventional DNA engineering techniques. The transfection of the abnormal DNA of the present invention at the fertilized egg cell stage is preserved to be present in all of the germinal and somatic cells of the mammals to be subjected. The fact that the abnormal DNA of the present invention is present in the germinal cells of the animal after DNA transfection means that all of the offspring of the prepared animal have the abnormal DNA of the present invention in all of the germinal and somatic cells. Such an offspring passaged the exogenous DNA of the present invention contains the abnormal DNA of the present invention in all of the germinal and somatic cells. A homozygous animal having the introduced DNA on both of homologous chromosomes can be acquired and then by mating these male and female animals, all the offspring can be bled to have the DNA.

Since non-human mammal having the abnormal DNA of the present invention may express the abnormal DNA of the present invention at a high level, the animal may be the function inactivation type inadaptability of the polypeptide or the receptor protein of the present invention by inhibiting the function of the endogenous normal DNA and can be utilized as its disease model animal. For example, using the abnormal DNA-transferred animal of the present invention, it is possible to elucidate the mechanism of inadaptability of the polypeptide or the receptor protein of the present invention and to perform to study a method for treatment of this disease.

More specifically, the transgenic animal of the present invention expressing the abnormal DNA of the present invention to a high level is also expected to serve as an experimental model for the elucidation of the mechanism of the functional inhibition (dominant negative effect) of normal polypeptide by the abnormal polypeptide of the present invention in the function inactive type inadaptability of the polypeptide of the present invention or the receptor protein of the present invention.

A mammal bearing the abnormal exogenous DNA of the present invention is also expected to serve for screening a candidate drug for the treatment of the function inactive type inadaptability of the polypeptide of the present invention or the receptor protein of the present invention, since the polypeptide of the present invention or the receptor protein of the present invention is increased in such an animal in its free form.

Other potential applications of two kinds of the transgenic animals described above include:

(1) use as a cell source for tissue culture;

(2) elucidation of the relation to a polypeptide that is specifically expressed or activated by the polypeptide of the present invention or the receptor protein of the present invention, by direct analysis of DNA or RNA in tissue of the DNA transgenic animal of the present invention or by analysis of the polypeptide tissue expressed by the DNA;

(3) research in the function of cells derived from tissues that are cultured usually only with difficulty, using cells of tissue bearing the DNA cultured by a standard tissue culture technique;

(4) screening for a drug that enhances the functions of cells using the cells described in (3) above; and, (5) isolation and purification of the variant polypeptide of the present invention and preparation of an antibody thereto.

Furthermore, clinical conditions of a disease associated wit the polypeptide of the present invention or the receptor protein of the present invention, including the function inactive type inadaptability of the polypeptide of the polypeptide of the present invention or the receptor protein of the present invention can be determined using the DNA transgenic animal of the present invention. In addition, pathological findings on each organ in a disease model associated with the polypeptide of the present invention or the receptor protein of the present invention can be obtained in more detail, leading to the development of a new method for treatment as well as the research and therapy of any secondary diseases associated with the disease.

It is also possible to obtain a free DNA-transfected cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve as identification of cells capable of producing the polypeptide of the present invention or the receptor protein of the present invention, and as studies on association with apoptosis, differentiation or propagation or on the mechanism of signal transduction in these properties to inspect any abnormality therein. Thus the DNA transgenic animal of the present invention can provide an effective research material for the polypeptide of the present invention or the receptor protein of the present invention and for elucidating the function and effect thereof.

To develop a therapeutic drug for the treatment of diseases associated with the polypeptide of the present invention or the receptor protein of the present invention, including the function inactive type inadaptability of the polypeptide of the present invention or the receptor protein of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the polypeptide of the present invention or the receptor protein of the present invention, using the DNA transgenic animal of the present invention or a vector capable of expressing the exogenous DNA of the present invention.

(8) Knockout Animal

The present invention provides a non-human mammal embryonic stem cell bearing the DNA of the present invention inactivated and a non-human mammal deficient in expressing the DNA of the present invention.

Thus, the present invention provides:

(1) a non-human embryonic stem cell in which the DNA of the present invention is inactivated;

(2) an embryonic stem cell according to (1), wherein the DNA is inactivated by introducing a reporter gene (e.g., β-galactosidase gene derived from *Escherichia coli*);

(3) an embryonic stem cell according to (1), which is resistant to neomycin;

(4) an embryonic stem cell according to (1), wherein the non-human mammal is a rodent;

(5) an embryonic stem cell according to (4), wherein the rodent is mouse;

(6) a non-human mammal deficient in expressing the DNA of the present invention, wherein the DNA of the present invention is inactivated;

(7) a non-human mammal according to (5), wherein the DNA is inactivated by inserting a reporter gene (e.g., β-galactosidase derived from *Escherichia coli*) therein and the reporter gene is capable of being expressed under control of a promoter for the DNA of the present invention;

(8) a non-human mammal according to (6), which is a rodent;

(9) a non-human mammal according to (8), wherein the rodent is mouse; and,

(10) a method for screening a compound that accelerates or inhibits the promoter activity for the DNA of the present invention, which comprises administering a test compound to the mammal of (7) and detecting expression of the reporter gene.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the polypeptide of the present invention or the receptor protein of the present invention (hereinafter sometimes referred to as the knockout DNA of the present invention) by substantially inactivating the activities of the polypeptide of the present invention or the receptor protein of the present invention encoded by the DNA (hereinafter merely referred to as ES cell).

As the non-human mammal, the same examples as described above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon site thereby to disable the functions of exon, or integrating to a chromosome of the subject animal by, e.g., homologous recombination, a DNA sequence which terminates gene transcription (e.g., polyA additional signal, etc.) in the intron between exons to, thus inhibit the synthesis of complete messenger RNA and eventually destroy the gene (hereinafter simply referred to as targeting vector). The thus-obtained ES cells to Southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to select the knockout ES cell of the present invention.

The parent ES cells to inactivate the DNA of the present invention by homologous recombination, etc. may be of a strain already established as described above, or may be originally established in accordance with a modification of the known method by Evans and Kaufman supra. For example, in the case of mouse ES cells, currently it is common practice to use ES cells of the 129 strain. However, since their immunological background is obscure, the C57BL/6 mouse or the BDF1 mouse (F1 hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The BDF1 mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera and are therefore preferred. It is also desirable that sexes be identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Second selection can be achieved by, for example, number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and 90% air) in the presence of LIF (1-10000 U/ml) on appropriate feeder cells such as STO fibroblasts, treated with a trypsin/EDTA solution (normally about 0.001 to about 0.5% trypsin/about 0.1 to about 5 mM EDTA, preferably about 0.1% trypsin/l mM EDTA) at the time of passage to obtain separate single cells, which are then seeded on fleshly prepared feeder cells. This passage is normally conducted every 1 to 3 days; it is desirable that cells be observed at passage and cells found to be morphologically abnormal in culture, if any, be abandoned.

Where ES cells are allowed to reach a high density in mono-layers or to form cell aggregates in suspension under appropriate conditions, they will spontaneously differentiate to various cell types, for example, pariental and visceral muscles, cardiac muscle or the like (M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985). The cells deficient in expression of the DNA of the present invention, which are obtainable from the differentiated ES cells of the present invention are useful for studying the functions of the polypeptide of the present invention or the receptor protein of the present invention cytologically or molecular biologically.

The non-human mammal deficient in expression of the DNA of the present invention can be identified from a normal animal by measuring the mRNA amount in the subject animal by a publicly known method, and indirectly comparing the degrees of expression.

As the non-human mammal, the same examples supra apply.

With respect to the non-human mammal deficient in expression of the DNA of the present invention, the DNA of the present invention can be made knockout by transfecting a targeting vector, prepared as described above, to non-human mammal embryonic stem cells or oocytes thereof, and conducting homologous recombination in which a targeting vector DNA sequence, wherein the DNA of the present invention is inactivated by the transfection, is replaced with the DNA of the present invention on a chromosome of a non-human mammal embryonic stem cell or embryo thereof.

The knockout cells with the DNA of the present invention disrupted can be identified by Southern hybridization analysis with a DNA fragment on or near the DNA of the present invention as a probe, or by PCR analysis using a DNA sequence on the targeting vector and another DNA sequence which is not included in the targeting vector as primers. When non-human mammalian embryonic stem cells are used, a cell line wherein the DNA of the present invention is inactivated by homologous recombination is cloned; the resulting cloned cell line is injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the peptide of the present invention. The individuals deficient in homozygous expression of the polypeptide of the present invention or the receptor protein of the present invention can be obtained from offspring of the intercross between the heterozygotes.

When an oocyte or egg cell is used, a DNA solution may be injected, e.g., to the prenucleus by microinjection thereby to obtain a transgenic non-human mammal having a targeting vector introduced in a chromosome thereof. From such transgenic non-human mammals, those having a mutation at the locus of the DNA of the present invention can be obtained by selection based on homologous recombination.

As described above, individuals in which the DNA of the present invention is rendered knockout permit passage rearing under ordinary rearing conditions, after the individuals obtained by their crossing have proven to have been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell in which the DNA of the present invention is inactivated is very useful for preparing a non-human mammal deficient in expression of the DNA of the present invention.

Since the non-human mammal in which the DNA of the present invention is inactivated lacks various biological activities derived from the polypeptide of the present invention or the receptor protein of the present invention, such an animal can be a disease model suspected of inactivated biological activities of the polypeptide of the present invention or the receptor protein of the present invention and thus, offers an effective study to investigate causes for and therapy for these diseases.

(8a) Method for Screening Of Compounds having Therapeutic/Prophylactic Effects for Diseases Caused by Deficiency, Damages, Etc. of the DNA of the Present Invention The non-human mammal deficient in expression of the DNA of the present invention can be employed for screening of compounds having therapeutic/prophylactic effects for diseases caused by deficiency, damages, etc. of the DNA of the present invention.

That is, the present invention provides a method for screening of a compound having therapeutic/prophylactic effects for diseases caused by deficiency, damages, etc. of the DNA of the present invention, which comprises administering a test compound to the non-human mammal deficient in expression of the DNA of the present invention and observing and measuring a change occurred in the animal.

As the non-human mammal deficient in expression of the DNA of the present invention which can be employed for the screening method, the same examples as given hereinabove apply.

Examples of the test compounds include peptides, proteins, non-peptide compounds, synthetic compounds, fermentation products, cell extracts, vegetable extracts, animal tissue extracts, blood plasma and the like and these compounds may be novel compounds or publicly known compounds.

Specifically, the non-human mammal deficient in expression of the DNA of the present invention is treated with a test compound, comparison is made with an intact animal for control and a change in each organ, tissue, disease conditions, etc. of the animal is used as an index to assess the therapeutic/prophylactic effects of the test compound.

For treating an animal to be test with a test compound, for example, oral administration, intravenous injection, etc. are applied and the treatment is appropriately selected depending upon conditions of the test animal, properties of the test compound, etc. Further, an amount of administration for a test compound can be selected depending on the administration route, nature of the test compound and the like.

For example, the non-human mammal deficient in expression of the DNA of the present invention is subjected to a sugar loading treatment, a test compound is administered before or after the sugar loading treatment and, blood sugar level, body weight change, etc. of the animal is measured with passage of time, in the case of screening a compound having a therapeutic/prophylactic effect for diseases such as hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer, rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorder, pollakiuria, uremia, neurodegenerative disease, etc.; or a compound having a therapeutic and prophylactic effect for macular edema cystoid; and furthermore, a compound useful as a therapeutic and prophylactic effect as:

(1) therapeutic agents for tumors such as acromegaly, TSH-producing tumor, non-secretory (non-functional) pituitary tumor, ectopic ACTH (adrenocorticotropine)-producing tumor, medullary thyroid cancer, VIP-producing tumor, glucagon-producing tumor, gastrin-producing tumor, insulinoma, carcinoid tumor, etc.;

(2) therapeutic agents for insulin-dependent or insulin-independent diabetes mellitus, or various diseases associated with the diabetes, i.e., diabetic complications (e.g., diabetic retinopathy, diabetic nephropathy, diabetic neuropathy, Down's syndrome, orthostatic hypotension, etc.);

(3) agents for improving hyperinsulinism or for the treatment of obesity, bulimia, etc. caused by the suppression of appetite;

(4) therapeutic agents for acute pancreatitis, chronic pancreatitis, pancreatic/intestinal fistula, hemorrhagic ulcer, peptic ulcer, gastritis, hyperchylia, reflux esophagitis, etc.;

(5) agents for alleviating various conditions accompanied by *Helicobacter pylori* bacterial infections (e.g., an agent for suppressing accentuated gastrin secretion, etc.);

(6) agents for suppressing secretion of amylase accompanied by endoscopic cholangio pancreatography and for the postoperative treatment in pancreas surgery;

(7) agents for the treatment of diarrhea caused by reduced absorption or accentuated secretion in small intestine or abnormal motility of digestive tract (Short bowel syndrome, etc.), diarrhea caused by drugs in chemotherapy of cancer, etc., diarrhea caused by congenital small intestine atrophy, diarrhea caused by neuro-endocrinal tumor such as VIP-producing tumor, etc., diarrhea caused by AIDS, diarrhea caused by graft-versus-host reaction accompanied by spinal transplant, etc., diarrhea caused by diabetes mellitus, diarrhea caused by blocking nervous plexus in the abdominal cavity, diarrhea caused by systemic screlosis, diarrhea caused by eosinophilia, etc.;

(8) agents for the treatment of Dumping syndrome, hypersensitive colitis, Crohn's disease, inflammatory bowel disease, etc.;

(9) agents for the treatment of tumor or cancer (e.g., thyroid cancer, colon cancer, breast cancer, prostatic cancer, small cell lung cancer, non-small cell lung cancer, pancreatic cancer, gastric cancer, bile duct cancer, liver cancer, bladder cancer, ovary cancer, melanoma, osteosarcoma, chondrosarcoma, malignant pheochromocytoma, neuroblastoma, brain tumor, thymoma, kidney cancer, etc.), leukemia (e.g., leukemia/chronic lymphoid leukemia of basophil leukocyte, chronic myeloid leukemia, Hodgkin's disease, non-Hodgkin's lymphoma, etc.), these agents may also be used alone or in combination with other carcinostatic agents (e.g., tamoxifen, LHRH agonist, LHRH antagonist, interferon-α, β and γ, interleukin-2, etc.);

(10) agents for the prevention and treatment of hypertrophic cardiomyopathy, arteriosclerosis, valvular disease, myocardial infarction (especially myocardial infarction after percutaneous transluminal angioplasty) or regeneration of blood vessels;

(11) agents for the treatment of hemorrhage in esophagal venous cancer, cirrhosis or peripheral vessel disease;

(12) agents for the treatment of disease accompanied by regulation of secretion of physiologically active substances acting on the immune system, such as systemic or regional inflammation (e.g., multiple arthritis, rheumatoid arthritis, psoriasis, sunburn, eczema, allergy (e.g., asthma, atopic dermatitis, allergic rhinitis, etc.), etc.;

(13) agents for the treatment of, for example, dementia (e.g., Alzheimer's disease, Alzheimer's senile dementia, vascular/multiple dementia, etc.), schizophrenia, epilepsy, depression, general anxiety disorder, sleeping disorder, multiple sclerosis, etc.;

(14) agents for the treatment of eye disease (e.g., glaucoma, etc.), etc.;

(15) agents for the prevention and treatment of acute bacterial meningitis, acute viral encephalitis, adult respiratory distress syndrome, bacterial pneumonia, severe systemic fungal infectious disease, tuberculosis, spinal injury, bone fracture, hepatic insufficiency, pneumonia, alcoholic hepatitis, hepatitis A, hepatitis B, hepatitis C, AIDS infectious disease, human papilloma virus infectious disease, influenza infectious disease, cancer metastasis, multiple myeloma, osteomalacia, osteoporosis, Behcet's disease of bone, nephritis, renal insufficiency, sepsis, septic shock, hypercalcemia, hypercholesterolemia, hyperglyceridemia, hyperlipemia, systemic lupus erythematosus, transient cerebral ischemia, alcoholic hepatitis, etc.;

(16) further use in healing organ transplantation, burn, wound, alopecia, etc:;

(17) analgesics for suppression or alleviation of chronic or acute pains (pains accompanied by, e.g., postoperative pain, inflammatory pain, toothache, bone disease (e.g., arthritis, rheumatoid, osteoporosis, etc.)).

In the screening method supra, when a test compound is administered to an animal to be tested and found to reduce the blood sugar level of the animal to at least about 10%, preferably at least about 30% and more preferably at least about 50%, the test compound can be selected to be a compound having a therapeutic and prophylactic effect for the diseases supra.

The compound obtained using the above screening method is a compound selected from the test compounds described above and exhibits a therapeutic and prophylactic effect for the diseases caused by deficiencies, damages, etc. of the polypeptide of the present invention or the receptor protein of the present invention. Therefore, the compound can be employed as a safe and low toxic drug for the treatment and prevention of these diseases. Furthermore, compounds derived from such a compound obtained by the screening supra can be likewise employed.

The compound obtained by the screening above may be used in the form of salts with physiologically acceptable acids (e.g., inorganic acids or organic acids) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

A pharmaceutical composition comprising the compound obtained by the above screening method or salts thereof may be manufactured in a manner similar to the method for preparing the composition comprising the polypeptide of the present invention described hereinabove.

Since the pharmaceutical composition thus obtained is safe and low toxic, it can be administered to human and another mammal (e.g., rat, mouse, guinea pig, rabbit, sheep, swine, bovine, horse, cat, dog, monkey, etc.).

Although the amount of the compound or its salt to be administered varies depending upon particular disease, subject to be administered, route of administration, etc. in general, for oral administration to an adult (as 60 kg body weight), the compound is administered in an amount of about 0.1 mg/day to about 100 mg/day, preferably about 1.0 mg/day to about 50 mg/day, more preferably about 1.0 mg to about 20 mg. For parenteral administration to an adult (as 60 kg body weight), it is advantageous to administer the composition in the form of an injectable preparation in an amount of about 0.01 mg/day to about 30 mg/day, preferably about 0.1 mg/day to about 20 mg/day, more preferably about 0.1 mg/day to about 10 mg/day, though the single dosage varies depending upon particular subject, particular disease, etc. As for other animals, the composition can be administered in the above amount with converting it into that for the body weight of 60 kg.

(8b) Method for Screening a Compound that Accelerates or Inhibits the Activities of a Promoter to the DNA of the Present Invention The present invention provides a method for screening a compound that accelerates or inhibits the activities of a promoter to the DNA of the present invention or salts thereof, which comprises administering a test compound to a non-human mammal deficient in expression of the DNA of the present invention and detecting expression of the reporter gene.

In the screening method supra, the non-human mammal deficient in expression of the DNA of the present invention is selected from the aforesaid non-human mammal deficient in expression of the DNA of the present invention, as an animal in which the DNA of the present invention is inactivated by introducing a reporter gene and the reporter gene is expressed under control of a promoter to the DNA of the present invention.

The same examples of the test compound apply to specific compounds used for the screening.

As the reporter gene, the same specific examples apply to this screening method. Preferably employed are ¤-galactosidase (lacZ), soluble alkaline phosphatase gene, luciferase gene and the like.

Since a reporter gene is present under control of a promoter to the DNA of the present invention in the non-human mammal deficient in expression of the DNA of the present invention wherein the DNA of the present invention is substituted with the reporter gene, the activity of the promoter can be detected by tracing expression of a substance encoded by the reporter gene.

When a part of the DNA region encoding the polypeptide of the present invention or the receptor protein of the present invention is substituted with, e.g., β-galactosidase gene (lacZ) derived from *Escherichia coli*, β-galactosidase is expressed in a tissue where the polypeptide of the present invention or the receptor protein of the present invention should originally be expressed, instead of the polypeptide or receptor protein of the present invention. Thus, the state of expression of the polypeptide or the receptor protein of the present invention can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the polypeptide of the present invention or the receptor protein of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening method supra are compounds that are selected from the test compounds described above and that accelerate or inhibit the promoter activity to the DNA of the present invention.

The compound obtained by the screening method above may be used in the form of salts with physiologically acceptable acids (e.g., inorganic acids or organic acids) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

Since the compounds or salts thereof that accelerate or inhibit the promoter activity to the DNA of the present invention can accelerate or inhibit the expression of the polypeptide of the present invention or the receptor protein of the present invention or can accelerate or inhibit the functions of the polypeptide of the present invention or the receptor protein of the present invention, they are useful as safe and low toxic drugs for the treatment/prevention of diseases such as hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer, rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorder, pollakiuria, uremia, neurodegenerative disease, etc.

In addition, the compounds or salts thereof that accelerate or inhibit the promoter activity to the DNA of the present invention can also be used as a safe and low toxic therapeutic/prophylactic agent for macular edema cystoid.

Moreover, the compounds or salts thereof that accelerate or inhibit the promoter activity to the DNA of the present invention are useful as safe and low toxic therapeutic/prophylactic agents for diseases, which are specifically given below:

(1) therapeutic agents for tumors such as acromegaly, TSH-producing tumor, non-secretory (non-functional) pituitary tumor, ectopic ACTH (adrenocorticotropine)-producing tumor, medullary thyroid cancer, VIP-producing tumor, glucagon-producing tumor, gastrin-producing tumor, insulinoma, carcinoid tumor, etc.;

(2) therapeutic agents for insulin-dependent or insulin-independent diabetes mellitus, or various diseases associated with the diabetes, i.e., diabetic complications (e.g., diabetic retinopathy, diabetic nephropathy, diabetic neuropathy, Down's syndrome, orthostatic hypotension, etc.);

(3) agents for improving hyperinsulinism or for the treatment of obesity, bulimia, etc. caused by the suppression of appetite;

(4) therapeutic agents for acute pancreatitis, chronic pancreatitis, pancreatic/intestinal fistula, hemorrhagic ulcer, peptic ulcer, gastritis, hyperchylia, reflux esophagitis, etc.;

(5) agents for alleviating various conditions accompanied by *Helicobacter pylori* bacterial infections (e.g., an agent for suppressing accentuated gastrin secretion, etc.);

(6) agents for suppressing secretion of amylase accompanied by endoscopic cholangio pancreatography and for the postoperative treatment in pancreas surgery;

(7) agents for the treatment of diarrhea caused by reduced absorption or accentuated secretion in small intestine or abnormal motility of digestive tract (Short bowel syndrome, etc.), diarrhea caused by drugs in chemotherapy of cancer, etc., diarrhea caused by congenital small intestine atrophy, diarrhea caused by neuro-endocrinal tumor such as VIP-producing tumor, etc., diarrhea caused by AIDS, diarrhea caused by graft-versus-host reaction accompanied by spinal transplant, etc., diarrhea caused by diabetes mellitus, diarrhea caused by blocking nervous plexus in the abdominal cavity, diarrhea caused by systemic screlosis, diarrhea caused by eosinophilia, etc.;

(8) agents for the treatment of Dumping syndrome, hypersensitive colitis, Crohn's disease, inflammatory bowel disease, etc.;

(9) agents for the treatment of tumor or cancer (e.g., thyroid cancer, colon cancer, breast cancer, prostatic cancer, small cell lung cancer, non-small cell lung cancer, pancreatic cancer, gastric cancer, bile duct cancer, liver cancer, bladder cancer, ovary cancer, melanoma, osteosarcoma, chondrosarcoma, malignant pheochromocytoma, neuroblastoma, brain tumor, thymoma, kidney cancer, etc.), leukemia (e.g., leukemia/chronic lymphoid leukemia of basophil leukocyte, chronic myeloid leukemia, Hodgkin's disease, non-Hodgkin's lymphoma, etc.), these agents may also be used alone or in combination with other carcinostatic agents (e.g., tamoxifen, LHRH agonist, LHRH antagonist, interferon-α, β and γ, interleukin-2, etc.);

(10) agents for the prevention and treatment of hypertrophic cardiomyopathy, arteriosclerosis, valvular disease, myocardial infarction (especially myocardial infarction after percutaneous transluminal angioplasty) or regeneration of blood vessels;

(11) agents for the treatment of hemorrhage in esophagal venous cancer, cirrhosis or peripheral vessel disease;

(12) agents for the treatment of disease accompanied by regulation of secretion of physiologically active substances acting on the immune system, such as systemic or regional inflammation (e.g., multiple arthritis, rheumatoid arthritis, psoriasis, sunburn, eczema, allergy (e.g., asthma, atopic dermatitis, allergic rhinitis, etc.), etc.;

(13) agents for the treatment of, for example, dementia (e.g., Alzheimer's disease, Alzheimer's senile dementia, vascular/multiple dementia, etc.), schizophrenia, epilepsy, depression, general anxiety disorder, sleeping disorder, multiple sclerosis, etc.;

(14) agents for the treatment of eye disease (e.g., glaucoma, etc.), etc.;

(15) agents for the prevention and treatment of acute bacterial meningitis, acute viral encephalitis, adult respiratory distress syndrome, bacterial pneumonia, severe systemic fungal infectious disease, tuberculosis, spinal injury, bone fracture, hepatic insufficiency, pneumonia, alcoholic hepatitis, hepatitis A, hepatitis B, hepatitis C, AIDS infectious disease, human papilloma virus infectious disease, influenza infectious disease, cancer metastasis, multiple myeloma, osteomalacia, osteoporosis, Behcet's disease of bone, nephritis, renal insufficiency, sepsis, septic shock, hypercalcemia, hypercholesterolemia, hyperglyceridemia, hyperlipemia, systemic lupus erythematosus, transient cerebral ischemia, alcoholic hepatitis, etc.;

(16) further use in healing organ transplantation, burn, wound, alopecia, etc.;

(17) analgesics for suppression or alleviation of chronic or acute pains (pains accompanied by, e.g., postoperative pain, inflammatory pain, toothache, bone disease (e.g., arthritis, rheumatoid, osteoporosis, etc.)). In addition, compound derived from the compounds obtained by the screening above may be likewise employed.

A pharmaceutical composition comprising the compounds or salts thereof obtained by the screening method supra may be manufactured in a manner similar to the method for preparing the composition comprising the polypeptide of the present invention described hereinabove.

Since the pharmaceutical composition thus obtained is safe and low toxic, it can be administered to human or another mammal (e.g., rat, mouse, guinea pig, rabbit, sheep, swine, bovine, horse, cat, dog, monkey, etc.).

The dose of the compound or salts thereof varies depending on target disease, subject to be administered, method for administration, etc.; for example, in oral administration of the compound that accelerates the promoter activity to the DNA of the present invention, the dose is normally about 0.1 to about 100 mg, preferably about 1.0 to about 50 mg, more preferably about 1.0 to about 20 mg per day for adult (as 60 kg body weight). In parenteral administration, the single dose varies depending on subject to be administered, target disease, etc. but it is advantageous to administer, for example, the compound that accelerates the functions of the polypeptide of the present invention intravenously at a daily dose of about 0.01 to about 30 mg, preferably about 0.1 to about 20 mg, more preferably about 0.1 to about 10 mg for adult (as 60 kg body weight). For other animal species, the corresponding dose as converted per 60 kg weight can be administered.

Turning to the compound that inhibits the promoter activity to the DNA of the present invention when it is orally administered, the dose is normally about 0.1 to about 100 mg, preferably about 1.0 to about 50 mg, more preferably about 1.0 to about 20 mg per day for adult (as 60 kg body weight). In parenteral administration, the single dose varies depending on subject to be administered, target disease, etc. When the compound that inhibits the promoter activity to the DNA of the present invention is administered to an adult (as 60 kg body weight) generally in the form of injection, it is advantageous to administer the compound intravenously at a daily dose of about 0.01 to about 30 mg, preferably about 0.1 to about 20 mg, more preferably about 0.1 to about 10 mg. For other animal species, the corresponding dose as converted per 60 kg weight can be administered.

As stated above, the non-human mammal deficient in expression of the DNA of the present invention is extremely useful for screening the compound or its salt that accelerates or inhibits the activity of a promoter to the DNA of the present invention and can greatly contribute to the elucidation of causes for various diseases suspected of deficiency in expression of the DNA of the present invention and for the development of prophylactic/therapeutic agent for these diseases.

Furthermore, a so-called transgenic animal (gene transferred animal) can be prepared by using DNA containing a promoter region of the polypeptide of the present invention or the receptor protein of the present invention, ligating genes encoding various proteins downstream and injecting the same into oocyte of an animal. It is then possible to synthesize the polypeptide or protein therein specifically and study its activity in vivo. When an appropriate reporter gene is ligated to the promoter site above and a cell line that express the gene is established, the resulting system can be utilized for exploring a low molecular compound having the action of specifically promoting or inhibiting the in vivo productivity of the polypeptide of the present invention or the receptor protein of the present invention, per se.

(9) Identification of receptor to the polypeptide of the present invention

The receptor to the polypeptide of the present invention can be identified as follows. Most receptors for the physiologically active peptides are of seven-transmembrane type and presently many orphan receptors, which ligands are unknown, are reported. Thus, specific receptors can be identified by expressing these orphan receptors in appropriate cells such as CHO cells, HEK293 cells, etc. and adding the polypeptide of the present invention to the expressed receptors to examine if such a cell stimulating activity as inducing a specific signal transduction is exhibited. Furthermore, a gene encoding the receptor can be isolated by inserting genome or cDNA library into appropriate animal cells and adding thereto a radioisotope-labeled polypeptide of the present invention to examine its binding.

Since a gene encoding the physiologically active peptide is characterized often by repeating a sequence motif of the peptide, the present invention further provides a method for identification of an unknown physiologically active peptide or its amides or esters, or salts thereof, by utilizing the characteristic property and also provides a physiologically active peptide obtained by the method, its amides or esters, or salts thereof.

Specific examples of the sequence motif possessed by the physiologically active peptide are RFG (R/K) sequence or RSG (R/K) sequence or RLG (R/K) sequence which is characteristic of the polypeptide of the present invention bearing an RF amide, RS amide or RL amide structure, and a base sequence encoding the amino acid sequence. The DNA sequence capable of encoding such a short amino acid sequence appears accidentally with a considerably high frequency also in those other than the DNA sequence of the physiologically active peptide. By exploring a sequence characterized by repeating such a sequence, DNA encoding a physiologically active peptide can be discovered in a high probability.

More specifically, the desired gene can be obtained by retrieval of database using as a probe the RFG(R/K) sequence or RSG(R/K) sequence or RLG(K/R) sequence or a sequence containing the amino acid sequence and a sequence containing the base sequence encoding the same. Examples of the probe include:

```
RFGK:
                                        (SEQ ID NO:20)
5'-(C/A)G(A/C/G/T)TT(T/C)GG(A/C/G/T)AA(A/G)-3'

RFGR:
                                        (SEQ ID NO:21)
5'-(C/A)G(A/C/G/T)TT(T/C)GG(A/C/G/T)(A/C)G

(A/C/G/T)-3'

RsSGK:
                                        (SEQ ID NO:22)
5'-(C/A)G(A/C/G/T)(A/T)(C/G)(A/C/G/T)GG(A/C/G/T)AA

(A/G)-3'

RSGR:
                                        (SEQ ID NO:23)
5'-(C/A)G(A/C/G/T)(A/T)(C/G)(A/C/G/T)GG(A/C/G/T)

(A/C)G(A/C/G/T)-3'

RLGK:
                                        (SEQ ID NO:24)
5'-(C/A)G(A/C/G/T)(T/C)T(A/C/G/T)GG(A/C/G/T)AA

(A/G)-3'

RLGR:
                                        (SEQ ID NO:25)
5'-(C/A)G(A/C/G/T)(T/C)T(A/C/G/T)GG(A/C/G/T)(A/C)G

(A/C/G/T)-3'
```

and the like, as the DNA sequence corresponding to RFG(K/R), RSG(K/R) and RLG(K/R).

The desired gene may also be obtained by screening cDNA or genomic library using the sequence motif above. Moreover, mRNA of the desired gene is purified by using the probes supra as in a gene trapper to acquire cDNA from the mRNA purified. Further by using other sequence motif (an amino acid sequence repeatedly encoded by the gene or a base sequence encoding the amino acid sequence), these probes may also be used for identification of a physiologically active peptide having other than the RF amide, RS amide or RL amide structure.

The peptide having the RF amide, RS amide or RL amide structure possesses a common structure of RF amide, RS amide or RL amide at the C-terminal region of the peptide. It is thus possible to explore a peptide having an unknown RF amide, RS amide or RL amide structure, using an antibody containing the RF amide, RS amide or RL amide structure. Most receptors to the peptide having the RF amide, RS amide or RL amide structure are of seven-transmembrane type. Therefore, a ligand to orphan receptor can be determined by using an anti-RF amide antibody, anti-RS amide antibody or anti-RL amide antibody, wherein a condensed or fractionated animal tissue extract is added to cells capable of expressing an orphan receptor with the ligand being not determined. Since many peptides that contain a common structure other than those having the RF amide, RS amide or RL amide structure are present, this method is applicable also to peptides other than those having the RF amide, RS amide or RL amide structure.

(10) Determination of a Ligand (Agonist) to the Receptor Protein of the Present Invention The receptor protein of the present invention is useful as a reagent for searching and determining a ligand (agonist) to the receptor protein of the present invention and salts thereof.

That is, the present invention provides a method for determining a ligand to the receptor protein of the present invention, which comprises bringing the receptor protein of the present invention in contact with a test compound.

Examples of compounds to be tested include publicly known ligands (e.g., angiotensin, bombesin, canavinoid, cholecystokinin, glutamine, serotonin, melatonin, neuropeptide Y, opioid, purines, vasopressin, oxytocin, PACAP, secretin, glucagon, calcitonin, adrenomedulin, somatostatin, GHRH, CRF, ACTH, GRP, PTH, VIP (vasoactive intestinal and related polypeptide), somatostatin, dopamine, motilin, amylin, bradykinin, CGRP (calcitonin gene-related peptide), leukotrienes, pancreastatin, prostaglandins, thromboxane, adenosine, adrenaline, α and β-chemokines (e.g., IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelin, enterogastrin, histamin, neurotensin, TRH, pancreatic polypeptide, galanin, etc.) as well as other substances, for example, tissue extracts and cell culture supernatants from human and mammals (e.g., mice, rats, swine, bovine, sheep, monkeys, etc.). For example, the tissue extract or cell culture supernatant is added to the receptor protein of the present invention and fractionated while assaying the cell stimulating activities to finally give a single ligand.

(4) Assay of the Binding Amount or the Cell Stimulating Activity of the Polypeptide of the Present Invention and a Test Compound to the Receptor Protein of the Present Invention Either by using the receptor protein of the present invention or by constructing an expression system of the receptor protein of recombinant type and making use of the receptor-binding assay system using the expression system, the binding amount or the cell stimulating activity of the compound (e.g., a peptide, protein, non-peptide compound, synthetic compound, fermentation product, etc.) that binds to the receptor protein of the present invention to exhibit the cell stimulating activity (e.g., the activity that promotes or inhibits arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, etc.), can be assayed.

In the assay method above, the characteristic feature comprises contacting the receptor protein of the present invention with a compound to be tested, and measuring, e.g., the binding amount, the cell stimulating activity, etc. of the test compound to the receptor protein of the present invention.

More specifically, the present invention provides the following:

(1) A method for determining a ligand to the receptor protein of the present invention, which contacting a labeled test compound with the is receptor protein of the present invention and measuring the amount of the labeled test compound bound to the receptor protein;

(2) A method for determining a ligand to the receptor protein of the present invention, which comprises contacting a labeled test compound with a cell containing the receptor protein of the present invention or with a membrane fraction of the cell and measuring the amount of the labeled test compound bound to the cell or the membrane fraction;

(3) A method for determining a ligand to the receptor protein of the present invention, which comprises culturing a transformant containing the DNA encoding the receptor protein of the present invention, contacting a labeled test compound with the receptor protein expressed on the cell membrane by said culturing, and measuring the amount of the labeled test compound bound to the receptor protein;

(4) A method for determining a ligand to the receptor protein of the present invention, which comprises contacting a test compound with a cell containing the receptor protein of the present invention and measuring the receptor protein-mediated cell stimulating activity (e.g., the activity that promotes or inhibits arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, etc.); and, (5) A method for determining a ligand to the receptor protein of the present invention, which comprises culturing a transformant containing DNA encoding the receptor protein of the present invention, contacting a labeled test compound with the receptor protein expressed on the cell membrane by said culturing, and measuring the receptor protein-mediated cell stimulating activity (e.g., the activity that promotes or inhibits arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, etc.).

In particular, it is preferred to perform the methods (1) to (3) described above, thereby to confirm that a test compound can bind to the receptor protein of the present invention, followed by the methods (4) and (5) described above.

Any protein exemplified to be usable as the receptor protein of the present invention can be used for determining ligands. However, the receptor protein that is abundantly expressed using animal cells is appropriate.

The receptor protein of the present invention can be manufactured by the method for expression described above, preferably by expressing DNA encoding the receptor protein in mammalian or insect cells. DNA fragments encoding the desired portion of the protein include, but are not limited to, complementary DNA. For example, gene fragments or synthetic DNA may also be used. For introducing a DNA fragment encoding the receptor protein of the present invention into host animal cells and efficiently expressing the same, it is preferred to insert the DNA fragment downstream the polyhedrin promoter of nuclear polyhedrosis virus (NPV), which is a baculovirus having insect hosts, an SV40-derived promoter, a retrovirus promoter, a metallothionein promoter, a human heat shock promoter, a cytomegalovirus promoter, an SRa promoter or the like. The amount and quality of the receptor expressed can be determined by a publicly known method. For example, this determination can be made by the method described in the literature [Nambi, P. et al., J. Biol. Chem., Vol. 267, pp. 19555-19559 (1992)].

Accordingly, the subject containing the receptor protein in the method for determining the ligand may be the receptor protein purified by publicly known method, a cell containing the receptor protein or membrane fraction of such a cell.

Where cells containing the receptor protein of the present invention are used in the method of the present invention for determination of ligands, the cells may be fixed using glutaraldehyde, formalin etc. he fixation can be made by a publicly known method.

The cells containing the receptor protein of the present invention are host cells that have expressed the receptor protein of the present invention, which host cells include *Escherichia coli, Bacillus subtilis*, yeast, insect cells, animal cells and the like.

The cell membrane fraction is a fraction abundant in cell membrane obtained by cell disruption and subsequent fractionation by a publicly known method. Useful cell disruption methods include cell squashing using a Potter-Elvehjem homogenizer, disruption using a Waring blender or Polytron (manufactured by Kinematica Inc.), disruption by ultrasonication, and disruption by cell spraying through thin nozzles under an increased pressure using a French press or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the receptor protein expressed and membrane components such as cell-derived phospholipids and membrane proteins.

The amount of the receptor protein in the cell containing the receptor protein and in the membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To perform the methods (1) through (3) for determination of a ligand to the receptor protein of the present invention, an appropriate receptor fraction and a labeled test compound are required.

The receptor protein fraction is preferably a fraction of naturally occurring receptor protein or a recombinant receptor fraction having an activity equivalent to that of the natural protein. Herein, the equivalent activity is intended to mean a ligand binding activity, a signal transduction activity or the like that is equivalent to that possessed by naturally occurring receptor proteins.

Preferred examples of labeled test compounds include angiotensin, bombesin, canavinoid, cholecystokinin, glutamine, serotonin, melatonin, neuropeptide Y, opioid, purines, vasopressin, oxytocin, PACAP, secretin, glucagon, calcitonin, adrenomedulin, somatostatin, GHRH, CRF, ACTH, GRP, PTH, VIP (vasoactive intestinal and related polypeptide), somatostatin, dopamine, motilin, amylin, bradykinin, CGRP (calcitonin gene-related peptide), leukotrienes, pancreastatin, prostaglandins, thromboxane, adenosine, adrenaline, α and β-chemokines (e.g., IL-8, GROα, GROβ, GROγ, NAP-2, ENA-78, PF4, IP10, GCP-2, MCP-1, HC14, MCP-3, I-309, MIP1α, MIP-1β, RANTES, etc.), endothelin, enterogastrin, histamine, neurotensin, TRH, pancreatic polypeptide, galanin, etc., which are labeled with [$^3$H], [$^{125}$I], [$^{14}$C], [$^{35}$S], etc.

Specifically, first, a standard receptor preparation is prepared by suspending a cell containing the receptor protein of the present invention or the membrane fraction thereof in a buffer appropriate for use in the determination method. Any buffer can be used so long as it does not interfere with ligand-receptor binding, such buffers including a phosphate buffer or a Tris-HCl buffer having pH of 4 to 10 (preferably pH of 6 to 8). For the purpose of minimizing non-specific binding, a surfactant such as CHAPS, Tween-80™ (manufactured by Kao-Atlas Inc.), digitonin or deoxycholate, and various proteins such as bovine serum albumin or gelatin, may optionally be added to the buffer. Further for the purpose of suppressing the degradation of the receptor or ligand by a protease, a protease inhibitor such as PMSF, leupeptin, E-64 (manufactured by Peptide Institute, Inc.) and pepstatin may also be added. A given amount (5,000 to 500,000 cpm) of a test compound labeled with [$^{3}$H], [$^{125}$I], [$^{14}$C], [$^{35}$S] or the like is added to 0.01 ml to 10 ml of the receptor solution. To determine the amount of non-specific binding (NSB), a reaction tube containing an unlabeled test compound in a large excess is also provided. The reaction is carried out at approximately 0° C. to 50° C., preferably about 4° C. to 37° C. for about 20 minutes to about 24 hours, preferably about 30 minutes to 3 hours. After completion of the reaction, the reaction mixture is filtrated through glass fiber filter paper, etc. and washed with an appropriate volume of the same buffer. The residual radioactivity in the glass fiber filter paper is then measured by means of a liquid scintillation counter or γ-counter. A test compound exceeding 0 cpm in count obtained by subtracting nonspecific binding (NSB) from the total binding (B) (B minus NSB) may be selected as the compound that promotes the activity of the polypeptide of the present invention.

The method (4) or (5) above for determination of a ligand to the receptor protein of the present invention can be performed as follows. The receptor protein-mediated cell stimulating activity (e.g., the activity that promotes or inhibits arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, etc.) can be determined by a publicly known method, or using an assay kit commercially available. Specifically, cells containing the receptor protein are first cultured on a multi-well plate, etc. Prior to the ligand determination, the medium is replaced with fresh medium or with an appropriate non-cytotoxic buffer, followed by culturing for a given period of time in the presence of a test compound, etc. Subsequently, the cells are extracted or the supernatant is recovered and the resulting product is quantified by appropriate procedures. Where it is difficult to detect the production of the indicator substance for the cell stimulating activity (e.g., arachidonic acid) due to a degrading enzyme contained in the cells, an inhibitor against such a degrading enzyme may be added prior to the assay. For detecting activities such as the activity of inhibiting the cAMP production, the baseline production in the cells is increased by forskolin or the like and the suppressing effect on the increased baseline production can then be detected.

The kit of the present invention for determination of the ligand that binds to the receptor protein of the present invention comprises the receptor protein of the present invention, cells containing the receptor protein of the present invention, or the membrane fraction, etc. of the cells containing the receptor protein of the present invention.

Examples of the ligand determination kit of the present invention are given below.

1. Reagents for Determining Ligands (1) Assay and Wash Buffers

Hanks' Balanced Salt Solution (manufactured by Gibco Co.) supplemented with 0.05% bovine serum albumin (Sigma Co.).

The solution is sterilized by filtration through a 0.45 μm filter and stored at 4° C. Alternatively, the solution may be prepared at use.

(2) Standard G Protein-Coupled Receptor Protein

CHO cells on which the receptor protein of the present invention has been expressed are subjected to passage culture on a 12-well plate in a density of $5\times10^{5}$ cells/well followed by culturing at 37° C. under 5% $CO_2$ and 95% air for 2 days.

(3) Labeled Test Compounds

Compounds labeled with commercially available [$^{3}$H], [$^{125}$I], [$^{14}$C], [$^{35}$S], etc. or compounds labeled by appropriate methods.

An aqueous solution of the compound is stored at 4° C. or −20° C. The solution is diluted to 1 μM with an assay buffer at use. A sparingly water-soluble test compound is dissolved in dimethylformamide, DMSO, methanol, etc.

(4) Non-Labeled Compounds

A non-labeled form of the same compound as the labeled compound is prepared in a concentration 100 to 1,000-fold higher than that of the labeled compound.

2. Method for Assay (1) CHO cells expressing the receptor protein of the present invention are cultured in a 12-well culture plate. After washing twice with 1 ml of an assay buffer, 490 μl of the assay buffer is added to each well.

(2) After 5 μl of the labeled test compound is added, the resulting mixture is cultured at room temperature for an hour. To determine the non-specific binding, 5 μl of the non-labeled compound is added to the system.

(3) The reaction mixture is removed and the wells are washed 3 times with 1 ml of washing buffer. The labeled test compound bound to the cell is dissolved in 0.2N NaOH-1% SDS and then mixed with 4 ml of liquid scintillator A (manufactured by Wako Pure Chemical Industries, Ltd.).

(4) The radioactivity is measured using a liquid scintillation counter (manufactured by Beckman Co.).

In the specification and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
I: inosine
R: adenine (A) or guanine (G)
Y: thymine (T) or cytosine (C)
M: adenine (A) or cytosine (C)
K: guanine (G) or thymine (T)
S: guanine (G) or cytosine (C)
W: adenine (A) or thymine (T)
B: guanine (G), guanine (G) or thymine (T)
D: adenine (A), guanine (G) or thymine (T)
V: adenine (A), guanine (G) or cytosine (C)
N: adenine (A), guanine (G), cytosine (C) or thymine (T), or unknown or other base
RNA: ribonucleic acid
mRNA: messenger ribonucleic acid
dATP: deoxyadenosine triphosphate
dTTP: deoxythymidine triphosphate dGTP: deoxyguanosine triphosphate
dCTP: deoxycytidine triphosphate
ATP: adenosine triphosphate
EDTA: ethylenediaminetetraacetic acid
SDS: sodium dodecyl sulfate
BHA: benzhydrylamine
pMBHA: p-methyobenzhydrylamine
Tos: p-toluenesulfonyl
Bzl: benzyl
Bom: benzyloxymethyl
Boc: t-butyloxycarbonyl
DCM: dichloromethane
HOBt: 1-hydroxybenztriazole
DCC: N,N'-dicyclohexylcarbodiimide
TFA: trifluoroacetic acid
DIEA: diisopropylethylamine
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
pGlu: pyroglutamic acid.

The sequence identification numbers in the sequence listing of the specification indicates the following sequence, respectively.

[SEQ ID NO: 1]

This shows the amino acid sequence of the polypeptide (human type) of the present invention, obtained in Example 1, which will be later described.

[SEQ ID NO: 2]

This shows the base sequence of DNA encoding the polypeptide of the present invention shown by SEQ ID NO: 1.

[SEQ ID NO: 3]

This shows the base sequence of primer F5 used in Example 1 later described.

[SEQ ID NO: 4]

This shows the base sequence of primer F6 used in Example 1 later described.

[SEQ ID NO: 5]

This shows the base sequence of primer F1 used in Example 1 later described.

[SEQ ID NO: 6]

This shows the base sequence of primer R5 used in Example 1 later described.

[SEQ ID NO: 7]

This shows the base sequence of primer hR1 used in Example 3 later described.

[SEQ ID NO: 8]

This shows the amino acid sequence of the polypeptide (human type) of the present invention obtained in Example 3 later described.

[SEQ ID NO: 9]

This shows the base sequence of DNA encoding the polypeptide of the present invention represented by SEQ ID NO: 8.

[SEQ ID NO: 10]

This shows the base sequence of primer bF6 used in Example 4 later described.

[SEQ ID NO: 11]

This shows the base sequence of primer bF7 used in Example 4 later described.

[SEQ ID NO: 12]

This shows the base sequence of primer bR6 used in Example 4 later described.

[SEQ ID NO: 13]

This shows the base sequence of primer bR7 used in Example 4 later described.

[SEQ ID NO: 14]

This shows the amino acid sequence of the polypeptide (bovine type) obtained in Example 4, which will be later described.

[SEQ ID NO: 15]

This shows the base sequence of the DNA encoding the polypeptide of the present invention shown by SEQ ID NO: 14.

[SEQ ID NO: 16]

This shows the base sequence of primer rLPR1 used in Example 5, which will be later described.

[SEQ ID NO: 17]

This shows the base sequence of primer rLPF1 employed in Example 5, which will be later described.

[SEQ ID NO: 18]

This shows the amino acid sequence of the polypeptide (rat type) of the present invention obtained in Example 5, which will be later described (before cloning).

[SEQ ID NO: 19]

This shows the base sequence of the DNA encoding the polypeptide of the present invention shown by SEQ ID NO: 18.

[SEQ ID NO: 20]

This shows the base sequence encoding RFGK sequence.

[SEQ ID NO: 21]

This shows the base sequence encoding RFGR sequence.

[SEQ ID NO: 22]

This shows the base sequence encoding RSGK sequence.

[SEQ ID NO: 23]

This shows the base sequence encoding RSGR sequence.

[SEQ ID NO: 24]

This shows the base sequence encoding RLGK sequence.

[SEQ ID NO: 25]

This shows the base sequence encoding RLGR sequence.

[SEQ ID NO: 26]

This shows the base sequence of primer FF2 used in Example 6, which will be later described.

[SEQ ID NO: 27]

This shows the base sequence of primer rR4 used in Example 6, which will be later described.

[SEQ ID NO: 28]

This shows the base sequence of primer mF1 used in Example 6, which will be later described.

[SEQ ID NO: 29]

This shows the base sequence of primer mF3 used in Example 6, which will be later described.

[SEQ ID NO: 30]

This shows the base sequence of primer mRl used in Example 6, which will be later described.

[SEQ ID NO: 31]

This shows the base sequence of primer moF used in Example 6, which will be later described.

[SEQ ID NO: 32]

This shows the base sequence of primer moR used in Example 6, which will be later described.

[SEQ ID NO: 33]

This shows the amino acid sequence of the polypeptide (mouse type) of the present invention obtained in Example 6, which will be later described.

[SEQ ID NO: 34]

This shows the base sequence of the DNA encoding the polypeptide of the present invention bearing the amino acid sequence shown by SEQ ID NO: 33.

[SEQ ID NO: 35]

This shows the base sequence of primer 1 used for cloning the cDNA encoding the rat "area around brainstem"-derived novel G protein-coupled receptor protein rOT7T022L obtained in Example 7, which will be later described.

[SEQ ID NO: 36]

This shows the base sequence of primer 2 used for cloning the cDNA encoding the rat cerebellum-derived novel G protein-coupled receptor protein rOT7T022L obtained in Example 7, which will be later described.

[SEQ ID NO: 37]

This shows the amino acid sequence of the rat cerebellum-derived novel G protein-coupled receptor protein rOT7T022L obtained in Example 7, which will be later described.

[SEQ ID NO: 38]

This shows the base sequence of the cDNA encoding the rat cerebellum-derived novel G protein-coupled receptor protein rOT7T022L obtained in Example 7, which will be later described.

[SEQ ID NO: 39]

This shows the amino acid sequence of the peptide obtained in Example 7 (3), which will be later described.

[SEQ ID NO: 40]

This shows the amino acid sequence of the peptide obtained in Example 7 (4), which will be later described.

[SEQ ID NO: 41]

This shows the amino acid sequence of the peptide obtained in Example 7 (5), which will be later described.

[SEQ ID NO: 42]

This shows the base sequence encoding the peptide bearing the is amino acid sequence of the $81^{st}$ (Met) to $92^{nd}$ (Phe) in the amino acid sequence shown by SEQ ID NO: 1.

[SEQ ID NO: 43]

This shows the base sequence encoding the peptide bearing the amino acid sequence of the $101^{st}$ (Ser) to $112^{nd}$ (Ser) in the amino acid sequence shown by SEQ ID NO: 1.

[SEQ ID NO: 44]

This shows the base sequence encoding the peptide bearing the amino acid sequence of the $124^{th}$ (Val) to $131^{st}$ (Phe) in the amino acid sequence shown by SEQ ID NO: 1.

[SEQ ID NO: 45]

This shows the base sequence encoding the peptide bearing the amino acid sequence of the $1^{st}$ (Met) to $92^{nd}$ (Phe) in the amino acid sequence shown by SEQ ID NO: 1.

[SEQ ID NO: 46]

This shows the base sequence encoding the peptide bearing the amino acid sequence of the $1^{st}$ (Met) to $112^{nd}$ (Ser) in the amino acid sequence shown by SEQ ID NO: 1.

[SEQ ID NO: 47]

This shows the base sequence encoding the peptide bearing the amino acid sequence of the $1^{st}$ (Met) to $131^{st}$ (Phe) in the amino acid sequence shown by SEQ ID NO: 1.

[SEQ ID NO: 48]

This shows the base sequence of primer ratF2 used in Example 5.

[SEQ ID NO: 49]

This shows the base sequence of primer ratR used in Example 5.

[SEQ ID NO: 50]

This shows the amino acid sequence of the polypeptide (rat type) of the present invention obtained in Example 5, which will be later described (after cloning).

[SEQ ID NO: 51]

This shows the base sequence of the DNA encoding the polypeptide of the present invention bearing the amino acid sequence shown by SEQ ID NO: 50.

[SEQ ID NO: 52]

This shows the base sequence of primer bFF used in Example 9.

[SEQ ID NO: 53]

This shows the base sequence of primer bFR used in Example 9.

[SEQ ID NO: 54]

This shows the amino acid sequence coding the protein (polypeptide) represented by h0T7T022 obtained Example 11.

[SEQ ID NO: 55]

This shows the base sequence of the DNA encoding the protein (polypeptide) represented by h0T7T022 bearing the amino acid sequence shown by SEQ ID NO: 54.

[SEQ ID NO: 56]

This shows the base sequence of the DNA encoding the protein (polypeptide) represented by h0T7T022 bearing the amino acid sequence shown by SEQ ID NO: 54.

[SEQ ID NO: 57]

This shows the base sequence of primer 1 used in Example 11.

[SEQ ID NO: 58]

This shows the base sequence of primer 2 used in Example 11.

[SEQ ID NO: 59]

This shows the base sequence of primer #1 used in Example 17.

[SEQ ID NO: 60]

This shows the base sequence of primer #2 used in Example 17.

[SEQ ID NO: 61]

This shows the base sequence of primer #3 used in Example 17.

[SEQ ID NO: 62]

This shows the base sequence of primer #4 used in Example 17.

*Escherichia coli* transformant JM109/p hRF1 obtained in Example 2 later described was on deposit with the Ministry of International Trade and Industry, Agency of Industrial Science and Technology, National Institute of Bioscience and Human Technology (NIBH) as the Accession Number FERM BP-6702 on Apr. 14, 1999 and with Institute for Fermentation, Osaka (IFO) as the Accession Number IFO 16265 on Mar. 5, 1999.

*Escherichia coli* transformant DH10B/pAK-rOT022L obtained in Example 7 later described was on deposit with the Ministry of International Trade and Industry, Agency of Industrial Science and Technology, National Institute of Bioscience and Human Technology (NIBH) as the Accession Number FERM BP-6558 on Nov. 2, 1998 and with Institute for Fermentation, Osaka (IFO) as the Accession Number IFO 16211 on Oct. 16, 1998.

*Escherichia coli* transformant JM109/pbRF2 obtained in Example 9 later described was on deposit with the Ministry of International Trade and Industry, Agency of Industrial Science and Technology, National Institute of Bioscience and Human Technology (NIBH) as the Accession Number FERM BP-6811 on Aug. 2, 1999 and with Institute for Fermentation, Osaka (IFO) as the Accession Number IFO 16288 on Jun. 18, 1999.

*Escherichia coli* transformant JM109/phRF2 obtained in Example 8 later described was on deposit with the Ministry of International Trade and Industry, Agency of Industrial Science and Technology, National Institute of Bioscience and Human Technology (NIBH) as the Accession Number FERM BP-6812 on Aug. 2, 1999 and with Institute for Fermentation, Osaka (IFO) as the Accession Number IFO 16289 on Jun. 18, 1999.

*Escherichia coli* transformant JM109/μmLP4 obtained in Example 6 later described was on deposit with the Ministry of International Trade and Industry, Agency of Industrial Science and Technology, National Institute of Bioscience and Human Technology (NIBH) as the Accession Number FERM BP-6813 on Aug. 2, 1999 and with Institute for Fermentation, Osaka (IFO) as the Accession Number IFO 16290 on Jun. 18, 1999.

*Escherichia coli* transformant JM109/prLPL6 obtained in Example 5 later described was on deposit with the Ministry of International Trade and Industry, Agency of Industrial Science and Technology, National Institute of Bioscience and Human Technology (NIBH) as the Accession Number FERM BP-6814 on Aug. 2, 1999 and with Institute for Fermentation, Osaka (IFO) as the Accession Number IFO 16291 on Jun. 18, 1999.

*Escherichia coli* transformant DH5 α/pCR2.1-h0T022T obtained in Example 11 later described was on deposit with the Ministry of International Trade and Industry, Agency of Industrial Science and Technology, National Institute of Bioscience and Human Technology (NIBH) as the Accession Number FERM BP-6930 on Nov. 8, 1999 and with Institute for Fermentation, Osaka (IFO) as the Accession Number IFO 16330 on Oct. 27, 1999.

*Escherichia coli* transformant DH5 α/pCR2.1-h0T022G obtained in Example 11 later described was on deposit with the Ministry of International Trade and Industry, Agency of Industrial Science and Technology, National Institute of Bioscience and Human Technology (NIBH) as the Accession Number FERM BP-6931 on Nov. 8, 1999 and with Institute for Fermentation, Osaka (IFO) as the Accession Number IFO 16331 on Oct. 27, 1999.

*Escherichia coli* transformant MM294(DE3)/pTFCR-FRP-1 obtained in Example 18 later described was on deposit with the Ministry of International Trade and Industry, Agency of Industrial Science and Technology, National Institute of Bioscience and Human Technology (NIBH) as the Accession Number FERM BP-7313 on Sep. 28, 2000 and with Institute for Fermentation (IFO) as the Accession Number IFO 16476 on Sep. 19, 2000.

Anti-rat type RFRP-1 monoclonal antibody IF3 obtained in Example 12 later described was on deposit with the Ministry of International Trade and Industry, Agency of Industrial Science and Technology, National Institute of Bioscience and Human Technology (NIBH) as the Accession Number FERM BP-7463 on Feb. 21, 2001 and with Institute for Fermentation (IFO) as the Accession Number IFO 50527 on Jan. 16, 2001.

EXAMPLES

The present invention is described in detail below with reference to Examples, but not intended to limit the scope of the present invention thereto. The gene manipulation procedures using *Escherichia coli* were performed according to the methods described in the Molecular Cloning.

Example 1

Synthesis of cDNA from Human Fetal Brain Poly(A)$^+$RNA Fraction and Amplification of Physiologically Active Peptide cDNA by RT-PCR Oligo dT primer (Gibco BRL Inc.) was added as a primer to 1 μg of human fetal brain poly(A)$^+$RNA fraction available from Clonetech and cDNA was synthesized with reverse transcriptase from Moloney murine leukemia virus (Gibco BRL Inc.) using a buffer attached thereto. After completion of the reaction, the product was extracted with phenol:chloroform (1:1) and the extract was precipitated with ethanol. The precipitate was dissolved in 30 μl of TE. Using a 1 μl of aliquot of the thus prepared cDNA as a template, amplification was performed by PCR using the following two primers (F5 and F6).

```
                                    (SEQ ID NO:3)
F5: 5'-GGGCTGCACATAGAGACTTAATTTTAG-3'

                                    (SEQ ID NO:4)
F6: 5'-CTAGACCACCTCTATATAACTGCCCAT-3'
```

The reaction solution was composed of 20 μM each of the synthetic DNA primers (F5 and F6), 0.25 mM dNTPs, 0.5 μl of Ex Taq DNA polymerase and 5 μl of a buffer attached to the enzyme, which were mixed together to make the total volume of the reaction solution 50 μl. Using Thermal Cycler (Perkin-Elmer Co.) for amplification, one cycle was set to include 98° C. for 10 seconds, 63° C. for 20 seconds and 72° C. for 40 seconds. This cycle was repeated 40 times in total.

Using a 1 μl aliquot of the PCR product as a template, the following two primers (F1 and R5) were amplified by nested PCR.

```
                                         (SEQ ID NO:5)
F1: 5'-GCACATAGAGACTTAATTTTAGATTTAGAC-3'

                                         (SEQ ID NO:6)
R5: 5'-CATGCACTTTGACTGGTTTCCAGGTAT-3'
```

The reaction solution was composed of 20 μM each of the synthetic DNA primers (F1 and R5), 0.25 mM dNTPs, 0.5 μl of Ex Taq DNA polymerase and 5 μl of a buffer attached to the enzyme, to which were mixed together to make the total volume of the reaction solution 50 μl. Using Thermal Cycler (Perkin-Elmer Co.) for amplification, one cycle was set to include 98° C. for 10 seconds, 60° C. for 20 seconds and 72° C. for 40 seconds. This cycle was repeated 40 times in total. The amplification product was confirmed by 1.2% agarose electrophoresis and ethidium bromide staining.

Example 2

Subcloning of the PCR Products into Plasmid Vectors and Selection of Novel Physiologically Active Peptide Candidate Clone by Decoding Base Sequence of the Inserted cDNA Region The PCR products obtained after the PCR procedure in Example 1 were separated by using a 1.2% agarose gel. After DNA fragments were proven to be amplified to the desired size, the DNAs were recovered using Quiagen PCR purification kit (Quiagen). According to the protocol attached to TA Cloning Kit (Invitrogen Co.), the recovered DNAs were subcloned to plasmid vector pCR™2.1. The recombinant vectors were introduced into *Escherichia coli* JM109 competent cells (Takara Shuzo Co., Ltd.) for transformation. Then, the resulting transformant clones bearing a cDNA-inserted fragment were selected in an LB agar culture medium supplemented with ampicillin, IPTG and X-gal. Only transformant clones that showed white color were picked up with a sterilized toothpick to obtain transformant *Escherichia coli* JM109/phRF1.

After the individual clones were cultured overnight in an LB culture medium containing ampicillin, the clones were treated with an automated plasmid extracting machine (Kurabo Co., Ltd.) to prepare plasmid DNAs. An aliquot of the DNAs thus prepared was cleaved by EcoRI to confirm the size of the cDNA fragment inserted. An aliquot of the remaining DNAs was further treated with RNase, extracted with phenol/chloroform followed by concentrating the aliquot through ethanol precipitation. Sequencing was carried out by using DyeDeoxy Terminator Cycle Sequencing Kit (ABI Inc.), the DNAs were decoded using an automated fluorescent sequencer. The data of the base sequences obtained were read by DNASIS (Hitachi System Engineering Co., Ltd.). The base sequence determined is shown in FIG. 1.

The base sequence thus determined was subjected to homology retrieval and sequence analysis based on FIG. 1. The results reveal that the novel physiologically active peptide was encoded by the cDNA fragment inserted in the plasmid of the transformant *Escherichia coli* JM109/phRF1.

Example 3

Acquisition of Splicing Variant of the Physiologically Active Peptide cDNA from Human Fetal Brain cDNA Using as a template 1 ml of the human fetal brain cDNA prepared in Example 1, amplification was performed by PCR using the following two primers (F5 and hR1).

```
                                          (SEQ ID NO:3)
F5: 5'-GGGCTGCACATAGAGACTTAATTTTAG-3'

                                          (SEQ ID NO:7)
hR1: 5'-CAGCTTTAGGGACAGGCTCCAGGTTTC-3'
```

The reaction solution was composed of 20 pM each of the synthetic DNA primers (F5 and hR1), 0.25 mM dNTPs, 0.5 ml of Ex Taq DNA polymerase and a buffer attached to the enzyme, which were mixed together to make the total volume of the reaction solution 50 ml. Using Thermal Cycler (Perkin-Elmer Co.) for amplification, one cycle was set to include 98° C. for 10 seconds, 65° C. for 20 seconds and 72° C. for 20 seconds. This cycle was repeated 40 times in total. The amplification product was confirmed by 1.2% agarose electrophoresis and ethidium bromide staining. After the PCR product was proven to be amplified, the reaction product was purified using QUIA Quick PCR Purification Kit (Quiagen), followed by sequencing. The sequencing reaction was conducted using BigDye Deoxy Terminator Cycle Sequence Kit (ABI Inc.). The DNAs were decoded using an automated fluorescent sequencer (ABI377). The data of the base sequences obtained were read by DNASIS (Hitachi System Engineering Co., Ltd.). As a result, cDNA with the 3' terminus different from the cDNA obtained in Example 2 was obtained. The cDNA thus obtained in this Example was found to be a splicing variant of the cDNA obtained in Example 2. The base sequence determined (SEQ ID NO: 9) and the deduced amino acid sequence (SEQ ID NO: 8), are shown in FIG. 3.

Example 4

Acquisition of Physiologically Active Peptide cDNA from Bovine Hypothalamus poly(A)$^+$RNA Bovine type physiologically active peptide cDNA was obtained from bovine hypothalamus poly(A)$^+$RNA using Marathon cDNA Amplification Kit (Clontech). Using as a template bovine hypothalamus cDNA prepared in accordance with the manual attached to the Kit, the following four primers (bF6, bF7, bR6 and bR7) were synthesized and employed in combination with two primers AP1 and AP2 attached to the Kit to effect amplification by PCR.

```
                                          (SEQ ID NO:10)
bF6: 5'-GCCTAGAGGAGATCTAGGCTGGGAGGA-3'

                                          (SEQ ID NO:11)
bF7: 5'-GGGAGGAACATGGAAGAAGAAAGGAGC-3'
```

-continued

```
                                          (SEQ ID NO:12)
bR6: 5'-GATGGTGAATGCATGGACTGCTGGAGC-3'

                                          (SEQ ID NO:13)
bR7: 5'-TTCCTCCCAAATCTCAGTGGCAGGTTG-3'
```

For amplification of the 5' terminus (N-terminal region), a first PCR was carried out using the synthetic primers (bR6 and AP1). The reaction solution composed of 20 pM each of the synthetic DNA primers, 0.25 mM dNTPs, 0.5 ml of Klen Taq DNA polymerase and a buffer attached to the enzyme was made the total volume of the reaction solution 25 ml. Using Thermal Cycler (Perkin-Elmer Co.) for amplification, one cycle was set to include 98° C. for 10 seconds and 72° C. for 2 minutes, which cycle was repeated 5 times, further cycle was set to include 98° C. for 10 seconds and 70° C. for 2 minutes, which cycle was repeated 5 times, and another cycle set to include 98° C. for 10 seconds and 68° C. for 2 minutes and 30 seconds, which cycle was repeated 25 times. Then, the reaction solution of the first PCR was diluted to 10-fold, 1 ml of the aliquot was used as a template to perform a second PCR using (bF7 and AP2) as primers. The reaction solution composed of 20 pM each of the primers, 0.25 mM dNTPs, 0.5 ml of Klen Taq DNA polymerase and a buffer attached to the enzyme was made the total volume of the reaction solution 25 ml. Using a Thermal Cycler (Perkin-Elmer Co.) for amplification, one cycle was set to include 98° C. for 10 seconds and 72° C. for 2 minutes, which cycle was repeated 5 times, followed by another cycle set to include 98° C. for 10 seconds and 70° C. for 2 minutes, which cycle was repeated 5 times and then a further cycle set to 98° C. for 10 seconds and 68° C. for 2 minutes and 30 seconds, which cycle was repeated times.

For amplification of the 3' terminus (C-terminal region), a first PCR was carried out using the synthetic primers (bF6 and AP1). The reaction solution composed of 20 pM each of the primers, 0.25 mM dNTPs, 0.5 ml of Klen Taq DNA polymerase and a buffer attached to the enzyme was made the total volume of the reaction solution 25 ml. Using Thermal Cycler (Perkin-Elmer Co.) for amplification, one cycle was set to include 98° C. for 10 seconds and 72° C. for 2 minutes, which cycle was repeated 5 times, and another cycle set to include 98° C. for 10 seconds and 70° C. for 2 minutes, which cycle was repeated 5 times and a further cycle set to include 98° C. for 10 seconds and 68° C. for 2 minutes and 30 seconds, which cycle was repeated 25 times. Then, the reaction solution of the first PCR was diluted to 10-fold, 1 ml of the aliquot was used as a template to perform a second PCR using (bF7 and AP2) as primers. The reaction solution composed of 20 pM each of the primers, 0.25 mM dNTPs, 0.5 ml of Klen Taq DNA polymerase and a buffer attached to the enzyme was made the total volume of the reaction solution 25 ml. Using Thermal Cycler (Perkin-Elmer Co.) for amplification, one cycle was set to include 98° C. for 10 seconds and 72° C. for 2 minutes, which cycle was repeated 5 times, followed by another cycle set to include 98° C. for 10 seconds and 70° C. for 2 minutes, which cycle was repeated 5 times and then a further cycle set to 98° C. for 10 seconds and 68° C. for 2 minutes and 30 seconds, which cycle was repeated 35 times. The amplification products at the 5' and 3' termini were confirmed by 1.2% agarose gel electrophoresis and ethidium bromide staining, respectively. After the PCR product was confirmed to be amplified, the reaction product was purified using QIA quick PCR purification Kit (Quiagen), followed by sequencing. The sequencing reaction was conducted using BigDye Deoxy Terminator Cycle Sequence Kit (ABI). The DNAs were decoded using an automated fluorescent sequencer (ABI377).

The data of the base sequences obtained were read by DNASIS (Hitachi System Engineering Co., Ltd.). The base sequence determined (SEQ ID NO: 15) and the deduced amino acid sequence (SEQ ID NO: 14), are shown in FIG. 4.

Example 5

Acquisition of Physiologically Active Peptide cDNA from Rat Brain Poly(A)$^+$RNA Rat type physiologically active peptide cDNA was obtained from rat brain poly(A)$^+$RNA using Marathon cDNA Amplification Kit (Clontech). Using as a template rat brain cDNA prepared in accordance with the manual attached to the Kit, the following two primers were synthesized and employed in combination with two primers AP1 and AP2 attached to the Kit to effect amplification by PCR.

```
                                          (SEQ ID NO:16)
rLPR1: 5'-CCCTGGGGCTTCTTCTGTCTTCTATGT-3'

                                          (SEQ ID NO:17)
rLPF1: 5'-AGCGATTCATTTTATTGACTTTAGCA-3'
```

For amplification of the 5' terminus (N-terminal region), a first PCR was carried out using the primer set of rLPR1 and AP1. The reaction solution composed of 20 pM each of the primers, 0.1 mM dNTPs, 0.25 ml of Klen Taq DNA polymerase was made the total volume of the reaction solution 25 ml with a buffer attached to the enzyme. Using Thermal Cycler (Perkin-Elmer Co.) for amplification, one cycle was set to include 98° C. for 10 seconds and 72° C. for 2 minutes, which cycle was repeated 5 times, another cycle set to include 98° C. for 10 seconds and 70° C. for 2 minutes, which cycle was repeated 5 times and then a further cycle set to include 98° C. for 10 seconds and 68° C. for 2 minutes and 30 seconds, which cycle was repeated 25 times. Then, a second PCR was performed using the first PCR solution as a template, the first set of primers and the same compositions of he reaction solution. For amplification, one cycle was set to include 98° C. for 10 seconds and 72° C. for 2 minutes, which cycle was repeated 5 times, followed by another cycle set to include 98° C. for 10 seconds and 70° C. for 2 minutes, which cycle was repeated 5 times and then a further cycle set to 98° C. for 10 seconds (68° C. for 2 minutes and 30 seconds), which cycle was repeated 38 times.

For amplification of the 3' terminus (C-terminal region), a first PCR was carried out using the primer set of rLPF1 and AP1. The composition of the reaction solution was the same as that for amplification of the 5'-terminus (N-terminal region). For amplification, one cycle was set to include 98° C. for 10 seconds and 72° C. for 2 minutes, which cycle was repeated 5 times, another cycle set to include 98° C. for 10 seconds and 72° C. for 2 minutes, which cycle was repeated 5 times and a further cycle set to include 98° C. for 10 seconds, 65° C. for 20 seconds and 72° C. for 2 minutes, which cycle was repeated 25 times. Then, the reaction solution of the first PCR was used as a template to perform a second PCR using rLPF1 and AP2 primers. The composition of the reaction solution was the same as that for the first PCR. Using Thermal Cycler (Perkin-Elmer Co.) for amplification, one cycle was set to include 98° C. for 10 seconds and 72° C. for 2 minutes, which cycle was repeated 5 times, followed by another cycle set to include 98° C. for 10 seconds and 70° C. for 2 minutes, which cycle was repeated 5 times and then a further cycle set to 98° C. for 10 seconds, 65° C. for 20 seconds and 72° C. for 2 minutes, which cycle was repeated 38 times. The amplification products at the 5' and 3' termini were confirmed by 1.2% agarose gel electrophoresis and ethidium bromide staining, respectively. The PCR product band was purified using QIA quick Gel Extrication Kit (Quiagen), followed by sequencing. The sequencing was conducted in a manner similar to Example 3. The base sequence determined (SEQ ID NO: 19) and the deduced amino acid sequence (SEQ ID NO: 18) are shown in FIG. 5. Based on the sequences, two primers were synthesized around the initiation and termination codons.

```
                                           (SEQ ID NO:48)
ratF2: 5'-AATGGAAATTATTTCATCAAAGCGATTCAT-3'

                                           (SEQ ID NO:49)
ratR: 5'-CACCTATACTGACAGGAATGATGGCTCTCC-3'
```

Using as a template cDNA that was synthesized from rat hypothalamus poly(A)$^+$ RNA using AMV reverse transferase (Takara Shuzo Co., Ltd.) and random 9mer (Takara Shuzo Co., Ltd.), PCR was carried out by repeating 33 times a cycle set to include 98° C. for 10 seconds and 68° C. for 40 seconds. Using the reaction solution as a template, PCR was carried out by repeating 38 times a cycle set to include 98° C. for 10 seconds and 68° C. for 1 minute to obtain the PCR product of about 690 bp. The PCR product was inserted to cloning vector pCR2.1 TOPO following the instructions attached to TA cloning kit (Invitrogen Inc.), which was then introduced into *Escherichia coli* JM109 to obtain transformant *E. coli* JM109/prLPL6. The base sequence was determined in a manner similar to Example 3 (SEQ ID NO: 51), from which the amino acid sequence (SEQ ID NO: 50) was deduced.

Example 6

Acquisition of Mouse Type Physiologically Active Peptide cDNA from Mouse Brain Poly(A)$^+$RNA by the Marathon PCR Method and Confirmation of its Sequence To acquire mouse type physiologically active peptide cDNA from mouse brain poly(A)$^+$RNA, firstly 1 μg of mouse brain poly(A)$^+$RNA was reacted with SuperScript II RNase H-reverse transcriptase (Gibco BRL) at 42° C. for an hour in the presence of 2.5 pmols of oligo d(T) primer (Takara Shuzo Co., Ltd.), 0.5 mM dNTPs and 10 mM DTT to synthesize cDNA. Using the cDNA as a template, PCR was carried out using the following primers and Klen Taq DNA polymerase (Clontech), while repeating 39 times a cycle set to include 98° C. for 10 seconds, 56° C. for 20 seconds and 72° C. for 25 seconds.

```
                                           (SEQ ID NO:26)
FF2: 5'-GACTTAATTTTAGATTTAGACAAAATGGAA-3'

                                           (SEQ ID NO:27)
rR4: 5'-TTCTCCCAAACCTTTGGGGCAGGTT-3'
```

Further using the same primer set, PCR was carried out by repeating 25 times a cycle set to include 98° C. for 10 seconds, 60° C. for 20 seconds and 72° C. for 25 seconds. The amplification product was confirmed by 1.2% agarose gel electrophoresis and ethidium bromide staining. The band was purified using QIA quick Gel Extrication Kit (Quiagen), followed by sequencing in a manner similar to Example 3. To obtain the 5' and 3' terminal sequences of the mouse type physiologically active peptide cDNA fragment, cDNA was synthesized from 1 μg of mouse brain poly(A)$^+$ RNA in a manner similar to Example 5, using Marathon cDNA Amplification Kit (Clontech) to use the cDNA as a template. The following three primers were synthesized and used in combination with AP1 primer attached to the kit for PCR.

```
                                           (SEQ ID NO:28)
mF1: 5'-ACAGCAAAGAAGGTGACGGAAAATACTC-3'

                                           (SEQ ID NO:29)
mF3: 5'-ATAGATGAGAAAAGAAGCCCCGCAGCAC-3'

                                           (SEQ ID NO:30)
mR1: 5'-GTGCTGCGGGGCTTCTTTTCTCATCTAT-3'
```

For amplification of the 5' terminus, a first PCR was carried out using the primer set of mR1 and AP1. For amplification of the 3' terminus (C-terminal region), a first PCR was carried out using the primer set of mF1 and AP1. The reaction solution composed of 200 pM each of the primers, 0.1 mM dNTP, 0.25 ml of Klen Taq DNA polymerase was made the total volume of the reaction solution 25 ml with a buffer attached to the enzyme. For amplification, one cycle was set to include 98° C. for 10 seconds and 72° C. for 2 minutes, which cycle was repeated 5 times, another cycle set to include 98° C. for 10 seconds and 70° C. for 2 minutes, which cycle was repeated 5 times and a further cycle set to include 98° C. for 10 seconds and 68° C. for 2 minutes and 30 seconds, which cycle was repeated 25 times. Then, the reaction solution of the first PCR was used as a template to perform a second PCR. Amplification at the 5' terminus was performed using the same primer set as in the first PCR and for amplification at the 3' terminus, the same composition of the reaction solution as in the first PCR was prepared, using the primer set of mF3 and AP1. PCR was carried out by repeating 5 times a cycle set to include 98° C. for 10 seconds and 72° C. for 2 minutes, 5 times another cycle set to include 98° C. for 10 seconds and 70° C. for 2 minutes, and then 38 times a further cycle set to 98° C. for 10 seconds and 68° C. for 2 minutes and 30 seconds.

The amplification products at the 5' and 3' termini were confirmed by 1.2% agarose gel electrophoresis and ethidium bromide staining, respectively. The PCR product band was purified using QIA quick Gel Extrication Kit (Quiagen), followed by sequencing. The sequencing was conducted in a manner similar to Example 3.

Based on the sequences, two primers were further synthesized.

```
                                           (SEQ ID NO:31)
moF: 5'-TTTAGACTTAGACGAAATGGA-3'

                                           (SEQ ID NO:32)
moR: 5'-GCTCCGTAGCCTCTTGAAGTC-3'
```

Using as a template the above-described cDNA that was synthesized from mouse brain poly(A)$^+$ RNA using SuperScript II RNase H-reverse, PCR was carried out to amplify a fragment containing mouse physiologically active peptide full-length cDNA. The reaction was carried out using Klen Taq DNA polymerase (Clontech), by repeating 35 times a cycle set to include 98° C. for 10 seconds, 56° C. for 20 seconds and 72° C. for 15 seconds. The amplification product of about 600 bp was confirmed by 2% agarose electrophoresis and ethidium bromide staining. The band was purified using QIA quick Gel Extrication Kit (Quiagen), subcloned to cloning vector pCR2.1-TOPO (TOPO TA cloning kit, Invitrogen Inc.) and then introduced into *Escherichia coli* JM109 to obtain transformant *E. coli* JM109/μmLP4. The base sequence was determined in a manner similar to Example 3. The base sequence thus determined (SEQ ID NO: 34) and the deduced amino acid sequence (SEQ ID NO: 33) therefrom, are shown in FIG. 7.

Example 7

(1) Cloning of the cDNA Encoding the Rat "Area Around Brainstem"-derived G Protein-coupled Receptor Protein and Determination of the Base Sequence.

Using rat cerebellum-derived cDNA as a template and two primers, namely, primer 1 (SEQ ID NO: 35) and primer 2 (SEQ ID NO: 36), PCR was carried out. The reaction solution in the above reaction comprised of 1/10 volume of the cDNA, 1/50 of Advantage cDNA Polymerase Mix (CLONTEC Inc.), 0.2 μM of primer 1 (SEQ ID NO: 35), 0.2 μM of primer 2 (SEQ ID NO: 36), 200 μM dNTPs and a buffer attached to the enzyme to make the final volume 50 μl. The PCR was carried out by cycles of (1) 94° C. for 2 minutes, (2) then a cycle set to include 94° C. for 30 seconds followed by 72° C. for 2 minutes, which was repeated 3 times, (3) a cycle set to include 94° C. for 30 seconds followed by 68° C. for 2 minutes, which was repeated 3 times, (4) a cycle set to include 94° C. for 30 seconds followed by 64° C. for 30 seconds and 68° C. for 2 minutes, which was repeated 30 times, and (5) finally, extension reaction at 68° C. for 8 minutes. After completion of the PCR reaction, the product was subcloned to plasmid vector pCR2.1 (Invitrogen Inc.) following the instructions attached to the TA cloning kit (Invitrogen Inc.), which was then introduced into *Escherichia coli* DH5 α, and the clones containing the cDNA were selected on LB agar plates containing ampicillin. The sequence of each clone was analyzed to give the cDNA sequence (SEQ ID NO: 38) encoding the novel G protein-coupled receptor protein. The novel G protein-coupled receptor protein containing the amino acid sequence (SEQ ID NO: 1) deduced therefrom was designated rOT7T022L.

Plasmid pAK-rOT7T022L in which the cDNA (SEQ ID NO: 38) encoding the rat cerebellum-derived G protein-coupled receptor protein rOT7T022L of the present invention was subcloned was introduced into *Escherichia coli* DH10B according to a publicly known method to give transformant *Escherichia coli* DH10B/pAK-rOT7T022L.

(2) Establishment of G Protein-coupled Receptor Protein rOT7T022L-expressing CHO Cell CHOdhfr$^-$ cells of $1\times10^6$ were inoculated on Petri's dish of a 10 mm diameter for tissue culture followed by incubation for 24 hours. Using 20 μg of rOT7T022L-expressing vector pAK-rOT7T022L obtained (1), DNA-liposome complex was formed by the liposome method using a gene transfer kit (Gene Transfer, Nippon Gene Co.). After a fresh medium was exchanged for the medium, the DNA-liposome complex was added to the medium and incubated overnight. The medium was replaced with a fresh medium and further incubation was performed for one day followed by incubation for 2 days for transformant selection. The cells in the Petri's dish were recovered by treatment with trypsin-EDTA. By culturing again in a dilute cell density, the ratio of transformants was increased thereby to obtain stable clone of cell line CHO-rOT7T022L capable of expressing rOT7T022L in a high level.

(3) Synthesis of Met-Pro-His-Ser-Phe-Ala-Asn-Leu-Pro-Leu-Arg-Phe-$NH_2$ (SEQ ID NO: 39)

Commercially available p-methyl BHA resin, 0.5 mmole, (manufactured by Applied Biosystems, now Perkin-Elmer Inc.) was charged in a reaction tank of peptide synthesizer (430A manufactured by Applied Biosystems). After swelling with DCM, first amino acid Boc-Phe was activated with the HOBt/DCC method and then introduced into p-methyl BHA resin. The resin was treated with 50% TFA/DCM to remove Boc, wherein the amino group was liberated and neutralized with DIEA. Next amino acid Boc-Arg(Tos) was condensed to the amino group by the HOBt/DCC method. Ninhydrin test was conducted to examine if any unreacted amino group was present. After it was confirmed that the reaction was completed, Boc-Leu, Boc-Pro, Boc-Leu, Boc-Asn, Boc-Ala, Boc-Phe, Boc-Ser(Bzl), Boc-His(Bom), Boc-Pro and Boc-Met were introduced in this order. The resin in which all amino acids of the sequence were introduced was treated with 50% TFA/DCM to remove the Boc groups on the resin. Thereafter the resin was dried to give 0.73 g of Met-Pro-His (Bom)-Ser(Bzl)-Phe-Ala-Asn-Leu-Pro-Leu-Arg(Tos)-Phe-pMBHA-resin.

In a Teflon-made hydrogen fluoride reactor the resin, 0.25 g, was reacted in 15 ml of hydrogen fluoride together with 5.1 g of p-cresol at 0° C. for 60 minutes. After removing the hydrogen fluoride by distillation in vacuum, 100 ml of diethyl ether was added to the residue, stirred and filtrated through a glass filter followed by drying. The dried product was suspended in 50 ml of 50% acetic acid aqueous solution and stirred. After the peptide was extracted, it was separated from the resin and concentrated to about 5 ml in vacuum. The concentrate was applied to a column of Sephadex G-25 (2×90 cm) and developed with 50% acetic acid aqueous solution. Main fractions were collected and lyophilized. Next, the crudely purified peptide was dissolved in 1.5 ml of 5% thioglycolic acid/50% acetic acid. The solution was kept at 50° C. for 12 hours to reduce the Met-oxidized peptide. The peptide was applied to a reversed phase column filled up with LiChroprep (trade name) RP-18 (manufactured by MERCK Inc.) followed by repeating purification with gradient elution using 0.1% aqueous TFA and 33% acetonitrile aqueous solution containing 0.1% TFA. Fractions eluted at the acetonitrile concentration of about 27% were collected and lyophilized to give 26 mg of white powders.

Mass spectrum $(M+H)^+$ 1428.7 (calcd. 1428.8)

Elution time on HPLC: 18.0 mins.

Column conditions:

Column: Wakosil (trademark) 5C18 (4.6×100 mm)

Eluant: linear density gradient elution (25 mins.) with solution A to solution B, using solution A (5% aqueous acetonitrile solution containing 0.1% TFA) and solution B (55% aqueous acetonitrile solution containing 0.1% TFA)

Flow rate: 1.0 ml/min.

(4) Synthesis of Val-Pro-Asn-Leu-Pro-Gln-Arg-Phe-$NH_2$ (SEQ ID NO:40)

As in Example 7 (3) described above, Boc-Phe, Boc-Arg (Tos), Boc-Gln, Boc-Pro, Boc-Leu, Boc-Asn, Boc-Pro and Boc-Val were condensed in this order to give 0.43 g of Boc-Val-Pro-Asn-Leu-Pro-Gln-Arg(Tos)-Phe-pMBHA-resin. In a manner similar to the above, 0.22 g of the resin was treated with hydrogen fluoride and purified by column chromatography to give 46 mg of the product as white powders.

Mass spectrum $(M+H)^+$ 969.5 (calcd. 969.6)
Elution time on HPLC: 11.8 mins.

Column conditions:
Column: Wakosil (trademark) 5C18 (4.6×100 mm)
Eluant: linear density gradient elution (25 mins.) with solution A to solution B, using solution A (5% aqueous acetonitrile solution containing 0.1% TFA) and solution B (55% aqueous acetonitrile solution containing 0.1% TFA)
Flow rate: 1.0 ml/min.

(5) Synthesis of Ser-Ala-Gly-Ala-Thr-Ala-Asn-Leu-Pro-Arg-Ser-$NH_2$ (SEQ ID NO: 41)

As in Example 7 (3) described above, Boc-Ser(Bzl), Boc-Arg(Tos), Boc-Leu, Boc-Pro, Boc-Leu, Boc-Asn, Boc-Ala, Boc-Thr(Bzl), Boc-Ala, Boc-Gly, Boc-Ala and Boc-Ser(Bzl) were condensed in this order to give 0.62 g of Boc-Ser(Bzl)-Ala-Gly-Ala-Thr(Bzl)-Ala-Asn-Leu-Pro-Leu-Arg(Tos)-Ser (Bzl)-pMBHA-resin. In a manner similar to the above, 0.23 g of the resin was treated with hydrogen fluoride and purified by column chromatography to give 71 mg of the product as white powders.

Mass spectrum $(M+H)^+$ 1156.4 (calcd. 1156.6)
Elution time on HPLC: 11.8 mins.

Column conditions:
Column: Wakosil (trademark) 5C18 (4.6×100 mm)
Eluant: linear density gradient elution (25 mins.) with solution A to solution B, using solution A (5% aqueous acetonitrile solution containing 0.1% TFA) and solution B (55% aqueous acetonitrile solution containing 0.1% TFA)
Flow rate: 1.0 ml/min.

Figure 2:
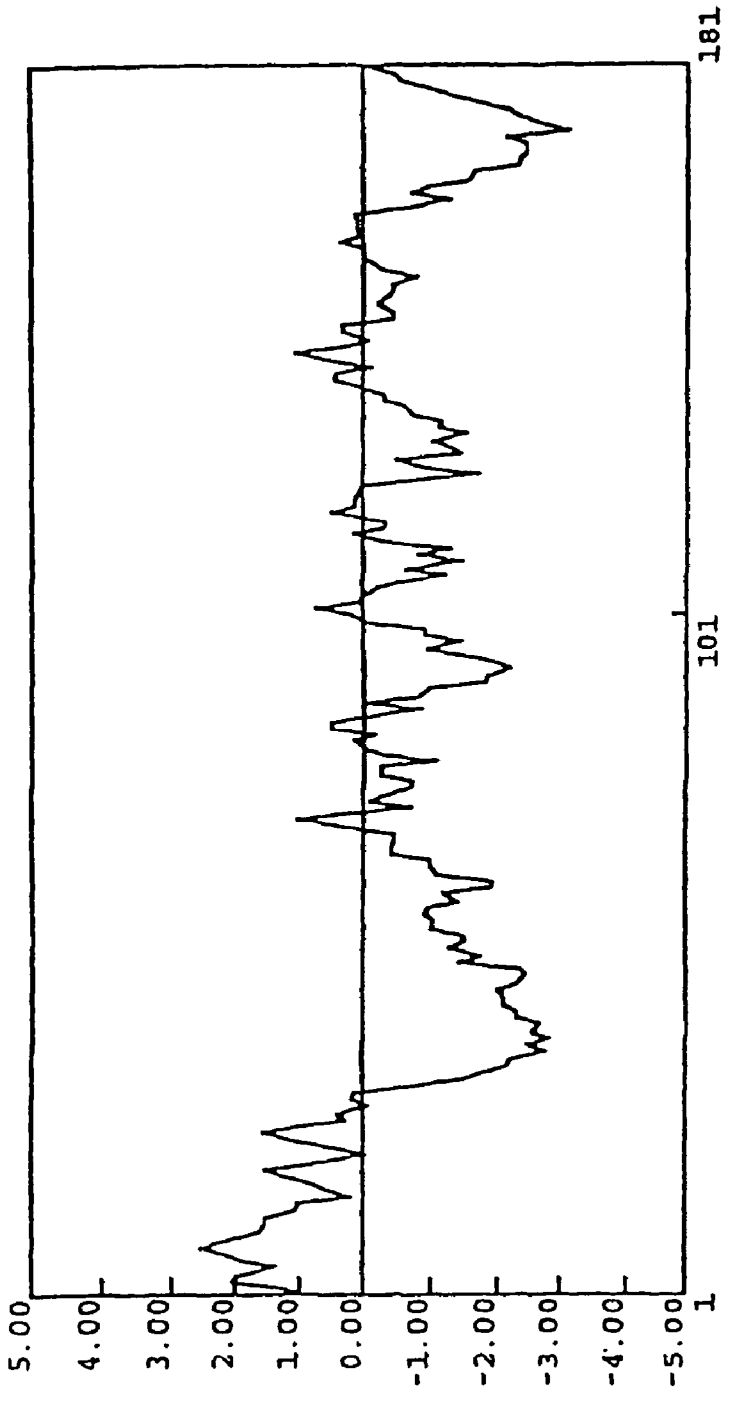
FIG. 2 shows the hydrophobic plotting of the polypeptide of the present invention.
Figure 8:
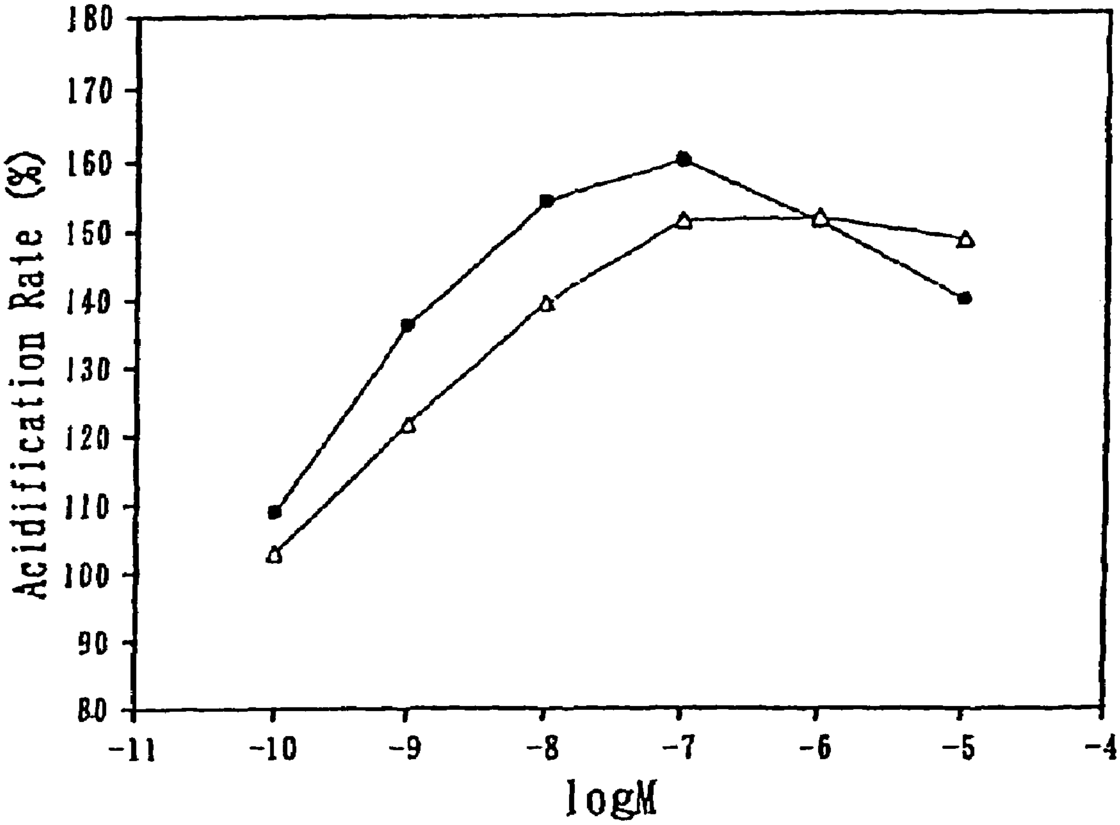
FIG. 8 shows the reactivity of peptides to r0T7T022L receptor-expressed CHO cells, assayed by Cytosensor in Example 7, in which ●-● and Δ-Δ denote MPHSFANLPLRF amide (SEQ ID NO: 39) and VPNLPQRF amide (SEQ ID NO: 40), respectively.

(6) Reaction of rOT7T022L (SEQ ID NO: 37) and Peptide MPHSFANLPLRFamide (SEQ ID NO: 39) and Peptide VPNLPQRFamide (SEQ ID NO: 40) with Site Sensor The rOT7T022L receptor-expressing CHO cells obtained in Example 7 (2) above were inoculated on capsules for site sensor in $2.7\times10^5$ cells/capsule. After incubation overnight, the site sensor was mounted to a workstation for the site sensor. A medium for assay (low buffered RMP11640 medium supplemented with 0.1% bovine serum albumin), which was set in the flow path of the site sensor, was supplied to the cells in a pump cycle of ON (80 seconds) and OFF (40 seconds). A rate of change in extracellular cells from 8 to 30 seconds after the pump stopped was calculated as an acidification rate. A change of the acidification rate with passage of time was monitored; when stable reading was obtained, the flow path was switched to expose each peptide to the cells for 7 minutes and 2 seconds. In the acidification rate of each well, the data for 3 cycles immediately before the peptide exposure was made 100% for standardization. Comparison of cell reactions reveals that rOT7T022L-expressing CHO cells strongly showed dose-dependent reaction with peptide MPHSFANLPLRFamide (SEQ ID NO: 39) and peptide VPNLPQRFamide (SEQ ID NO: 40) (FIG. 8).

Example 8

Construction of Transformant Bearing Splicing Variant cDNA for Human Novel Physiologically Active Peptide Candidate The reaction product obtained after PCR in Example 3 supra was separated using 1.2% agarose gel. After DNA fragments were proven to be amplified to the desired size, the DNAs were recovered using QIA Quick PCR purification kit (Qiagen). According to the protocol attached to TA Cloning Kit (Invitrogen Co.), the recovered DNAs were subcloned to plasmid vector pCR™2.1. The recombinant vectors were introduced into *Escherichia coli* JM109 competent cells (Takara Shuzo Co.) for transformation. Then, the resulting clones bearing the cDNA-inserted fragment were selected in an LB agar culture medium supplemented with ampicillin, IPTG and X-gal. Only transformant clones that showed white color were picked up with a sterilized toothpick. Each clone was cultured overnight in an LB culture medium supplemented with ampicillin and plasmid DNA was prepared using an automated plasmid extracting machine (Kurabo Co., Ltd.). An aliquot of the DNAs thus prepared was cleaved by EcoRI to confirm the size of the cDNA fragment inserted. An aliquot of the remaining DNAs was further treated with RNase, extracted with phenol/chloroform followed by concentrating the aliquot through ethanol precipitation. The reaction for sequencing was carried out by using DyeDeoxy Terminator Cycle Sequencing Kit (ABI Inc.), the DNAs were decoded using an automated fluorescent sequencer to obtain transformant *Escherichia coli* JM109/phRF2.

Example 9

Construction of Transformant Bovine Novel Physiologically is Active Peptide cDNA Using as a template 1 ml of the bovine hypothalamus cDNA prepared in Example 4, amplification was performed by PCR using the following two primers (bFF and bFR).

```
                                  (SEQ ID NO: 52)
bFF: 5'-TTCTAGATTTTGGACAAAATGGAAATT-3'

                                  (SEQ ID NO: 53)
bFR: 5'-CGTCTTTAGGGACAGGCTCCAGATTTC-3'
```

The reaction solution was composed of 20 pM each of the synthetic primers (bFF and bFR), 0.25 mM dNTPs, 0.5 ml of Ex Taq DNA polymerase and a buffer attached to the enzyme, which were mixed together to make the total volume 50 ml. Using Thermal Cycler (Perkin-Elmer Co.) for amplification, one cycle was set to include 98° C. for 10 seconds, 65° C. for 20 seconds and 72° C. for 20 seconds, which cycle was repeated 40 times. The amplification product was confirmed by 1.2% agarose electrophoresis and ethidium bromide staining. The reaction product obtained after PCR in Example 3 was separated using 1.2% agarose gel. After the DNA fragments were proven to be amplified to the desired size, the DNAs were recovered using Quigen PCR Purification Kit (Qiagen). According to the protocol attached to TA Cloning Kit (Invitrogen Co.), the recovered DNAs were subcloned to plasmid vector pCR™2.1. The recombinant DNA was introduced into *Escherichia coli* JM109 competent cells (Takara Shuzo Co., Ltd.) for transformation. Then, the resulting clones bearing a cDNA-inserted fragment were selected in an LB agar culture medium supplemented with ampicillin, IPTG and X-gal. Only clones that showed white color were picked up with a sterilized toothpick. Each clone was cultured overnight in an LB culture medium supplemented with ampicillin and plasmid DNA was prepared using an automated plasmid extracting machine (Kurabo Co., Ltd.). An aliquot of the DNAs thus prepared was cleaved by EcoRI to confirm the size of the cDNA fragment inserted. The DNAs prepared were further treated with RNase, extracted with phenol/chloroform and the extract was concentrated by ethanol precipitation. The reaction for sequencing was carried out by using DyeDeoxy Terminator Cycle Sequencing Kit (ABI Inc.), the DNAs were decoded using an automated fluorescent sequencer to obtain transformant *Escherichia coli* JM109/pbRF2.

Example 10

Activity of Suppressing cAMP Production of Peptide MPHSFANLPLRFamide (SEQ ID NO: 39) and Peptide VPNLPQRFamide (SEQ ID NO: 40) for rOT7T022L(SEQ ID NO: 37)-expressing CHO Cells It was confirmed by the site sensor experiment of Example 7 (6) that peptide MPHSFANLPLRFamide (SEQ ID NO: 39) and peptide VPNLPQRFamide (SEQ ID NO: 40) synthesized in Example 7 (3) and (4) specifically reacted with the rOT7T022L receptor. Next, the cAMP production suppression activity of the peptides for the rOT7T022L-expressing CHO cells were evaluated.

Figure 9:
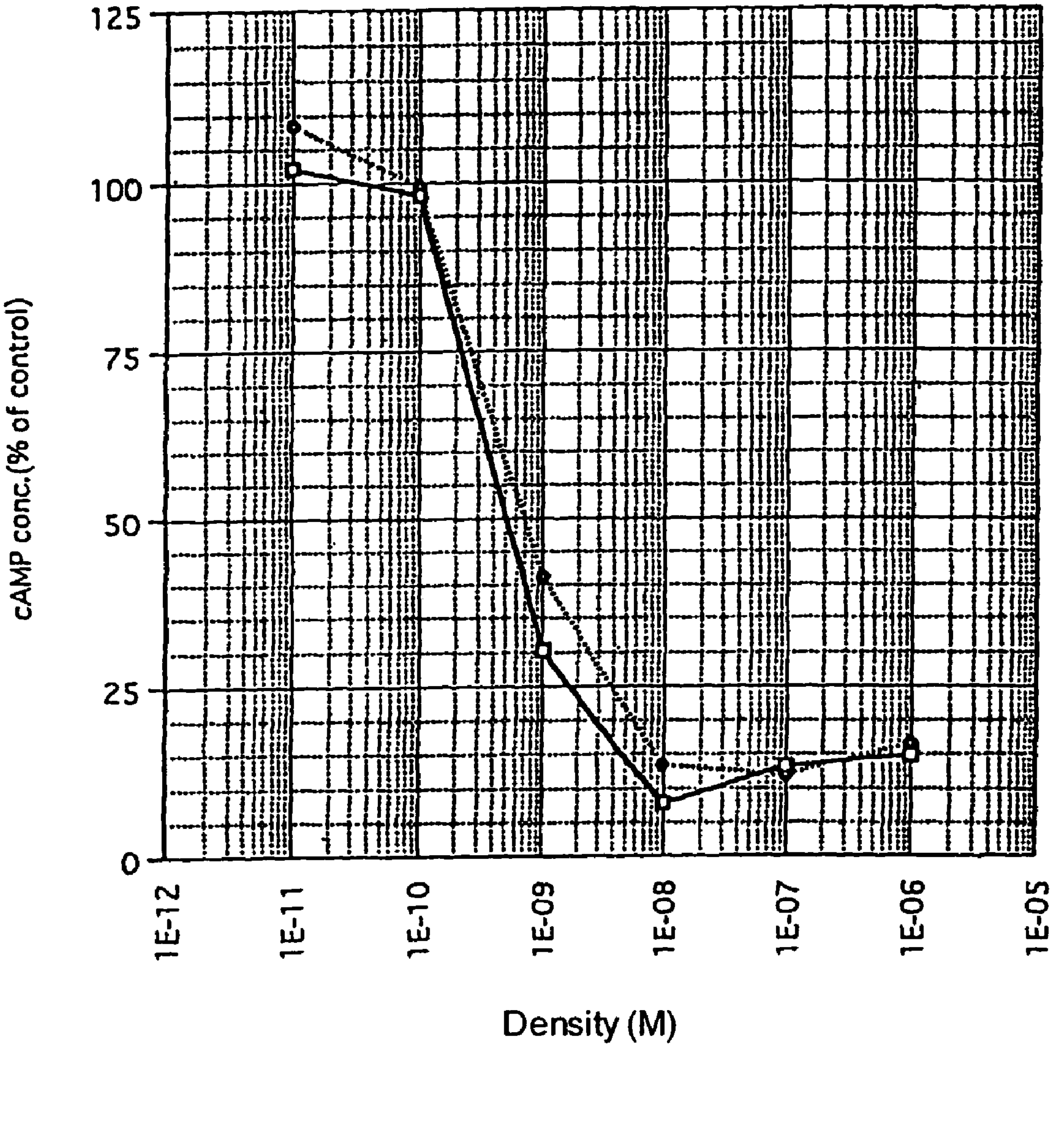
FIG. 9 shows the activity of MPHSFANLPLRF amide (SEQ ID NO: 39) and VPNLPQRF amide (SEQ ID NO: 40) for suppressing cAMP production against the r0T7T022L-expressed CHO cells, assayed in Example 10, in which □-□ and ●-● denote MPHSFANLPLRF amide (SEQ ID NO: 39) and VPNLPQRF amide (SEQ ID NO: 40), respectively.

The rOT7T022L-expressing CHO cells obtained in Example 7 (2) above was inoculated in a 24-well plate in a concentration of $1.0\times10^5$ cells/well, followed by incubation at 37° C. for 2 days. After the cells were washed with Hanks' buffer (HBSS) supplemented with 0.05% BSA and 0.2 mM IBMX, the system was allowed to stand at 37° C. for 30 minutes in the same buffer. Thirty minutes after, an assay buffer was prepared by adding the cells to Hanks' buffer supplemented with $10^{-6}$ M Forskolin and at the same time, the peptides described above were added thereto in various concentrations. Incubation was performed at 37° C. for 30 minutes. According to the method given in cAMP EIA Kit (Amersham Inc.), the cAMP level in the cells of each well was measured 30 minutes after. As shown in FIG. 9, peptide MPHSFANLPLRFamide (SEQ ID NO: 39) and peptide VPNLPQRFamide (SEQ ID NO: 40) showed a potent effect of cAMP production suppression on rOT7T022L receptor-expressing CHO cells at $IC_{50}$ of 0.5 nM and 0.7 nM, respectively, indicating that the peptide concentrations were very low.

Example 11

Cloning of the cDNA Encoding Human Hypothalamus G Protein-coupled Receptor Protein and Determination of its Base Sequence Using human hypothalamus cDNA (CLONTECH Inc.) as a template and two primers: primer 1, 5'-GTCGACATGG AGGGGGAGCC CTCCCAGCCT C-3' (SEQ ID NO: 57) and primer 2, 5'-ACTAGTTCAG ATATCCCAGG CTG-GMTGG-3' (SEQ ID NO: 58), PCR was carried out. The reaction solution in the above reaction comprised of 1/10 volume of the cDNA, which was used as a template, 1/50 volume of Advantage cDNA Polymerase Mix (CLONTECH Inc.), 0.2 μM of primer 1 (SEQ ID NO: 57), 0.2 μM of primer 2 (SEQ ID NO: 58), 200 μM dNTPs, 4% dimethylsulfoxide and a buffer attached to the enzyme to make the final volume 25 μl. The PCR was carried out by (1) a cycle of 94° C. for 2 minutes, (2) then a cycle set to include 94° C. for 20 seconds followed by 72° C. for 1 minute and 30 seconds, which was repeated 3 times, (3) a cycle set to include 94° C. for 20 seconds followed by 67° C. for 1 minute and 30 seconds, which was repeated 3 times, (4) a cycle set to include 94° C. for 20 seconds followed by 62° C. for 20 seconds and 68° C. for 1 minute and 30 seconds, which was repeated 38 times, and (5) finally, extension reaction at 68° C. for 7 minutes. After completion of the PCR reaction, the reaction product was subcloned to plasmid vector pCR2.1 (Invitrogen Inc.) following the instructions attached to the TA cloning kit (Invitrogen Inc.), which was then introduced into *Escherichia coli* DH5 a, and the clones carrying the cDNA were selected in an LB agar medium containing ampicillin. The sequence of each clone was analyzed to give the cDNA sequences (SEQ ID NO: 55 and SEQ ID NO: 56) encoding the novel G protein-coupled receptor protein. The two sequences are different by one base in the 597th residue but the deduced amino acid sequences are the same (SEQ ID NO: 57). Novel G protein-coupled receptor protein containing the amino acid sequence was designated hOT7T022. The two transformants were named *Escherichia coli* DH5 α/pCR2.1-hOT022T (containing cDNA shown by SEQ ID NO: 55) and *Escherichia coli* DH5 α/pCR2.1-hOT022G (containing cDNA shown by SEQ ID NO: 56).

Example 12

Preparation of Anti-rat RFRP-1 Monoclonal Antibody

A monoclonal antibody was prepared using a peptide added with one Cys residue to the C-terminal 12 amino acids (the C-terminal carboxyl group has been amidated: the 83 (Val)-94 (Phe) amino acid sequence in the amino acid sequence shown by SEQ ID NO: 50) at the N-terminus (C-VPHSMNLPLRF—$NH_2$) of rat type RFRP-1 as an antigen. Using maleimide, 0.6 mg of an antigen peptide was conjugated to bovine serum albumin (BSA). After 100 μg of the conjugate was subcutaneously injected in mouse 3 times for immunization, 50 μg of the conjugate was injected for booster immunization via the tail vein. On 4 days following the final immunization, mouse splenocytes were collected and fused with mouse myeloma cells (P3-X63Ag8-U1: Matsumoto et al., BBRC (1999), vol. 257, 264-268) using polyethylene glycol. Following the cell fusion, hybridoma cell 1F3 was selected and mass culture was conducted using INTREGRA CL-1000 to give the supernatant of 1F3. From the culture supernatant, anti-rat RFRP-1 monoclonal antibody was obtained using HiTrap rProtein A column (Pharmacia). Detection with Mouse mAb isotyping kit (Amersham) revealed that the subtype of this monoclonal antibody was IgG1 κ chain.

Example 13

Construction of Competitive EIA

First, the peptide used as an antigen in Example 12 was conjugated with horseradish peroxidase (HRP) using maleimide to prepare HRP-rat RFRP-1. Using this HRP-rat RFRP-1 and anti-rat RFRP-1 monoclonal antibody prepared in Example 12, competitive EIA was constructed.

To each well of a 96-well plate coated with 1.5 μg/well of anti-mouse IgGAM (Cappel) and blocked with Block ACE (Dai-Nippon Pharmaceutical Co., Ltd.), 50 μl of anti-rat RFRP-1 monoclonal antibody, which had been diluted with buffer (phosphate buffered saline (PBS) containing 2 mM EDTA, 0.4% BSA, 0.1M NaCl and 0.1% micro-O-protect), was added and 50 ml of a sample dissolved in the same buffer was also added to the plate. After incubation at 4° C. for 16 hours, 50 μl of anti-rat RFRP-1 monoclonal antibody diluted with the buffer was added to each well, followed by incubation at room temperature for 2 hours. After the plate was washed with PBS containing 0.1% Tween 20 (Sigma), the activity of HRP bound to each well was detected via colorforming reaction using TMB microwell peroxidase substrate system (Kirkegaard & Perry Labs), and absorbance was assayed at 450 nm. Change in absorbance when the RFRP-1-related peptide was added as the sample is shown in FIG. 11.

Example 14

Effects of Ligand Polypeptide on Pituitary Hormone Level in Plasma

The effect of the peptide shown by SEQ ID NO: 39 administered into the third ventricle on pituitary hormone level in plasma, was explored. Mature male Wistar rats (body weights at operation: about 290-350 g) were anesthetized with 50 mg/kg of pentobarbital, i.p., and each rat was immobilized in a rat brain stereotaxic apparatus. The incisor bar was set 3.3 mm lower from the interaural line. The skull was exposed, and using a dental drill a hole was made on the bone for implantation of a guide cannula.

In addition, an anchor screw was buried in one position around the hole. A stainless-steel guide cannula, AG-12 (0.4 mm inner diameter, 0.5 mm outer diameter, EICOM Co., Ltd.), was inserted in such a manner that its tip would be situated in the upper part of the third ventricle. Following the atlas of Paxinos and Watson (1986), the stereotaxic coordinates were set to AP: +7.2 mm (from the interaural line), L: 0.0 mm, and H: +2.0 mm (from the interaural line). The guide cannula was secured to the skull using instant adhesive, dental cement and an anchor screw. A stainless-steel dummy cannula, AD-12 (0.35 mm outer diameter, EICOM Co., Ltd.), was then passed through the guide cannula and locked in position with a cap nut (EICOM Co., Ltd.). After the operation the rats were housed in individual cages and kept for at least a week for postoperative recuperation before starting the experiment.

The operated rat was anesthetized with 50 mg/kg of pentobarbital, i.p., and immobilized in the dorsal position on a necropsy pad. A catheter (SP35, Natsume Seisakusho Co., Ltd.) was inserted into the right jugular vein. On the following day, 400 μl of blood was drawn through the jugular vein catheter. To prevent clotting, a syringe was filled beforehand with 20 μl of saline containing 200 U/ml of heparin. The cap nut and dummy cannula were removed from the rat skull and instead, a stainless steel microinjection cannula AMI13 (0.17 mm inner diameter, 0.35 mm outer diameter, EICOM Co., Ltd.) connected to a Teflon tube (50 cm long, 0.1 mm inner diameter, 0.4 mm outer diameter, EICOM Co., Ltd.) was inserted. The length of the microinjection cannula was adjusted beforehand so that its tip would be exposed from the guide cannula by 1 mm. One end of the Teflon tube was connected to a microsyringe pump and either PBS or the peptide shown by SEQ ID NO: 39 dissolved in PBS was injected, in a total volume of 10 μl, into the third ventricle at a flow rate of 5 μl/min. After a 1 minute standby time following the infusion, the microinjection cannula was disconnected and the dummy cannula was locked in position again with a cap nut. Immediately before the initiation of intraventricular administration and 10, 20, 30, 40, and 60 minutes after the initiation of administration, 400 μl aliquots of blood were collected via the cannula inserted into the jugular vein. Each blood sample collected was centrifuged (5,000 rpm, 10 min.) with a high-speed refrigerated microcentrifuge (MR-150, Tommy Seiko) and the supernatant (plasma) was recovered. The amount of prolactin in the plasma was determined by radioimmunoassay.

Figure 10:
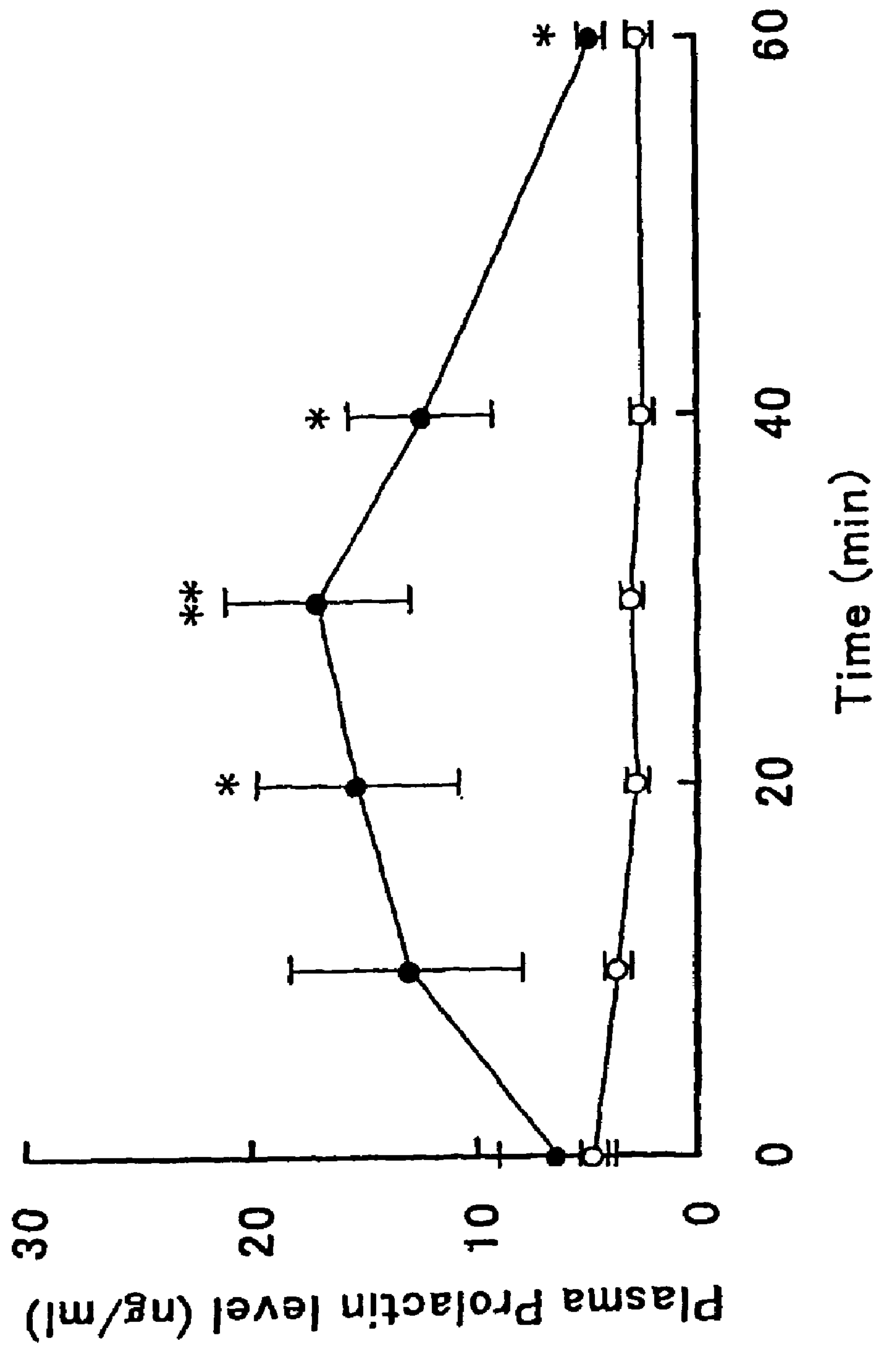
FIG. 10 shows the measurement results of prolactin level contained in plasma, which was carried out in EXAMPLE 14, wherein ●-● denote the prolactin level in the group receiving PBS in which the peptide represented by SEQ ID NO: 39 was dissolved, and ○-○ denotes the prolactin level in the control group receiving PBS alone.

The results were shown in terms of a mean±S.E.M. To examine if there was a significant difference between the group administered with the peptide shown by SEQ ID NO: 39 dissolved in PBS and the control group administered with PBS alone, Student's t-test was used. According to the two-tailed test, the risk percentage of 5% or less was assumed to be statistically significant. As shown in FIG. 10, the plasma prolactin level tended to increase at 10 minutes after the administration of 10 nmols of the peptide shown by SEQ ID NO: 39 into the third ventricle and significantly increased at 20, 30 and 40 minutes. Even at 60 minutes after the administration, a significant difference was noted, as compared to the control group. As to the levels of GH, LH, ACTH, and TSH in plasma, none showed any significant change.

Example 15

Purification Endogenous RGRP-1 from Bovine Hypothalamus

An RFRP-1-like immune activity was detected in crude fraction of the peptide from bovine hypothalamus by the competitive EIA constructed in Example 13. Using this RFRP-1-like immune activity as an indicator, endogenous RFRP-1 was purified from bovine hypothalamus.

First, 2.0 kg of frozen bovine hypothalamus was ground and boiled in 8.0 L of ultra pure water (milliQ water), acetic acid was added at a concentration of 1 M and the mixture was homogenized using a Polytron. Trifluoroacetic acid (TFA) was added to the supernatant at a concentration of 0.05%. The mixture was then applied to reversed phase C18 column (Prep C18 125 angstrom; Waters). The peptide bound to the column was stepwise eluted with 10, 30 and 50% acetonitrile containing 0.5% TFA. The 30% acetonitrile fraction was diluted with 2-fold volume of 20 mM ammonium acetate (pH 4.7), and the dilution was applied to ion exchange column HiPrep CM-Sepharose FF (Pharmacia). The peptide bound to the ion exchange column was stepwise eluted with 0.1, 0.2, 0.5 and 1.0 M NaCl in 20 mM ammonium acetate (pH 4.7) containing 10% acetonitrile. Then, 3-fold volume of chilled acetone was added to the 0.1 M NaCl fraction with the most abundant RFRP-1-like immune activity, and the precipitates were removed by centrifugation. The supernatant was concentrated in an evaporator. To the concentrated fraction was added TFA in a concentration of 0.1%, and the mixture was applied to reversed phase HPLC column RESOURCE RPC (Pharmacia) for further fractionation. The fractionation of RESOURCE RPC was carried out on a concentration gradient of 10-30% acetonitrile, in which the main RFRP-1-like activity was detected in the fraction of about 22% acetonitrile. The active fraction was separated by cation exchange column TSK gel CM-SW (Toso) using a concentration gradient of 0.2-0.6 M NaCl in 20 mM ammonium acetate (pH 4.7) containing 10% acetonitrile. The main RFRP-1-like activity was detected in the fraction of about 0.3 M NaCl. TFA was added to the fraction of CM-2SW column containing the RFRP-1-like immune activity in a concentration of 0.1%, and the mixture was applied to reversed phase column diphenyl 219TP5415 (Vydac) for further fractionation. By fractionation on a concentration gradient of 21-25% acetonitrile, the RFRP-1-like immune activity was eluted with 23% acetonitrile. The fraction containing this RFRP-1-like immune activity was subjected to final purification on reversed phase column μRPC C2/C18 SC 2.1/10, using a concentration gradient of 22-23% acetonitrile. Thus, a single peak coincident with the RFRP-1-like immune activity was detected (FIG. 12).

Example 16

N-Terminal Amino Acid Sequencing of the Finally Purified Product and Determination of its Molecular Weight by Mass Spectrum The N-terminal amino acids of the finally purified product obtained in Example 15 were sequenced with a protein sequencer (model 491 cLC; Applied Biosystems). As a result, the amino acid sequence shown by S-L-T-F-E-E-V-K-D-X-A-P-K-l-K-M-N-K-P-V- (wherein X is an unidentified amino acid residue) (SEQ ID NO: 63) was obtained.

Also, the molecular weight of the finally purified product using ESI-MS (Thermoquest) was found to be 3997.0.

These analytical results reveal that the finally purified product from bovine hypothalamus coincided with the peptide composed of 35 amino acids from 58 (Ser) to 92 (Phe) in amino acid sequence shown by SEQ ID NO: 14.

Example 17

Preparation of Structural Gene of a Peptide having the Amino Acid Sequence Shown by SEQ ID NO: 1, Wherein the C-terminal Carboxyl Group has been Amidated (Hereinafter Sometimes Referred to as hRFRP-1(37))

Using 4 DNA fragments (#1: SEQ ID NO: 15; #4: SEQ ID NO: 18; #1: SEQ ID NO: 18; manufactured by Kikotech Co., Ltd.) (#2: SEQ ID NO: 16; #3: SEQ ID NO: 17; manufactured by Amersham Pharmacia Biotech, Inc.) shown by SEQ ID NO: 59 through SEQ ID NO: 62, the structural gene of hRFRP-1(37) was prepared by a publicly known method.

a) Phosphorylation of DNA Oligomers

In 100 µL of a reaction solution for phosphorylation [50 mM Tris-HCl (pH 7.6), 10 mM MgCl$_2$, 1 mM spermidine, 10 mM dithiothreitol, 0.1 mg/mL bovine serum albumin, 1 mM ATP, 10 U T4 polynucleotide kinase (Nippon Gene)], 1 µg each of the two oligomers, except for #1 and #4 supposed to form the 5' ends, were reacted at 37° C. for 1 hour to phosphorylate the 5'-ends. After phenol treatment, the aqueous phase was recovered and 2-fold volume of ethanol was added thereto. Then, the mixture was cooled to −70° C. and centrifuged to precipitate DNA.

b) Ligation of DNA Fragments

The phosphorylated DNA fragments obtained in a) above and 1 µg each of #1 and #4 were combined and added to 10 mM Tris/HCl, 2 mM EDTA (pH 8.0) to make a total volume of 120 µL. The mixture was kept at 80° C. for 10 minutes and then gradually cooled to room temperature for annealing. Using TaKaRa DNA Ligation Kit ver. 2 (Takara Shuzo), ligation was carried out. To 30 µL of the annealing solution, 30 µL of Solution II supplied with the kit was added. After thoroughly mixing them, 60 µL of Solution I supplied with the kit was added and the mixture was reacted at 37° C. for 1 hour to effect ligation. After phenol treatment, the aqueous phase was recovered and 2-fold volume of ethanol was added thereto. Then, the mixture was cooled to −70° C. and centrifuged to precipitate DNA.

c) Phosphorylation of the 5' Ends

The precipitate was dissolved in 10 µL of TE buffer (10 mM Tris-HCl (pH 8.0), 1 mM EDTA), and the solution was reacted at 37° C. for 1 hour in 100 µL of a reaction solution for phosphorylation [50 mM Tris-HCl (pH 7.6), 10 mM MgCl$_2$, 1 mM spermidine, 10 mM dithiothreitol, 0.1 mg/mL bovine serum albumin, 1 mM ATP, 10 U T4 polynucleotide kinase (Nippon Gene)] to phosphorylate the 5' ends. After phenol treatment, the aqueous phase was recovered and 2-fold volume of ethanol was added thereto. Then, the mixture was cooled to −70° C. and centrifuged to precipitate DNA.

Example 18

Preparation of hRFRP-1(37) Expression Plasmid

The pTFC (described in JPA 2000-270871) as the expression vector was digested with NdeI and AvaI (Takara Shuzo Co., Ltd.) at 37° C. for 4 hours and electrophoresed on a 1% agarose gel. A4.4 kb DNA fragment was extracted using QIAquick Gel Extraction Kit (Qiagen) and dissolved in 25 µL of TE buffer. The NedI and AvaI fragment of this pTFC and the structural gene of hRFRP-1(37) prepared as above were ligated using TaKaRa DNA Ligation Kit ver. 2 (Takara Shuzo). Using a 10 µl aliquot of the reaction solution, E. coli JM 109 competent cells (Toyobo Co., Ltd.) were transformed and the transformants were seeded on an LB agar medium containing 10 µg/ml of tetracycline followed by incubation at 37° C. overnight. The tetracycline-resistant colony formed was selected. This transformant was incubated overnight in LB medium, and plasmid pTFCRFRP-1 was prepared using QIAprep8 Miniprep Kit (Qiagen). The base sequence of this pTFCRFRP-1 structural gene part was verified using Model 377 DNA sequencer of Applied Systems, Inc. E. coli MM294 (DE3) was transformed by plasmid pTFCRFRP-1 to give RFRP-1-CS23-fused protein expressed *Escherichia coli* MM294 (DE3)/pTFCRFRP-1 (FIG. 13).

Example 19

The transformant obtained in Example 18 was subjected to shaking culture at 37° C. for 8 hours in a 2 liter volume of flask charged with 1 L of LB medium containing 5.0 mg/L of tetracycline (1% peptone, 0.5% yeast extract, 0.5% sodium chloride). The culture broth obtained was transferred to a fermentation tank of 50 L volume charged with 19 liters of the main fermentation medium (1.68% sodium monohydrogenphosphate, 0.3% potassium dihydrogenphosphate, 0.1% ammonium chloride, 0.05% sodium chloride, 0.05% magnesium sulfate, 0.02% defoaming agent, 0.00025% ferrous sulfate, 0.00025% thiamine hydrochloride, 1.5% glucose, 1.5% Casamino acid) to initiate aeration spinner culture at 30° C. At the point of time when the turbidity showed a Klett value of about 500 was obtained, isopropyl-β-D-thiogalactopyranoside was added at a final concentration of 12 mg/L followed by incubation for additional 4 hours. After the incubation, the culture was centrifuged to give about 500 g of the wet cells. The cells were frozen and stored at −80° C.

Example 20

Acquisition of hRFRP-1(37)

To 500 g of the cells obtained in EXAMPLE 6 was added 1000 ml of 0.2 mM Tris/HCl (pH 8.0) solution, and the mixture was agitated for about 4 hours followed by centrifugation (10000 rpm, 60 minutes). The supernatant was diluted with 29 liters of 50 mM Tris/HCl (pH 8.0) supplemented with 0.6 M arginine and 1 mM dithiothreitol. After standing at 10° C. overnight, the pH was adjusted to 6.0 with conc. hydrochloric acid. The mixture was passed through an AF-Heparin Toyopearl 650M column (11.3 cm ID×13 cmL, Toso) equilibrated with 50 mM phosphate buffer (pH 6.0) for adsorption. After the column was rinsed, elution was carried out with 50 mM phosphate buffer, 2M NaCl, pH 6.0 to recover 1000 ml of the polypeptide of the present invention hRFRP-1(37)-CS23 fusion protein-containing eluate.

This eluate was concentrated using Pellicon Mini Cassette (Millipore Corp.) with constant addition of 0.1 M acetic acid to give a solution of hRFRP-1(37)-CS23 fusion protein in 0.1 M acetic acid. Urea was added to this solution at a final concentration of 6 M, followed by addition of 445 mg of 1-cyano-4-dimethylaminopyridinium (DMAP-CN), and the reaction was carried out at room temperature for 15 minutes. After completion of the reaction, the reaction mixture was applied onto a Sephadex G-25 column (46 mm ID×600 mmL, Pharmacia) equilibrated with 10% acetic acid and elution was carried out with the same 10% acetic acid as used for the equilibration at a flow rate of 6 ml/min to give an S-cyanated hRFRP-1(37)-CS23 fusion protein fraction. This eluate was concentrated and desalted using Pellicon Mini Cassette (Millipore Corp.) to give a desalted solution of hRFRP-1(37)-CS23 fusion protein. Urea was added to this desalted solution urea at a final concentration of 6 M, followed by further addition of 25% aqueous ammonia at a final concentration of 3 M. The reaction was carried out at room temperature for 15 minutes. After completion of the reaction, the reaction mixture was adjusted to pH 6.0 with acetic acid to give hRFRP-1(37). This reaction mixture was applied onto an SP-5PW column (5.5 mm ID×30 mmL, Toso) equilibrated with 50 mM phosphate buffer (pH 6.5) containing 3 M urea for adsorption. After the column was rinsed, elution was carried out on a gradient of 0 to 50% B (B=50 mM MES buffer+1 M NaCl+3 M urea) to recover hRFRP-1(35). This hRFRP-1(37) fraction was further applied onto an ODS-120T column (21.5 mm ID×300 mmL, Toso) equilibrated with 0.1% trifluoroacetic acid (TFA) for adsorption. After the column was rinsed, elution was carried out a gradient concentration of 30 to 60% B (B=80% acetonitrile/0.1% TFA). The resulting hRFRP-1(37) is fractions were pooled (elution time: 45 minutes) and lyophilized to give about lyophilized powders of hRFRP-1(37).

Example 21

Comparison in the Agonist Activity Between Various RF Amide Peptides on Human 0T7T022 Receptor-expressing CHO Cells Human 0T7T022 receptor-expressing CHO cells obtained by a modification of the method described in WO 00/29441 were inoculated on a 24-well plate in a concentration of $3\times10^5$ cells/well. After incubation overnight, the cells were rinsed with Hanks' buffer (HBSS) supplemented with 0.05% BSA and 0.2 mM IBMX, and then preincubated at 37° C. for 30 minutes in the same buffer. Next, the buffer was exchanged by Hanks' buffer (HBSS) supplemented with 0.05% BSA and 0.2 mM IBMX, or HBSS further added with 1 μM forskolin only, or HBSS added with 1 μM forskolin and peptide of various concentrations, followed by incubation at 37° C. for 30 minutes. After completion of the incubation, cAMP in the cells of each well was extracted and quantified according to the method of cAMP EIA Kit (Amersham Inc.). An inhibition rate of the increased cAMP level in the cells by the forskolin treatment was calculated with the respective concentrations of the peptide. The dose-response curve as shown in FIG. 14 was obtained. The $ED_{50}$ levels of the peptides were hRFRP-1-12 (peptide having the 81 (Met) to 92 (Phe) amino acid sequence in SEQ ID NO: 1 (○)) (4.5 nM); hRFRP-1-37 (peptide having the 56 (Ser) to 92 (Phe) amino acid sequence in SEQ ID NO: 1 (■)) (21 nM); rRFRP-1-37 (peptide having the 58 (Ser) to 94 (Phe) amino acid sequence in SEQ ID NO: 50 (◇)) (30 nM); hRFRP-2-12 (peptide having the 101 (Phe) to 112 (Ser) amino acid sequence in SEQ ID NO: 1 (▲)); hRFRP-3-8 (peptide having the 124 (Val) to 131 (Phe) amino acid sequence in SEQ ID NO: 1 (□)) (9.9 nM); PQRFamide (peptide shown by Pro-Gln-Arg-Phe-$NH_2$ (◆) (SEQ ID NO: 64)) (1000 nM or more); LPLRFamide (peptide shown by Leu-Pro-Leu-Arg-Phe-$NH_2$ (●) (SEQ ID NO: 65)) (36 nM); and NPFF (peptide shown by Asn-Pro-Phe-Phe (Δ) (SEQ ID NO: 66)) (140 nM), respectively.

Example 22

Study of the Effects of Pertussis Toxin by RFRP Peptide on is the Activation of Human 0T7T022 Receptor Human 0T7T022 receptor-expressing CHO cells obtained in Example 21 were inoculated on a 24-well plate in a concentration of $1\times10^5$ cells/well. After culturing overnight, the medium was exchanged by a medium added with 100 ng/ml pertussis toxin (Sigma, Inc.) or with a control medium followed by further incubation overnight. The cells were rinsed with Hanks' buffer (HBSS) supplemented with 0.05% BSA and 0.2 mM IBMX and then preincubated at 37° C. for 30 minutes in the same buffer. Next, the cells were incubated at 37° C. for 30 minutes after the buffer was exchanged by Hanks' buffer alone (HBSS) supplemented with 0.05% BSA and 0.2 mM IBMX (black column), or by HBSS further added with 1 μM forskolin only (white column), or by HBSS added with 1 μM forskolin and 0.1 μM RFRP-1-12 (peptide having the 81 (Met) to 92 (Phe) amino acid sequence in SEQ ID NO: 1) (hatched column). After completion of the incubation, cAMP in the cells of each well was extracted and quantified according to the method of cAMP EIA Kit (Amersham, Inc.). As shown in FIG. 15, since the cAMP production inhibiting activity by RFRP-1-12 was lost in the cells treated with pertussis toxin, it was demonstrated that the 0T7T022 receptor-mediated cAMP production inhibiting activity is conjugated to pertussis toxin-sensitive G protein a subunit, Gi (suppressive) or Go.

INDUSTRIAL APPLICABILITY

The polypeptide, receptor protein, etc. of the present invention exhibits, e.g., a nerve cell stimulating activity and thus can be employed as a pharmaceutical composition for the treatment of neuropathy. The polypeptide or receptor protein of the present invention is useful as a reagent for screening a compound that accelerates or inhibits the activities of the polypeptide or receptor protein of the present invention, or its salts. These compounds obtained by the screening are expected to be useful as an agent for the treatment/prevention of neuropathy. Furthermore, antibodies to the polypeptide or receptor protein of the present invention can recognize the polypeptide or receptor protein of the present invention specifically and can be used for quantification of the polypeptide or receptor protein of the present invention in a test sample fluid.

What is claimed is:

1. A method for screening a compound that alters the binding property between a ligand and a protein or a salt thereof, which comprises:

(i) providing an isolated protein or a salt thereof comprising an amino acid sequence selected from the group consisting of:

(a) SEQ ID NO: 54;

(b) SEQ ID NO: 54 of which 1 to 30 amino acids are deleted;

(c) SEQ ID NO: 54 to which 1 to 30 amino acids are added;

(d) SEQ ID NO: 54 in which 1 to 30 amino acids are substituted by other amino acids; and (e) a combination of the amino acid sequences of(b) to (d);

wherein said protein is capable of binding a partial peptide of a polypeptide containing the amino acid sequence of SEQ ID NO: 1, comprising (1) amino acid residues 81 (Met) to 92 (Phe) of SEQ ID NO: 1 or (2) amino acid residues 124 (Val) to 131 (Phe) of SEQ ID NO: 1, its amide or ester, or a salt thereof;

(ii) contacting (a) the isolated protein or a salt thereof with (b) a polypeptide comprising (1) amino acid residues 81 (Met) to 92 (Phe) of SEQ ID NO: 1 or (2) amino acid residues 124 (Val) to 131 (Phe) of SEQ ID NO: 1, its amide or ester, or a salt thereof, and measuring binding activity between the isolated protein or a salt thereof and the polypeptide or its amide or ester, or a salt thereof;

(iii) contacting (a) the isolated protein or a salt thereof and a test compound with (b) a polypeptide comprising (1) amino acid residues 81 (Met) to 92 (Phe) of SEQ ID NO: 1 or (2) amino acid residues 124 (Val) to 131 (Phe) of SEQ ID NO: 1, its amide or ester, or a salt thereof, and measuring binding activity between the isolated protein or a salt thereof and the polypeptide or its amide or ester, or a salt thereof; and (iv) comparing the activity of case (ii) with the activity of case (iii).

* * * * *

SEQUENCE LISTING

<160> NUMBER OF SEQ ID NOS: 66

<210> SEQ ID NO 1
<211> LENGTH: 180
<212> TYPE: PRT
<213> ORGANISM: Human

<400> SEQUENCE: 1

```
Met Glu Ile Ile Ser Ser Lys Leu Phe Ile Leu Leu Thr Leu Ala Thr
 1               5                  10                  15

Ser Ser Leu Leu Thr Ser Asn Ile Phe Cys Ala Asp Glu Leu Val Met
            20                  25                  30

Ser Asn Leu His Ser Lys Glu Asn Tyr Asp Lys Tyr Ser Glu Pro Arg
        35                  40                  45

Gly Tyr Pro Lys Gly Glu Arg Ser Leu Asn Phe Glu Glu Leu Lys Asp
    50                  55                  60

Trp Gly Pro Lys Asn Val Ile Lys Met Ser Thr Pro Ala Val Asn Lys
65                  70                  75                  80

Met Pro His Ser Phe Ala Asn Leu Pro Leu Arg Phe Gly Arg Asn Val
                85                  90                  95

Gln Glu Glu Arg Ser Ala Gly Ala Thr Ala Asn Leu Pro Leu Arg Ser
            100                 105                 110

Gly Arg Asn Met Glu Val Ser Leu Val Arg Arg Val Pro Asn Leu Pro
        115                 120                 125

Gln Arg Phe Gly Arg Thr Thr Thr Ala Lys Ser Val Cys Arg Met Leu
    130                 135                 140

Ser Asp Leu Cys Gln Gly Ser Met His Ser Pro Cys Ala Asn Asp Leu
145                 150                 155                 160

Phe Tyr Ser Met Thr Cys Gln His Gln Glu Ile Gln Asn Pro Asp Gln
                165                 170                 175

Lys Gln Ser Arg
            180
```

<210> SEQ ID NO 2
<211> LENGTH: 540
<212> TYPE: DNA
<213> ORGANISM: Human

<400> SEQUENCE: 2

```
atggaaatta tttcatcaaa actattcatt ttattgactt tagccacttc aagcttgtta      60

acatcaaaca ttttttgtgc agatgaatta gtgatgtcca atcttcacag caaagaaaat     120

tatgacaaat attctgagcc tagaggatac ccaaaagggg aaagaagcct caattttgag     180

gaattaaaag attggggacc aaaaaatgtt attaagatga gtacacctgc agtcaataaa     240

atgccacact ccttcgccaa cttgccattg agatttggga ggaacgttca agaagaaaga     300

agtgctggag caacagccaa cctgcctctg agatctggga agaaatatgga ggtgagcctc     360

gtgagacgtg ttcctaacct gccccaaagg tttgggagaa caacaacagc caaaagtgtc     420

tgcaggatgc tgagtgattt gtgtcaagga tccatgcatt caccatgtgc caatgactta     480

ttttactcca tgacctgcca gcaccaagaa atccagaatc ccgatcaaaa acagtcaagg     540
```

<210> SEQ ID NO 3
<211> LENGTH: 27
<212> TYPE: DNA
<213> ORGANISM: Artificial  Sequence -continued
<220> FEATURE:
<223> OTHER INFORMATION: primer

<400> SEQUENCE: 3
gggctgcaca tagagactta attttag 27

<210> SEQ ID NO 4
<211> LENGTH: 27
<212> TYPE: DNA
<213> ORGANISM: Artificial Sequence
<220> FEATURE:
<223> OTHER INFORMATION: primer

<400> SEQUENCE: 4
ctagaccacc tctatataac tgcccat 27

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
gcacatagag acttaatttt agatttagac 30

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6
catgcacttt gactggtttc caggtat 27

<210> SEQ ID NO 7
<211> LENGTH: 27
<212> TYPE: DNA
<213> ORGANISM: Artificial Sequence
<220> FEATURE:
<223> OTHER INFORMATION: primer

<400> SEQUENCE: 7
cagctttagg gacaggctcc aggtttc 27

<210> SEQ ID NO 8
<211> LENGTH: 196
<212> TYPE: PRT
<213> ORGANISM: Human

<400> SEQUENCE: 8

```
Met Glu Ile Ile Ser Ser Lys Leu Phe Ile Leu Leu Thr Leu Ala Thr
 1               5                  10                  15

Ser Ser Leu Leu Thr Ser Asn Ile Phe Cys Ala Asp Glu Leu Val Met
            20                  25                  30

Ser Asn Leu His Ser Lys Glu Asn Tyr Asp Lys Tyr Ser Glu Pro Arg
        35                  40                  45

Gly Tyr Pro Lys Gly Glu Arg Ser Leu Asn Phe Glu Glu Leu Lys Asp
    50                  55                  60

Trp Gly Pro Lys Asn Val Ile Lys Met Ser Thr Pro Ala Val Asn Lys
65                  70                  75                  80

Met Pro His Ser Phe Ala Asn Leu Pro Leu Arg Phe Gly Arg Asn Val
```

-continued

```
                85                  90                  95

Gln Glu Glu Arg Ser Ala Gly Ala Thr Ala Asn Leu Pro Leu Arg Ser
            100                 105                 110

Gly Arg Asn Met Glu Val Ser Leu Val Arg Arg Val Pro Asn Leu Pro
        115                 120                 125

Gln Arg Phe Gly Arg Thr Thr Thr Ala Lys Ser Val Cys Arg Met Leu
    130                 135                 140

Ser Asp Leu Cys Gln Gly Ser Met His Ser Pro Cys Ala Asn Asp Leu
145                 150                 155                 160

Phe Tyr Ser Met Thr Cys Gln His Gln Glu Ile Gln Asn Pro Asp Gln
                165                 170                 175

Lys Gln Ser Arg Arg Leu Leu Phe Lys Lys Ile Asp Asp Ala Glu Leu
            180                 185                 190

Lys Gln Glu Lys
        195


<210> SEQ ID NO 9
<211> LENGTH: 588
<212> TYPE: DNA
<213> ORGANISM: Human

<400> SEQUENCE: 9

atggaaatta tttcatcaaa actattcatt ttattgactt tagccacttc aagcttgtta      60

acatcaaaca ttttttgtgc agatgaatta gtgatgtcca atcttcacag caaagaaaat     120

tatgacaaat attctgagcc tagaggatac ccaaaagggg aaagaagcct caattttgag     180

gaattaaaag attggggacc aaaaaatgtt attaagatga gtacacctgc agtcaataaa     240

atgccacact ccttcgccaa cttgccattg agatttggga ggaacgttca agaagaaaga     300

agtgctggag caacagccaa cctgcctctg agatctggaa gaaatatgga ggtgagcctc     360

gtgagacgtg ttcctaacct gccccaaagg tttgggagaa caacaacagc caaaagtgtc     420

tgcaggatgc tgagtgattt gtgtcaagga tccatgcatt caccatgtgc caatgactta     480

ttttactcca tgacctgcca gcaccaagaa atccagaatc ccgatcaaaa acagtcaagg     540

agactgctat tcaagaaaat agatgatgca gaattgaaac aagaaaaa                 588


<210> SEQ ID NO 10
<211> LENGTH: 27
<212> TYPE: DNA
<213> ORGANISM: Artificial  Sequence
<220> FEATURE:
<223> OTHER INFORMATION: primer

<400> SEQUENCE: 10

gcctagagga gatctaggct gggagga                                          27


<210> SEQ ID NO 11
<211> LENGTH: 27
<212> TYPE: DNA
<213> ORGANISM: Artificial  Sequence
<220> FEATURE:
<223> OTHER INFORMATION: primer

<400> SEQUENCE: 11

gggaggaaca tggaagaaga aaggagc                                          27


<210> SEQ ID NO 12
<211> LENGTH: 27
<212> TYPE: DNA
```

-continued

<213> ORGANISM: Artificial Sequence
<220> FEATURE:
<223> OTHER INFORMATION: primer

<400> SEQUENCE: 12
gatggtgaat gcatggactg ctggagc 27

<210> SEQ ID NO 13
<211> LENGTH: 27
<212> TYPE: DNA
<213> ORGANISM: Artificial Sequence
<220> FEATURE:
<223> OTHER INFORMATION: primer

<400> SEQUENCE: 13
ttcctcccaa atctcagtgg caggttg 27

<210> SEQ ID NO 14
<211> LENGTH: 196
<212> TYPE: PRT
<213> ORGANISM: Bovine

<400> SEQUENCE: 14

```
Met Glu Ile Ile Ser Leu Lys Arg Phe Ile Leu Leu Met Leu Ala Thr
 1               5                  10                  15

Ser Ser Leu Leu Thr Ser Asn Ile Phe Cys Thr Asp Glu Ser Arg Met
            20                  25                  30

Pro Asn Leu Tyr Ser Lys Lys Asn Tyr Asp Lys Tyr Ser Glu Pro Arg
        35                  40                  45

Gly Asp Leu Gly Trp Glu Lys Glu Arg Ser Leu Thr Phe Glu Glu Val
    50                  55                  60

Lys Asp Trp Ala Pro Lys Ile Lys Met Asn Lys Pro Val Val Asn Lys
65                  70                  75                  80

Met Pro Pro Ser Ala Ala Asn Leu Pro Leu Arg Phe Gly Arg Asn Met
                85                  90                  95

Glu Glu Glu Arg Ser Thr Arg Ala Met Ala His Leu Pro Leu Arg Leu
            100                 105                 110

Gly Lys Asn Arg Glu Asp Ser Leu Ser Arg Trp Val Pro Asn Leu Pro
        115                 120                 125

Gln Arg Phe Gly Arg Thr Thr Thr Ala Lys Ser Ile Thr Lys Thr Leu
    130                 135                 140

Ser Asn Leu Leu Gln Gln Ser Met His Ser Pro Ser Thr Asn Gly Leu
145                 150                 155                 160

Leu Tyr Ser Met Ala Cys Gln Pro Gln Glu Ile Gln Asn Pro Gly Gln
                165                 170                 175

Lys Asn Leu Arg Arg Arg Gly Phe Gln Lys Ile Asp Asp Ala Glu Leu
            180                 185                 190

Lys Gln Glu Lys
        195
```

<210> SEQ ID NO 15
<211> LENGTH: 588
<212> TYPE: DNA
<213> ORGANISM: Bovine

<400> SEQUENCE: 15
atggaaatta tttcattaaa acgattcatt ttattgatgt tagccacttc aagcttgtta 60
acatcaaaca tcttctgcac agacgaatca aggatgccca atctttacag caaaaagaat 120

-continued

```
tatgacaaat attccgagcc tagaggagat ctaggctggg agaaagaaag aagtcttact    180

tttgaagaag taaaagattg ggctccaaaa attaagatga ataaacctgt agtcaacaaa    240

atgccacctt ctgcagccaa cctgccactg agatttggga ggaacatgga agaagaaagg    300

agcactaggg cgatggccca cctgcctctg agactcggaa aaaatagaga ggacagcctc    360

tccagatggg tcccaaatct gccccagagg tttggaagaa caacaacagc caaaagcatt    420

accaagaccc tgagtaattt gctccagcag tccatgcatt caccatctac caatgggcta    480

ctctactcca tggcctgcca gccccaagaa atccagaatc ctggtcaaaa gaacctaagg    540

agacggggat tccagaaaat agatgatgca gaattgaaac aagaaaaa                588
```

<210> SEQ ID NO 16
<211> LENGTH: 27
<212> TYPE: DNA
<213> ORGANISM: Artificial Sequence
<220> FEATURE:
<223> OTHER INFORMATION: primer

<400> SEQUENCE: 16

```
ccctggggct tcttctgtct tctatgt                                         27
```

<210> SEQ ID NO 17
<211> LENGTH: 26
<212> TYPE: DNA
<213> ORGANISM: Artificial Sequence
<220> FEATURE:
<223> OTHER INFORMATION: primer

<400> SEQUENCE: 17

```
agcgattcat tttattgact ttagca                                          26
```

<210> SEQ ID NO 18
<211> LENGTH: 203
<212> TYPE: PRT
<213> ORGANISM: Rat

<400> SEQUENCE: 18

```
Met Glu Ile Ile Ser Ser Lys Arg Phe Ile Leu Leu Thr Leu Ala Thr
 1               5                  10                  15

Ser Ser Phe Leu Thr Ser Asn Thr Leu Cys Ser Asp Glu Leu Met Met
            20                  25                  30

Pro His Phe His Ser Lys Glu Gly Tyr Gly Lys Tyr Tyr Gln Leu Arg
        35                  40                  45

Gly Ile Pro Lys Gly Val Lys Glu Arg Ser Val Thr Phe Gln Glu Leu
    50                  55                  60

Lys Asp Trp Gly Ala Lys Lys Asp Ile Lys Met Ser Pro Ala Pro Ala
 65                  70                  75                  80

Asn Lys Val Pro His Ser Ala Ala Asn Leu Pro Leu Arg Phe Gly Arg
                85                  90                  95

Asn Ile Glu Asp Arg Arg Ser Pro Arg Ala Arg Ala Asn Met Glu Ala
            100                 105                 110

Gly Thr Met Ser His Phe Pro Ser Leu Pro Gln Arg Phe Gly Arg Thr
        115                 120                 125

Thr Ala Arg Arg Ile Thr Lys Thr Leu Ala Gly Leu Pro Gln Lys Ser
    130                 135                 140

Leu His Ser Leu Ala Ser Ser Glu Ser Leu Tyr Ala Met Thr Arg Gln
145                 150                 155                 160

His Gln Glu Ile Gln Ser Pro Gly Gln Glu Gln Pro Arg Lys Arg Val
```

-continued

```
            165                 170                 175

Phe Thr Glu Thr Asp Asp Ala Glu Arg Lys Gln Glu Lys Ile Gly Asn
        180                 185                 190

Leu Gln Pro Val Leu Gln Gly Ala Met Lys Leu
    195                 200
```

<210> SEQ ID NO 19
<211> LENGTH: 609
<212> TYPE: DNA
<213> ORGANISM: Rat

<400> SEQUENCE: 19

```
atggaaatta tttcatcaaa gcgattcatt ttattgactt tagcaacttc aagcttctta     60

acttcaaaca ccctttgttc agatgaatta atgatgcccc attttcacag caaagaaggt    120

tatggaaaat attaccagct gagaggaatc ccaaaagggg taaaggaaag aagtgtcact    180

tttcaagaac tcaaagattg gggggcaaag aaagatatta agatgagtcc agcccctgcc    240

aacaaagtgc cccactcagc agccaacctt cccctgaggt ttgggaggaa catagaagac    300

agaagaagcc ccagggcacg ggccaacatg gaggcaggga ccatgagcca ttttcccagc    360

ctgccccaaa ggtttgggag aacaacagcc agacgcatca ccaagacact ggctggtttg    420

ccccagaaat ccctgcactc cctggcctcc agtgaatcgc tctatgccat gacccgccag    480

catcaagaaa ttcagagtcc tggtcaagag caacctagga aacgggtgtt cacggaaaca    540

gatgatgcag aaaggaaaca agaaaaaata ggaaacctcc agccagtcct tcaaggggct    600

atgaagctg                                                            609
```

<210> SEQ ID NO 20
<211> LENGTH: 12
<212> TYPE: DNA
<213> ORGANISM: Artificial Sequence
<220> FEATURE:
<223> OTHER INFORMATION: base sequence encoding RFGR sequence
<220> FEATURE:
<221> NAME/KEY: variation
<222> LOCATION: 3
<223> OTHER INFORMATION: n means any of a, g, t or c.
<220> FEATURE:
<221> NAME/KEY: variation
<222> LOCATION: 9
<223> OTHER INFORMATION: n means any of a, g, t or c.

<400> SEQUENCE: 20

```
mgnttyggna ar                                                         12
```

<210> SEQ ID NO 21
<211> LENGTH: 12
<212> TYPE: DNA
<213> ORGANISM: Artificial Sequence
<220> FEATURE:
<223> OTHER INFORMATION: base sequence encoding RSGK sequence
<220> FEATURE:
<221> NAME/KEY: variation
<222> LOCATION: 3
<223> OTHER INFORMATION: n means any of a, g, t or c.
<220> FEATURE:
<221> NAME/KEY: variation
<222> LOCATION: 9
<223> OTHER INFORMATION: n means any of a, g, t or c.
<220> FEATURE:
<221> NAME/KEY: variation
<222> LOCATION: 12
<223> OTHER INFORMATION: n means any of a, g, t or c.

<400> SEQUENCE: 21

-continued

```
mgnttyggnm gn                                                         12


<210> SEQ ID NO 22
<211> LENGTH: 12
<212> TYPE: DNA
<213> ORGANISM: Artificial  Sequence
<220> FEATURE:
<223> OTHER INFORMATION: base sequence encoding RSGR sequence
<220> FEATURE:
<221> NAME/KEY: variation
<222> LOCATION: 3
<223> OTHER INFORMATION: n means any of a, g, t or c.
<220> FEATURE:
<221> NAME/KEY: variation
<222> LOCATION: 6
<223> OTHER INFORMATION: n means any of a, g, t or c.
<220> FEATURE:
<221> NAME/KEY: variation
<222> LOCATION: 9
<223> OTHER INFORMATION: n means any of a, g, t or c.

<400> SEQUENCE: 22

mgnwsnggna ar                                                         12


<210> SEQ ID NO 23
<211> LENGTH: 12
<212> TYPE: DNA
<213> ORGANISM: Artificial  Sequence
<220> FEATURE:
<223> OTHER INFORMATION: base sequence encoding RLGK sequence
<220> FEATURE:
<221> NAME/KEY: variation
<222> LOCATION: 3
<223> OTHER INFORMATION: n means any of a, g, t or c.
<220> FEATURE:
<221> NAME/KEY: variation
<222> LOCATION: 6
<223> OTHER INFORMATION: n means any of a, g, t or c.
<220> FEATURE:
<221> NAME/KEY: variation
<222> LOCATION: 9
<223> OTHER INFORMATION: n means any of a, g, t or c.
<220> FEATURE:
<221> NAME/KEY: variation
<222> LOCATION: 12
<223> OTHER INFORMATION: n means any of a, g, t or c.

<400> SEQUENCE: 23

mgnwsnggnm gn                                                         12


<210> SEQ ID NO 24
<211> LENGTH: 12
<212> TYPE: DNA
<213> ORGANISM: Artificial  Sequence
<220> FEATURE:
<223> OTHER INFORMATION: base sequence encoding RLGK sequence
<220> FEATURE:
<221> NAME/KEY: variation
<222> LOCATION: 3
<223> OTHER INFORMATION: n means any of a, g, t or c.
<220> FEATURE:
<221> NAME/KEY: variation
<222> LOCATION: 6
<223> OTHER INFORMATION: n means any of a, g, t or c.
<220> FEATURE:
<221> NAME/KEY: variation
<222> LOCATION: 9
<223> OTHER INFORMATION: n means any of a, g, t or c.

<400> SEQUENCE: 24

mgnytnggna ar                                                         12
```

-continued

<210> SEQ ID NO 25
<211> LENGTH: 12
<212> TYPE: DNA
<213> ORGANISM: Artificial Sequence
<220> FEATURE:
<223> OTHER INFORMATION: base sequence encoding RLGR sequence
<220> FEATURE:
<221> NAME/KEY: variation
<222> LOCATION: 3
<223> OTHER INFORMATION: n means any of a, g, t or c.
<220> FEATURE:
<221> NAME/KEY: variation
<222> LOCATION: 6
<223> OTHER INFORMATION: n means any of a, g, t or c.
<220> FEATURE:
<221> NAME/KEY: variation
<222> LOCATION: 9
<223> OTHER INFORMATION: n means any of a, g, t or c.
<220> FEATURE:
<221> NAME/KEY: variation
<222> LOCATION: 12
<223> OTHER INFORMATION: n means any of a, g, t or c.

<400> SEQUENCE: 25
mgnytnggnm gn 12

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26
gacttaattt tagatttaga caaaatggaa 30

<210> SEQ ID NO 27
<211> LENGTH: 25
<212> TYPE: DNA
<213> ORGANISM: Artificial Sequence
<220> FEATURE:
<223> OTHER INFORMATION: primer

<400> SEQUENCE: 27
ttctcccaaa cctttggggc aggtt 25

<210> SEQ ID NO 28
<211> LENGTH: 28
<212> TYPE: DNA
<213> ORGANISM: Artificial Sequence
<220> FEATURE:
<223> OTHER INFORMATION: primer

<400> SEQUENCE: 28
acagcaaaga aggtgacgga aaatactc 28

<210> SEQ ID NO 29
<211> LENGTH: 28
<212> TYPE: DNA
<213> ORGANISM: Artificial Sequence
<220> FEATURE:
<223> OTHER INFORMATION: primer

<400> SEQUENCE: 29
atagatgaga aaagaagccc cgcagcac 28

<210> SEQ ID NO 30
<211> LENGTH: 28

-continued

<212> TYPE: DNA
<213> ORGANISM: Artificial Sequence
<220> FEATURE:
<223> OTHER INFORMATION: primer

<400> SEQUENCE: 30
gtgctgcggg gcttcttttc tcatctat 28

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
tttagactta gacgaaatgg a 21

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
gctccgtagc ctcttgaagt c 21

<210> SEQ ID NO 33
<211> LENGTH: 188
<212> TYPE: PRT
<213> ORGANISM: Mouse

<400> SEQUENCE: 33

```
Met Glu Ile Ile Ser Leu Lys Arg Phe Ile Leu Leu Thr Val Ala Thr
 1               5                  10                  15

Ser Ser Phe Leu Thr Ser Asn Thr Phe Cys Thr Asp Glu Phe Met Met
            20                  25                  30

Pro His Phe His Ser Lys Glu Gly Asp Gly Lys Tyr Ser Gln Leu Arg
        35                  40                  45

Gly Ile Pro Lys Gly Glu Lys Glu Arg Ser Val Ser Phe Gln Glu Leu
    50                  55                  60

Lys Asp Trp Gly Ala Lys Asn Val Ile Lys Met Ser Pro Ala Pro Ala
65                  70                  75                  80

Asn Lys Val Pro His Ser Ala Ala Asn Leu Pro Leu Arg Phe Gly Arg
                85                  90                  95

Thr Ile Asp Glu Lys Arg Ser Pro Ala Ala Arg Val Asn Met Glu Ala
            100                 105                 110

Gly Thr Arg Ser His Phe Pro Ser Leu Pro Gln Arg Phe Gly Arg Thr
        115                 120                 125

Thr Ala Arg Ser Pro Lys Thr Pro Ala Asp Leu Pro Gln Lys Pro Leu
    130                 135                 140

His Ser Leu Gly Ser Ser Glu Leu Leu Tyr Val Met Ile Cys Gln His
145                 150                 155                 160

Gln Glu Ile Gln Ser Pro Gly Gly Lys Arg Thr Arg Arg Gly Ala Phe
                165                 170                 175

Val Glu Thr Asp Asp Ala Glu Arg Lys Pro Glu Lys
            180                 185
```

<210> SEQ ID NO 34

-continued

```
<211> LENGTH: 564
<212> TYPE: DNA
<213> ORGANISM: Mouse

<400> SEQUENCE: 34

atggaaatta tttcattaaa acgattcatt ttattgactg tggcaacttc aagcttctta      60

acatcaaaca ccttctgtac agatgagttc atgatgcctc attttcacag caaagaaggt     120

gacggaaaat actcccagct gagaggaatc ccaaaagggg aaaaggaaag aagtgtcagt     180

tttcaagaac taaaagattg gggggcaaag aatgttatta agatgagtcc agcccctgcc     240

aacaaagtgc cccactcagc agccaacctg cccctgagat ttggaaggac catagatgag     300

aaaagaagcc ccgcagcacg ggtcaacatg gaggcaggga ccaggagcca tttccccagc     360

ctgccccaaa ggtttgggag aacaacagcc agaagcccca agacacccgc tgatttgcca     420

cagaaacccc tgcactcact gggctccagc gagttgctct acgtcatgat ctgccagcac     480

caagaaattc agagtcctgg tggaaagcga acgaggagag gagcgtttgt ggaaacagat     540

gatgcagaaa ggaaaccaga aaaa                                            564


<210> SEQ ID NO 35
<211> LENGTH: 27
<212> TYPE: DNA
<213> ORGANISM: Artificial  Sequence
<220> FEATURE:
<223> OTHER INFORMATION: primer

<400> SEQUENCE: 35

agtcgacagt atggaggcgg agccctc                                          27


<210> SEQ ID NO 36
<211> LENGTH: 29
<212> TYPE: DNA
<213> ORGANISM: Artificial  Sequence
<220> FEATURE:
<223> OTHER INFORMATION: primer

<400> SEQUENCE: 36

gactagttca aatgttccag gccgggatg                                        29


<210> SEQ ID NO 37
<211> LENGTH: 432
<212> TYPE: PRT
<213> ORGANISM: Rat

<400> SEQUENCE: 37

Met Glu Ala Glu Pro Ser Gln Pro Pro Asn Gly Ser Trp Pro Leu Gly
1               5                   10                  15

Gln Asn Gly Ser Asp Val Glu Thr Ser Met Ala Thr Ser Leu Thr Phe
            20                  25                  30

Ser Ser Tyr Tyr Gln His Ser Ser Pro Val Ala Ala Met Phe Ile Ala
        35                  40                  45

Ala Tyr Val Leu Ile Phe Leu Leu Cys Met Val Gly Asn Thr Leu Val
    50                  55                  60

Cys Phe Ile Val Leu Lys Asn Arg His Met Arg Thr Val Thr Asn Met
65                  70                  75                  80

Phe Ile Leu Asn Leu Ala Val Ser Asp Leu Leu Val Gly Ile Phe Cys
                85                  90                  95

Met Pro Thr Thr Leu Val Asp Asn Leu Ile Thr Gly Trp Pro Phe Asp
            100                 105                 110
```

-continued

```
Asn Ala Thr Cys Lys Met Ser Gly Leu Val Gln Gly Met Ser Val Ser
        115                 120                 125

Ala Ser Val Phe Thr Leu Val Ala Ile Ala Val Glu Arg Phe Arg Cys
    130                 135                 140

Ile Val His Pro Phe Arg Glu Lys Leu Thr Leu Arg Lys Ala Leu Phe
145                 150                 155                 160

Thr Ile Ala Val Ile Trp Ala Leu Ala Leu Leu Ile Met Cys Pro Ser
                165                 170                 175

Ala Val Thr Leu Thr Val Thr Arg Glu Glu His His Phe Met Leu Asp
            180                 185                 190

Ala Arg Asn Arg Ser Tyr Pro Leu Tyr Ser Cys Trp Glu Ala Trp Pro
        195                 200                 205

Glu Lys Gly Met Arg Lys Val Tyr Thr Ala Val Leu Phe Ala His Ile
    210                 215                 220

Tyr Leu Val Pro Leu Ala Leu Ile Val Val Met Tyr Val Arg Ile Ala
225                 230                 235                 240

Arg Lys Leu Cys Gln Ala Pro Gly Pro Ala Arg Asp Thr Glu Glu Ala
                245                 250                 255

Val Ala Glu Gly Gly Arg Thr Ser Arg Arg Arg Ala Arg Val Val His
            260                 265                 270

Met Leu Val Met Val Ala Leu Phe Phe Thr Leu Ser Trp Leu Pro Leu
        275                 280                 285

Trp Val Leu Leu Leu Leu Ile Asp Tyr Gly Glu Leu Ser Glu Leu Gln
    290                 295                 300

Leu His Leu Leu Ser Val Tyr Ala Phe Pro Leu Ala His Trp Leu Ala
305                 310                 315                 320

Phe Phe His Ser Ser Ala Asn Pro Ile Ile Tyr Gly Tyr Phe Asn Glu
                325                 330                 335

Asn Phe Arg Arg Gly Phe Gln Ala Ala Phe Arg Ala Gln Leu Cys Trp
            340                 345                 350

Pro Pro Trp Ala Ala His Lys Gln Ala Tyr Ser Glu Arg Pro Asn Arg
        355                 360                 365

Leu Leu Arg Arg Arg Val Val Val Asp Val Gln Pro Ser Asp Ser Gly
    370                 375                 380

Leu Pro Ser Glu Ser Gly Pro Ser Ser Gly Val Pro Gly Pro Gly Arg
385                 390                 395                 400

Leu Pro Leu Arg Asn Gly Arg Val Ala His Gln Asp Gly Pro Gly Glu
                405                 410                 415

Gly Pro Gly Cys Asn His Met Pro Leu Thr Ile Pro Ala Trp Asn Ile
            420                 425                 430


<210> SEQ ID NO 38
<211> LENGTH: 1299
<212> TYPE: DNA
<213> ORGANISM: Rat

<400> SEQUENCE: 38

atggaggcgg agccctccca gcctcccaac ggcagctggc ccctgggtca gaacgggagt      60

gatgtggaga ccagcatggc aaccagcctc accttctcct cctactacca acactcctct     120

ccggtggcag ccatgttcat cgcggcctac gtgctcatct tcctcctctg catggtgggc     180

aacaccctgg tctgcttcat tgtgctcaag aaccggcaca tgcgcactgt caccaacatg     240

tttatcctca acctggccgt cagcgacctg ctggtgggca tcttctgcat gcccacaacc     300

cttgtggaca accttatcac tggttggcct tttgacaacg ccacatgcaa gatgagcggc     360
```

-continued

```
ttggtgcagg gcatgtccgt gtctgcatcg gttttcacac tggtggccat cgctgtggaa    420

aggttccgct gcatcgtgca ccctttccgc gagaagctga cccttcggaa ggcgctgttc    480

accatcgcgg tgatctgggc tctggcgctg ctcatcatgt gtccctcggc ggtcactctg    540

acagtcaccc gagaggagca tcacttcatg ctggatgctc gtaaccgctc ctacccgctc    600

tactcgtgct gggaggcctg gcccgagaag ggcatgcgca aggtctacac cgcggtgctc    660

ttcgcgcaca tctacctggt gccgctggcg ctcatcgtag tgatgtacgt gcgcatcgcg    720

cgcaagctat gccaggcccc cggtcctgcg cgcgacacgg aggaggcggt ggccgagggt    780

ggccgcactt cgcgccgtag ggcccgcgtg gtgcacatgc tggtcatggt ggcgctcttc    840

ttcacgttgt cctggctgcc actctgggtg ctgctgctgc tcatcgacta tggggagctg    900

agcgagctgc aactgcacct gctgtcggtc tacgccttcc ccttggcaca ctggctggcc    960

ttcttccaca gcagcgccaa ccccatcatc tacggctact tcaacgagaa cttccgccgc   1020

ggcttccagg ctgccttccg tgcacagctc tgctggcctc cctgggccgc ccacaagcaa   1080

gcctactcgg agcggcccaa ccgcctcctg cgcaggcggg tggtggtgga cgtgcaaccc   1140

agcgactccg gcctgccatc agagtctggc cccagcagcg gggtcccagg gcctggccgg   1200

ctgccactgc gcaatgggcg tgtggcccat caggatggcc cgggggaagg gccaggctgc   1260

aaccacatgc ccctcaccat cccggcctgg aacatttga                          1299
```

<210> SEQ ID NO 39
<211> LENGTH: 12
<212> TYPE: PRT
<213> ORGANISM: Artificial Sequence
<220> FEATURE:
<223> OTHER INFORMATION: the C-terminus of the polypeptide is amide (-CONH2) form

<400> SEQUENCE: 39

```
Met Pro His Ser Phe Ala Asn Leu Pro Leu Arg Phe
 1               5                   10
```

<210> SEQ ID NO 40
<211> LENGTH: 8
<212> TYPE: PRT
<213> ORGANISM: Artificial Sequence
<220> FEATURE:
<223> OTHER INFORMATION: the C-terminus of the polypeptide is amide (-CONH2) form

<400> SEQUENCE: 40

```
Val Pro Asn Leu Pro Gln Arg Phe
 1               5
```

<210> SEQ ID NO 41
<211> LENGTH: 11
<212> TYPE: PRT
<213> ORGANISM: Artificial Sequence
<220> FEATURE:
<223> OTHER INFORMATION: the C-terminus of the polypeptide is amide (-CONH2) form

<400> SEQUENCE: 41

```
Ser Ala Gly Ala Thr Ala Asn Leu Pro Arg Ser
 1              5                   10
```

<210> SEQ ID NO 42
<211> LENGTH: 36
<212> TYPE: DNA

-continued

<213> ORGANISM: Human

<400> SEQUENCE: 42
atgccacact ccttcgccaa cttgccattg agattt 36

<210> SEQ ID NO 43
<211> LENGTH: 36
<212> TYPE: DNA
<213> ORGANISM: Human

<400> SEQUENCE: 43
agtgctggag caacagccaa cctgcctctg agatct 36

<210> SEQ ID NO 44
<211> LENGTH: 24
<212> TYPE: DNA
<213> ORGANISM: Human

<400> SEQUENCE: 44
gttcctaacc tgccccaaag gttt 24

<210> SEQ ID NO 45
<211> LENGTH: 276
<212> TYPE: DNA
<213> ORGANISM: Human

<400> SEQUENCE: 45
atggaaatta tttcatcaaa actattcatt ttattgactt tagccacttc aagcttgtta 60
acatcaaaca ttttttgtgc agatgaatta gtgatgtcca atcttcacag caaagaaaat 120
tatgacaaat attctgagcc tagaggatac ccaaaagggg aaagaagcct caattttgag 180
gaattaaaag attggggacc aaaaaatgtt attaagatga gtacacctgc agtcaataaa 240
atgccacact ccttcgccaa cttgccattg agattt 276

<210> SEQ ID NO 46
<211> LENGTH: 336
<212> TYPE: DNA
<213> ORGANISM: Human

<400> SEQUENCE: 46
atggaaatta tttcatcaaa actattcatt ttattgactt tagccacttc aagcttgtta 60
acatcaaaca ttttttgtgc agatgaatta gtgatgtcca atcttcacag caaagaaaat 120
tatgacaaat attctgagcc tagaggatac ccaaaagggg aaagaagcct caattttgag 180
gaattaaaag attggggacc aaaaaatgtt attaagatga gtacacctgc agtcaataaa 240
atgccacact ccttcgccaa cttgccattg agatttggga ggaacgttca agaagaaaga 300
agtgctggag caacagccaa cctgcctctg agatct 336

<210> SEQ ID NO 47
<211> LENGTH: 393
<212> TYPE: DNA
<213> ORGANISM: Human

<400> SEQUENCE: 47
atggaaatta tttcatcaaa actattcatt ttattgactt tagccacttc aagcttgtta 60
acatcaaaca ttttttgtgc agatgaatta gtgatgtcca atcttcacag caaagaaaat 120
tatgacaaat attctgagcc tagaggatac ccaaaagggg aaagaagcct caattttgag 180
gaattaaaag attggggacc aaaaaatgtt attaagatga gtacacctgc agtcaataaa 240

-continued

```
atgccacact ccttcgccaa cttgccattg agatttggga ggaacgttca agaagaaaga    300

agtgctggag caacagccaa cctgcctctg agatctgga agaaatatgga ggtgagcctc    360

gtgagacgtg ttcctaacct gccccaaagg ttt                                 393


<210> SEQ ID NO 48
<211> LENGTH: 27
<212> TYPE: DNA
<213> ORGANISM: Artificial  Sequence
<220> FEATURE:
<223> OTHER INFORMATION: primer

<400> SEQUENCE: 48

ccctggggct tcttctgtct tctatgt                                         27


<210> SEQ ID NO 49
<211> LENGTH: 26
<212> TYPE: DNA
<213> ORGANISM: Artificial  Sequence
<220> FEATURE:
<223> OTHER INFORMATION: primer

<400> SEQUENCE: 49

agcgattcat tttattgact ttagca                                          26


<210> SEQ ID NO 50
<211> LENGTH: 203
<212> TYPE: PRT
<213> ORGANISM: Rat

<400> SEQUENCE: 50

Met Glu Ile Ile Ser Ser Lys Arg Phe Ile Leu Leu Thr Leu Ala Thr
 1               5                  10                  15

Ser Ser Phe Leu Thr Ser Asn Thr Leu Cys Ser Asp Glu Leu Met Met
            20                  25                  30

Pro His Phe His Ser Lys Glu Gly Tyr Gly Lys Tyr Tyr Gln Leu Arg
        35                  40                  45

Gly Ile Pro Lys Gly Val Lys Glu Arg Ser Val Thr Phe Gln Glu Leu
    50                  55                  60

Lys Asp Trp Gly Ala Lys Lys Asp Ile Lys Met Ser Pro Ala Pro Ala
 65                  70                  75                  80

Asn Lys Val Pro His Ser Ala Ala Asn Leu Pro Leu Arg Phe Gly Arg
                85                  90                  95

Asn Ile Glu Asp Arg Arg Ser Pro Arg Ala Arg Ala Asn Met Glu Ala
            100                 105                 110

Gly Thr Met Ser His Phe Pro Ser Leu Pro Gln Arg Phe Gly Arg Thr
        115                 120                 125

Thr Ala Arg Arg Ile Thr Lys Thr Leu Ala Gly Leu Pro Gln Lys Ser
    130                 135                 140

Leu His Ser Leu Ala Ser Ser Glu Leu Leu Tyr Ala Met Thr Arg Gln
145                 150                 155                 160

His Gln Glu Ile Gln Ser Pro Gly Gln Glu Gln Pro Arg Lys Arg Val
                165                 170                 175

Phe Thr Glu Thr Asp Asp Ala Glu Arg Lys Gln Glu Lys Ile Gly Asn
            180                 185                 190

Leu Gln Pro Val Leu Gln Gly Ala Met Lys Leu
        195                 200
```

-continued

<210> SEQ ID NO 51
<211> LENGTH: 609
<212> TYPE: DNA
<213> ORGANISM: Rat

<400> SEQUENCE: 51
atggaaatta tttcatcaaa gcgattcatt ttattgactt tagcaacttc aagcttctta 60
acttcaaaca ccctttgttc agatgaatta atgatgcccc attttcacag caaagaaggt 120
tatggaaaat attaccagct gagaggaatc ccaaaagggg taaaggaaag aagtgtcact 180
tttcaagaac tcaaagattg gggggcaaag aaagatatta agatgagtcc agcccctgcc 240
aacaaagtgc cccactcagc agccaacctt cccctgaggt ttgggaggaa catagaagac 300
agaagaagcc ccagggcacg ggccaacatg gaggcaggga ccatgagcca ttttcccagc 360
ctgccccaaa ggtttgggag aacaacagcc agacgcatca ccaagacact ggctggtttg 420
ccccagaaat ccctgcactc cctggcctcc agtgaattgc tctatgccat gacccgccag 480
catcaagaaa ttcagagtcc tggtcaagag caacctagga aacgggtgtt cacggaaaca 540
gatgatgcag aaaggaaaca agaaaaaata ggaaacctcc agccagtcct tcaaggggct 600
atgaagctg 609

<210> SEQ ID NO 52
<211> LENGTH: 27
<212> TYPE: DNA
<213> ORGANISM: Artificial Sequence
<220> FEATURE:
<223> OTHER INFORMATION: primer

<400> SEQUENCE: 52
ttctagattt tggacaaaat ggaaatt 27

<210> SEQ ID NO 53
<211> LENGTH: 27
<212> TYPE: DNA
<213> ORGANISM: Artificial Sequence
<220> FEATURE:
<223> OTHER INFORMATION: primer

<400> SEQUENCE: 53
cgtctttagg gacaggctcc agatttc 27

<210> SEQ ID NO 54
<211> LENGTH: 430
<212> TYPE: PRT
<213> ORGANISM: Human

<400> SEQUENCE: 54

Met Glu Gly Glu Pro Ser Gln Pro Pro Asn Ser Ser Trp Pro Leu Ser
1 5 10 15

Gln Asn Gly Thr Asn Thr Glu Ala Thr Pro Ala Thr Asn Leu Thr Phe
20 25 30

Ser Ser Tyr Tyr Gln His Thr Ser Pro Val Ala Ala Met Phe Ile Val
35 40 45

Ala Tyr Ala Leu Ile Phe Leu Leu Cys Met Val Gly Asn Thr Leu Val
50 55 60

Cys Phe Ile Val Leu Lys Asn Arg His Met His Thr Val Thr Asn Met
65 70 75 80

Phe Ile Leu Asn Leu Ala Val Ser Asp Leu Leu Val Gly Ile Phe Cys
85 90 95

-continued

```
Met Pro Thr Thr Leu Val Asp Asn Leu Ile Thr Gly Trp Pro Phe Asp
            100                 105                 110

Asn Ala Thr Cys Lys Met Ser Gly Leu Val Gln Gly Met Ser Val Ser
        115                 120                 125

Ala Ser Val Phe Thr Leu Val Ala Ile Ala Val Glu Arg Phe Arg Cys
    130                 135                 140

Ile Val His Pro Phe Arg Glu Lys Leu Thr Leu Arg Lys Ala Leu Val
145                 150                 155                 160

Thr Ile Ala Val Ile Trp Ala Leu Ala Leu Leu Ile Met Cys Pro Ser
                165                 170                 175

Ala Val Thr Leu Thr Val Thr Arg Glu Glu His His Phe Met Val Asp
            180                 185                 190

Ala Arg Asn Arg Ser Tyr Pro Leu Tyr Ser Cys Trp Glu Ala Trp Pro
        195                 200                 205

Glu Lys Gly Met Arg Arg Val Tyr Thr Thr Val Leu Phe Ser His Ile
    210                 215                 220

Tyr Leu Ala Pro Leu Ala Leu Ile Val Val Met Tyr Ala Arg Ile Ala
225                 230                 235                 240

Arg Lys Leu Cys Gln Ala Pro Gly Pro Ala Pro Gly Gly Glu Glu Ala
                245                 250                 255

Ala Asp Pro Arg Ala Ser Arg Arg Arg Ala Arg Val Val His Met Leu
            260                 265                 270

Val Met Val Ala Leu Phe Phe Thr Leu Ser Trp Leu Pro Leu Trp Ala
        275                 280                 285

Leu Leu Leu Leu Ile Asp Tyr Gly Gln Leu Ser Ala Pro Gln Leu His
    290                 295                 300

Leu Val Thr Val Tyr Ala Phe Pro Phe Ala His Trp Leu Ala Phe Phe
305                 310                 315                 320

Asn Ser Ser Ala Asn Pro Ile Ile Tyr Gly Tyr Phe Asn Glu Asn Phe
                325                 330                 335

Arg Arg Gly Phe Gln Ala Ala Phe Arg Ala Arg Leu Cys Pro Arg Pro
            340                 345                 350

Ser Gly Ser His Lys Glu Ala Tyr Ser Glu Arg Pro Gly Gly Leu Leu
        355                 360                 365

His Arg Arg Val Phe Val Val Val Arg Pro Ser Asp Ser Gly Leu Pro
    370                 375                 380

Ser Glu Ser Gly Pro Ser Ser Gly Ala Pro Arg Pro Gly Arg Leu Pro
385                 390                 395                 400

Leu Arg Asn Gly Arg Val Ala His His Gly Leu Pro Arg Glu Gly Pro
                405                 410                 415

Gly Cys Ser His Leu Pro Leu Thr Ile Pro Ala Trp Asp Ile
            420                 425                 430
```

<210> SEQ ID NO 55
<211> LENGTH: 1290
<212> TYPE: DNA
<213> ORGANISM: Human

<400> SEQUENCE: 55

```
atggaggggg agccctccca gcctcccaac agcagttggc ccctaagtca gaatgggact      60

aacactgagg ccaccccggc tacaaacctc accttctcct cctactatca gcacacctcc     120

cctgtggcgg ccatgttcat tgtggcctat gcgctcatct tcctgctctg catggtgggc     180

aacaccctgg tctgtttcat cgtgctcaag aaccggcaca tgcatactgt caccaacatg     240
```

-continued

```
ttcatcctca acctggctgt cagtgacctg ctggtgggca tcttctgcat gcccaccacc    300

cttgtggaca acctcatcac tgggtggccc ttcgacaatg ccacatgcaa gatgagcggc    360

ttggtgcagg gcatgtctgt gtcggcttcc gttttcacac tggtggccat tgctgtggaa    420

aggttccgct gcatcgtgca ccctttccgc gagaagctga ccctgcggaa ggcgctcgtc    480

accatcgccg tcatctgggc cctggcgctg ctcatcatgt gtccctcggc cgtcacgctg    540

accgtcaccc gtgaggagca ccacttcatg gtggacgccc gcaaccgctc ctaccctctc    600

tactcctgct gggaggcctg gcccgagaag ggcatgcgca gggtctacac cactgtgctc    660

ttctcgcaca tctacctggc gccgctggcg ctcatcgtgg tcatgtacgc ccgcatcgcg    720

cgcaagctct gccaggcccc gggcccggcc cccgggggcg aggaggctgc ggacccgcga    780

gcatcgcggc gcagagcgcg cgtggtgcac atgctggtca tggtggcgct gttcttcacg    840

ctgtcctggc tgccgctctg ggcgctgctg ctgctcatcg actacgggca gctcagcgcg    900

ccgcagctgc acctggtcac cgtctacgcc ttccccttcg cgcactggct ggccttcttc    960

aacagcagcg ccaaccccat catctacggc tacttcaacg agaacttccg ccgcggcttc   1020

caggccgcct tccgcgcccg cctctgcccg cgcccgtcgg ggagccacaa ggaggcctac   1080

tccgagcggc ccggcgggct tctgcacagg cgggtcttcg tggtggtgcg gcccagcgac   1140

tccgggctgc cctctgagtc gggccctagc agtggggccc ccaggcccgg ccgcctcccg   1200

ctgcggaatg ggcgggtggc tcaccacggc ttgcccaggg aagggcctgg ctgctcccac   1260

ctgcccctca ccattccagc ctgggatatc                                    1290
```

<210> SEQ ID NO 56
<211> LENGTH: 1290
<212> TYPE: DNA
<213> ORGANISM: Human

<400> SEQUENCE: 56

```
atggaggggg agccctccca gcctcccaac agcagttggc ccctaagtca gaatgggact     60

aacactgagg ccaccccggc tacaaacctc accttctcct cctactatca gcacacctcc    120

cctgtggcgg ccatgttcat tgtggcctat gcgctcatct tcctgctctg catggtgggc    180

aacaccctgg tctgtttcat cgtgctcaag aaccggcaca tgcatactgt caccaacatg    240

ttcatcctca acctggctgt cagtgacctg ctggtgggca tcttctgcat gcccaccacc    300

cttgtggaca acctcatcac tgggtggccc ttcgacaatg ccacatgcaa gatgagcggc    360

ttggtgcagg gcatgtctgt gtcggcttcc gttttcacac tggtggccat tgctgtggaa    420

aggttccgct gcatcgtgca ccctttccgc gagaagctga ccctgcggaa ggcgctcgtc    480

accatcgccg tcatctgggc cctggcgctg ctcatcatgt gtccctcggc cgtcacgctg    540

accgtcaccc gtgaggagca ccacttcatg gtggacgccc gcaaccgctc ctacccgctc    600

tactcctgct gggaggcctg gcccgagaag ggcatgcgca gggtctacac cactgtgctc    660

ttctcgcaca tctacctggc gccgctggcg ctcatcgtgg tcatgtacgc ccgcatcgcg    720

cgcaagctct gccaggcccc gggcccggcc cccgggggcg aggaggctgc ggacccgcga    780

gcatcgcggc gcagagcgcg cgtggtgcac atgctggtca tggtggcgct gttcttcacg    840

ctgtcctggc tgccgctctg ggcgctgctg ctgctcatcg actacgggca gctcagcgcg    900

ccgcagctgc acctggtcac cgtctacgcc ttccccttcg cgcactggct ggccttcttc    960

aacagcagcg ccaaccccat catctacggc tacttcaacg agaacttccg ccgcggcttc   1020

caggccgcct tccgcgcccg cctctgcccg cgcccgtcgg ggagccacaa ggaggcctac   1080
```

-continued

```
tccgagcggc ccggcgggct tctgcacagg cgggtcttcg tggtggtgcg gcccagcgac   1140

tccgggctgc cctctgagtc gggccctagc agtggggccc ccaggcccgg ccgcctcccg   1200

ctgcggaatg ggcgggtggc tcaccacggc ttgcccaggg aagggcctgg ctgctcccac   1260

ctgcccctca ccattccagc ctgggatatc                                     1290
```

<210> SEQ ID NO 57
<211> LENGTH: 31
<212> TYPE: DNA
<213> ORGANISM: Artificial Sequence
<220> FEATURE:
<223> OTHER INFORMATION: primer

<400> SEQUENCE: 57

```
gtcgacatgg agggggagcc ctcccagcct c                                     31
```

<210> SEQ ID NO 58
<211> LENGTH: 29
<212> TYPE: DNA
<213> ORGANISM: Artificial Sequence
<220> FEATURE:
<223> OTHER INFORMATION: primer

<400> SEQUENCE: 58

```
actagttcag atatcccagg ctggaatgg                                        29
```

<210> SEQ ID NO 59
<211> LENGTH: 58
<212> TYPE: DNA
<213> ORGANISM: Artificial Sequence
<220> FEATURE:
<223> OTHER INFORMATION: Primer

<400> SEQUENCE: 59

```
tatgagcctg aactttgaag aactgaaaga ttggggtccg aaaaatgtga ttaaaatg        58
```

<210> SEQ ID NO 60
<211> LENGTH: 61
<212> TYPE: DNA
<213> ORGANISM: Artificial Sequence
<220> FEATURE:
<223> OTHER INFORMATION: Primer

<400> SEQUENCE: 60

```
agcaccccgg cggtgaataa aatgccgcat agctttgcga atctgccgct gcgtttttgc      60

c                                                                      61
```

<210> SEQ ID NO 61
<211> LENGTH: 62
<212> TYPE: DNA
<213> ORGANISM: Artificial Sequence
<220> FEATURE:
<223> OTHER INFORMATION: Primer

<400> SEQUENCE: 61

```
ggtgctcatt ttaatcacat ttttcggacc ccaatctttc agttcttcaa agttcaggct      60

ca                                                                     62
```

<210> SEQ ID NO 62
<211> LENGTH: 59
<212> TYPE: DNA
<213> ORGANISM: Artificial Sequence
<220> FEATURE:

-continued

```
<223> OTHER INFORMATION: Primer

<400> SEQUENCE: 62

tcggggcaaa aacgcagcgg cagattcgca aagctatgcg gcattttatt caccgccgg      59


<210> SEQ ID NO 63
<211> LENGTH: 20
<212> TYPE: PRT
<213> ORGANISM: bovine
<220> FEATURE:
<221> NAME/KEY: misc_feature
<222> LOCATION: (10)..(10)
<223> OTHER INFORMATION: Xaa represents an unidentified amino acid
      residue

<400> SEQUENCE: 63

Ser Leu Thr Phe Glu Glu Val Lys Asp Xaa Ala Pro Lys Ile Lys Met
1               5                   10                  15

Asn Lys Pro Val
            20


<210> SEQ ID NO 64
<211> LENGTH: 4
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: AMIDATION

<400> SEQUENCE: 64

Pro Gln Arg Phe
1


<210> SEQ ID NO 65
<211> LENGTH: 5
<212> TYPE: PRT
<213> ORGANISM: Artificial
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 65

Leu Pro Leu Arg Phe
1               5


<210> SEQ ID NO 66
<211> LENGTH: 4
<212> TYPE: PRT
<213> ORGANISM: Artificial
<220> FEATURE:
<223> OTHER INFORMATION: Synthetic peptide

<400> SEQUENCE: 66

Asn Pro Phe Phe
1
```